(12) United States Patent
Ohba et al.

(10) Patent No.: US 12,102,641 B2
(45) Date of Patent: *Oct. 1, 2024

(54) SULFONAMIDE OR SULFINAMIDE COMPOUND HAVING EFFECT OF INDUCING BRD4 PROTEIN DEGRADATION AND PHARMACEUTICAL USE THEREOF

(71) Applicant: MITSUBISHI TANABE PHARMA CORPORATION, Osaka (JP)

(72) Inventors: Kiyomi Ohba, Osaka (JP); Yasuki Niwa, Osaka (JP); Tetsuji Matsudaira, Osaka (JP); Maiko Hamada, Osaka (JP); Ryuta Yamazaki, Tokyo (JP); Tatsuya Ibuki, Tokyo (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 189 days.

This patent is subject to a terminal disclaimer.

(21) Appl. No.: 17/796,258

(22) PCT Filed: Feb. 5, 2021

(86) PCT No.: PCT/JP2021/004231
§ 371 (c)(1),
(2) Date: Jul. 28, 2022

(87) PCT Pub. No.: WO2021/157684
PCT Pub. Date: Aug. 12, 2021

(65) Prior Publication Data
US 2023/0146717 A1 May 11, 2023

(30) Foreign Application Priority Data
Feb. 6, 2020 (JP) .................. 2020-019227

(51) Int. Cl.
A61K 31/5517 (2006.01)
A61P 35/00 (2006.01)

(52) U.S. Cl.
CPC .......... *A61K 31/5517* (2013.01); *A61P 35/00* (2018.01)

(58) Field of Classification Search
None
See application file for complete search history.

(56) References Cited

U.S. PATENT DOCUMENTS

| 11,890,288 | B2 * | 2/2024 | Ohba | A61K 31/5517 |
| 2021/0002295 | A1 | 1/2021 | Gray et al. | |
| 2021/0024540 | A1 | 1/2021 | Uchida et al. | |
| 2021/0284654 | A1 | 9/2021 | Yamazaki et al. | |

FOREIGN PATENT DOCUMENTS

| WO | WO 2019/118851 A1 | 6/2019 |
| WO | WO 2019/189778 A1 | 10/2019 |
| WO | WO 2020/009176 A1 | 1/2020 |

OTHER PUBLICATIONS

U.S. Appl. No. 18/355,554, filed Jul. 20, 2023.
Crawford et al., "Bromodomain 4 Activation Predicts Breast Cancer Survival," *Proc. Nat. Acad. Sci. USA*., 105(17): 6380-6385 (2008).
Dai et al., "Prostate Cancer-associated SPOP Mutations Confer Resistance to BET Inhibitors through Stabilization of BRD4," *Nat. Med.*, 23(9): 1063-1071 (2017).
Herrmann et al., "Small-molecule Inhibition of BRD4 as a New Potent Approach to Eliminate Leukemic Stem- and Progenitor Cells in Acute Myeloid Leukemia (AML)," *Oncotarget*, 3(12): 1588-1599 (2012).
Hu et al., "BRD4 Inhibitor Inhibits Colorectal Cancer Growth and Metastasis," *Int. J. Mol. Sci.*, 16(1): 1928-1948 (2015).
Iliopoulos et al., "Tumour Suppression by the Human von Hippel-Lindau Gene Product," *Nat. Med.*, 1(8): 822-826 (1995).
Kanno et al., "BRD4 Assists Elongation of Both Coding and Enhancer RNAs by Interacting with Acetylated Histones," *Nat. Struct. Mol. Biol.*, 21(12): 1047-1057 (2014).
Li et al., "In Vivo Target Protein Degradation Induced by PROTACs Based on E3 Ligase DCAF15," *Signal Transduction and Targeted Therapy*, 5(1): 129 (2020).
Liao et al., "High Level of BRD4 Promotes Non-small Cell Lung Cancer Progression," *Oncotarget*, 7(8): 9491-9500 (2016).
Liu et al., "Drug Discovery Targeting Bromodomain-Containing Protein 4," *J. Med. Chem.*, 60(11): 4533-4558 (2017).
Lu et al., "Hijacking the E3 Ubiquitin Ligase Cereblon to Efficiently Target BRD4," *Chem. Biol.*, 22(6): 755-763 (2015).
Nguyen et al., "Targeting the E3 Ubiquitin Ligases DCAF15 and Cereblon for Cancer Therapy," *Semin. Cancer. Biol.*, 67: 53-60 (2020).
Raina et al., "PROTAC-induced BET Protein Degradation as a Therapy for Castration-resistant Prostate Cancer," *Proc. Nat. Acad. Sci. USA.*, 113(26): 7124-7129 (2016).
Schapira et al., "Targeted Protein Degradation: Expanding the Toolbox," *Nat. Rev. Drug. Discov.*, 18(12): 949-963 (2019).

(Continued)

*Primary Examiner* — Brian J Davis
(74) *Attorney, Agent, or Firm* — Leydig, Voit & Mayer, Ltd.

(57) ABSTRACT

Provided is a compound or a pharmaceutically acceptable salt thereof which is superior in an action inducing degradation of BRD4 protein and useful as a therapeutic agent for cancer. A compound represented by the following formula (I) or a pharmaceutically acceptable salt thereof:

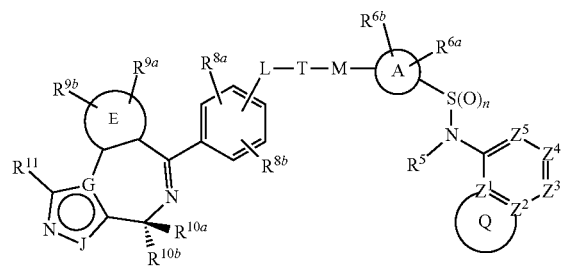

wherein each symbol is as defined in the DESCRIPTION.

19 Claims, 2 Drawing Sheets

(56) References Cited

OTHER PUBLICATIONS

Segura et al., "BRD4 Sustains Melanoma Proliferation and Represents a New Target for Epigenetic Therapy," *Cancer Res.*, 73(20): 6264-6276 (2013).
Shu et al., "Response and Resistance to BET Bromodomain Inhibitors in Triple-negative Breast Cancer," *Nature.*, 529(7586): 413-417 (2016).
Stathis et al., "Clinical Response of Carcinomas Harboring the BRD4-NUT Oncoprotein to the Targeted Bromodomain Inhibitor OTX015/MK-8628," *Cancer Discov.*, 6(5): 492-500 (2016).
Taniguchi, "The Bromodomain and Extra-Terminal Domain (BET) Family: Functional Anatomy of BET Paralogous Proteins," *Int. J. Mol. Sci.*, 17(11): 1849 (2016).
Toure et al., "Small-molecule PROTACS: New Approaches to Protein Degradation," *Angew. Chem. Int. Ed. Engl.*, 55(6): 1966-1973 (2016).
Ucar et al., "Amplification of the Bromodomain-containing Protein 4 Gene in Ovarian High-grade Serous Carcinoma is Associated with Worse Prognosis and Survival," *Mol. Clin. Oncol.*, 3(6): 1291-1294 (2015).
Vasan et al., "A View on Drug Resistance in Cancer," *Nature.* 575(7782): 299-309 (2019).
Yan et al., "Bromodomain 4 Protein is a Predictor of Survival for Urothelial Carcinoma of Bladder," *Int. J. Clin. Exp. Pathol.*, 7(7): 4231-4238 (2014).
Zhang et al., "BRD4 Promotes Tumor Growth and Epithelial-mesenchymal Transition in Hepatocellular Carcinoma," *Int. J. Immunopathol. Pharmacol.*, 28(1): 36-44 (2015).
Zhang et al., "Acquired Resistance to BET-PROTACs (Proteolysis-Targeting Chimeras) Caused by Genomic Alterations in Core Components of E3 Ligase Complexes," *Mol. Cancer. Ther.*, 18(7): 1302-1311 (2019).
Zhu et al., "Bromodomain Protein 4 is a Novel Predictor of Survival for Gastric Carcinoma," *Oncotarget*, 8(19): 31092-31100 (2017).
Japan Patent Office, International Search Report in International Patent Application No. PCT/JP2021/004231 (Apr. 20, 2021).

* cited by examiner

SULFONAMIDE OR SULFINAMIDE COMPOUND HAVING EFFECT OF INDUCING BRD4 PROTEIN DEGRADATION AND PHARMACEUTICAL USE THEREOF

TECHNICAL FIELD

The present invention relates to a sulfonamide or sulfinamide compound or a pharmaceutically acceptable salt thereof, which is superior in a cytotoxic action on cancer cells, an action inducing degradation of BRD4 protein in cancer cells, and an inhibitory action on the binding of BRD4 protein and acetylated histone, and useful as an anticancer drug, a BRD4 protein degradation inducing agent or a BRD4 protein inhibitor.

BACKGROUND ART

Eukaryotic DNA forms a chromatin structure and is stored in the nucleus. Nucleosome which is a constitutional unit thereof has a structure in which DNA is wound around histone octamer formed by 2 molecules each of 4 kinds of histones, H2A, H2B, H3, H4. Dozens of residues on the N-terminal side of histones is called a histone tale, and various post-translational modifications such as acetylation, methylation, phosphorylation, ubiquitination are present therein. Post-translational modification, also called histone code, is one of the mechanisms responsible for controlling epigenetic gene expression, which determines when or where genetic information on DNA is expressed. Histone modification is reversible, and functionally controlled by a modifying enzyme (writer) that writes modification group into histone, a demodifying enzyme (eraser) that removes modification group, and a histone reader (reader) that specifically reads modified histone. It is known that such control mechanism greatly contributes to ontogenesis and cell differentiation, while epigenetics abnormalities are involved in various diseases.

The bromodomain is a reader protein consisting of about 110 amino acids that recognize acetylated lysine of histone. About 50 kinds of proteins possessing a bromodomain have been known to date, and they function as scaffold proteins for various transcription factors by binding to acetylated lysine of histone and also show various functions in the cell such as being responsible for chromatin reconstitution and transcriptional regulation through its own histone acetyltransferase activity and kinase activity and the like. BRD2, BRD3, BRD4 and BRDT contained in the BET (bromodomain and extraterminal) family protein of the bromodomain-containing protein (sometimes to be indicated as BET protein in the present specification and Claims) possess two highly conserved bromodomains on the N-terminal side and Extra C-Terminal domain on the C-terminal side within the family, and respective BET proteins are known to function both independently and cooperatively (non-patent document 1).

Among the BET family proteins, BRD4 is expected to be the target of drug discovery in cancer treatment because it regulates the expression of c-MYC which is a proto-oncogene (non-patent document 2) and has been reported to have a correlation with prognosis in various carcinomas such as gastric cancer (non-patent document 3), ovarian cancer (non-patent document 4), lung cancer (non-patent document 5), liver cancer (non-patent document 6), urothelial cancer (non-patent document 7), testicular cancer (non-patent document 8), skin cancer (non-patent document 9), prostate cancer (non-patent document 10), breast cancer (non-patent document 11), colorectal cancer (non-patent document 12) and leukemia (non-patent document 13).

To date, a BRD4 inhibitor that inhibits the binding of BRD4 to histone has been clinically developed as an anticancer drug targeting BRD4 (non-patent document 14). However, BRD4 inhibitors do not show a sufficient effect since they cause accumulation of BRD4 (non-patent document 15), and resistance is acquired by expression of proteins that stabilize BRD4 expression and proteins that enhance BRD4-mediated transcriptional activity in a bromodomain-independent manner (non-patent documents 16, 17). Thus, the development of an anticancer drug targeting BRD4 by a new means is required.

In recent years, a technology in which an artificial complex of E3 ligase and a target protein is formed in the cell by using a compound in which a ligand for an E3 ligase [Von Hippel-Lindau (VHL), Cereblon (CRBN), Cellular Inhibitor of Apoptosis Protein 1 (cIAP1)] having ubiquitin ligase activity and a binder that binds to the target protein are linked, and degradation of the target protein is induced by using the ubiquitin-proteasome system, which is an intracellular protein degradation mechanism (chemical knockdown) has been attracting attention as a new drug discovery technique (non-patent document 18). ARV-771 utilizing a ligand for VHL, ARV-825 utilizing a ligand for CRBN and the like have heretofore been reported as BRD4 protein degradation inducing agents utilizing this technique (non-patent documents 15, 19).

In cancer chemotherapy, the emergence of natural tolerance that renders anticancer drugs ineffective from the beginning of treatment and acquired resistance that decreases the effect of anticancer drugs when they are used continuously for a long period of time has become a major issue (non-patent document 20). It is expected that the treatment results of cancer chemotherapy will be improved by overcoming the resistance to anticancer drugs, and the existence of various resistance mechanisms has been clarified so far (non-patent document 20). Regarding BRD4 protein degradation inducing agents, it has been reported that acquired resistance is induced in cancer cells due to the dysfunction of the complex of E3 ligase VHL or CRBN that causes proteolysis action (non-patent document 21). In tumors such as renal cell cancer and the like caused by mutation in the VHL gene (non-patent document 22), it is considered that natural resistance to BRD4 protein degradation inducing agents using a ligand for VHL occurs, and the development of a novel BRD4 protein degradation inducing agent that uses a new ligand for E3 ligase and overcomes the resistance to the conventional BRD4 protein degradation inducing agents is desired. In recent years, many target protein degradation inducing compounds have been reported in which a new ligand for E3 ligase and a binder for the target protein are bound (non-patent document 23). For example, a BRD4 protein degradation inducing agent newly using E3 ligase DCAF15 has been reported (non-patent document 24). However, it is difficult to say that the BRD4 proteolysis inducing action and cytotoxic action thereof are sufficient. The combination of a ligand for E3 ligase and a binder for the target protein is currently limited (non-patent document 23), and it is desired to find a combination of an appropriate ligand for E3 ligase and a linker structure that is necessary for exhibiting a BRD4 proteolysis inducing action and a cytotoxic action sufficient as an anticancer drug on the binders for BRD4 protein.

DOCUMENT LIST

Non-Patent Documents non-patent document 1: Taniguchi Y., Int J Mol Sci. 2016, 17: E1849
non-patent document 2: Kanno T., Nat Struct Mol Biol. 2014, 21: 1047-1057
non-patent document 3: Zhu Y., Oncotarget. 2017, 8: 31092-31100
non-patent document 4: Ucar D., Mol Clin Oncol. 2015, 3: 1291-1294
non-patent document 5: Liao Y F., Oncotarget. 2016, 7: 9491-9500
non-patent document 6: Zhang P., Int J Immunopathol Pharmacol. 2015, 28: 36-44
non-patent document 7: Yan Y., Int J Clin Exp Pathol. 2014, 7: 4231-4238
non-patent document 8: Stathis A., Cancer Discov. 2016, 6: 492-500
non-patent document 9: Segura M F., Cancer Res. 2013, 73: 6264-6276
non-patent document 10: Dai X., Nat Med. 2017, 23: 1063-1071
non-patent document 11: Crawford N P., Proc Natl Acad Sci USA. 2008, 105: 6380-6385
non-patent document 12: Hu Y., Int J Mol Sci. 2015, 16: 1928-1948
non-patent document 13: Herrmann H., Oncotarget. 2012, 3: 1588-1599
non-patent document 14: Liu Z., J Med Chem. 2017, 60: 4533-4558
non-patent document 15: Lu J., Chem Biol. 2015, 22: 755-763
non-patent document 16: Dai X., Nat Med. 2017, 23: 1063-1071
non-patent document 17: Shu S., Nature. 2016, 529: 413-417
non-patent document 18: Toure M., Angew Chem Int Ed Engl. 2016, 55: 1966-1973
non-patent document 19: Raina K., Proc Natl Acad Sci USA. 2016, 113: 7124-7129
non-patent document 20: Neil V., Nature. 2019, 575: 299-309
non-patent document 21: Zhang L., Mol Cancer Ther. 2019, 18: 1302-1311.
non-patent document 22: Iliopoulos O., Nat Med. 1995, 1: 822-826.
non-patent document 23: Schapira M., Nat Rev Drug Discov. 2019, 18: 949-963.
non-patent document 24: Li L., Signal Transduct Target Ther. 2020, 5: 129.

SUMMARY OF INVENTION

Technical Problem

The present invention aims to provide a compound or a pharmaceutically acceptable salt thereof that uses a ligand for E3 ligase DCAF15, is superior in a BRD4 proteolysis-inducing action, and is useful as a therapeutic agent for cancer.

Solution to Problem

The present inventors have conducted intensive studies in an attempt to solve the aforementioned problem and found a compound that uses a ligand for E3 ligase DCAF15 and has a BRD4 proteolysis-inducing action, and found that a therapeutic agent for cancer can be provided. They have found a linker structure particularly optimal for the ligand for DCAF15 and completed the present invention. That is, the gist of the present invention is as follows.

[1] A compound represented by the formula (I):

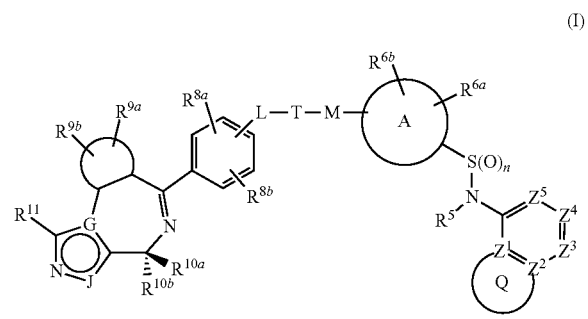

wherein
A and Q are each independently a ring selected from an aromatic hydrocarbocycle; an aromatic heterocycle containing 1 to 3 atoms selected from oxygen, sulfur and nitrogen; a cycloalkane ring; and an aliphatic heterocycle containing 1 to 3 atoms selected from oxygen, sulfur and nitrogen;
the ring is optionally substituted by a group selected from
a halogen atom;
a hydroxy group;
a cyano group;
a hydroxycarbonyl group;
an oxo group;
a thioxo group;
an alkyl group optionally substituted by a group selected from a halogen atom, a hydroxy group, an alkoxy group and a cyano group;
an alkoxy group optionally substituted by a group selected from a halogen atom, a hydroxy group, an alkoxy group and a cyano group;
an alkoxycarbonyl group optionally substituted by a group selected from a halogen atom, a hydroxy group, an alkoxy group and a cyano group;
—CO—N($R^{7a}$)($R^{7b}$);
—N($R^{7a}$)($R^{7b}$); and
—N($R^{7c}$)—CO—$R^{7d}$;
$Z^1$ is a group selected from C and N,
$Z^2$ is a group selected from C and N,
$Z^3$ is a group selected from =$CR^{Z3}$— and =N—,
$Z^4$ is a group selected from =$CR^{Z4}$— and =N—,
$Z^5$ is a group selected from =$CR^{Z5}$— and =N—,
$R^{Z3}$, $R^{Z4}$, and $R^{Z5}$ are each independently a group selected from
a hydrogen atom; a halogen atom; a hydroxy group; a cyano group; a hydroxycarbonyl group; an alkyl group optionally substituted by a group selected from a halogen atom, a hydroxy group, an alkoxy group and a cyano group; a cycloalkyl group optionally substituted by a group selected from a halogen atom, a hydroxy group, an alkoxy group and a cyano group; an alkoxy group optionally substituted by a group selected from a halogen atom, a hydroxy group, an alkoxy group and a cyano group; an alkoxycarbonyl group optionally substituted by a group selected from a halogen atom, a hydroxy group, an alkoxy group and a cyano group;

—CO—N($R^{7a}$)($R^{7b}$); —N($R^{7a}$)($R^{7b}$); —N($R^{7c}$)—CO—$R^{7d}$; an aromatic hydrocarbon group; and a 5- or 6-membered aromatic heterocyclic group containing 1 to 3 atoms selected from oxygen, sulfur and nitrogen;

a partial structure:

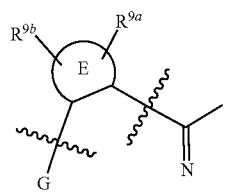

is any of the following formulas (Ea), (Eb) and (Ec):

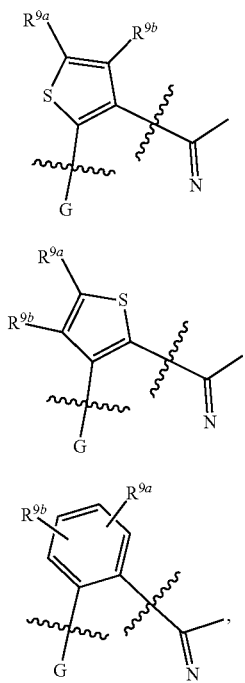

L, T, and M are each independently a single bond, a group selected from

—O—; —S—; —$NR^{7a}$—; —CO—; —SO—; —$SO_2$—; —CO—$NR^{7c}$—; —$NR^{7c}$—CO—; —$SO_2$—$NR^{7c}$—; —$NR^{7c}$—$SO_2$—; —$NR^{7a}$—CO—$NR^{7b}$—; —$(OCH_2CH_2)_m$—; —O—$R^{7r}$—; —$R^{7r}$—O—; —S—$R^{7r}$—; —$R^{7r}$—S—; —$NR^{7a}$—$R^{7r}$—; —$R^{7r}$—$NR^{7a}$—; —CO—$NR^{7c}$—$R^{7r}$—; —$R^{7r}$—CO—$NR^{7c}$—; —$SO_2$—$NR^{7c}$—$R^{7r}$—; and —$R^{7r}$—$SO_2$—$NR^{7c}$—; or a group selected from a divalent aromatic hydrocarbon group; a divalent aliphatic heterocyclic group; an optionally partly hydrogenated divalent aromatic heterocyclic group; an alkylene group; a cycloalkylene group; an alkenylene group; and an alkynylene group;

the group is optionally substituted by a substituent selected from a halogen atom; a hydroxy group; a cyano group; an oxo group; a hydroxycarbonyl group; an alkyl group optionally substituted by a group selected from a halogen atom, a hydroxy group, an alkoxy group and a cyano group; and an alkoxy group optionally substituted by a group selected from a halogen atom, a hydroxy group, an alkoxy group and a cyano group;

-L-T-M- does not indicate a group selected from —O—O—, —S—S—, —$NR^{7a}$—$NR^{7a}$—, —O—S—, —S—O—, —O—$NR^{7a}$—, —$NR^{7a}$—O—, —S—$NR^{7a}$— and —$NR^{7a}$—S—, as a whole or partial structure, G is N or C,
J is N or O,
a partial structure:

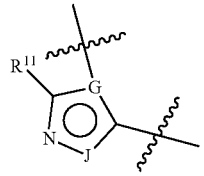

is a partial structure selected from

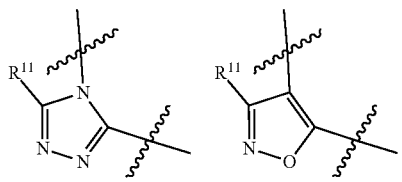

n is 1 or 2,
m is an integer of 1 to 6,
$R^5$ is a group selected from a hydrogen atom; and an alkyl group optionally substituted by a group selected from a halogen atom, a hydroxy group, an alkoxy group and a cyano group;
$R^{6a}$ and $R^{6b}$ are each independently a group selected from a hydrogen atom; a halogen atom; a hydroxy group; a cyano group; an alkyl group optionally substituted by a group selected from a halogen atom, a hydroxy group, an alkoxy group and a cyano group; and an alkoxy group optionally substituted by a group selected from a halogen atom, a hydroxy group, an alkoxy group and a cyano group;
$R^{7a}$ and $R^{7b}$ are each independently a hydrogen atom; or an alkyl group optionally substituted by a group selected from a halogen atom, a hydroxy group, an alkoxy group and a cyano group, or
$R^{7a}$ and $R^{7b}$ that are bonded to the same nitrogen atom are bonded to optionally form, together with the nitrogen atom, an aliphatic heterocycle having one nitrogen atom and optionally substituted by a group selected from a halogen atom, a hydroxy group, an alkoxy group and a cyano group,
$R^{7c}$ and $R^{7d}$ are each independently a hydrogen atom; or an alkyl group optionally substituted by a group selected from a halogen atom, a hydroxy group, an alkoxy group and a cyano group,
$R^{7r}$ is a group selected from an alkylene group optionally substituted by a group selected from a halogen atom, a hydroxy group, an alkoxy group and a cyano group; an alkenylene group optionally substituted by a group selected from a halogen atom, a hydroxy group, an alkoxy group and a cyano group; or an alkynylene group optionally substituted by a group selected from a halogen atom, a hydroxy group, an alkoxy group and a cyano group, $R^{8a}$ and $R^{8b}$ are each independently a group selected from a hydrogen atom; a halogen atom; a hydroxy group; a cyano group; an alkyl group optionally substituted by a group selected from a halogen atom, a hydroxy group, an alkoxy group and a cyano group; and an alkoxy group optionally substituted by a group selected from a halogen atom, a hydroxy group, an alkoxy group and a cyano group;

$R^{9a}$ and $R^{9b}$ are each independently a group selected from a hydrogen atom; a halogen atom; a hydroxy group; a cyano group; a hydroxycarbonyl group; an alkyl group optionally substituted by a group selected from a halogen atom, a hydroxy group, an alkoxy group and a cyano group; an alkoxy group optionally substituted by a group selected from a halogen atom, a hydroxy group, an alkoxy group and a cyano group; an alkoxycarbonyl group optionally substituted by a substituent selected from a halogen atom, a hydroxy group, an alkoxy group and a cyano group; and —CO—N($R^{7a}$)($R^{7b}$), or $R^{9a}$ and $R^{9b}$ are optionally joined to show, an alkylene group optionally substituted by a group selected from a halogen atom, a hydroxy group, an alkoxy group and a cyano group; or an alkenylene group optionally substituted by a group selected from a halogen atom, a hydroxy group, an alkoxy group and a cyano group, and optionally form a fused ring with the adjacent ring E, $R^{10a}$ and $R^{10b}$ are each independently a substituent selected from a hydrogen atom; a hydroxy group; a cyano group; —N($R^{7a}$)($R^{7b}$); —N($R^{7c}$)—CO—O$R^{7d}$; and an alkyl group;

the alkyl group is optionally substituted by a substituent selected from a halogen atom; a hydroxy group; a cyano group; an alkoxy group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; a hydroxycarbonyl group; and —CO—N($R^{7a}$)($R^{7b}$); or $R^{10a}$ and $R^{10b}$ are optionally joined to show an alkylene group optionally substituted by a group selected from a halogen atom, a hydroxy group, an alkoxy group and a cyano group and form a ring, and $R^{11}$ is a group selected from a hydrogen atom; and an alkyl group optionally substituted by a group selected from a halogen atom, a hydroxy group, an alkoxy group and a cyano group;

or a pharmaceutically acceptable salt thereof (sometimes to be abbreviated as "compound (I)" in the present specification).

[2] The compound of [1], wherein a partial structure:

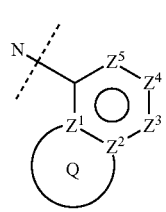

is represented by the following formula:

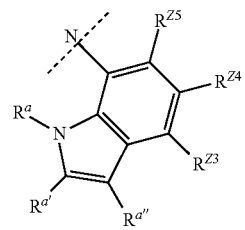

wherein
$R^a$ is a hydrogen atom; or an alkyl group optionally substituted by a substituent selected from a halogen atom, a hydroxy group, an alkoxy group and a cyano group;

$R^{a'}$ is a hydrogen atom; a halogen atom; a hydroxy group; a cyano group; an alkyl group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; or —CO—N($R^{7a}$)($R^{7b}$), $R^{a''}$ is a hydrogen atom; a halogen atom; a cyano group; an alkyl group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; or —CO—N($R^{7a}$)($R^{7b}$), or a pharmaceutically acceptable salt thereof.

[3] The compound of [2], wherein A is a ring selected from an aromatic hydrocarbocycle, a 5- or 6-membered aromatic heterocycle containing 1 to 3 atoms selected from oxygen, sulfur and nitrogen, and a cycloalkane ring, $R^{Z3}$ is a group selected from a hydrogen atom; a halogen atom; a hydroxy group; a cyano group; a hydroxycarbonyl group; an alkyl group optionally substituted by a group selected from a halogen atom, a hydroxy group, an alkoxy group and a cyano group; a cycloalkyl group optionally substituted by a group selected from a halogen atom, a hydroxy group, an alkoxy group and a cyano group; an alkoxy group optionally substituted by a group selected from a halogen atom, a hydroxy group, an alkoxy group and a cyano group; an alkoxycarbonyl group optionally substituted by a group selected from a halogen atom, a hydroxy group, an alkoxy group and a cyano group;

$R^{Z4}$ and $R^{Z5}$ are each independently a group selected from a hydrogen atom; a halogen atom; a cyano group; an alkyl group optionally substituted by a substituent selected from a halogen atom, a hydroxy group, an alkoxy group and a cyano group; an alkoxy group optionally substituted by a group selected from a halogen atom, a hydroxy group, an alkoxy group and a cyano group;

a partial structure:

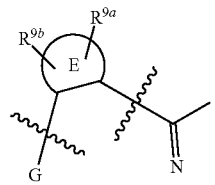

is represented by the following formula (Ea) or (Ec):

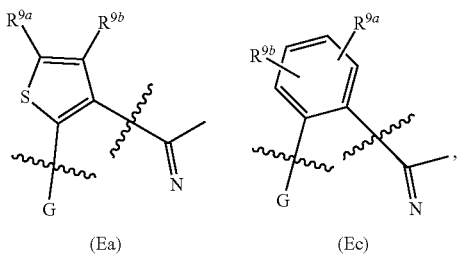

(Ea)         (Ec)

a partial structure:

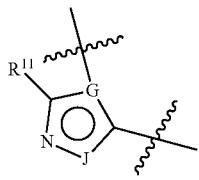

is represented by

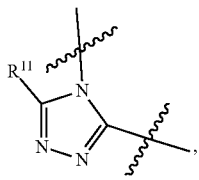

a partial structure:

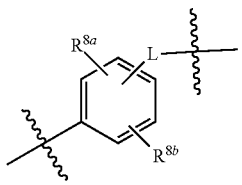

is represented by

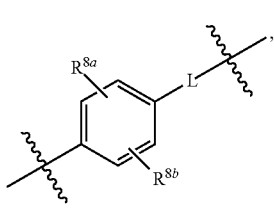

L is a group selected from a divalent aromatic hydrocarbon group; a divalent aliphatic heterocyclic group; an optionally partly hydrogenated divalent aromatic heterocyclic group; an alkylene group; a cycloalkylene group; an alkenylene group; and an alkynylene group; the group is optionally substituted by a substituent selected from a halogen atom; a hydroxy group; a cyano group; a hydroxycarbonyl group; an alkyl group optionally substituted by a group selected from a halogen atom, a hydroxy group, an alkoxy group and a cyano group; and an alkoxy group optionally substituted by a group selected from a halogen atom, a hydroxy group, an alkoxy group and a cyano group;

T is a single bond, —CO—, —CO—NR$^{7c}$—, —NR$^{7c}$—CO—, or —O—, or an alkylene group optionally substituted by a substituent selected from a halogen atom; a hydroxy group; a cyano group; an oxo group; a hydroxycarbonyl group; an alkyl group optionally substituted by a substituent selected from a halogen atom, a hydroxy group, an alkoxy group and a cyano group; and an alkoxy group optionally substituted by substituent selected from a halogen atom, a hydroxy group, an alkoxy group and a cyano group;

M is a single bond, or a group selected from —O—; —S—; —NR$^{7a}$—; —CO—; —SO—; —SO$_2$—; —CO—NR$^{7c}$—; —NR$^{7c}$—CO—; —SO$_2$—NR$^{7c}$—; —NR$^{7c}$—SO$_2$—; —NR$^{7a}$—CO—NR$^{7b}$—; —(OCH$_2$CH$_2$)$_m$—; —O—R$^{7r}$—; —R$^{7r}$—O—; —S—R$^{7r}$—; —R$^{7r}$-S—; —NR$^{7a}$—R$^{7r}$—; —R$^{7r}$—NR$^{7a}$—; —CO—NR$^{7c}$—R$^{7r}$—; —R$^{7r}$—CO—NR$^{7c}$—; an alkylene group optionally substituted by a substituent selected from a halogen atom, a hydroxy group, an alkoxy group and a cyano group; an alkynylene group optionally substituted by a substituent selected from a halogen atom, a hydroxy group, an alkoxy group and a cyano group; and a divalent aliphatic heterocyclic group optionally substituted by a substituent selected from a) a halogen atom, b) a hydroxy group, c) a cyano group, d) an oxo group, e) an alkyl group optionally substituted by a substituent selected from a halogen atom, a hydroxy group, an alkoxy group and a cyano group, and f) an alkoxy group optionally substituted by a substituent selected from a halogen atom, a hydroxy group, an alkoxy group and a cyano group, $R^5$ is a hydrogen atom, $R^{6a}$ and $R^{6b}$ are each independently a group selected from a hydrogen atom; a halogen atom; a hydroxy group; a cyano group; and an alkyl group optionally substituted by a substituent selected from a halogen atom, a hydroxy group and a cyano group;

$R^{7c}$ is a hydrogen atom, $R^{8a}$ and $R^{8b}$ are each independently a group selected from a hydrogen atom; a halogen atom; a hydroxy group; and a cyano group;

$R^{9a}$ and $R^{9b}$ are each independently a group selected from a hydrogen atom; a halogen atom; a cyano group; an alkyl group optionally substituted by a substituent selected from a halogen atom, a hydroxy group and a cyano group;

$R^{9a}$ and $R^{9b}$ are each independently a substituent selected from a hydrogen atom; —N(R$^{7c}$)—CO—OR$^{7d}$; and an alkyl group; the alkyl group is optionally substituted by a substituent selected from
a halogen atom; a hydroxy group; a cyano group; an alkoxy group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; —CO—N(R$^{7a}$)(R$^{7b}$); and a hydroxycarbonyl group, or a pharmaceutically acceptable salt thereof.

[4] The compound of [2] or [3], wherein A is a ring selected from a benzene ring; a pyridine ring; and a cycloalkane ring, $R^a$ is a hydrogen atom; or an alkyl group optionally substituted by a substituent selected from a halogen atom, a hydroxy group, and a cyano group, $R^{a'}$ is a hydrogen atom; or an alkyl group optionally substituted by a substituent selected from a halogen atom, a hydroxy group, and a cyano group, $R^{a''}$ is a hydrogen atom; a halogen atom; an alkyl group optionally substituted by a substituent selected from a halogen atom, a hydroxy group, and a cyano group; or a cyano group, $R^{Z3}$ is a hydrogen atom; a halogen atom; a cyano group; an alkyl group optionally substituted by a substituent selected from a halogen atom, a hydroxy group and a cyano group; a cycloalkyl group optionally substituted by a substituent selected from a halogen atom, a hydroxy group and a cyano group; or an alkoxy group optionally substituted by a substituent selected from a halogen atom, a hydroxy group and a cyano group;

$R^{Z4}$ and $R^{Z5}$ are each independently a hydrogen atom; or an alkyl group optionally substituted by a substituent selected from a halogen atom, a hydroxy group and a cyano group, a partial structure:

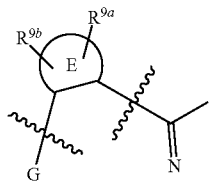

is represented by the following formula (Ea):

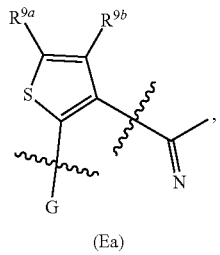

(Ea)

L is a group selected from an alkynyl group optionally substituted by a substituent selected from a halogen atom, a hydroxy group and a cyano group; a divalent aromatic hydrocarbon group optionally substituted by a substituent selected from a) a halogen atom, b) a hydroxy group, c) a cyano group, d) an alkyl group optionally substituted by a substituent selected from a halogen atom, a hydroxy group and a cyano group, and e) an alkoxy group optionally substituted by a substituent selected from a halogen atom, a hydroxy group and a cyano group; a divalent aliphatic heterocyclic group containing one nitrogen atom optionally substituted by a substituent selected from a halogen atom, a hydroxy group and a cyano group; and an optionally partially hydrogenated, divalent aromatic heterocyclic group containing 1-2 atoms selected from a nitrogen atom, an oxygen atom and a sulfur atom, the aromatic heterocyclic group is optionally substituted by a substituent selected from a halogen atom, a hydroxy group, a cyano group and an oxo group, T is a single bond; —CO—; —CO—NR$^{7c}$—; —NR$^{7c}$—CO—; or —O—, M is a single bond, or a group selected from —R$^{7r}$—O—; —R$^{7r}$—NR$^{7a}$—; an alkylene group optionally substituted by a substituent selected from a halogen atom, a hydroxy group, and a cyano group; an alkynylene group optionally substituted by a substituent selected from a halogen atom, a hydroxy group, and a cyano group; and a divalent aliphatic heterocyclic group, $R^{6a}$ and $R^{6b}$ are each independently a group selected from a hydrogen atom; a halogen atom; a cyano group; and an alkyl group optionally substituted by a substituent selected from a halogen atom, a hydroxy group and a cyano group, $R^{7a}$ and $R^{7b}$ are each independently a hydrogen atom; or an alkyl group optionally substituted by a substituent selected from a halogen atom, a hydroxy group and a cyano group, $R^{7c}$ is a hydrogen atom, $R^{7d}$ is an alkyl group optionally substituted by a substituent selected from a halogen atom, a hydroxy group and a cyano group, $R^{7r}$ is an alkylene group optionally substituted by a substituent selected from a halogen atom, a hydroxy group, and a cyano group, $R^{8a}$ and $R^{8b}$ are each a hydrogen atom, $R^{9a}$ and $R^{9b}$ are each independently an alkyl group optionally substituted by a substituent selected from a halogen atom, a hydroxy group and a cyano group, $R^{10a}$ is a group selected from a hydrogen atom; and an alkyl group optionally substituted by a substituent selected from a halogen atom, a hydroxy group, a cyano group, —NH—CO—OR$^{7d}$, —CO—N(R$^{7a}$)(R$^{7b}$), an alkoxycarbonyl group and a hydroxycarbonyl group, $R^{10b}$ is a hydrogen atom, and $R^{11}$ is an alkyl group optionally substituted by a substituent selected from a halogen atom, a hydroxy group and a cyano group, or a pharmaceutically acceptable salt thereof.

[5] The compound of any one of [2] to [4], wherein $R^a$ is a hydrogen atom; or an alkyl group, $R^{a'}$ is a hydrogen atom; or an alkyl group, $R^{a''}$ is a hydrogen atom; a halogen atom; an alkyl group; or a cyano group, $R^{Z3}$ is a hydrogen atom; a halogen atom; a cyano group; an alkyl group optionally substituted by 1-3 substituents selected from a halogen atom and hydroxy group; a cycloalkyl group; or an alkoxy group, $R^{Z4}$ and $R^{Z5}$ are each independently a hydrogen atom; or an alkyl group, a partial structure:

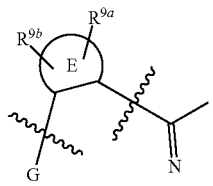

is represented by the following formula (Ea):

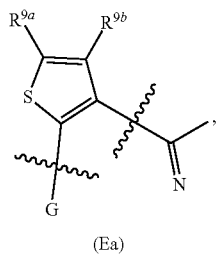

(Ea)

L is a group selected from an alkynylene group; a divalent aromatic hydrocarbon group optionally substituted by 1-2 substituents selected from a halogen atom, a hydroxy group, an alkyl group optionally substituted by 1 to 3 halogen atoms, and an alkoxy group; a divalent aliphatic heterocyclic group containing one nitrogen atom; and optionally partially hydrogenated, divalent aromatic heterocyclic group containing 1-2 atoms selected from a nitrogen atom, an oxygen atom and a sulfur atom, the aromatic heterocyclic group is optionally substituted by an oxo group when it is a partially hydrogenated, divalent aromatic heterocyclic group containing 1-2 atoms selected from a nitrogen atom, an oxygen atom and a sulfur atom, T is a single bond, or
—CO—; —CO—NR$^{7c}$—; —NR$^{7c}$—CO—; or —O—, M is a single bond, or a group selected from —R$^{7r}$—O—; —R$^{7r}$—NR$^{7a}$—; an alkylene group optionally substituted by one hydroxy group; an alkynylene group; and a divalent aliphatic heterocyclic group, R$^{6a}$ and R$^{6b}$ are each independently a group selected from a hydrogen atom; a halogen atom; a cyano group; and an alkyl group, R$^{7a}$ and R$^{7b}$ are each independently a hydrogen atom; or an alkyl group, R$^{7c}$ is a hydrogen atom, R$^{7d}$ is an alkyl group, R$^{7r}$ is an alkylene group, R$^{8a}$ and R$^{8b}$ are each a hydrogen atom, R$^{9a}$ and R$^{9b}$ are each independently an alkyl group optionally substituted by one hydroxy group, R$^{10a}$ is a group selected from a hydrogen atom; and an alkyl group optionally substituted by one substituent selected from —NH—CO—OR$^{7d}$, —CO—N(R$^{7a}$)(R$^{7b}$), a cyano group, an alkoxycarbonyl group and a hydroxycarbonyl group, R$^{10b}$ is a hydrogen atom, and R$^{11}$ is an alkyl group, or a pharmaceutically acceptable salt thereof.

[6] The compound of any one of [2] to [5], wherein A is a benzene ring,

R$^a$ is a hydrogen atom,

R$^{10a}$ is an alkyl group optionally substituted by one alkoxycarbonyl group,

L is a group selected from a divalent aromatic hydrocarbon group optionally substituted by 1-2 substituents selected from a halogen atom, an alkyl group optionally substituted by 1 to 3 halogen atoms, and an alkoxy group; and optionally partially hydrogenated, divalent aromatic heterocyclic group containing 1-2 atoms selected from a nitrogen atom, an oxygen atom and a sulfur atom, and M is an alkylene group optionally substituted by one substituent selected from a hydroxy group and a cyano group, or a pharmaceutically acceptable salt thereof.

[7] The compound of any one of [2] to [6], wherein R$^{a'}$ is a hydrogen atom,

R$^{a''}$ is a cyano group,

R$^{Z3}$ is an alkyl group optionally substituted by 1 to 3 halogen atoms or a hydroxy group; or an alkoxy group, R$^{Z4}$ is a hydrogen atom, and R$^{Z5}$ is a hydrogen atom, or a pharmaceutically acceptable salt thereof.

[8] The compound of any one of [2] to [7], wherein R$^{8a}$ and R$^{8b}$ are each a hydrogen atom, R$^{9a}$ and R$^{9b}$ are each independently an alkyl group optionally substituted by one hydroxy group, R$^{10a}$ is an alkyl group optionally substituted by one alkoxycarbonyl group, R$^{10b}$ is a hydrogen atom, and R$^{11}$ is an alkyl group, or a pharmaceutically acceptable salt thereof.

[9] The compound of any one of [2] to [8], wherein L is a phenylene group optionally substituted by 1-2 substituents selected from a halogen atom and an alkyl group; or a pyrazinediyl group, T is —CO—NR$^{7c}$—, R$^{7c}$ is a hydrogen atom, and M is —CH$_2$— or —CH(CH$_3$)—, or a pharmaceutically acceptable salt thereof.

[10] A compound selected from methyl [(6S)-4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate, methyl [(6S)-4-{4'-[(2-{4-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate, methyl [(6S)-4-{4'-[({4-[(3-cyano-4-methoxy-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate, methyl [(6S)-4-(4'-{[(1R)-1-{4-[(3-cyano-4-methyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate, methyl [(6S)-4-{4'-[({4-[(3-cyano-4-ethyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate, methyl [(6S)-4-{4'-[({4-[(3-cyano-4-methyl-1H-indol-7-yl)sulfamoyl]phenyl}methyl) carbamoyl]-2'-fluoro[1,1'-biphenyl]-4-yl}-2,3,9-trimethyl-6H-thieno[3,2-f][1,2,4]triazolo[4,3-a][1,4]diazepin-6-yl]acetate, methyl [(6S)-4-{4'-[(2-{4-[(3-cyano-4-methyl-1H-indol-7-yl)sulfamoyl]phenyl}ethyl)carbamoyl]-2'-fluoro[1,1'-biphenyl]-4-yl}-2,3,9-trimethyl-6H-thieno[3,2-f][1,2,4]triazolo[4,3-a][1,4]diazepin-6-yl]acetate, methyl [(6S)-4-{2'-chloro-4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate, methyl [(6S)-4-{4'-[({4-[(3-cyano-4-methyl-1H-indol-7-yl)sulfamoyl]phenyl}methyl) carbamoyl]-3'-methyl[1,1'-biphenyl]-4-yl}-2,3,9-trimethyl-6H-thieno[3,2-f][1,2,4]triazolo[4,3-a][1,4]diazepin-6-yl]acetate, methyl [(6S)-4-(4-{6-[({4-[(3-cyano-4-methyl-1H-indol-7-yl)sulfamoyl]phenyl}methyl)carbamoyl]pyridin-3- yl}phenyl)-2,3,9-trimethyl-6H-thieno[3,2-f][1,2,4]tri-
azolo[4,3-a][1,4]diazepin-6-yl]acetate,
t-butyl [(6S)-4-{4'-[({4-[(3-cyano-4-methyl-1H-indol-7-yl)
sulfamoyl]phenyl}methyl)carbamoyl][1,1'-biphenyl]-4-
yl}-2,3,9-trimethyl-6H-thieno[3,2-f][1,2,4]triazolo[4,3-a]
[1,4]diazepin-6-yl]acetate,
t-butyl [(6S)-4-{4'-[(2-{4-[(3-cyano-4-methyl-1H-indol-7-
yl)sulfamoyl]phenyl}ethyl)carbamoyl][1,1'-biphenyl]-4-
yl}-2,3,9-trimethyl-6H-thieno[3,2-f][1,2,4]triazolo[4,3-a]
[1,4]diazepin-6-yl]acetate,
methyl [(6S)-4-(4-{5-[({4-[(3-cyano-4-methyl-1H-indol-7-
yl)sulfamoyl]phenyl}methyl)carbamoyl]pyrazin-2-
yl}phenyl)-2,3,9-trimethyl-6H-thieno[3,2-f][1,2,4]tri-
azolo[4,3-a][1,4]diazepin-6-yl]acetate,
methyl [(6S)-4-(4'-{[(1R)-1-{4-[(3-cyano-4-methyl-1H-in-
dol-7-yl)sulfamoyl]phenyl}ethyl]carbamoyl}-3'-fluoro[1,
1'-biphenyl]-4-yl)-2,3,9-trimethyl-6H-thieno[3,2-f][1,2,
4]triazolo[4,3-a][1,4]diazepin-6-yl]acetate,
methyl [(6S)-4-(3'-chloro-4'-{[(1R)-1-{4-[(3-cyano-4-
methyl-1H-indol-7-yl)sulfamoyl]phenyl}ethyl]carbam-
oyl}[1,1'-biphenyl]-4-yl)-2,3,9-trimethyl-6H-thieno[3,2-
f][1,2,4]triazolo[4,3-a][1,4]diazepin-6-yl]acetate,
5-chloro-N-({4-[(3-cyano-4-methyl-1H-indol-7-yl)sulfa-
moyl]phenyl}methyl)-2-fluoro-4'-[(6S)-2,3,6,9-tetram-
ethyl-6H-thieno[3,2-f][1,2,4]triazolo[4,3-a][1,4]diaz-
epin-4-yl][1,1'-biphenyl]-4-carboxamide,
methyl [(6S)-4-{4'-[({4-[(3-cyano-4-methyl-1H-indol-7-yl)
sulfamoyl]phenyl}methyl)carbamoyl]-2',3'-difluoro[1,1'-
biphenyl]-4-yl}-2,3,9-trimethyl-6H-thieno[3,2-f][1,2,4]
triazolo[4,3-a][1,4]diazepin-6-yl]acetate,
methyl [(6S)-4-(4'-{[(1R)-1-{4-[(3-cyano-4-methyl-1H-in-
dol-7-yl)sulfamoyl]phenyl}ethyl]carbamoyl}-2'-fluoro[1,
1'-biphenyl]-4-yl)-2,3,9-trimethyl-6H-thieno[3,2-f][1,2,
4]triazolo[4,3-a][1,4]diazepin-6-yl]acetate,
methyl {(6S)-4-[4-(6-{[(1R)-1-{4-[(3-cyano-4-methyl-1H-
indol-7-yl)sulfamoyl]phenyl}ethyl]carbamoyl}pyridin-3-
yl)phenyl]-2,3,9-trimethyl-6H-thieno[3,2-f][1,2,4]tri-
azolo[4,3-a][1,4]diazepin-6-yl}acetate,
methyl [(6S)-4-(4'-{[(1R)-1-{4-[(3-cyano-4-methyl-1H-in-
dol-7-yl)sulfamoyl]phenyl}ethyl]carbamoyl}-2',5'-dif-
luoro[1,1'-biphenyl]-4-yl)-2,3,9-trimethyl-6H-thieno[3,2-
f][1,2,4]triazolo[4,3-a][1,4]diazepin-6-yl]acetate,
methyl [(6S)-4-(4'-{[(1R)-1-{4-[(3-cyano-4-methyl-1H-in-
dol-7-yl)sulfamoyl]phenyl}ethyl]carbamoyl}-2'-fluoro-
5'-methyl[1,1'-biphenyl]-4-yl)-2,3,9-trimethyl-6H-thieno
[3,2-f][1,2,4]triazolo[4,3-a][1,4]diazepin-6-yl]acetate,
methyl [(6S)-4-(4'-{[(1R)-1-{4-[(3-cyano-4-methyl-1H-in-
dol-7-yl)sulfamoyl]phenyl}ethyl]carbamoyl}-2',3'-dif-
luoro[1,1'-biphenyl]-4-yl)-2,3,9-trimethyl-6H-thieno[3,2-
f][1,2,4]triazolo[4,3-a][1,4]diazepin-6-yl]acetate,
methyl [(6S)-4-{4'-[(2-{4-[(3-cyano-4-methyl-1H-indol-7-
yl)sulfamoyl]phenyl}ethyl)carbamoyl]-2',3'-difluoro[1,
1'-biphenyl]-4-yl}-2,3,9-trimethyl-6H-thieno[3,2-f][1,2,
4]triazolo[4,3-a][1,4]diazepin-6-yl]acetate,
methyl [(6S)-4-(4-{5-[(2-{4-[(3-cyano-4-methyl-1H-indol-
7-yl)sulfamoyl]phenyl}ethyl)carbamoyl]pyrazin-2-
yl}phenyl)-2,3,9-trimethyl-6H-thieno[3,2-f][1,2,4]tri-
azolo[4,3-a][1,4]diazepin-6-yl]acetate,
methyl {(6S)-4-[4-(5-{[(1R)-1-{4-[(3-cyano-4-methyl-1H-
indol-7-yl)sulfamoyl]phenyl}ethyl]carbamoyl}pyrazin-
2-yl)phenyl]-2,3,9-trimethyl-6H-thieno[3,2-f][1,2,4]tri-
azolo[4,3-a][1,4]diazepin-6-yl}acetate,
methyl [(6S)-4-{4-{5-[({4-[(3-cyano-4-ethyl-1H-indol-7-yl)
sulfamoyl]phenyl}methyl)carbamoyl]pyrazin-2-
yl}phenyl)-2,3,9-trimethyl-6H-thieno[3,2-f][1,2,4]tri-
azolo[4,3-a][1,4]diazepin-6-yl]acetate, methyl {(6S)-4-[4-(5-{[(1R)-1-{4-[(3-cyano-4-ethyl-1H-in-
dol-7-yl)sulfamoyl]phenyl}ethyl]carbamoyl}pyrazin-2-
yl)phenyl]-2,3,9-trimethyl-6H-thieno[3,2-f][1,2,4]tri-
azolo[4,3-a][1,4]diazepin-6-yl}acetate,
methyl [(6S)-4-(4-{5-[(2-{4-[(3-cyano-4-ethyl-1H-indol-7-
yl)sulfamoyl]phenyl}ethyl)carbamoyl]pyrazin-2-
yl}phenyl)-2,3,9-trimethyl-6H-thieno[3,2-f][1,2,4]tri-
azolo[4,3-a][1,4]diazepin-6-yl]acetate,
methyl [(6S)-4-(4-{6-[({4-[(3-cyano-4-ethyl-1H-indol-7-yl)
sulfamoyl]phenyl}methyl)carbamoyl]pyridin-3-
yl}phenyl)-2,3,9-trimethyl-6H-thieno[3,2-f][1,2,4]tri-
azolo[4,3-a][1,4]diazepin-6-yl]acetate,
methyl {(6S)-4-[4-(6-{[(1R)-1-{4-[(3-cyano-4-ethyl-1H-in-
dol-7-yl)sulfamoyl]phenyl}ethyl]carbamoyl}pyridin-3-
yl)phenyl]-2,3,9-trimethyl-6H-thieno[3,2-f][1,2,4]tri-
azolo[4,3-a][1,4]diazepin-6-yl}acetate,
methyl [(6S)-4-(4-{6-[(2-{4-[(3-cyano-4-ethyl-1H-indol-7-
yl)sulfamoyl]phenyl}ethyl)carbamoyl]pyridin-3-
yl}phenyl)-2,3,9-trimethyl-6H-thieno[3,2-f][1,2,4]tri-
azolo[4,3-a][1,4]diazepin-6-yl]acetate,
methyl [(6S)-4-{4'-[({4-[(3-cyano-4-ethyl-1H-indol-7-yl)
sulfamoyl]phenyl}methyl)carbamoyl]-2',3'-difluoro[1,1'-
biphenyl]-4-yl}-2,3,9-trimethyl-6H-thieno[3,2-f][1,2,4]
triazolo[4,3-a][1,4]diazepin-6-yl]acetate,
methyl [(6S)-4-(4'-{[(1R)-1-{4-[(3-cyano-4-ethyl-1H-indol-
7-yl)sulfamoyl]phenyl}ethyl]carbamoyl}[1,1'-biphenyl]-
4-yl)-2,3,9-trimethyl-6H-thieno[3,2-f][1,2,4]triazolo[4,3-
a][1,4]diazepin-6-yl]acetate, and
t-butyl [(6S)-4-(4-{5-[({4-[(3-cyano-4-methyl-1H-indol-7-
yl)sulfamoyl]phenyl}methyl)carbamoyl]pyrazin-2-
yl}phenyl)-2,3,9-trimethyl-6H-thieno[3,2-f][1,2,4]tri-
azolo[4,3-a][1,4]diazepin-6-yl]acetate,
or a pharmaceutically acceptable salt thereof.
[11] A compound selected from methyl [(6S)-4-{4'-[({4-
[(3-cyano-4-methyl-1H-indol-7-yl)sulfamoyl]
phenyl}methyl)carbamoyl][1,1'-biphenyl]-4-yl}-2,3,9-trim-
ethyl-6H-thieno[3,2-f][1,2,4]triazolo[4,3-a][1,4]diazepin-6-
yl]acetate,
methyl [(6S)-4-{4'-[(2-{4-[(3-cyano-4-methyl-1H-indol-7-
yl)sulfamoyl]phenyl}ethyl)carbamoyl][1,1'-biphenyl]-4-
yl}-2,3,9-trimethyl-6H-thieno[3,2-f][1,2,4]triazolo[4,3-a]
[1,4]diazepin-6-yl]acetate,
methyl [(6S)-4-(4'-{[(1R)-1-{4-[(3-cyano-4-methyl-1H-in-
dol-7-yl)sulfamoyl]phenyl}ethyl]carbamoyl}[1,1'-biphe-
nyl]-4-yl)-2,3,9-trimethyl-6H-thieno[3,2-f][1,2,4]triazolo
[4,3-a][1,4]diazepin-6-yl]acetate,
methyl [(6S)-4-{4'-[({4-[(3-cyano-4-ethyl-1H-indol-7-yl)
sulfamoyl]phenyl}methyl)carbamoyl][1,1'-biphenyl]-4-
yl}-2,3,9-trimethyl-6H-thieno[3,2-f][1,2,4]triazolo[4,3-a]
[1,4]diazepin-6-yl]acetate,
methyl [(6S)-4-{2'-chloro-4'-[({4-[(3-cyano-4-methyl-1H-
indol-7-yl)sulfamoyl]phenyl}methyl)carbamoyl][1,1'-bi-
phenyl]-4-yl}-2,3,9-trimethyl-6H-thieno[3,2-f][1,2,4]tri-
azolo[4,3-a][1,4]diazepin-6-yl]acetate,
methyl [(6S)-4-(4-{6-[({4-[(3-cyano-4-methyl-1H-indol-7-
yl)sulfamoyl]phenyl}methyl)carbamoyl]pyridin-3-
yl}phenyl)-2,3,9-trimethyl-6H-thieno[3,2-f][1,2,4]tri-
azolo[4,3-a][1,4]diazepin-6-yl]acetate,
t-butyl [(6S)-4-{4'-[({4-[(3-cyano-4-methyl-1H-indol-7-yl)
sulfamoyl]phenyl}methyl)carbamoyl][1,1'-biphenyl]-4-
yl}-2,3,9-trimethyl-6H-thieno[3,2-f][1,2,4]triazolo[4,3-a]
[1,4]diazepin-6-yl]acetate,
t-butyl [(6S)-4-{4'-[(2-{4-[(3-cyano-4-methyl-1H-indol-7-
yl)sulfamoyl]phenyl}ethyl)carbamoyl][1,1'-biphenyl]-4-
yl}-2,3,9-trimethyl-6H-thieno[3,2-f][1,2,4]triazolo[4,3-a]
[1,4]diazepin-6-yl]acetate, methyl [(6S)-4-(4-{5-[({4-[(3-cyano-4-methyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl [(6S)-4-(4'-{[(1R)-1-{4-[(3-cyano-4-methyl-1H-indol-7-yl)sulfamoyl]phenyl}ethyl]carbamoyl}-3'-fluoro[1,1'-biphenyl]-4-yl)-2,3,9-trimethyl-6H-thieno[3,2-f][1,2,4]triazolo[4,3-a][1,4]diazepin-6-yl]acetate, 5-chloro-N-({4-[(3-cyano-4-methyl-1H-indol-7-yl)sulfamoyl]phenyl}methyl)-2-fluoro-4'-[(6S)-2,3,6,9-tetramethyl-6H-thieno[3,2-f][1,2,4]triazolo[4,3-a][1,4]diazepin-4-yl][1,1'-biphenyl]-4-carboxamide, methyl [(6S)-4-{4'-[({4-[(3-cyano-4-methyl-1H-indol-7-yl)sulfamoyl]phenyl}methyl)carbamoyl]-2',3'-difluoro[1,1'-biphenyl]-4-yl}-2,3,9-trimethyl-6H-thieno[3,2-f][1,2,4]triazolo[4,3-a][1,4]diazepin-6-yl]acetate, methyl {(6S)-4-[4-(6-{[(1R)-1-{4-[(3-cyano-4-methyl-1H-indol-7-yl)sulfamoyl]phenyl}ethyl]carbamoyl}pyridin-3-yl)phenyl]-2,3,9-trimethyl-6H-thieno[3,2-f][1,2,4]triazolo[4,3-a][1,4]diazepin-6-yl}acetate, methyl [(6S)-4-(4-{5-[(2-{4-[(3-cyano-4-methyl-1H-indol-7-yl)sulfamoyl]phenyl}ethyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl {(6S)-4-[4-(5-{[(1R)-1-{4-[(3-cyano-4-methyl-1H-indol-7-yl)sulfamoyl]phenyl}ethyl]carbamoyl}pyrazin-2-yl)phenyl]-2,3,9-trimethyl-6H-thieno[3,2-f][1,2,4]triazolo[4,3-a][1,4]diazepin-6-yl}acetate, methyl [(6S)-4-(4-{5-[({4-[(3-cyano-4-ethyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl {(6S)-4-[4-(5-{[(1R)-1-{4-[(3-cyano-4-ethyl-1H-indol-7-yl)sulfamoyl]phenyl}ethyl]carbamoyl}pyrazin-2-yl)phenyl]-2,3,9-trimethyl-6H-thieno[3,2-f][1,2,4]triazolo[4,3-a][1,4]diazepin-6-yl}acetate, methyl [(6S)-4-(4-{5-[(2-{4-[(3-cyano-4-ethyl-1H-indol-7-yl)sulfamoyl]phenyl}ethyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl [(6S)-4-(4-{6-[({4-[(3-cyano-4-ethyl-1H-indol-7-yl)sulfamoyl]phenyl}methyl)carbamoyl]pyridin-3-yl}phenyl)-2,3,9-trimethyl-6H-thieno[3,2-f][1,2,4]triazolo[4,3-a][1,4]diazepin-6-yl]acetate, methyl {(6S)-4-[4-(6-{[(1R)-1-{4-[(3-cyano-4-ethyl-1H-indol-7-yl)sulfamoyl]phenyl}ethyl]carbamoyl}pyridin-3-yl)phenyl]-2,3,9-trimethyl-6H-thieno[3,2-f][1,2,4]triazolo[4,3-a][1,4]diazepin-6-yl}acetate, and methyl [(6S)-4-(4-{6-[(2-{4-[(3-cyano-4-ethyl-1H-indol-7-yl)sulfamoyl]phenyl}ethyl)carbamoyl]pyridin-3-yl}phenyl)-2,3,9-trimethyl-6H-thieno[3,2-f][1,2,4]triazolo[4,3-a][1,4]diazepin-6-yl]acetate, or a pharmaceutically acceptable salt thereof.

[12] A pharmaceutical composition comprising the compound of any one of [1] to [11] or a pharmaceutically acceptable salt thereof.

[13] The pharmaceutical composition of [12] for inducing BRD4 proteolysis.

[14] The pharmaceutical composition of [12] or [13] for treating cancer.

[15] The pharmaceutical composition of [14], wherein the cancer is selected from acute myeloid leukemia, chronic myeloid leukemia, multiple myeloma, diffuse large B-cell lymphoma, adult T-cell leukemia lymphoma, Burkitt lymphoma, prostate cancer, ovarian cancer, bladder cancer, breast cancer, uterus cervix cancer, uterine sarcoma, gastric cancer, lung cancer, colorectal cancer, glioma, pancreatic cancer, liver cancer, bile duct cancer, renal cell cancer, and fibrosarcoma.

[16] The pharmaceutical composition of [15], wherein the cancer is selected from acute myeloid leukemia, chronic myeloid leukemia, acute lymphocytic leukemia, diffuse large B-cell lymphoma, multiple myeloma, Burkitt lymphoma, glioma, gastric cancer, colorectal cancer, pancreatic cancer, liver cancer, prostate cancer, non-small cell lung cancer, breast cancer, ovarian cancer and uterine sarcoma.

[17] The pharmaceutical composition of [16], wherein the cancer is selected from acute myeloid leukemia, diffuse large B-cell lymphoma, multiple myeloma, prostate cancer, ovarian cancer and breast cancer.

[18] Use of the pharmaceutical composition of any one of [12] to [17], in treating cancer.

[19] Use of the compound of any one of [1] to [11] or a pharmaceutically acceptable salt thereof in producing a pharmaceutical composition for treating cancer.

[20] A method for treating cancer, comprising administering the compound of any one of [1] to [11] or a pharmaceutically acceptable salt thereof, or the pharmaceutical composition of any one of [12] to [17].

Advantageous Effects of Invention

The compound of the present invention is superior in BRD4 proteolysis-inducing action and useful as a therapeutic agent for cancer.

DESCRIPTION OF EMBODIMENTS

Figure 1:
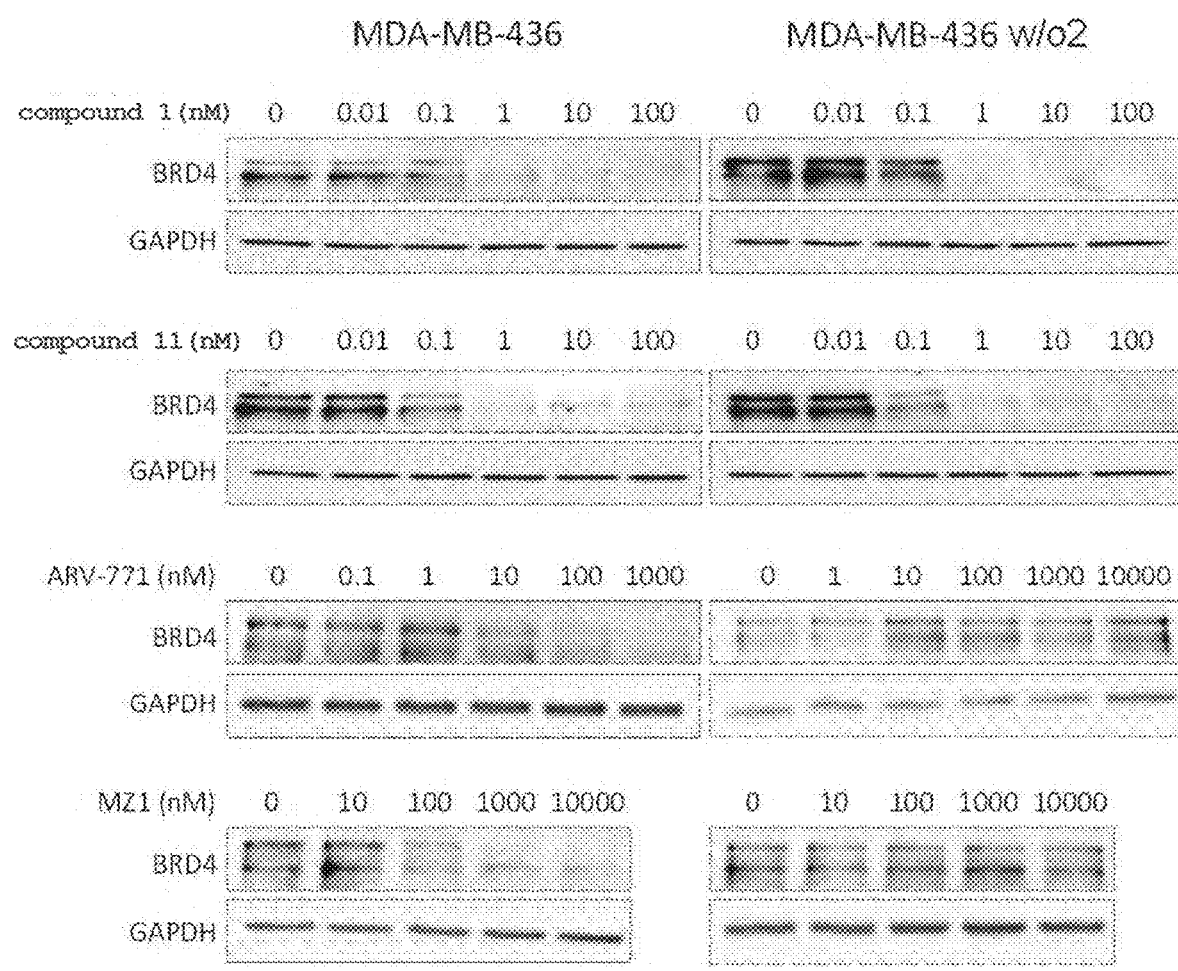
FIG. 1 shows the results of the BRD4 proteolysis-inducing action in Experimental Example 4.

The compound of the present invention is a compound represented by the formula (I) or a pharmaceutically acceptable salt thereof. In the present specification, the "compound represented by the formula (I) or a pharmaceutically acceptable salt thereof" is sometimes referred to generically as the compound of the present invention.

In the following, the meanings of the terms used in the present specification are described and the present invention is further described in detail. The following explanation of the terms does not limit the present invention in any manner.

In the present specification, examples of the "halogen atom" include fluorine atom, chlorine atom, bromine atom, and iodine atom.

In the present specification, examples of the "alkyl group" include "$C_{1-6}$ alkyl group" such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

In the present specification, examples of the "cycloalkyl group" include "$C_{3-10}$ cycloalkyl group" such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, adamantyl and the like.

In the present specification, examples of the "alkoxy group" include "$C_{1-6}$ alkoxy group" such as methoxy, ethoxy, propoxy, isopropoxy, butoxy, isobutoxy, sec-butoxy, tert-butoxy, pentyloxy, hexyloxy and the like.

In the present specification, examples of the "alkylene group" include "$C_{1-6}$ alkylene group" such as —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$C(CH_3)_2$—, —$C(CH_3)_2$—$CH_2$—$CH_2$—$CH_2$— and the like.

In the present specification, examples of the "alkenylene group" include "$C_{2-6}$ alkenylene group" such as —CH=CH—, —$CH_2$—CH=CH—, —CH=CH—$CH_2$—, —$C(CH_3)_2$—CH=CH—, —CH=CH—$C(CH_3)_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$—, —$CH_2$—$CH_2$—$CH_2$—CH=CH— and the like.

In the present specification, examples of the "alkynylene group" include "$C_{2-6}$ alkynylene group" such as —C≡C—, —$CH_2$—C≡C—, —C≡C—$CH_2$—, —$C(CH_3)_2$—C≡C—, —C≡C—$C(CH_3)_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$—, —$CH_2$—$CH_2$—$CH_2$—C≡C— and the like.

In the present specification, examples of the "cycloalkylene group" include "$C_{3-10}$ cycloalkylene group" such as cyclopropylene, cyclobutylene, cyclopentylene, cyclohexylene, cycloheptylene, cyclooctylene and the like.

In the present specification, examples of the "alkoxycarbonyl group" include "$C_{1-6}$ alkoxy-carbonyl group" such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

In the present specification, examples of the "cycloalkane ring" include "$C_{3-10}$ cycloalkane ring" such as cyclopropane, cyclobutane, cyclopentane, cyclohexane, cycloheptane, cyclooctane and the like.

In the present specification, examples of the "aromatic hydrocarbocycle" include "$C_{6-14}$ aromatic hydrocarbocycle" such as benzene, naphthalene, anthracene and the like.

In the present specification, examples of the "aromatic hydrocarbon group" include $C_{6-14}$ aryl group such as phenyl, 1-naphthyl, 2-naphthyl, 1-anthryl, 2-anthryl, 9-anthryl and the like.

In the present specification, examples of the "divalent aromatic hydrocarbon group" include $C_{6-14}$ arylene group such as phenylene, naphthylene, anthrylene and the like.

In the present specification, examples of the "aliphatic heterocycle containing 1 to 3 atoms selected from oxygen, sulfur and nitrogen" include 3- to 14-membered (preferably 4- to 10-membered) aliphatic heterocycle containing 1-3 atoms selected from oxygen, sulfur and nitrogen as a ring-constituting atom besides carbon atom. Preferable examples of the "aliphatic heterocycle" include 3- to 8-membered monocyclic aliphatic heterocycle such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like;

9- to 14-membered fused polycyclic (preferably bi or tricyclic) aliphatic heterocycle such as dihydrobenzofuran, dihydrobenzoimidazole, dihydrobenzoxazole, dihydrobenzothiazole, dihydrobenzoisothiazole, dihydronaphto[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxathiine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "aliphatic heterocycle containing one nitrogen atom" include aliphatic heterocycle containing one nitrogen atom among the above-mentioned "aliphatic heterocycles containing 1 to 3 atoms selected from oxygen, sulfur and nitrogen".

In the present specification, examples of the "divalent aliphatic heterocyclic group" include a divalent aliphatic heterocyclic group induced from the above-mentioned "aliphatic heterocycle".

In the present specification, examples of the "divalent aliphatic heterocyclic group containing one nitrogen atom" include a divalent aliphatic heterocyclic group induced from aliphatic heterocycle containing one nitrogen atom among the above-mentioned "aliphatic heterocycles".

In the present specification, examples of the "aromatic heterocycle containing 1 to 3 atoms selected from oxygen, sulfur and nitrogen" include 5- to 14-membered (preferably 5- to 10-membered) aromatic heterocycle containing 1-3 atoms selected from oxygen, sulfur and nitrogen as a ring-constituting atom besides carbon atom. Preferable examples of the "aromatic heterocycle" include 5- or 6-membered monocyclic aromatic heterocycle such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; 8- to 14-membered fused polycyclic (preferably bi or tricyclic) aromatic heterocycle such as benzothiophene, benzofuran, benzoimidazole, benzoxazole, benzoisoxazole, benzothiazole, benzoisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "5- or 6-membered aromatic heterocyclic group containing 1 to 3 atoms selected from oxygen, sulfur and nitrogen" include a 5- or 6-membered aromatic heterocyclic group containing 1-3 atoms selected from oxygen, sulfur and nitrogen as a ring-constituting atom besides carbon atom.

Preferable examples of the "aromatic heterocyclic group" include 5- or 6-membered monocyclic aromatic heterocyclic group such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like.

In the present specification, examples of the "optionally partly hydrogenated, divalent aromatic heterocyclic group" include divalent ring groups induced from the above-mentioned "aliphatic heterocycle" and the above-mentioned "aromatic heterocycle".

In the present specification, examples of the "optionally partially hydrogenated, divalent aromatic heterocyclic group containing 1-2 atoms selected from a nitrogen atom, an oxygen atom and a sulfur atom" include divalent ring group induced from the above-mentioned "aliphatic heterocycle" and the above-mentioned "aromatic heterocycle" containing 1-2 atoms selected from a nitrogen atom, an oxygen atom and a sulfur atom.

Preferable examples of the "partially hydrogenated, divalent aromatic heterocyclic group containing 1-2 atoms selected from a nitrogen atom, an oxygen atom and a sulfur atom" from among the "optionally partially hydrogenated, divalent aromatic heterocyclic group containing 1-2 atoms selected from a nitrogen atom, an oxygen atom and a sulfur atom" include tetrahydroisoquinolinediyl (particularly, 1,2,3,4-tetrahydroisoquinoline-2,6-diyl).

In the present specification, the number of substituents when "substituted" is one or two or more unless particularly indicated, and the kind of the substituents may be the same or different.

Preferable embodiments of the above-mentioned formula (I) are explained below.

A is preferably a ring selected from an aromatic hydrocarbocycle (e.g., benzene ring), a 5- or 6-membered aromatic heterocycle containing 1 to 3 atoms selected from oxygen, sulfur and nitrogen, and a cycloalkane ring (e.g., cyclobutane ring), more preferably, a ring selected from a benzene ring; a pyridine ring; and a cycloalkane ring (e.g., cyclobutane ring), further preferably, a benzene ring.

Q is preferably a 5- or 6-membered aromatic heterocycle (e.g., pyrrole ring) containing 1 to 3 atoms selected from oxygen, sulfur and nitrogen.

A partial structure:

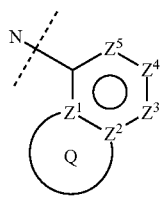

is preferably the following formula:

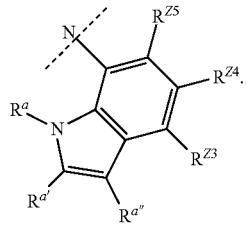

That is, $Z^1$ is preferably C, $Z^2$ is preferably C, $Z^3$ is preferably $=CR^{Z3}-$, $Z^4$ is preferably $=CR^{Z4}-$, $Z^5$ is preferably $=CR^{Z5}-$, and Q is preferably a pyrrole ring.

$R^{Z3}$ is preferably a group selected from a hydrogen atom; a halogen atom (e.g., chlorine atom, bromine atom); a hydroxy group; a cyano group; a hydroxycarbonyl group; an alkyl group (e.g., methyl, ethyl) optionally substituted by a group selected from a halogen atom (e.g., fluorine atom), a hydroxy group, an alkoxy group and a cyano group; a cycloalkyl group (e.g., cyclopropyl) optionally substituted by a group selected from a halogen atom, a hydroxy group, an alkoxy group and a cyano group; an alkoxy group (e.g., methoxy) optionally substituted by a group selected from a halogen atom, a hydroxy group, an alkoxy group and a cyano group; an alkoxycarbonyl group optionally substituted by a group selected from a halogen atom, a hydroxy group, an alkoxy group and a cyano group, more preferably, a hydrogen atom; a halogen atom; a cyano group; an alkyl group optionally substituted by 1 to 3 substituents selected from a halogen atom, a hydroxy group and a cyano group; a cycloalkyl group optionally substituted by 1 to 3 substituents selected from a halogen atom, a hydroxy group and a cyano group; or an alkoxy group optionally substituted by 1 to 3 substituents selected from a halogen atom, a hydroxy group and a cyano group, further preferably, an alkyl group optionally substituted by 1 to 3 halogen atoms or a hydroxy group; or an alkoxy group, particularly preferably an alkyl group, further more preferably a methyl group or an ethyl group.

Preferably, $R^{Z4}$ and $R^{Z5}$ are each independently a group selected from a hydrogen atom; a halogen atom; a cyano group; an alkyl group (e.g., methyl) optionally substituted by a substituent selected from a halogen atom, a hydroxy group, an alkoxy group and a cyano group; an alkoxy group optionally substituted by a group selected from a halogen atom, a hydroxy group, an alkoxy group and a cyano group; more preferably, each is independently a hydrogen atom; an alkyl group optionally substituted by a substituent selected from a halogen atom, a hydroxy group and a cyano group, further preferably, both are hydrogen atoms.

$R^a$ is preferably a hydrogen atom; or an alkyl group optionally substituted by a substituent selected from a halogen atom, a hydroxy group, and a cyano group, more preferably, a hydrogen atom; or an alkyl group, further preferably, a hydrogen atom.

$R^{a'}$ is preferably a hydrogen atom; an alkyl group (e.g., methyl) optionally substituted by a substituent selected from a halogen atom, a hydroxy group, and a cyano group, more preferably, a hydrogen atom; or an alkyl group, further preferably, a hydrogen atom.

$R^{a''}$ is preferably a hydrogen atom; a halogen atom (e.g., chlorine atom); an alkyl group (e.g., methyl) optionally substituted by a substituent selected from a halogen atom, a hydroxy group, and a cyano group; or a cyano group, more preferably, a hydrogen atom; a halogen atom; an alkyl group; or a cyano group, further preferably, a cyano group.

A partial structure:

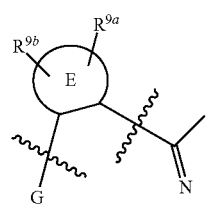

is preferably the following formula (Ea) or (Ec):

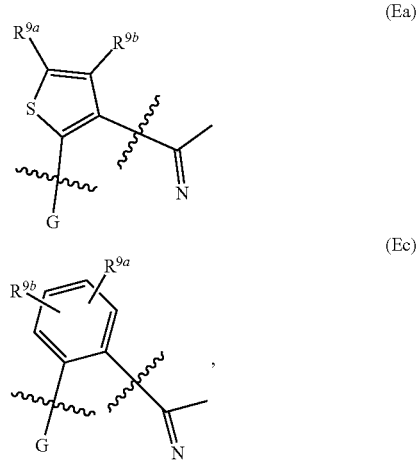

(Ea)

(Ec)

more preferably,

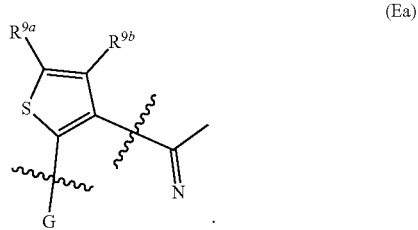

(Ea)

$R^{9a}$ and $R^{9b}$ are, for example, each independently a group selected from a hydrogen atom; a halogen atom; a cyano group; an alkyl group (e.g., methyl) optionally substituted by a substituent selected from a halogen atom, a hydroxy group and a cyano group; and an alkoxy group (e.g., methoxy) optionally substituted by a substituent selected from a halogen atom, a hydroxy group and a cyano group, preferably, each independently a hydrogen atom; a halogen atom; a cyano group; an alkyl group (e.g., methyl) optionally substituted by a substituent selected from a halogen atom, a hydroxy group and a cyano group; more preferably, each independently an alkyl group optionally substituted by a substituent selected from a halogen atom, a hydroxy group and a cyano group, further preferably, each independently an alkyl group optionally substituted by a hydroxy group, particularly preferably an unsubstituted alkyl group, further more preferably, a methyl group.

L is preferably a group selected from a divalent aromatic hydrocarbon group (e.g., phenylene); a divalent aliphatic heterocyclic group (e.g., pyrrolidinediyl); an optionally partly hydrogenated divalent aromatic heterocyclic group (e.g., thiophenediyl, pyridinediyl, tetrahydropyridinediyl, pyrazinediyl, benzofurandiyl, benzoxazinediyl, benzothiophenediyl, tetrahydroquinolinediyl); an alkylene group; a cycloalkylene group; an alkenylene group; and an alkynylene group (e.g., —C≡C—, —C≡C—CH$_2$—); the group is optionally substituted by a substituent selected from a halogen atom (e.g., fluorine atom, chlorine atom); a hydroxy group; a cyano group; a hydroxycarbonyl group; an alkyl group (e.g., methyl) optionally substituted by a group selected from a halogen atom (e.g., fluorine atom), a hydroxy group, an alkoxy group and a cyano group; and an alkoxy group (e.g., methoxy) optionally substituted by a group selected from a halogen atom, a hydroxy group, an alkoxy group and a cyano group; more preferably, a group selected from an alkynyl group optionally substituted by a substituent selected from a halogen atom, a hydroxy group and a cyano group; a divalent aromatic hydrocarbon group optionally substituted by a substituent selected from a) a halogen atom, b) a hydroxy group, c) a cyano group, d) an alkyl group optionally substituted by a substituent selected from a halogen atom, a hydroxy group and a cyano group, and e) an alkoxy group optionally substituted by a substituent selected from a halogen atom, a hydroxy group and a cyano group; a divalent aliphatic heterocyclic group containing one nitrogen atom optionally substituted by a substituent selected from a halogen atom, a hydroxy group and a cyano group; and optionally partially hydrogenated, divalent aromatic heterocyclic group containing 1-2 atoms selected from a nitrogen atom, an oxygen atom and a sulfur atom; the aromatic heterocyclic group is optionally substituted by a substituent selected from a halogen atom, a hydroxy group, a cyano group and an oxo group, further preferably, a group selected from an alkynylene group; a divalent aromatic hydrocarbon group optionally substituted by a substituent selected from a halogen atom, an alkyl group optionally substituted by a halogen atom, and an alkoxy group; a divalent aliphatic heterocyclic group containing one nitrogen atom; and optionally partially hydrogenated, divalent aromatic heterocyclic group containing 1-2 atoms selected from a nitrogen atom, an oxygen atom and a sulfur atom; the aromatic heterocyclic group is optionally substituted by an oxo group, particularly preferably, a group selected from an aromatic hydrocarbon group optionally substituted by a substituent selected from a halogen atom, an alkyl group optionally substituted by a halogen atom, and an alkoxy group; and an optionally partially hydrogenated, divalent aromatic heterocyclic group containing 1-2 atoms selected from a nitrogen atom, an oxygen atom and a sulfur atom; particularly further preferably, a group selected from a divalent aromatic hydrocarbon group optionally substituted by 1-2 halogen atoms; and a divalent aromatic heterocyclic group containing 1-2 nitrogen atoms, particularly preferably, a group selected from phenylene optionally substituted by 1-2 halogen atoms; pyridinediyl; and pyrazinediyl, still more preferably, a group selected from phenylene optionally substituted by 1-2 halogen atoms; and pyrazinediyl.

In another embodiment, L is preferably a divalent aromatic hydrocarbon group (e.g., phenylene), the group is optionally substituted by a substituent selected from a halogen atom (e.g., fluorine atom, chlorine atom); a hydroxy group; a cyano group; a hydroxycarbonyl group; an alkyl group (e.g., methyl) optionally substituted by a group selected from a halogen atom (e.g., fluorine atom), a hydroxy group, an alkoxy group and a cyano group; and an alkoxy group (e.g., methoxy) optionally substituted by a group selected from a halogen atom, a hydroxy group, an alkoxy group and a cyano group; more preferably, a divalent aromatic hydrocarbon group optionally substituted by a substituent selected from a) a halogen atom, b) a hydroxy group, c) a cyano group, d) an alkyl group optionally substituted by a substituent selected from a halogen atom, a hydroxy group and a cyano group, and e) an alkoxy group optionally substituted by a substituent selected from a halogen atom, a hydroxy group and a cyano group, particularly preferably, a divalent aromatic hydrocarbon group optionally substituted by a substituent selected from a halogen atom, an alkyl group optionally substituted by a halogen atom, and an alkoxy group, particularly further preferably, a divalent aromatic hydrocarbon group optionally substituted by 1-2 halogen atoms, particularly preferably, phenylene optionally substituted by 1-2 halogen atoms.

In another embodiment, L is preferably an optionally partly hydrogenated divalent aromatic heterocyclic group (e.g., thiophenediyl, pyridinediyl, tetrahydropyridinediyl, pyrazinediyl, benzofurandiyl, benzoxazinediyl, benzothiophenediyl, tetrahydroquinolinediyl); an alkylene group; a cycloalkylene group; an alkenylene group; or an alkynylene group (e.g., —C≡C—, —C≡C—CH$_2$—), the group is optionally substituted by a substituent selected from a halogen atom (e.g., fluorine atom, chlorine atom); a hydroxy group; a cyano group; a hydroxycarbonyl group; an alkyl group (e.g., methyl) optionally substituted by a group selected from a halogen atom (e.g., fluorine atom), a hydroxy group, an alkoxy group and a cyano group; and an alkoxy group (e.g., methoxy) optionally substituted by a group selected from a halogen atom, a hydroxy group, an alkoxy group and a cyano group; more preferably, optionally partially hydrogenated, divalent aromatic heterocyclic group containing 1-2 atoms selected from a nitrogen atom, an oxygen atom and a sulfur atom, the group is optionally substituted by a substituent selected from a halogen atom, a hydroxy group, a cyano group and an oxo group, further preferably, a group selected from an optionally partially hydrogenated, divalent aromatic heterocyclic group containing 1-2 atoms selected from a nitrogen atom, an oxygen atom and a sulfur atom; the aromatic heterocyclic group is optionally substituted by an oxo group, particularly preferably, a divalent aromatic hydrocarbon group optionally substituted by a substituent selected from a halogen atom, an alkyl group optionally substituted by a halogen atom, and an alkoxy group, particularly further preferably, a group selected from a divalent aromatic heterocyclic group containing 1-2 nitrogen atoms, particularly preferably, a group selected from pyridinediyl; and pyrazinediyl, further more preferably, pyrazinediyl.

T is preferably a single bond, —CO—, —CO—NR$^{7c}$—, —NR$^{7c}$—CO—, or —O—, or an alkylene group (e.g., —CH$_2$—) optionally substituted by a substituent selected from a halogen atom; a hydroxy group; a cyano group; an oxo group; a hydroxycarbonyl group; an alkyl group optionally substituted by a substituent selected from a halogen atom, a hydroxy group, an alkoxy group and a cyano group; and an alkoxy group optionally substituted by a substituent selected from a halogen atom, a hydroxy group, an alkoxy group and a cyano group; more preferably, a single bond; —CO—; —CO—NR$^{7c}$—; —NR$^{7c}$—CO—; or —O—, particularly preferably —CO—NR$^{7c}$—.

M is preferably a single bond, or a group selected from —O—; —S—; —NR$^{7a}$—; —CO—; —SO—; —SO$_2$—; —CO—NR$^{7c}$—; —NR$^{7c}$—CO—; —SO$_2$—NR$^{7c}$—; —NR$^{7c}$—SO$_2$—; —NR$^{7a}$—CO—NR$^{7b}$—; —(OCH$_2$CH$_2$)$_m$—; —O—R$^{7r}$—; —R$^{7r}$—O—; —S—R$^{7r}$—; —R$^{7r}$—S—; —NR$^{7a}$—R$^{7r}$—; —R$^{7r}$—NR$^{7a}$—; —CO—NR$^{7c}$—R$^{7r}$—; —R$^{7r}$—CO—NR$^{7c}$—; and an alkylene group (e.g., —CH$_2$—, —(CH$_2$)$_2$—, —(CH$_2$)$_3$—) optionally substituted by a substituent selected from a halogen atom, a hydroxy group, an alkoxy group and a cyano group; an alkynylene group (e.g., —CH$_2$—C≡C—) optionally substituted by a substituent selected from a halogen atom, a hydroxy group, an alkoxy group and a cyano group; and a divalent aliphatic heterocyclic group (e.g., piperidinediyl) optionally substituted by a substituent selected from a) a halogen atom, b) a hydroxy group, c) a cyano group, d) an oxo group, e) an alkyl group optionally substituted by a substituent selected from a halogen atom, a hydroxy group, an alkoxy group and a cyano group; and f) an alkoxy group optionally substituted by a substituent selected from a halogen atom, a hydroxy group, an alkoxy group and a cyano group; more preferably, a single bond, or a group selected from —R$^{7r}$—O—; —R$^{7r}$—NR$^{7a}$—; an alkylene group optionally substituted by a substituent selected from a halogen atom, a hydroxy group, and a cyano group; an alkynylene group optionally substituted by a substituent selected from a halogen atom, a hydroxy group, and a cyano group; and a divalent aliphatic heterocyclic group; further preferably, a single bond, or a group selected from —R$^{7r}$—O—; —R$^{7r}$—NR$^{7a}$—; an alkylene group optionally substituted by a substituent selected from a hydroxy group, and a cyano group; an alkynylene group; and a divalent aliphatic heterocyclic group; particularly preferably, an alkylene group optionally substituted by one substituent selected from a hydroxy group and a cyano group, particularly preferably, —CH$_2$— or —CH(CH$_3$)—, particularly more preferably, —CH$_2$— or

-L-T-M- does not indicate a group selected from —O—O—, —S—S—, —NR$^{7a}$—NR$^{7a}$—, —O—S—, —S—O—, —O—NR$^{7a}$—, —NR$^{7a}$—O—, —S—NR$^{7a}$— and —NR$^{7a}$—S—, as a whole or partial structure.

In -L-T-M-, preferably,

L is a group selected from an aromatic hydrocarbon group optionally substituted by 1-2 substituents selected from a halogen atom and an alkyl group; and a divalent aromatic heterocyclic group containing 1-2 nitrogen atoms, T is —CO—NR$^{7c}$—, R$^{7c}$ is a hydrogen atom, M is —CH$_2$—, —(CH$_2$)$_2$— or —CH(CH$_3$)—, more preferably, L is a group selected from a phenylene group optionally substituted by 1-2 substituents selected from a halogen atom and an alkyl group; pyridinediyl; and a pyrazinediyl group, T is —CO—NR$^{7c}$—, R$^{7c}$ is a hydrogen atom, M is —CH$_2$—, —(CH$_2$)$_2$— or —CH(CH$_3$)—, further preferably, L is a phenylene group optionally substituted by 1-2 halogen atoms; or a pyrazinediyl group, T is —CO—NR$^{7c}$—, R$^{7c}$ is a hydrogen atom, M is —CH$_2$— or —CH(CH$_3$)—, particularly preferably, L is a phenylene group optionally substituted by 1-2 halogen atoms; or a pyrazinediyl group, T is —CO—NR$^{7c}$—, R$^{7c}$ is a hydrogen atom, M is —CH$_2$—, or

A partial structure:

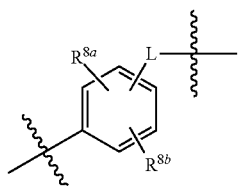

is preferably

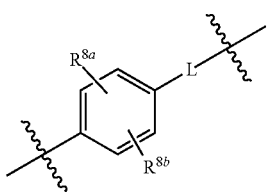

A partial structure:

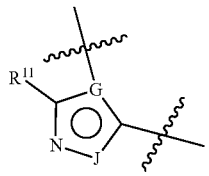

is preferably

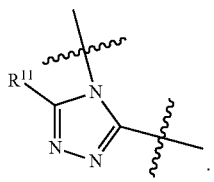

That is, G is preferably N, and J is preferably N.

$R^5$ is preferably a hydrogen atom.

$R^{6a}$ and $R^{6b}$ are preferably each independently a group selected from a hydrogen atom; a halogen atom (e.g., fluorine atom); a hydroxy group; a cyano group; and an alkyl group (e.g., methyl) optionally substituted by a substituent selected from a halogen atom, a hydroxy group and a cyano group; more preferably, each independently a group selected from a hydrogen atom; a halogen atom; a cyano group; and an alkyl group optionally substituted by a substituent selected from a halogen atom, a hydroxy group and a cyano group; further preferably, a group selected from a hydrogen atom; a halogen atom; a cyano group; and alkyl group.

$R^{7a}$ and $R^{7b}$ are preferably each independently a hydrogen atom; or an alkyl group (e.g., methyl, ethyl) optionally substituted by a substituent selected from a halogen atom, a hydroxy group and a cyano group, more preferably, each independently a hydrogen atom; or an alkyl group optionally substituted by a hydroxy group.

$R^{7c}$ is preferably a hydrogen atom.

$R^{7d}$ is preferably an alkyl group (e.g., methyl) optionally substituted by a substituent selected from a halogen atom, a hydroxy group and a cyano group, more preferably, an alkyl group.

$R^{7r}$ is preferably an alkylene group (e.g., —CH$_2$—, —(CH$_2$)$_2$—, —(CH$_2$)$_3$—) optionally substituted by a substituent selected from a halogen atom, a hydroxy group, and a cyano group, more preferably, an alkylene group.

$R^{8a}$ and $R^{8b}$ are preferably each independently a group selected from a hydrogen atom; a halogen atom; a hydroxy group; and a cyano group; more preferably, both are hydrogen atoms.

$R^{10a}$ and $R^{10b}$ are preferably each independently a substituent selected from a hydrogen atom; —N(R$^{7c}$)—CO—OR$^{7d}$; and an alkyl group (e.g., methyl); the alkyl group is optionally substituted by a substituent selected from a halogen atom; a hydroxy group; a cyano group; an alkoxy group optionally substituted by a substituent selected from a halogen atom, a hydroxy group, an alkoxy group and a cyano group; an alkoxycarbonyl group (e.g., methoxycarbonyl, t-butoxycarbonyl) optionally substituted by a substituent selected from a halogen atom, a hydroxy group, an alkoxy group and a cyano group; —CO—N(R$^{7a}$)(R$^{7b}$); and a hydroxycarbonyl group; more preferably, R$^{10a}$ is a group selected from a hydrogen atom; and an alkyl group optionally substituted by a substituent selected from a halogen atom, a hydroxy group, a cyano group, —NH—CO—OR$^{7d}$, —CO—N(R$^{7a}$)(R$^{7b}$), an alkoxycarbonyl group, and a hydroxycarbonyl group; and R$^{10b}$ is a hydrogen atom, further preferably, R$^{10a}$ is a group selected from a hydrogen atom; and an alkyl group optionally substituted by a substituent selected from —NH—CO—OR$^{7d}$, —CO—N(R$^{7a}$)(R$^{7b}$), a cyano group, an alkoxycarbonyl group, and a hydroxycarbonyl group; and R$^{10b}$ is a hydrogen atom, particularly preferably, R$^{10a}$ is an alkyl group optionally substituted by one alkoxycarbonyl group, and R$^{10b}$ is a hydrogen atom, further more preferably, R$^{10a}$ is a methyl group optionally substituted by one substituent selected from a tert-butoxycarbonyl group and a methoxycarbonyl group, most preferably a methyl group substituted by a methoxycarbonyl group.

$R^{11}$ is preferably an alkyl group (e.g., methyl) optionally substituted by a substituent selected from a halogen atom, a hydroxy group and a cyano group, more preferably, an alkyl group, particularly preferably a methyl group.

Preferable examples of a compound represented by the formula (I) include the following compounds.

[Compound I-A]

Compound (I) wherein A is a ring selected from an aromatic hydrocarbocycle, a 5- or 6-membered aromatic heterocycle containing 1 to 3 atoms selected from oxygen, sulfur and nitrogen and a cycloalkane ring, a partial structure:

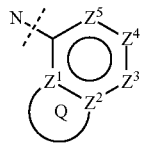

is the following formula:

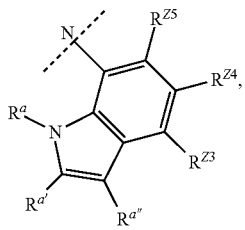

R$^a$ is a hydrogen atom; or an alkyl group optionally substituted by a substituent selected from a halogen atom, a hydroxy group, an alkoxy group and a cyano group, R$^{a'}$ is a hydrogen atom; a halogen atom; a hydroxy group; a cyano group; an alkyl group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; or —CO—N(R$^{7a}$)(R$^{7b}$), R$^{a''}$ is a hydrogen atom; a halogen atom; a cyano group; an alkyl group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; or —CO—N(R$^{7a}$)(R$^{7b}$), R$^{Z3}$ is a group selected from a hydrogen atom; a halogen atom; a hydroxy group; a cyano group; a hydroxycarbonyl group; an alkyl group optionally substituted by a group selected from a halogen atom, a hydroxy group, an alkoxy group and a cyano group; a cycloalkyl group optionally substituted by a group selected from a halogen atom, a hydroxy group, an alkoxy group and a cyano group; an alkoxy group optionally substituted by a group selected from a halogen atom, a hydroxy group, an alkoxy group and a cyano group; an alkoxycarbonyl group optionally substituted by a group selected from a halogen atom, a hydroxy group, an alkoxy group and a cyano group;

R$^{Z4}$ and R$^{Z5}$ are each independently a group selected from a hydrogen atom; a halogen atom; a cyano group; an alkyl group optionally substituted by a substituent selected from a halogen atom, a hydroxy group, an alkoxy group and a cyano group; an alkoxy group optionally substituted by a group selected from a halogen atom, a hydroxy group, an alkoxy group and a cyano group;

a partial structure:

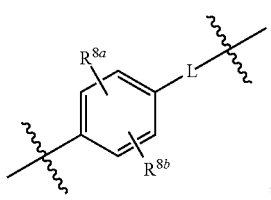

is the following formula (Ea) or (Ec):

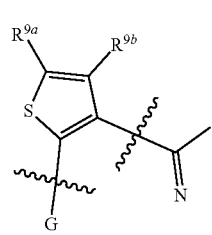

a partial structure:

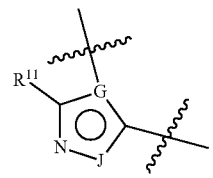

a partial structure:

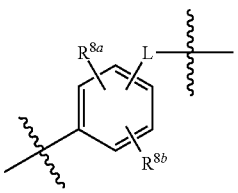

is

L is a group selected from a divalent aromatic hydrocarbon group; a divalent aliphatic heterocyclic group; an optionally partly hydrogenated divalent aromatic heterocyclic group; an alkylene group; a cycloalkylene group; an alkenylene group; and an alkynylene group; the group is optionally substituted by a substituent selected from a halogen atom; a hydroxy group; a cyano group; a hydroxycarbonyl group; an alkyl group optionally substituted by a group selected from a halogen atom, a hydroxy group, an alkoxy group and a cyano group; and an alkoxy group optionally substituted by a group selected from a halogen atom, a hydroxy group, an alkoxy group and a cyano group;

T is a single bond, —CO—, —CO—NR$^{7c}$—, —NR$^{7c}$—CO—, or —O—, or an alkylene group optionally substituted by a substituent selected from a halogen atom; a hydroxy group; a cyano group; an oxo group; a hydroxycarbonyl group; an alkyl group optionally substituted by a substituent selected from a halogen atom, a hydroxy group, an alkoxy group and a cyano group; and an alkoxy group optionally substituted by substituent selected from a halogen atom, a hydroxy group, an alkoxy group and a cyano group;

M is a single bond, or a group selected from —O—; —S—; —NR$^{7a}$—; —CO—; —SO—; —SO$_2$—; —CO—NR$^{7c}$—; —NR$^{7c}$—CO—; —SO$_2$—NR$^{7c}$—; —NR$^{7c}$—SO$_2$—; —NR$^{7a}$—CO—NR$^{7b}$—; —(OCH$_2$CH$_2$)$_m$—; —O—R$^{7r}$—; —R$^{7r}$—O—; —S—R$^{7r}$—; —R$^{7r}$—S—; —NR$^{7a}$—R$^{7r}$—; —R$^{7r}$—NR$^{7a}$—; —CO—NR$^{7c}$—R$^{7r}$—; —R$^{7r}$—CO—NR$^{7c}$—; an alkylene group optionally substituted by a substituent selected from a halogen atom, a hydroxy group, an alkoxy group and a cyano group; an alkynylene group optionally substituted by a substituent selected from a halogen atom, a hydroxy group, an alkoxy group and a cyano group; and a divalent aliphatic heterocyclic group optionally substituted by a substituent selected from a) a halogen atom, b) a hydroxy group, c) a cyano group, d) an oxo group, e) an alkyl group optionally substituted by a substituent selected from a halogen atom, a hydroxy group, an alkoxy group and a cyano group, and f) an alkoxy group optionally substituted by a substituent selected from a halogen atom, a hydroxy group, an alkoxy group and a cyano group, R$^5$ is a hydrogen atom, R$^{6a}$ and R$^{6b}$ are each independently a group selected from a hydrogen atom; a halogen atom; a hydroxy group; a cyano group; and an alkyl group optionally substituted by a substituent selected from a halogen atom, a hydroxy group and a cyano group;

R$^{7c}$ is a hydrogen atom,

R$^{8a}$ and R$^{8b}$ are each independently a group selected from a hydrogen atom; a halogen atom; a hydroxy group; and a cyano group;

R$^{9a}$ and R$^{9b}$ are each independently a group selected from a hydrogen atom; a halogen atom; a cyano group; an alkyl group optionally substituted by a substituent selected from a halogen atom, a hydroxy group and a cyano group;

R$^{10a}$ and R$^{10b}$ are each independently a substituent selected from a hydrogen atom; —N(R$^{7c}$)—CO—OR$^{7d}$; and an alkyl group; and the alkyl group is optionally substituted by a substituent selected from a halogen atom; a hydroxy group; a cyano group; an alkoxy group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; —CO—N(R$^{7a}$)(R$^{7b}$); and a hydroxycarbonyl group.

[Compound I-B]

Compound (I) wherein A is a ring selected from a benzene ring; a pyridine ring; and a cycloalkane ring, a partial structure:

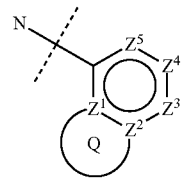

is the following formula:

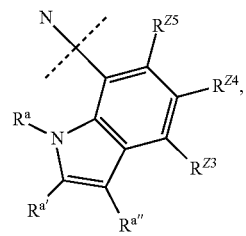

R$^a$ is a hydrogen atom; or an alkyl group optionally substituted by a substituent selected from a halogen atom, a hydroxy group, and a cyano group, R$^{a'}$ is a hydrogen atom; or an alkyl group optionally substituted by a substituent selected from a halogen atom, a hydroxy group, and a cyano group, R$^{a''}$ is a hydrogen atom; a halogen atom; an alkyl group optionally substituted by a substituent selected from a halogen atom, a hydroxy group, and a cyano group; or a cyano group, R$^{Z3}$ is a hydrogen atom; a halogen atom; a cyano group; an alkyl group optionally substituted by a substituent selected from a halogen atom, a hydroxy group and a cyano group; a cycloalkyl group optionally substituted by a substituent selected from a halogen atom, a hydroxy group and a cyano group; or an alkoxy group optionally substituted by a substituent selected from a halogen atom, a hydroxy group and a cyano group;

R$^{Z4}$ and R$^{Z5}$ are each independently a hydrogen atom; or an alkyl group optionally substituted by a substituent selected from a halogen atom, a hydroxy group and a cyano group, a partial structure:

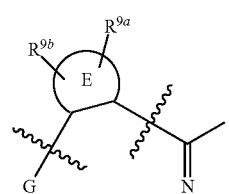

is the following formula (Ea):

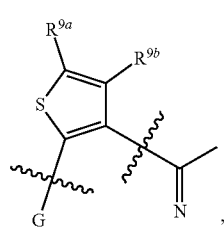

a partial structure:

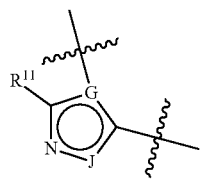

is

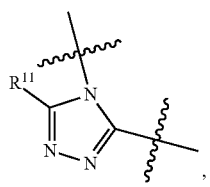

a partial structure:

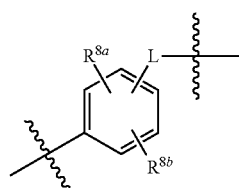

is

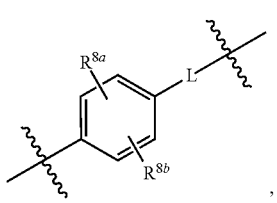

L is a group selected from an alkynyl group optionally substituted by a substituent selected from a halogen atom, a hydroxy group and a cyano group; a divalent aromatic hydrocarbon group optionally substituted by a substituent selected from a) a halogen atom, b) a hydroxy group, c) a cyano group, d) an alkyl group optionally substituted by a substituent selected from a halogen atom, a hydroxy group and a cyano group, and e) an alkoxy group optionally substituted by a substituent selected from a halogen atom, a hydroxy group and a cyano group; a divalent aliphatic heterocyclic group containing a nitrogen atom optionally substituted by a substituent selected from a halogen atom, a hydroxy group and a cyano group; and an optionally partially hydrogenated, divalent aromatic heterocyclic group containing 1-2 atoms selected from a nitrogen atom, an oxygen atom and a sulfur atom, the aromatic heterocyclic group is optionally substituted by a substituent selected from a halogen atom, a hydroxy group, a cyano group and an oxo group, T is a single bond; —CO—; —CO—NR$^{7c}$—; —NR$^{7c}$—CO—; or —O—, M is a single bond, or a group selected from —R$^{7r}$—O—; —R$^{7r}$—NR$^{7a}$—; an alkylene group optionally substituted by a substituent selected from a halogen atom, a hydroxy group, and a cyano group; an alkynylene group optionally substituted by a substituent selected from a halogen atom, a hydroxy group, and a cyano group; and a divalent aliphatic heterocyclic group, R$^{6a}$ and R$^{6b}$ are each independently a group selected from a hydrogen atom; a halogen atom; a cyano group; and an alkyl group optionally substituted by a substituent selected from a halogen atom, a hydroxy group and a cyano group, R$^{7a}$ and R$^{7b}$ are each independently a hydrogen atom; or an alkyl group optionally substituted by a substituent selected from a halogen atom, a hydroxy group and a cyano group, R$^{7c}$ is a hydrogen atom, R$^{7d}$ is an alkyl group optionally substituted by a substituent selected from a halogen atom, a hydroxy group and a cyano group, R$^{7r}$ is an alkylene group optionally substituted by a substituent selected from a halogen atom, a hydroxy group, and a cyano group, R$^{8a}$ and R$^{8b}$ are each a hydrogen atom, R$^{9a}$ and R$^{9b}$ are each independently an alkyl group optionally substituted by a substituent selected from a halogen atom, a hydroxy group and a cyano group, R$^{10a}$ is a group selected from a hydrogen atom; and an alkyl group optionally substituted by a substituent selected from a halogen atom, a hydroxy group, a cyano group, —NH—CO—OR$^{7d}$, —CO—N(R$^{7a}$)(R$^{7b}$), an alkoxycarbonyl group and a hydroxycarbonyl group, R$^{10b}$ is a hydrogen atom, and R$^{11}$ is an alkyl group optionally substituted by a substituent selected from a halogen atom, a hydroxy group and a cyano group.

[Compound I-C]

Compound (I) wherein A is a ring selected from a benzene ring; a pyridine ring; and a cycloalkane ring, a partial structure:

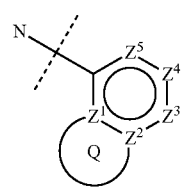

is the following formula:

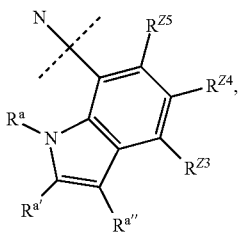

R$^a$ is a hydrogen atom; or an alkyl group,
R$^{a'}$ is a hydrogen atom; or an alkyl group,
R$^{a''}$ is a hydrogen atom; a halogen atom; an alkyl group; or a cyano group,
R$^{Z3}$ is a hydrogen atom; a halogen atom; a cyano group; an alkyl group optionally substituted by a halogen atom or a hydroxy group; a cycloalkyl group; or an alkoxy group,
R$^{Z4}$ and R$^{Z5}$ are each independently a hydrogen atom; or an alkyl group,
a partial structure:

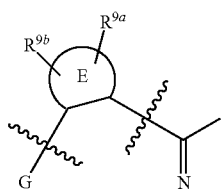

is the following formula (Ea):

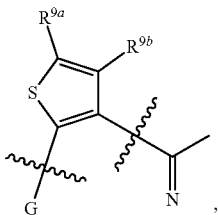 (Ea)

a partial structure:

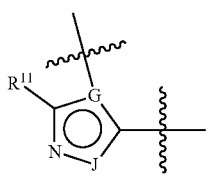

is

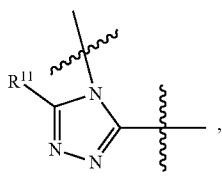

a partial structure:

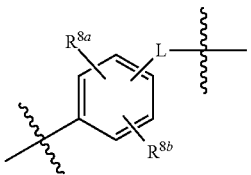

is

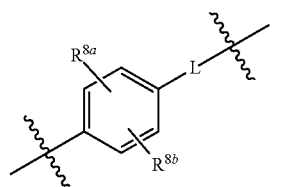,

L is a group selected from an alkynyl group optionally substituted by a substituent selected from a halogen atom, a hydroxy group and a cyano group; a divalent aromatic hydrocarbon group optionally substituted by a substituent selected from a) a halogen atom, b) a hydroxy group, c) a cyano group, d) an alkyl group optionally substituted by a substituent selected from a halogen atom, a hydroxy group and a cyano group, and e) an alkoxy group optionally substituted by a substituent selected from a halogen atom, a hydroxy group and a cyano group; a divalent aliphatic heterocyclic group containing one nitrogen atom optionally substituted by a substituent selected from a halogen atom, a hydroxy group and a cyano group; and an optionally partially hydrogenated, divalent aromatic heterocyclic group containing 1-2 atoms selected from a nitrogen atom, an oxygen atom and a sulfur atom,
the aromatic heterocyclic group is optionally substituted by a substituent selected from a halogen atom, a hydroxy group, a cyano group and an oxo group,
T is a single bond; —CO—; —CO—NR$^{7c}$—; —NR$^{7c}$—CO—; or —O—,
M is a single bond, or a group selected from —R$^{7r}$—O—; —R$^{7r}$—NR$^{7a}$—; an alkylene group optionally substituted by a substituent selected from a halogen atom, a hydroxy group, and a cyano group; an alkynylene group optionally substituted by a substituent selected from a halogen atom, a hydroxy group, and a cyano group; and a divalent aliphatic heterocyclic group,
R$^{6a}$ and R$^{6b}$ are each independently a group selected from a hydrogen atom; a halogen atom; a cyano group; and an alkyl group optionally substituted by a substituent selected from a halogen atom, a hydroxy group and a cyano group,
R$^{7a}$ and R$^{7b}$ are each independently a hydrogen atom; or an alkyl group optionally substituted by a substituent selected from a halogen atom, a hydroxy group and a cyano group,
R$^{7c}$ is a hydrogen atom,
R$^{7d}$ is an alkyl group optionally substituted by a substituent selected from a halogen atom, a hydroxy group and a cyano group,
R$^{7r}$ is an alkylene group optionally substituted by a substituent selected from a halogen atom, a hydroxy group, and a cyano group, $R^{8a}$ and $R^{8b}$ are each a hydrogen atom, $R^{9a}$ and $R^{9b}$ are each independently an alkyl group optionally substituted by a substituent selected from a halogen atom, a hydroxy group and a cyano group, $R^{10a}$ is a group selected from a hydrogen atom; and an alkyl group optionally substituted by a substituent selected from a halogen atom, a hydroxy group, a cyano group, —NH—CO—OR$^{7d}$, —CO—N($R^{7a}$)($R^{7b}$), an alkoxycarbonyl group and a hydroxycarbonyl group, $R^{10b}$ is a hydrogen atom, and $R^{11}$ is an alkyl group optionally substituted by a substituent selected from a halogen atom, a hydroxy group and a cyano group.

[Compound I-D]

Compound (I) wherein A is a benzene ring, a partial structure:

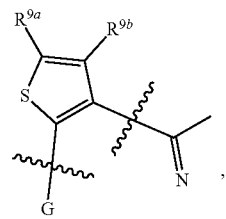

is the following formula:

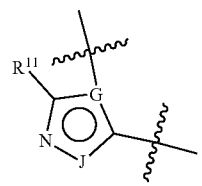

$R^a$ is a hydrogen atom, $R^{a'}$ is a hydrogen atom; or an alkyl group, $R^{a''}$ is a hydrogen atom; a halogen atom; an alkyl group; or a cyano group, $R^{Z3}$ is a hydrogen atom; a halogen atom; a cyano group; an alkyl group optionally substituted by a halogen atom or a hydroxy group; a cycloalkyl group; or an alkoxy group, $R^{Z4}$ and $R^{Z5}$ are each independently a hydrogen atom; or an alkyl group, a partial structure:

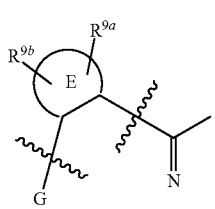

is the following formula (Ea):

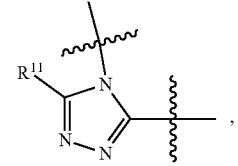

a partial structure:

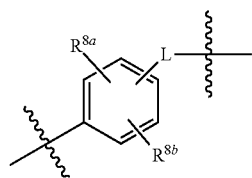

is

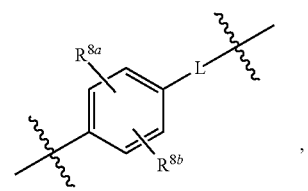

a partial structure:

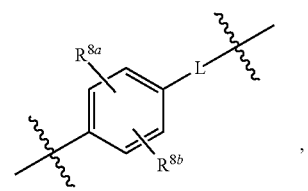

is

L is a group selected from a divalent aromatic hydrocarbon group optionally substituted by a substituent selected from a halogen atom, an alkyl group optionally substituted by a halogen atom, and an alkoxy group; and an optionally partially hydrogenated, divalent aromatic heterocyclic group containing 1-2 atoms selected from a nitrogen atom, an oxygen atom and a sulfur atom, T is a single bond; —CO—; —CO—NR$^{7c}$—; —NR$^{7c}$—CO—; or —O—, M is an alkylene group optionally substituted by a hydroxy group and a cyano group, $R^{6a}$ and $R^{6b}$ are each independently a group selected from a hydrogen atom; a halogen atom; a cyano group; and an alkyl group optionally substituted by a substituent selected from a halogen atom, a hydroxy group and a cyano group, $R^{7a}$ and $R^{7b}$ are each independently a hydrogen atom; or an alkyl group optionally substituted by a substituent selected from a halogen atom, a hydroxy group and a cyano group, $R^{7c}$ is a hydrogen atom, $R^{7d}$ is an alkyl group optionally substituted by a substituent selected from a halogen atom, a hydroxy group and a cyano group, $R^{7r}$ is an alkylene group optionally substituted by a substituent selected from a halogen atom, a hydroxy group, and a cyano group, $R^{8a}$ and $R^{8b}$ are each a hydrogen atom, $R^{9a}$ and $R^{9b}$ are each independently an alkyl group optionally substituted by a substituent selected from a halogen atom, a hydroxy group and a cyano group, $R^{10a}$ is an alkyl group optionally substituted by an alkoxycarbonyl group, $R^{10b}$ is a hydrogen atom, and $R^{11}$ is an alkyl group optionally substituted by a substituent selected from a halogen atom, a hydroxy group and a cyano group.

[Compound I-E]

Compound (I) wherein A is a benzene ring, a partial structure:

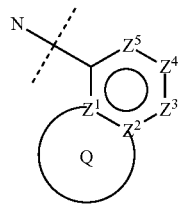

is the following formula:

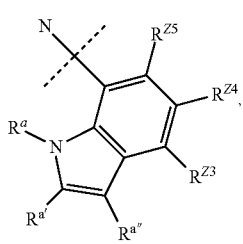

$R^a$ is a hydrogen atom, $R^{a'}$ is a hydrogen atom, $R^{a''}$ is a cyano group, $R^{Z3}$ is an alkyl group optionally substituted by 1 to 3 halogen atoms or a hydroxy group; or an alkoxy group, $R^{Z4}$ is a hydrogen atom, $R^{Z5}$ is a hydrogen atom, a partial structure:

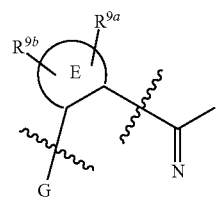

is the following formula (Ea):

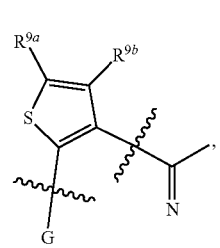

(Ea)

a partial structure:

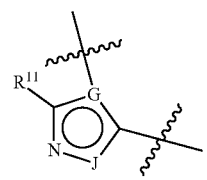

is

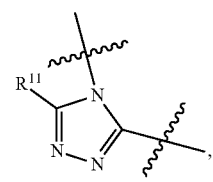

a partial structure:

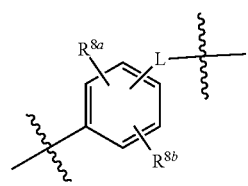

is

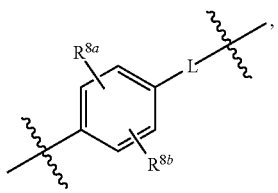

L is a group selected from a divalent aromatic hydrocarbon group optionally substituted by 1-2 substituents selected from a halogen atom, an alkyl group optionally substituted by 1 to 3 halogen atoms, and an alkoxy group; and optionally partially hydrogenated, divalent aromatic heterocyclic group containing 1-2 atoms selected from a nitrogen atom, an oxygen atom and a sulfur atom, T is a single bond; —CO—; —CO—NR$^{7c}$—; —NR$^{7c}$—CO—; or —O—, M is an alkylene group optionally substituted by one substituent selected from a hydroxy group and a cyano group, R$^{6a}$ and R$^{6b}$ are each independently a group selected from a hydrogen atom; a halogen atom; a cyano group; and an alkyl group optionally substituted by 1 to 3 substituents selected from a halogen atom, a hydroxy group and a cyano group, R$^{7a}$ and R$^{7b}$ are each independently a hydrogen atom; or an alkyl group optionally substituted by 1 to 3 substituents selected from a halogen atom, a hydroxy group and a cyano group, R$^{7c}$ is a hydrogen atom, R$^{7d}$ is an alkyl group optionally substituted by 1 to 3 substituents selected from a halogen atom, a hydroxy group and a cyano group, R$^{7r}$ is an alkylene group optionally substituted by 1 to 3 substituents selected from a halogen atom, a hydroxy group, and a cyano group, R$^{8a}$ and R$^{8b}$ are each a hydrogen atom, R$^{9a}$ and R$^{9b}$ are each independently an alkyl group optionally substituted by one substituent selected from a halogen atom, a hydroxy group and a cyano group, R$^{10a}$ is an alkyl group optionally substituted by one alkoxycarbonyl group, R$^{10b}$ is a hydrogen atom, and R$^{11}$ is an alkyl group optionally substituted by 1 to 3 substituents selected from a halogen atom, a hydroxy group and a cyano group.

[Compound I-F]

Compound (I) wherein A is a benzene ring, a partial structure:

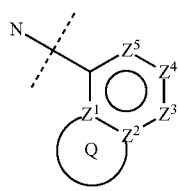

is the following formula:

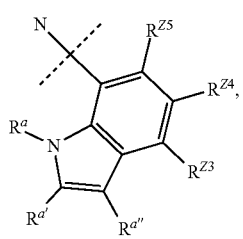

R$^{a'}$ is a hydrogen atom,
R$^{a''}$ is a cyano group,

R$^{Z3}$ is an alkyl group; or an alkoxy group,
R$^{Z4}$ is a hydrogen atom,
R$^{Z5}$ is a hydrogen atom, a partial structure:

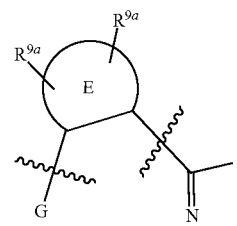

is the following formula (Ea):

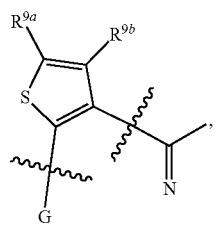

(Ea)

a partial structure:

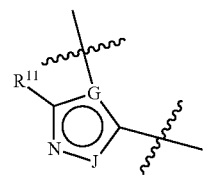

is

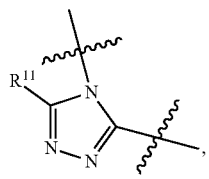

a partial structure:

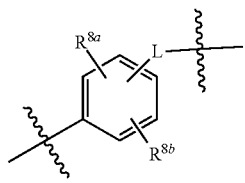

is

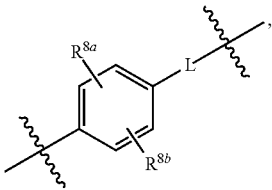

L is a group selected from a divalent aromatic hydrocarbon group optionally substituted by 1-2 substituents selected from a halogen atom and an alkyl group; and a divalent aromatic heterocyclic group containing 1-2 nitrogen atoms,
T is —CO—NR$^{7c}$—, R$^{7c}$ is a hydrogen atom,
M is —CH$_2$—, —(CH$_2$)$_2$—, or —CH(CH$_3$)—,
R$^{8a}$ and R$^{8b}$ are each a hydrogen atom,
R$^{9a}$ and R$^b$ are each independently an alkyl group,
R$^{10a}$ is an alkyl group optionally substituted by one alkoxycarbonyl group,
R$^{10b}$ is a hydrogen atom, and
R$^{11}$ is an alkyl group.

[Compound I-G]
Compound (I) wherein A is a benzene ring,
a partial structure:

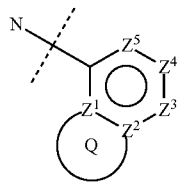

is the following formula:

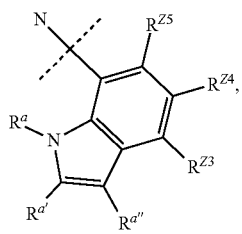

R$^{a'}$ is a hydrogen atom,
R$^{a''}$ is a cyano group,
R$^{Z3}$ is an alkyl group; or an alkoxy group,
R$^{Z4}$ is a hydrogen atom,
R$^{Z5}$ is a hydrogen atom,
a partial structure:

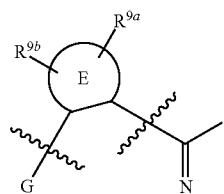

is the following formula (Ea):

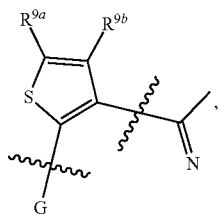

a partial structure:

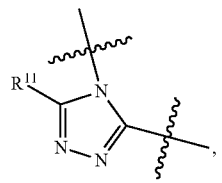

a partial structure:

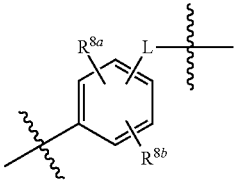

is

L is a group selected from a phenylene group optionally substituted by 1-2 substituents selected from a halogen atom and an alkyl group; a pyridinediyl group; and a pyrazinediyl group,
T is —CO—NR$^{7c}$—, R$^{7c}$ is a hydrogen atom,
M is —CH$_2$—, —(CH$_2$)$_2$—, or —CH(CH$_3$)—,
R$^{8a}$ and R$^{8b}$ are each a hydrogen atom,
R$^{9a}$ and R$^{9b}$ are each independently an alkyl group, $R^{10a}$ is an alkyl group optionally substituted by one alkoxycarbonyl group,
$R^{10b}$ is a hydrogen atom, and
$R^{11}$ is an alkyl group.

[Compound I-H]

Compound (I) wherein A is a benzene ring, a partial structure:

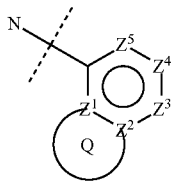

is the following formula:

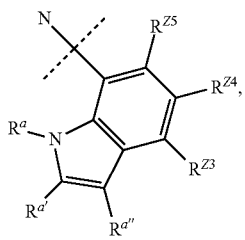

$R^{a'}$ is a hydrogen atom,
$R^{a''}$ is a cyano group,
$R^{Z3}$ is an alkyl group; or an alkoxy group,
$R^{Z4}$ is a hydrogen atom,
$R^{Z5}$ is a hydrogen atom, a partial structure:

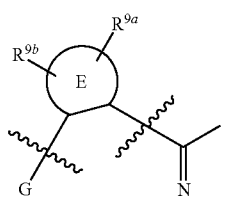

is the following formula (Ea):

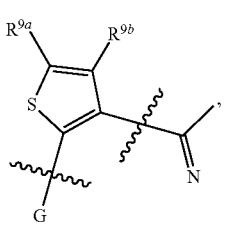

(Ea)

a partial structure:

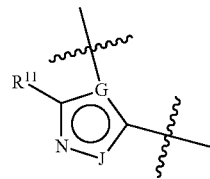

is

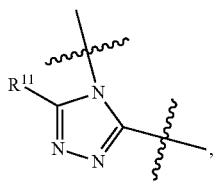

a partial structure:

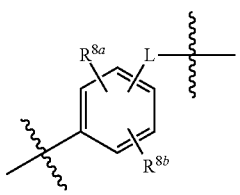

is

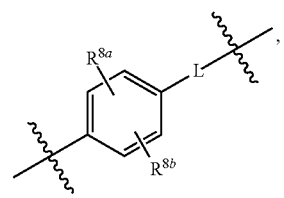

L is a group selected from a phenylene group optionally substituted by 1-2 substituents selected from a halogen atom and an alkyl group; and a pyrazinediyl group, T is —CO—NR$^{7c}$—, $R^{7c}$ is a hydrogen atom, M is —CH$_2$—, or —CH(CH$_3$)—, $R^{8a}$ and $R^{8b}$ are each a hydrogen atom, $R^{9a}$ and $R^{9b}$ are each independently an alkyl group, $R^{10a}$ is an alkyl group substituted by one alkoxycarbonyl group, $R^{10b}$ is a hydrogen atom, and $R^{11}$ is an alkyl group.

[Compound I-I]

Compound (I) wherein A is a benzene ring, a partial structure:

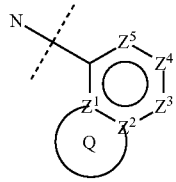

is the following formula:

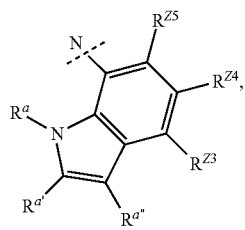

$R^a$ is a hydrogen atom, $R^{a'}$ is a hydrogen atom, $R^{a''}$ is a cyano group, $R^{Z3}$ is an alkyl group optionally substituted by 1 to 3 halogen atoms or a hydroxy group; or an alkoxy group, $R^{Z4}$ is a hydrogen atom, $R^{Z5}$ is a hydrogen atom, a partial structure:

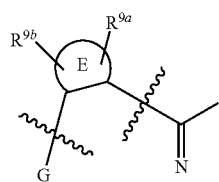

is the following formula (Ea):

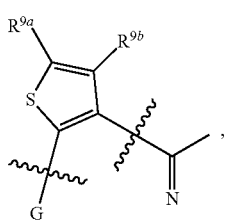

(Ea)

a partial structure:

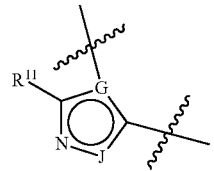

is

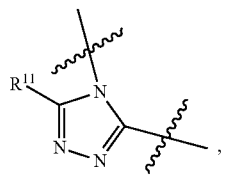

, a partial structure:

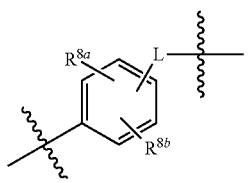

is

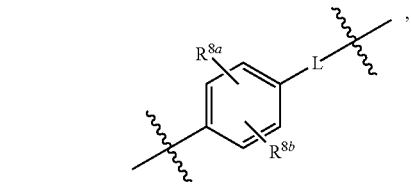

,

L is a divalent aromatic hydrocarbon group optionally substituted by 1-2 substituents selected from a halogen atom, an alkyl group optionally substituted by 1 to 3 halogen atoms, and an alkoxy group, T is a single bond; —CO—; —CO—$NR^{7c}$—; —$NR^{7c}$—CO—; or —O—, M is an alkylene group optionally substituted by one substituent selected from a hydroxy group and a cyano group, $R^{6a}$ and $R^{6b}$ are each independently a group selected from a hydrogen atom; a halogen atom; a cyano group; and an alkyl group optionally substituted by 1 to 3 substituents selected from a halogen atom, a hydroxy group and a cyano group, $R^{7a}$ and $R^{7b}$ are each independently a hydrogen atom; or an alkyl group optionally substituted by 1 to 3 substituents selected from a halogen atom, a hydroxy group and a cyano group, $R^{7c}$ is a hydrogen atom, $R^{7d}$ is an alkyl group optionally substituted by 1 to 3 substituents selected from a halogen atom, a hydroxy group and a cyano group, $R^{7r}$ is an alkylene group optionally substituted by 1 to 3 substituents selected from a halogen atom, a hydroxy group, and a cyano group, $R^{8a}$ and $R^{8b}$ are each a hydrogen atom,
$R^{9a}$ and $R^{9b}$ are each independently an alkyl group optionally substituted by one substituent selected from a halogen atom, a hydroxy group and a cyano group,
$R^{10a}$ is an alkyl group optionally substituted by one alkoxycarbonyl group,
$R^{10b}$ is a hydrogen atom, and
$R^{11}$ is an alkyl group optionally substituted by 1 to 3 substituents selected from a halogen atom, a hydroxy group and a cyano group.

[Compound I-J]

Compound (I) wherein A is a benzene ring,
a partial structure:

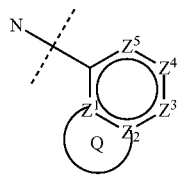

is the following formula:

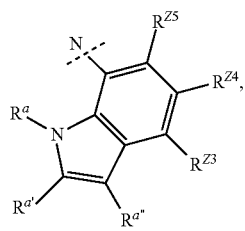

$R^a$ is a hydrogen atom,
$R^{a'}$ is a hydrogen atom,
$R^{a''}$ is a cyano group,
$R^{Z3}$ is an alkyl group optionally substituted by 1 to 3 halogen atoms or a hydroxy group; or an alkoxy group,
$R^{Z4}$ is a hydrogen atom,
$R^{Z5}$ is a hydrogen atom,
a partial structure:

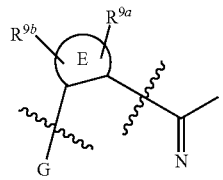

is the following formula (Ea):

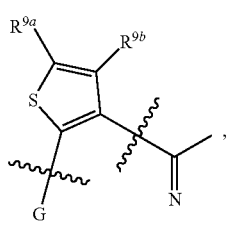

(Ea)

a partial structure:

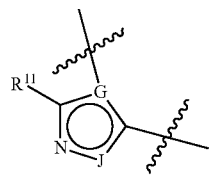

is

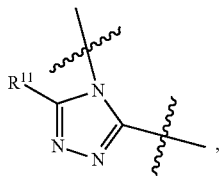

, a partial structure:

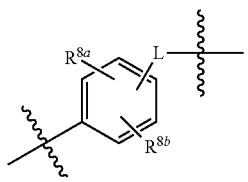

is

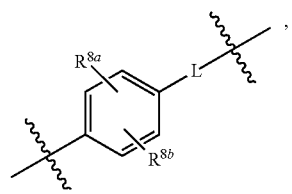

,

L is a divalent aromatic heterocyclic group containing 1-2 nitrogen atoms,
T is a single bond; —CO—; —CO—NR$^{7c}$—; —NR$^{7c}$—CO—; or —O—,
M is an alkylene group optionally substituted by one substituent selected from a hydroxy group and a cyano group,
$R^{6a}$ and $R^{6b}$ are each independently a group selected from a hydrogen atom; a halogen atom; a cyano group; and an alkyl group optionally substituted by 1 to 3 substituents selected from a halogen atom, a hydroxy group and a cyano group,
$R^{7a}$ and $R^{7b}$ are each independently hydrogen atom; or an alkyl group optionally substituted by 1 to 3 substituents selected from a halogen atom, a hydroxy group and a cyano group,
$R^{7c}$ is a hydrogen atom,
$R^{7d}$ is an alkyl group optionally substituted by 1 to 3 substituents selected from a halogen atom, a hydroxy group and a cyano group,
$R^{7r}$ is an alkylene group optionally substituted by 1 to 3 substituents selected from a halogen atom, a hydroxy group, and a cyano group, $R^{8a}$ and $R^{8b}$ are each a hydrogen atom, $R^{9a}$ and $R^{9b}$ are each independently an alkyl group optionally substituted by one substituent selected from a halogen atom, a hydroxy group and a cyano group, $R^{10a}$ is an alkyl group optionally substituted by one alkoxycarbonyl group, $R^{10b}$ is a hydrogen atom, and $R^{11}$ is an alkyl group optionally substituted by 1 to 3 substituents selected from a halogen atom, a hydroxy group and a cyano group.

Specific examples of a compound represented by the formula (I) include the compounds of the below-mentioned Examples 1-126, preferred are the compounds of Examples 1, 11, 15, 26, 43, 45, 46, 47, 50, 53, 63, 64, 65, 69, 70, 71, 74, 85, 92, 97, 98, 99, 100, 102, 103, 105, 106, 107, 108, 109, 110, 118, 127 and 148, more preferred are the compounds of Examples 1, 11, 26, 43, 47, 53, 63, 64, 65, 69, 71, 74, 92, 102, 103, 105, 106, 107, 108, 109 and 110, and further preferred are the compounds of Examples 1, 47, 74 and 106.

In the present invention, the "pharmaceutically acceptable salt" is not particularly limited as long as it is a pharmaceutically acceptable salt, and examples include salts with inorganic acids, salts with organic acids, salts with alkali metals, salts with alkaline earth metals, salts with inorganic bases, and salts with organic bases. Furthermore, hydrates which are water-containing salts and solvates which are solvent-containing salts are also included in the pharmaceutically acceptable salts in the present invention.

In the present specification, "pharmaceutically acceptable" means being generally safe and harmless, possibly biologically undesirable but preferable in other aspects, and useful in preparing pharmaceutical compositions including those useful not only for application as medicament for human but also for application in veterinary medicine.

The compounds of the present invention can be produced by the following methods A-F. While these methods and steps may be combined but the production method thereof is not limited thereto.

In the following, the case where $R^{10}$ is $R^{10a}$ or $R^{10b}$, and one of $R^{10a}$ and $R^{10b}$ is a hydrogen atom is described as an example. Even when both $R^{10a}$ and $R^{10b}$ are optionally substituted alkyl, the following method applies ($R^{10a}$, $R^{10b}$ are as defined above).

(Method A)

(1) The production method described here is suitable for producing an intermediate of a compound represented by the formula (I) wherein ring E is represented by the aforementioned formula (Ea), G is a nitrogen atom and J is a nitrogen atom, namely, the following compound (A-1).

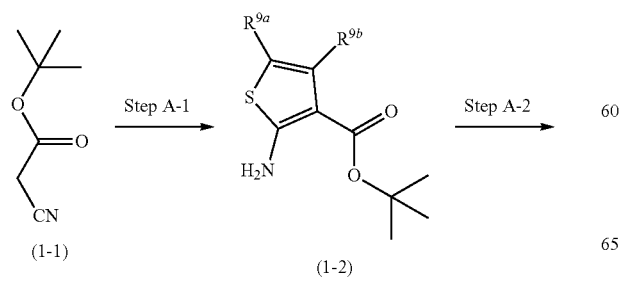

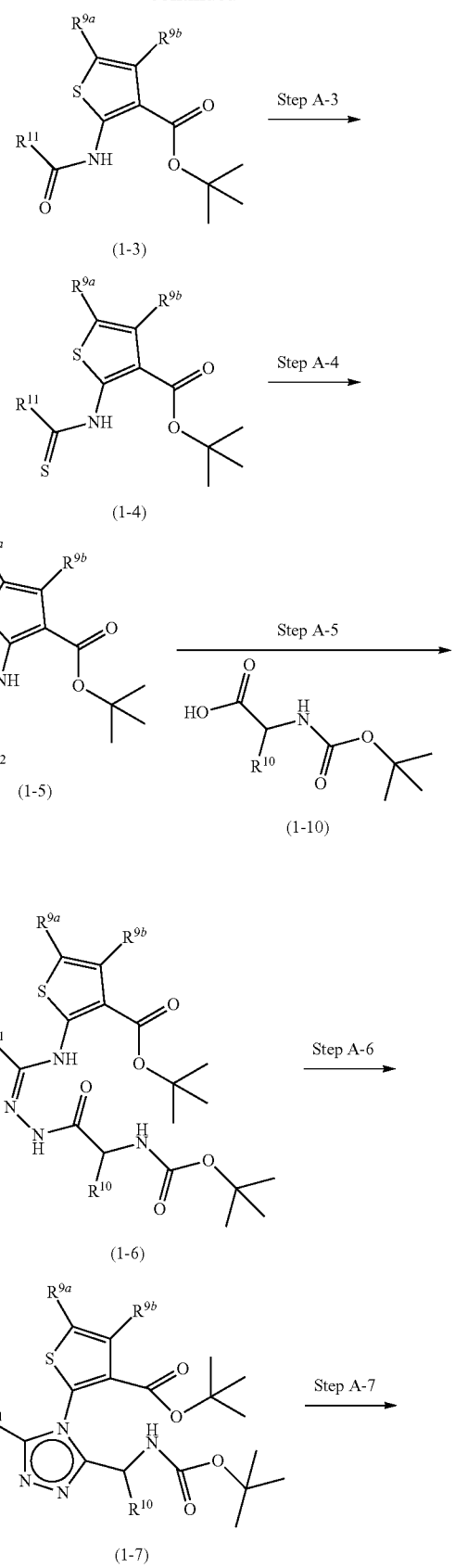

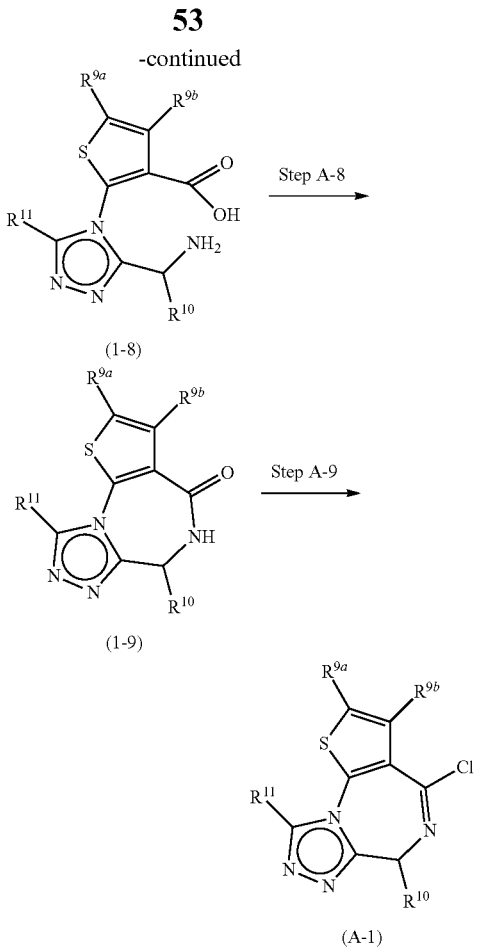

(1-8)

(1-9)

(A-1)

wherein each symbol is as defined above.

Step A-1

Compound (1-2) can be derived from compound (1-1) according to a known method (e.g., J. Med. Chem. 1973, 16, 214-219).

Step A-2

Compound (1-3) can be obtained by acylating compound (1-2). The reaction proceeds using a base in an appropriate solvent at generally from −20° C. to the refluxing temperature of the solvent. While the reaction time varies depending on the starting material and solvent to be used and the reaction temperature, it is generally from 0.5 hr to 24 hr. Examples the acylating agent include trifluoroacetic anhydride, acetic anhydride, propanoic anhydride, acetyl chloride and the like. Examples of the base include triethylamine, pyridine and the like. Examples of the solvent include tetrahydrofuran, dichloromethane, toluene, 1,4-dioxane and the like.

Step A-3

Compound (1-4) can be obtained by thioamidating compound (1-3). The thioamidation reaction proceeds using a sulfating agent in an appropriate solvent generally at room temperature to the refluxing temperature of the solvent. While the reaction time varies depending on the starting material and solvent to be used and the reaction temperature, it is generally from 0.5 hr to 24 hr. Examples of the sulfating agent include Lawesson reagent, diphosphorus pentasulfide and the like. Examples of the solvent include 1,2-dichloroethane, tetrahydrofuran, 1,4-dioxane and the like.

Step A-4

Compound (1-5) can be obtained by reacting compound (1-4) with hydrazine. The reaction with hydrazine proceeds using hydrazine monohydrate in an appropriate solvent generally at room temperature to the refluxing temperature of the solvent. While the reaction time varies depending on the starting material and solvent to be used and the reaction temperature, it is generally from 1 hr to 24 hr. Examples of the solvent include tetrahydrofuran, 1,4-dioxane, N,N-dimethylformamide and the like.

Step A-5

Compound (1-6) can be obtained by converting the carboxylate form (1-10) having a substituent for $R^{10}$ to acid halide by a halogenating agent, and reacting same with compound (1-5). The reaction proceeds using a base in an appropriate solvent generally from 0° C. to the refluxing temperature of the solvent. While the reaction time varies depending on the starting material and solvent to be used and the reaction temperature, it is generally from 1 hr to 24 hr. Examples of the halogenating agent include thionyl chloride, oxalyl chloride, phenylphosphonyl dichloride and the like. Examples of the base include triethylamine, pyridine and the like. Examples of the solvent include dichloromethane, 1,2-dichloroethane, chloroform, pyridine, toluene and the like.

Step A-6

Compound (1-7) can be obtained by a cyclization reaction of compound (1-6). It proceeds in an appropriate solvent generally at room temperature to the refluxing temperature of the solvent. While the reaction time varies depending on the starting material and solvent to be used and the reaction temperature, it is generally from 1 hr to 24 hr. Examples of the solvent include 2-propanol, 1-butanol, tetrahydrofuran and the like.

Step A-7

Compound (1-8) can be obtained by deprotection reaction of compound (1-7). The reaction proceeds using an acid in an appropriate solvent generally at room temperature to the refluxing temperature of the solvent. While the reaction time varies depending on the starting material and solvent to be used and the reaction temperature, it is generally from 1 hr to 24 hr. Examples of the acid include hydrochloric acid, trifluoroacetic acid and the like. Examples of the solvent include ethyl acetate, 1,4-dioxane, tetrahydrofuran, dichloromethane, chloroform and the like.

Step A-8

Compound (1-9) can be obtained by a cyclization reaction of compound (1-8). The reaction proceeds using a condensing agent in the presence of a suitable base in a suitable solvent at 0° C. to the refluxing temperature of the solvent. While the reaction time varies depending on the starting material and solvent to be used and the reaction temperature, it is generally from 1 hr to 24 hr. Examples of the condensing agent include 1-ethyl-3-(3-dimethylaminopropyl)carbodiimide hydrochloride (WSC·HCl), 1-[bis(dimethylamino)methylene]-1H-1,2,3-triazolo[4,5-b]pyridinium 3-oxidohexafluorophosphate (HATU), 4-(4,6-dimethoxy[1.3.5]triazin-2-yl)-4-methylmorpholinium chloride hydrate (DMT-MM), 2-chloro-1-methylpyridinium iodide and the like. Examples of the solvent include methanol, N,N-dimethylformamide, chloroform, dichloromethane, tetrahydrofuran and the like. The reaction is sometimes accelerated by adding 1-hydroxybenzotriazole (HOBt). Examples of the base include triethylamine, N,N-diisopropylethylamine, pyridine and the like.

Step A-9

Compound (A-1) can be obtained by halogenating compound (1-9). The reaction proceeds using a halogenating agent generally at room temperature to the refluxing temperature of the solvent. While the reaction time varies depending on the starting material and solvent to be used and the reaction temperature, it is generally from 1 hr to 24 hr. Examples of the halogenating agent include phosphoryl chloride and the like.

(2) The production method described here is suitable for producing an intermediate of a compound represented by the formula (I) wherein ring E is represented by the aforementioned formula (Ec), G is a nitrogen atom and J is a nitrogen atom, namely, the following compound (A-2).

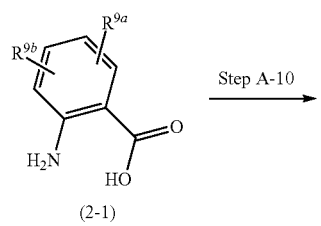
(2-1)

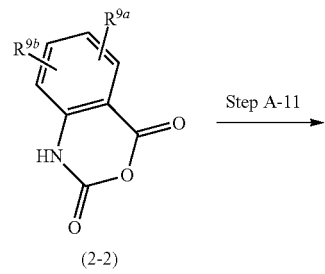
(2-2)

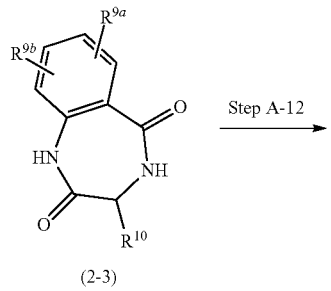
(2-3)

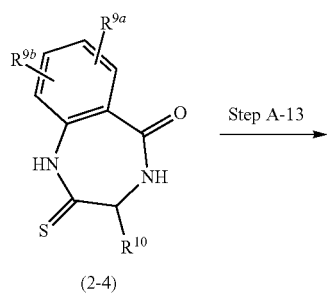
(2-4)

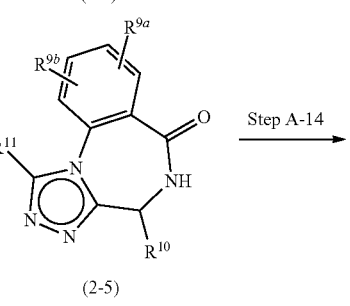
(2-5)

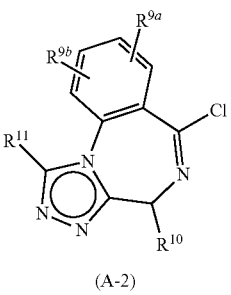
(A-2)

wherein each symbol is as defined above.

Compound (A-2) can be derived from compound (2-1) according to a known method (e.g., J. Med. Chem. 2016, 59, 1426).

(3) The production method described here is suitable for producing an intermediate of a compound represented by the formula (I) wherein G is a carbon atom and J is an oxygen atom, namely, the following compound (A-3).

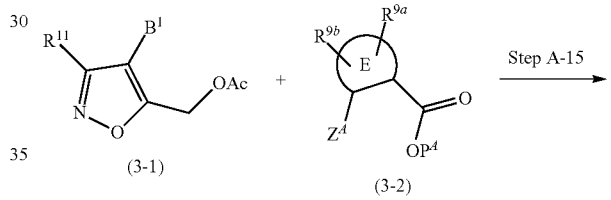
(3-1)        (3-2)

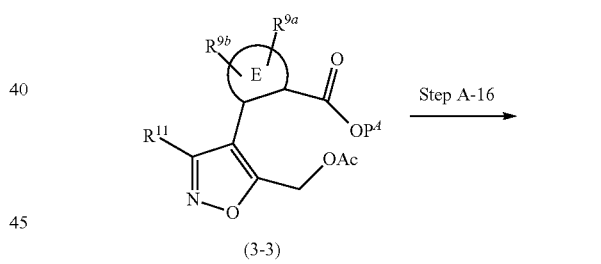
(3-3)

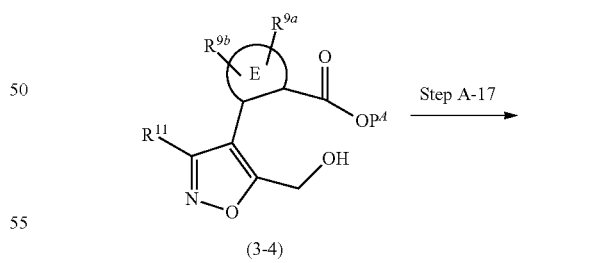
(3-4)

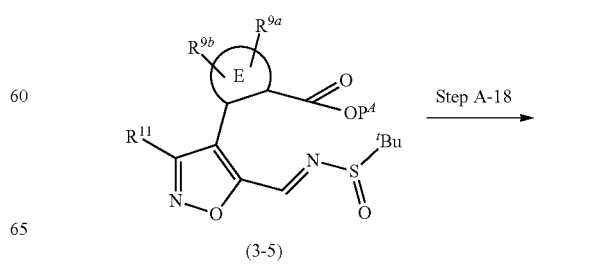
(3-5)

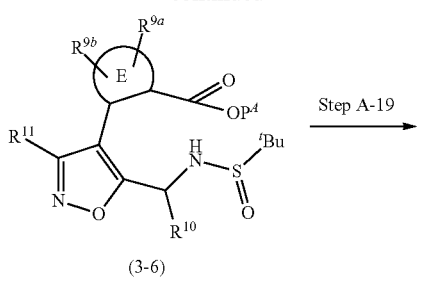

(3-6)

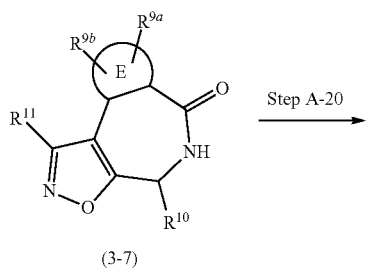

(3-7)

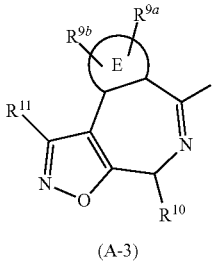

(A-3)

wherein $B^1$ is boronic acid or boronic acid ester optionally having substituent(s), $Z^A$ is a halogen atom, $P^A$ is a protecting group, and other symbols are as defined above.

In the formula, the boronic acid ester optionally having substituent(s) for $B^1$ is pinacolatoboron, neopentylglycolatoboron or the like, and the halogen atom for $Z^A$ is a chlorine atom, a bromine atom or an iodine atom. In the formula, the protecting group for $P^A$ protects carboxyl group and is not particularly limited as long as compound (3-7) is obtained. For example, alkyl (specifically methyl, ethyl) and the like can be mentioned.

Compound (A-3) can be derived from compound (3-1) according to a known method (e.g., WO 2012/075383).

(Method B)

(1) An intermediate of a compound represented by the formula (I), i.e., the following compound (B-1), can be synthesized by the following method.

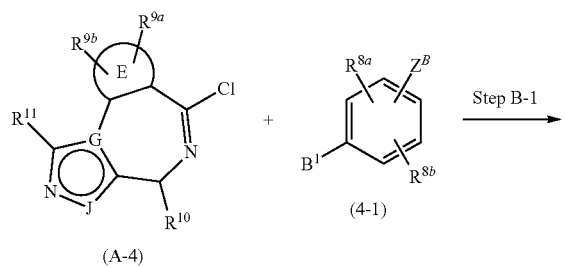

(A-4) + (4-1) → Step B-1

(B-1)

wherein $Z^B$ is a chlorine atom or a hydroxyl group, and other symbols are as defined above.

Step B-1

Compound (B-1) can be obtained by a coupling reaction of compound (A-4) with boronic acid derivative (4-1). The reaction preferably proceeds in the presence of a palladium catalyst, a phosphine ligand and a base in a suitable solvent at 0° C. to under heating, particularly at room temperature to the boiling point of the solvent. While the reaction time varies depending on the starting material and solvent to be used and the reaction temperature, it is generally from 1 hr to 24 hr. Examples of the palladium catalyst include palladium(II) acetate, palladium(II) chloride, tris(dibenzylideneacetone)dipalladium(0) or chloroform adduct thereof and the like. Examples of the phosphine ligand include triphenylphosphine, 2-(dicyclohexylphosphino)-2',4',6'-triisopropyl-1,1'-biphenyl, 2-(dicyclohexylphosphino)-3,6-dimethoxy-2',4',6'-triisopropyl-1,1'-biphenyl, 2-(dicyclohexylphosphino)-2,6-diisopropoxy-1,1'-biphenyl, 2-di-t-butylphosphino-2'-4'-6'-triisopropylbiphenyl, 2-dicyclohexylphosphino-2'-6'-dimethoxybiphenyl, 2-(dicyclohexylphosphino)-2-(N,N-dimethylamino)biphenyl, tri-ortho-tolylphosphine, 2-(dicyclohexylphosphino)biphenyl, 2-(di-t-butylphosphino)biphenyl, 2-(di-t-butylphosphino)-1,1-binaphthyl, tri-t-butylphosphine, tri-t-butylphosphonium tetrafluoroborate and the like. A reagent in which a palladium catalyst and a phosphine ligand form a complex may also be used and, for example, tetrakis(triphenylphosphine)palladium(0), 1,1-bis(diphenylphosphino)ferrocene-palladium(II) dichloride, dichlorobis(triphenylphosphine)palladium(II), dichlorobis(tricyclohexylphosphine)palladium(II), bis(tri-t-butylphosphine)palladium(0), chloro(2-dicyclohexylphosphino-2',4',6'-triisopropyl-1,1'-biphenyl) (2'-amino-1,1'-biphenyl-2-yl)palladium(II), [(2-dicyclohexylphosphino-3,6-dimethoxy-2',4',6'-triisopropyl-1,1'-biphenyl)-2-(2'-amino-1,1'-biphenyl)palladium(II) methanesulfonate, (2-dicyclohexylphosphino-2,6-diisopropoxy-1,1'-biphenyl) [2-(2'-amino-1,1'-biphenyl)]palladium(II) methanesulfonate, [(2-di-t-butylphosphino-3,6-dimethoxy-2',4',6'-triisopropyl-1,1'-biphenyl)-2-(2'-amino-1,1'-biphenyl) palladium(II) methanesulfonate, [1,3-bis(2,6-di-3-pentylphenyl)imidazol-2-ylidene](3-chloropyridyl) dichloropalladium(II), and the like. Examples of the base include t-butoxy sodium, potassium acetate, tripotassium phosphate, cesium carbonate, potassium carbonate, sodium hydrogen carbonate, lithium bis(trimethylsilyl)amide, triethylamine, diisopropylethylamine, dicyclohexylethylamine, potassium fluoride, cesium fluoride and the like. Examples of the solvent include ether solvents such as tetrahydrofuran, 1,2-dimethoxyethane, 1,4-dioxane and the like, alcohol solvents such as methanol, ethanol, propanol, butanol and the like, N,N-dimethylformamide, or a mixed solvent of the organic solvent and water and the like.

(2) The production method described here is suitable for producing an intermediate of a compound represented by the formula (I) wherein G is a nitrogen atom and J is a nitrogen atom, namely, the following compound (B-2).

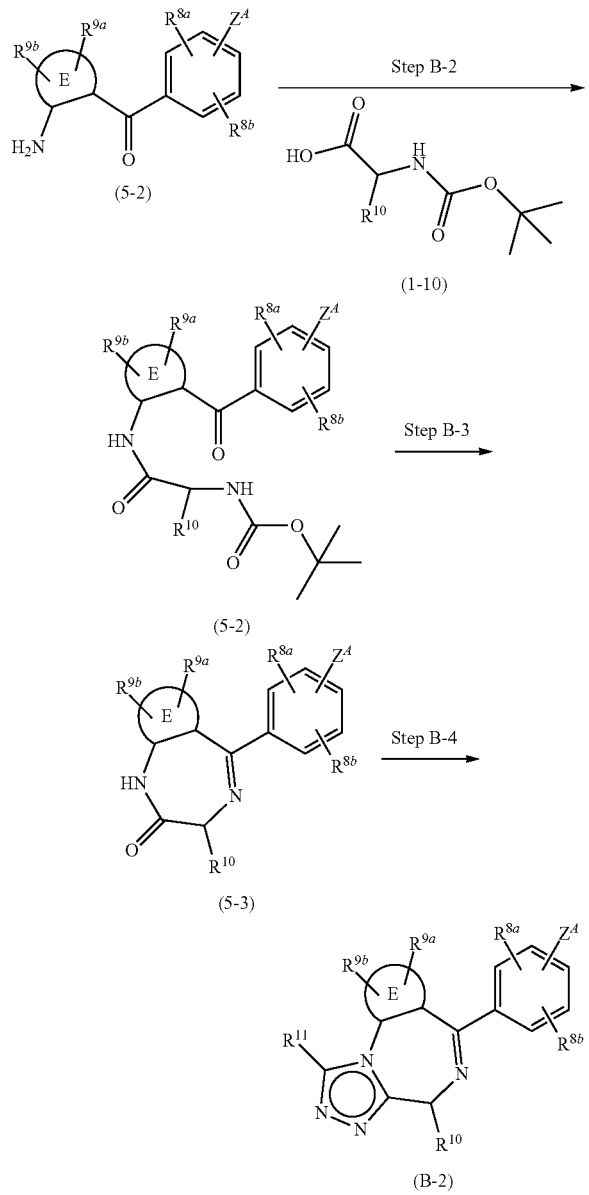

wherein each symbol is as defined above.

Step B-2

Compound (5-2) can be obtained by converting a carboxylate form (1-10) having a substituent for $R^{10}$ to acid halide by a halogenating agent and reacting same with compound (5-1). The reaction proceeds using a base in an appropriate solvent generally at −20° C. to the refluxing temperature of the solvent. While the reaction time varies depending on the starting material and solvent to be used and the reaction temperature, it is generally from 0.5 hr to 24 hr. Examples of the halogenating agent include thionyl chloride, oxalyl chloride, phenylphosphonyl dichloride and the like. Examples of the base include triethylamine, pyridine and the like. Examples of the solvent include dichloromethane, 1,2-dichloroethane, chloroform, pyridine, toluene and the like.

Step B-3

Compound (5-3) can be obtained by deprotection reaction and cyclization reaction of compound (5-2). The deprotection reaction proceeds using an acid in an appropriate solvent generally at 0° C. to the refluxing temperature of the solvent. While the reaction time varies depending on the starting material and solvent to be used and the reaction temperature, it is generally from 0.5 hr to 24 hr. Examples of the acid include trifluoroacetic acid, hydrochloric acid and the like. Examples of the solvent include dichloromethane, chloroform, tetrahydrofuran and the like. This reaction can also be performed using an acid alone. The cyclization reaction proceeds using an acid in an appropriate solvent generally at room temperature to the refluxing temperature of the solvent. While the reaction time varies depending on the starting material and solvent to be used and the reaction temperature, it is generally from 0.5 hr to 24 hr. Examples of the acid include trifluoroacetic acid, acetic acid and the like. Examples of the solvent include tetrahydrofuran, N,N-dimethylformamide, 1-butanol, 2-propanol and the like.

Step B-4

Compound (B-2) can be obtained from compound (5-3) by the following two methods.

A first one can be obtained by hydrazine addition, acylation and cyclization reaction. The reaction with hydrazine proceeds using a base and hydrazine in an appropriate solvent generally at 0° C. to room temperature. Examples of the base include sodium hydride, t-butoxy sodium, t-butoxy potassium and the like. The acylation reaction proceeds using an acylating agent in an appropriate solvent generally at room temperature to the refluxing temperature of the solvent. While the reaction time varies depending on the starting material and solvent to be used and the reaction temperature, it is generally from 0.5 hr to 24 hr. Examples of the acylating agent include trifluoroacetic anhydride, acetic anhydride, propanoic anhydride and the like. Examples of the solvent include tetrahydrofuran, 1,4-dioxane, N,N-dimethylformamide, dichloromethane and the like. The above-mentioned reaction can also be performed using acylhydrazide instead of using hydrazine and acid chloride or acid anhydride. Examples of the acylhydrazide include acetylhydrazine and the like. The cyclization reaction proceeds using an acid in an appropriate solvent generally at room temperature to the refluxing temperature of the solvent. While the reaction time varies depending on the starting material and solvent to be used and the reaction temperature, it is generally from 0.5 hr to 24 hr. Examples of the acid include acetic acid, trifluoroacetic acid and the like. Examples of the solvent include tetrahydrofuran, N,N-dimethylformamide, 1-butanol, 2-propanol and the like. This reaction proceeds after addition of hydrazine and using the corresponding ortho ester form in an appropriate solvent generally at room temperature to the refluxing temperature of the solvent. While the reaction time varies depending on the starting material and solvent to be used and the reaction temperature, it is generally from 0.5 hr to 24 hr. Examples of the ortho ester form include 1,1,1-triethoxyethane, 1,1,1-trimethoxypentane and the like. Examples of the solvent include toluene, tetrahydrofuran and the like.

A second one can be obtained by converting amide group to thioamide group, and performing hydrazine addition, acylation and cyclization reaction. The thioamidation reaction proceeds using a sulfating agent in an appropriate solvent generally at room temperature to the refluxing temperature of the solvent. While the reaction time varies depending on the starting material and solvent to be used and the reaction temperature, it is generally from 0.5 hr to 24 hr. Examples of the sulfating agent include Lawesson reagent, diphosphorus pentasulfide and the like. Examples of the solvent include 1,2-dichloroethane, tetrahydrofuran, 1,4-dioxane and the like. The hydrazine addition reaction proceeds using hydrazine in an appropriate solvent generally at room temperature to the refluxing temperature of the solvent. While the reaction time varies depending on the starting material and solvent to be used and the reaction temperature, it is generally from 1 hr to 24 hr. Examples of the solvent include tetrahydrofuran, 1,4-dioxane, N,N-dimethylformamide and the like. The acylation reaction proceeds using an acylating agent in an appropriate solvent generally at room temperature to the refluxing temperature of the solvent. While the reaction time varies depending on the starting material and solvent to be used and the reaction temperature, it is generally from 1 hr to 24 hr. Examples of the acylating agent include trifluoroacetic anhydride, acetic anhydride, propanoic anhydride and the like. The above-mentioned reaction can also be performed using acylhydrazide instead of using hydrazine and acid chloride or acid anhydride. Examples of the acylhydrazide include acetylhydrazine and the like. Examples of the solvent include tetrahydrofuran, N,N-dimethylformamide and the like. The cyclization reaction proceeds using an acid in an appropriate solvent generally at room temperature to the refluxing temperature of the solvent. While the reaction time varies depending on the starting material and solvent to be used and the reaction temperature, it is generally from 0.5 hr to 24 hr. Examples of the acid include acetic acid, trifluoroacetic acid and the like. Examples of the solvent include tetrahydrofuran, N,N-dimethylformamide, 1-butanol, 2-propanol and the like. This reaction proceeds after addition of hydrazine by using the corresponding ortho ester form in an appropriate solvent generally at room temperature to the refluxing temperature of the solvent. While the reaction time varies depending on the starting material and solvent to be used and the reaction temperature, it is generally from 0.5 hr to 24 hr. Examples of the ortho ester form include 1,1,1-triethoxyethane, 1,1,1-trimethoxypentane and the like. Examples of the solvent include toluene, tetrahydrofuran and the like.

(3) An intermediate of a compound represented by the formula (I) wherein G is a nitrogen atom and J is a nitrogen atom, namely, the following compound (B-2) can also be synthesized by the following method.

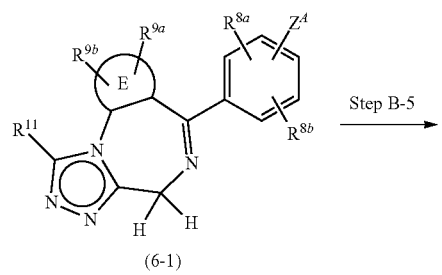

wherein $P^B$ is a protecting group, and other symbols are as defined above.

In the formula, $P^B$ is not particularly limited as long as it protects a carboxyl group. For example, alkyl (specifically methyl, ethyl, t-butyl and the like), aralkyl (benzyl and the like) and the like can be mentioned.

Compound (B-2) can also be synthesized from compound (6-1) according to a known method (e.g., methods described in WO 1993/007129, WO 1998/011111).

(4) The production method described here is suitable for producing an intermediate of a compound represented by the formula (I) wherein $R^{10}$ is —N($R^{7c}$)—CO—O$R^{7d}$, namely, the following compound (B-3), compound (B-4) ($R^{7c}$ and $R^{7d}$ are as defined above).

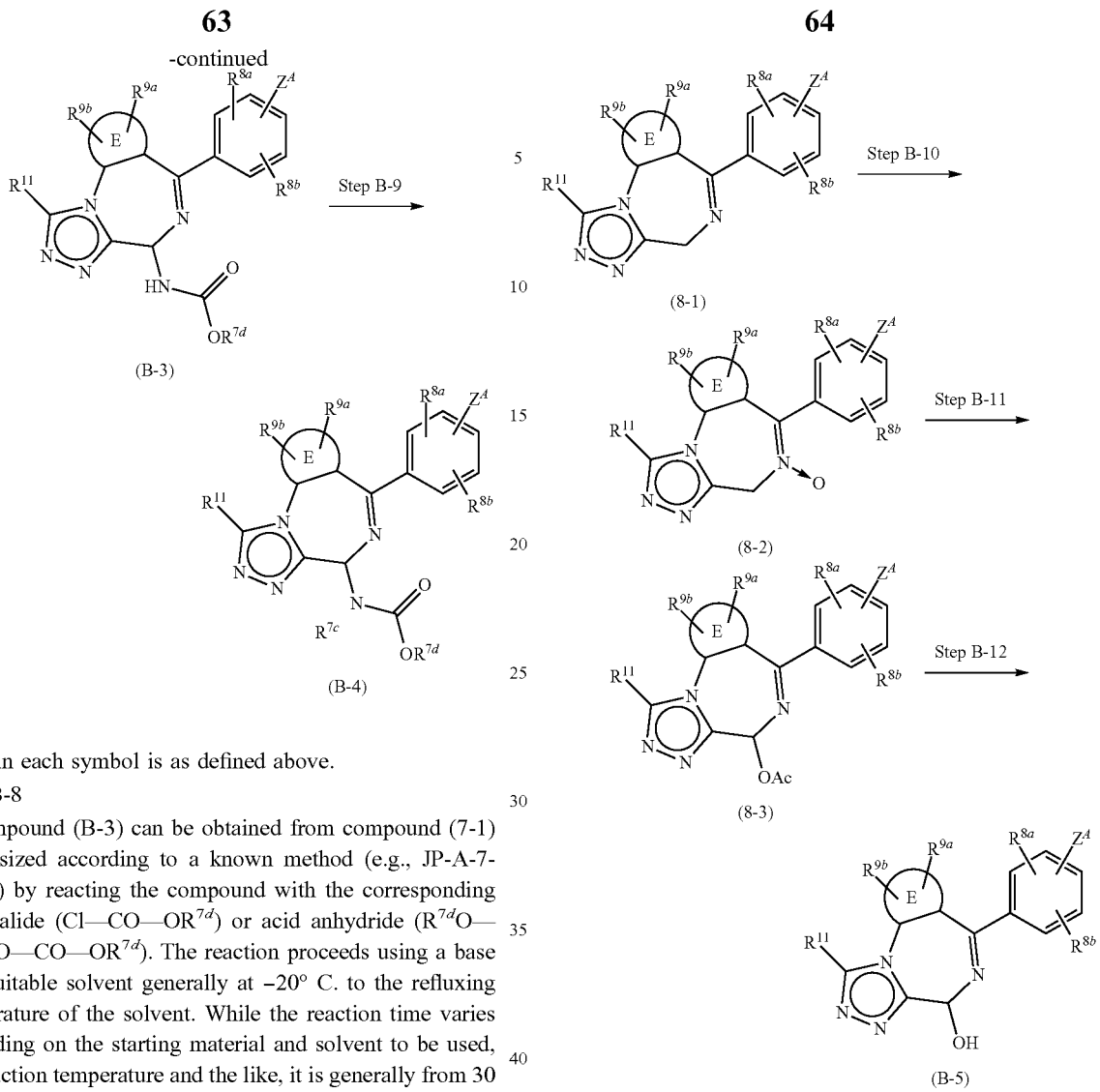

(B-3)

(B-4)

wherein each symbol is as defined above.

Step B-8

Compound (B-3) can be obtained from compound (7-1) synthesized according to a known method (e.g., JP-A-7-17941) by reacting the compound with the corresponding acid halide (Cl—CO—OR$^{7d}$) or acid anhydride (R$^{7d}$O—CO—O—CO—OR$^{7d}$). The reaction proceeds using a base in a suitable solvent generally at −20° C. to the refluxing temperature of the solvent. While the reaction time varies depending on the starting material and solvent to be used, the reaction temperature and the like, it is generally from 30 min to 24 hr. Examples of the base include triethylamine, N,N-diisopropylethylamine, pyridine and the like. Examples of the solvent include dichloromethane, 1,2-dichloroethane, chloroform, N-methylpyrrolidone, pyridine, toluene and the like. In this reaction, the base to be used can also be used as a solvent.

Step B-9

Compound (B-4) can be obtained by alkylating compound (B-3). The alkylation reaction proceeds using a base and an alkylating agent such as alkyl halide and the like in an appropriate solvent at generally 0° C. to the refluxing temperature of the solvent. While the reaction time varies depending on the starting material and solvent to be used and the reaction temperature, it is generally from 10 min to 24 hr. Examples of the base include inorganic bases such as sodium hydride, potassium hydroxide, potassium carbonate and the like, alkoxides such as potassium t-butoxide and the like, and the like. Examples of the solvent include N,N-dimethylformamide, tetrahydrofuran, dimethyl sulfoxide and the like.

(5) The production method described here is suitable for producing an intermediate of a compound represented by the formula (I) wherein R$^{10}$ is a hydroxyl group, namely, the following compound (B-5).

wherein each symbol is as defined above.

Compound (B-5) can be derived from compound (8-1) according to a known method (e.g., U.S. Pat. No. 4,959,361).

(6) The production method described here is suitable for producing an intermediate of a compound represented by the formula (I) wherein R$^{10}$ is —(CH$_2$)$_k$—CO—N(R$^{7a}$)(R$^{7b}$), namely, the following compound (B-6).

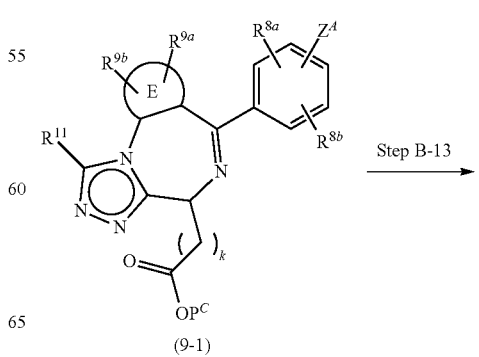

(9-1)

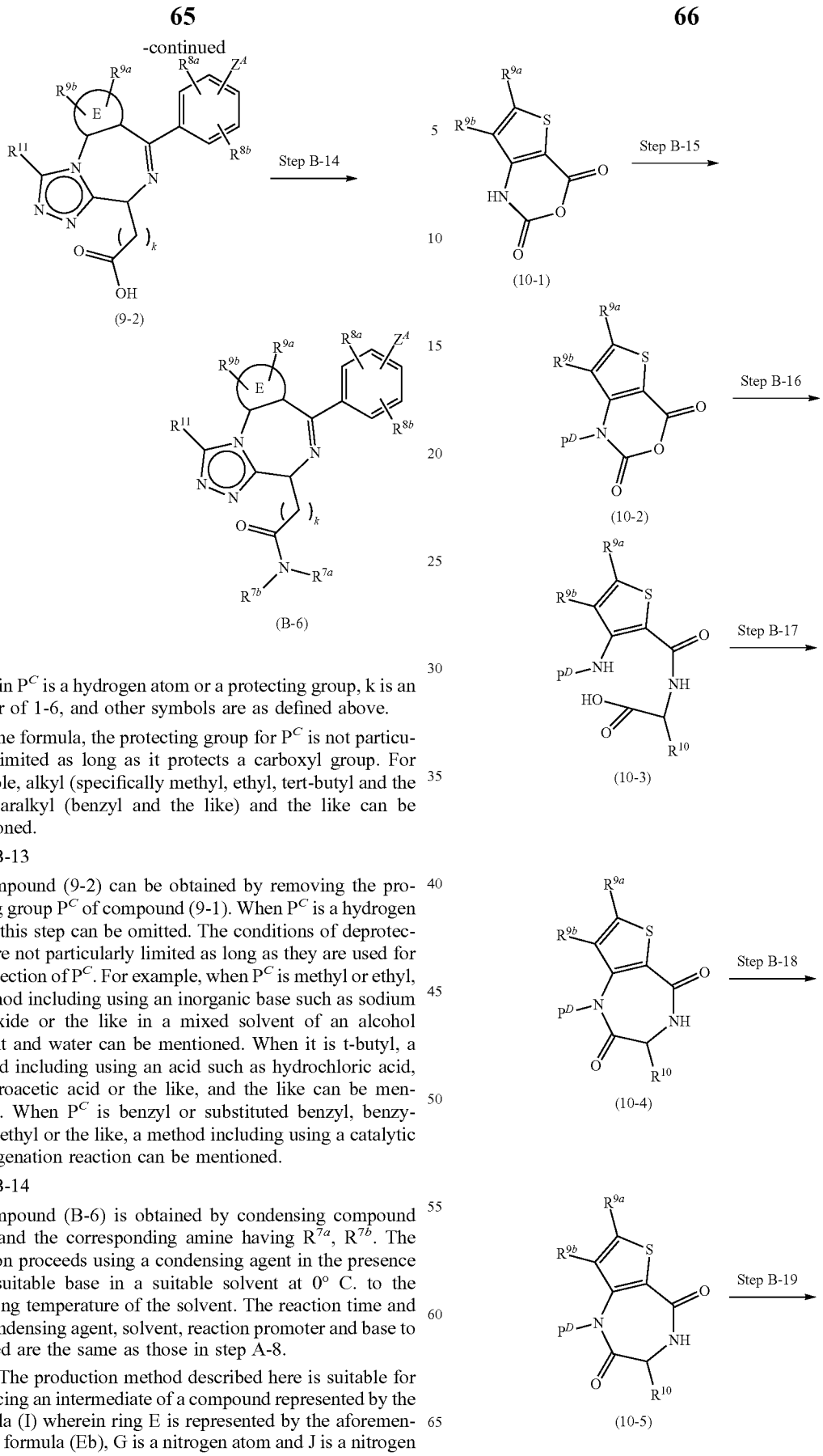

wherein $P^C$ is a hydrogen atom or a protecting group, k is an integer of 1-6, and other symbols are as defined above.

In the formula, the protecting group for $P^C$ is not particularly limited as long as it protects a carboxyl group. For example, alkyl (specifically methyl, ethyl, tert-butyl and the like), aralkyl (benzyl and the like) and the like can be mentioned.

Step B-13

Compound (9-2) can be obtained by removing the protecting group $P^C$ of compound (9-1). When $P^C$ is a hydrogen atom, this step can be omitted. The conditions of deprotection are not particularly limited as long as they are used for deprotection of $P^C$. For example, when $P^C$ is methyl or ethyl, a method including using an inorganic base such as sodium hydroxide or the like in a mixed solvent of an alcohol solvent and water can be mentioned. When it is t-butyl, a method including using an acid such as hydrochloric acid, trifluoroacetic acid or the like, and the like can be mentioned. When $P^C$ is benzyl or substituted benzyl, benzyloxymethyl or the like, a method including using a catalytic hydrogenation reaction can be mentioned.

Step B-14

Compound (B-6) is obtained by condensing compound (9-2) and the corresponding amine having $R^{7a}$, $R^{7b}$. The reaction proceeds using a condensing agent in the presence of a suitable base in a suitable solvent at 0° C. to the refluxing temperature of the solvent. The reaction time and the condensing agent, solvent, reaction promoter and base to be used are the same as those in step A-8.

(7) The production method described here is suitable for producing an intermediate of a compound represented by the formula (I) wherein ring E is represented by the aforementioned formula (Eb), G is a nitrogen atom and J is a nitrogen atom, namely, the following compound (B-7).

-continued

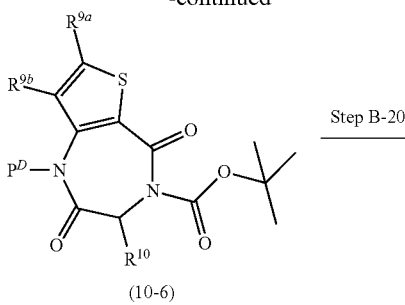

(10-6)

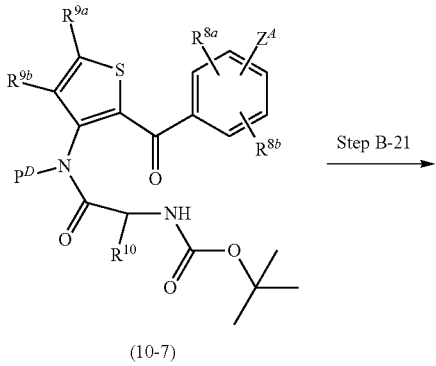

(10-7)

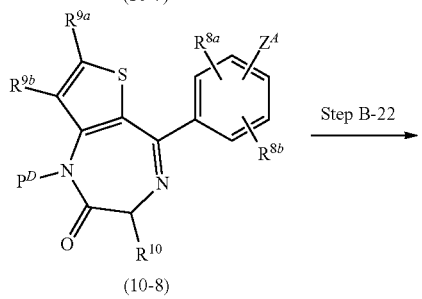

(10-8)

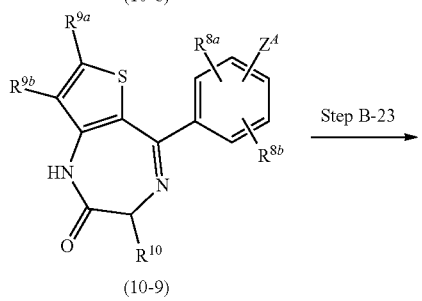

(10-9)

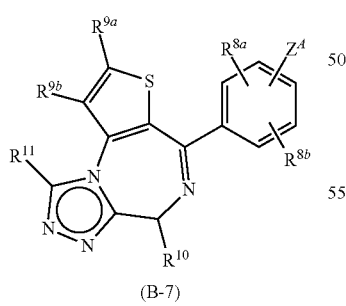

(B-7)

wherein $P^D$ is a protecting group, and other symbols are as defined above.

In the formula, $P^D$ is not particularly limited as long as it protects an amide group to produce compound (10-9). For example, 4-methoxybenzyl group, 2,4-dimethoxybenzyl group and the like can be mentioned.

Compound (B-7) can be synthesized from compound (10-1) according to the method described in SYNLETT, 2008, 15, 2360-2364 and J. Org. Chem., 2009, 74, 4975-4981.

(8) An intermediate of a compound represented by the formula (I) wherein ring E is represented by the aforementioned formula (Ea), G is a nitrogen atom, J is a nitrogen atom, and $R^{9a}$ is cyanomethyl, namely, the following compound (B-8) can also be synthesized by the following production method.

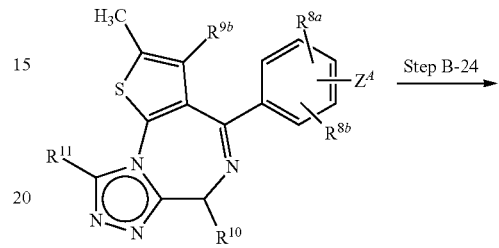

(11-1)

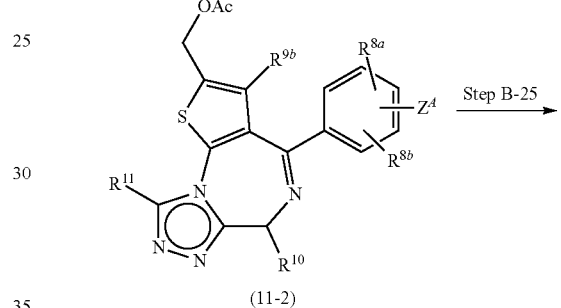

(11-2)

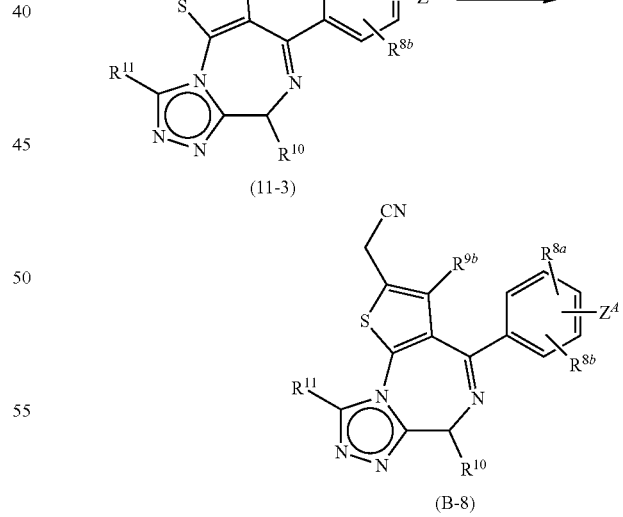

(11-3)

(B-8)

wherein each symbol is as defined above.

Step B-24

Compound (11-2) can be obtained by reacting compound (11-1) with a mixture of magnesium acetate dihydrate, acetic acid, acetic anhydride and concentrated sulfuric acid at room temperature for a suitable time.

Step B-25

Compound (11-3) is obtained by reacting compound (11-2) with a base. The reaction proceeds in an appropriate solvent generally at 0° C. to room temperature. While the reaction time varies depending on the starting material and solvent to be used, the reaction temperature, and the like, it is generally from 0.5 hr to 24 hr. Examples of the base include aqueous sodium hydroxide solution, aqueous potassium hydroxide solution and the like. Examples of the solvent include methanol, ethanol, tetrahydrofuran, 1,4-dioxane and the like.

Step B-26

Compound (B-8) can be obtained by converting a hydroxyl group of compound (11-3) to a leaving group and substituting same with a cyano group (cyanated). The conversion to the leaving group proceeds using a protecting agent and a base in an appropriate solvent generally at 0° C. to at room temperature. Examples of the protecting agent include p-toluenesulfonyl chloride, mesyl chloride and the like. While the reaction time varies depending on the starting material and solvent to be used, the reaction temperature, and the like, it is generally from 1 hr to 24 hr. Examples of the base include triethylamine, N,N-diisopropylethylamine and the like. Examples of the solvent include dichloromethane, tetrahydrofuran and the like. The cyanation reaction proceeds using a cyanating agent in an appropriate solvent generally at 0° C. to the refluxing temperature of the solvent. While the reaction time varies depending on the starting material and solvent to be used, the reaction temperature, and the like, it is generally from 1 hr to 24 hr. Examples of the cyanating agent include sodium cyanide, trimethylsilyl cyanide and the like. Examples of the solvent include dimethyl sulfoxide, acetonitrile, tetrahydrofuran and the like. When trimethylsilyl cyanide is used, tetrabutylammonium fluoride is used.

(9) An intermediate of a compound represented by the formula (I) wherein ring E is represented by the aforementioned formula (Ea), G is a nitrogen atom, J is a nitrogen atom, and $R^{9a}$ is alkyl having 1-6 carbon atoms and substituted by a cyano group, namely, the following compound (B-9) can also be synthesized by the following production method.

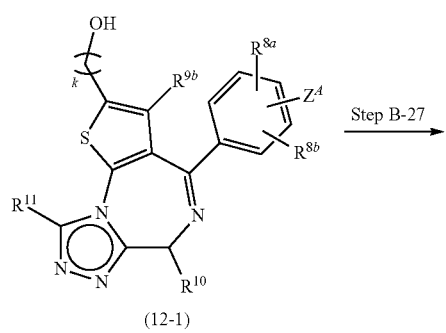

(12-1)

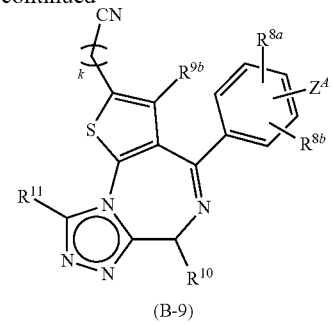

(B-9)

wherein k is an integer of 1-6, and other symbols are as defined above.

Step B-27

Compound (B-9) can be obtained by cyanating compound (12-1). As the reaction conditions, the conditions similar to those of the aforementioned Step B-26 can be mentioned.

(10) An intermediate of a compound represented by the formula (I) wherein ring E is represented by the aforementioned formula (Ea), G is a nitrogen atom, J is a nitrogen atom, and $R^{9a}$ is a cyano group, namely, the following compound (B-10) can be synthesized by the following production method.

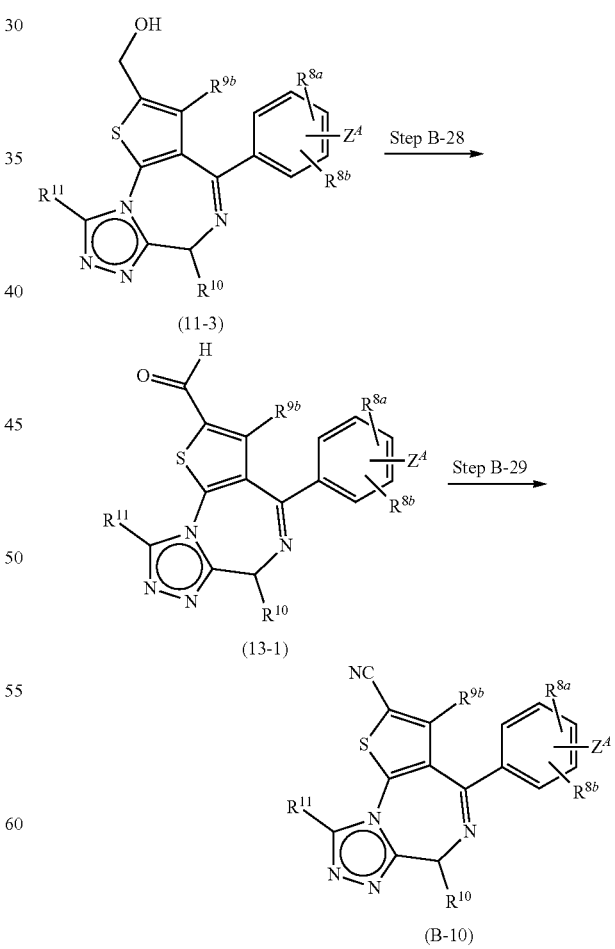

wherein each symbol is as defined above.

Step B-28

Compound (13-1) can be obtained by oxidizing compound (11-3). The reaction conditions are, for example, those for reacting a mixture of manganese dioxide and dichloromethane for a suitable time at room temperature.

Step B-29

Compound (B-10) can be obtained by cyanating compound (13-1). The reaction conditions are, for example, those for reacting a mixture of hydroxylamine hydrochloride and dimethyl sulfoxide for a suitable time under heating.

(11) An intermediate of a compound represented by the formula (I) wherein ring E is represented by the aforementioned formula (Ea), G is a nitrogen atom, J is a nitrogen atom, and $R^{9a}$ is a hydrogen atom, namely, the following compound (B-11) can be synthesized by the following production method.

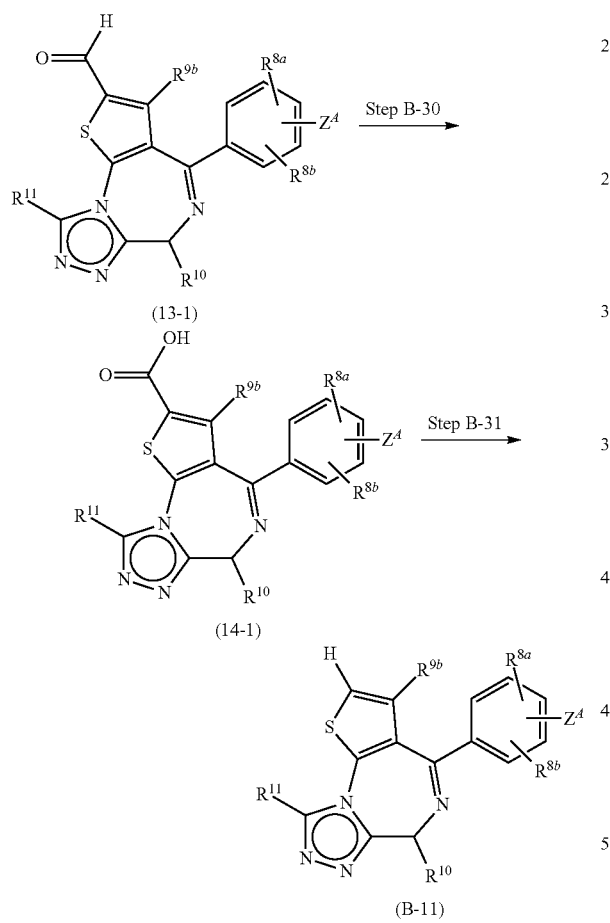

wherein each symbol is as defined above.

Step B-30

Compound (14-1) can be obtained by oxidizing compound (13-1). The reaction proceeds using an oxidant in an appropriate solvent generally at 0° C. to the refluxing temperature of the solvent. While the reaction time varies depending on the starting material and solvent to be used and the reaction temperature, it is generally from 0.5 hr to 24 hr. Examples of the oxidant include hydrogen peroxide, t-butyl hydroperoxide, sodium chlorite, potassium permanganate and the like. Examples of the solvent include methanol, acetonitrile, water and the like. The reaction proceeds, for example, by adding 35% hydrogen peroxide water, aqueous sodium chlorite solution to a mixture of acetonitrile and aqueous sodium dihydrogen phosphate solution at 0° C. to room temperature.

Step B-31

Compound (B-11) can be obtained by decarboxylating compound (14-1). The reaction conditions are, for example, those for reacting in quinoline in the presence of copper at 150° C.

(Method C)

(1) An intermediate of a compound represented by the formula (I), namely, the following compound (C-1) can also be synthesized by the following method.

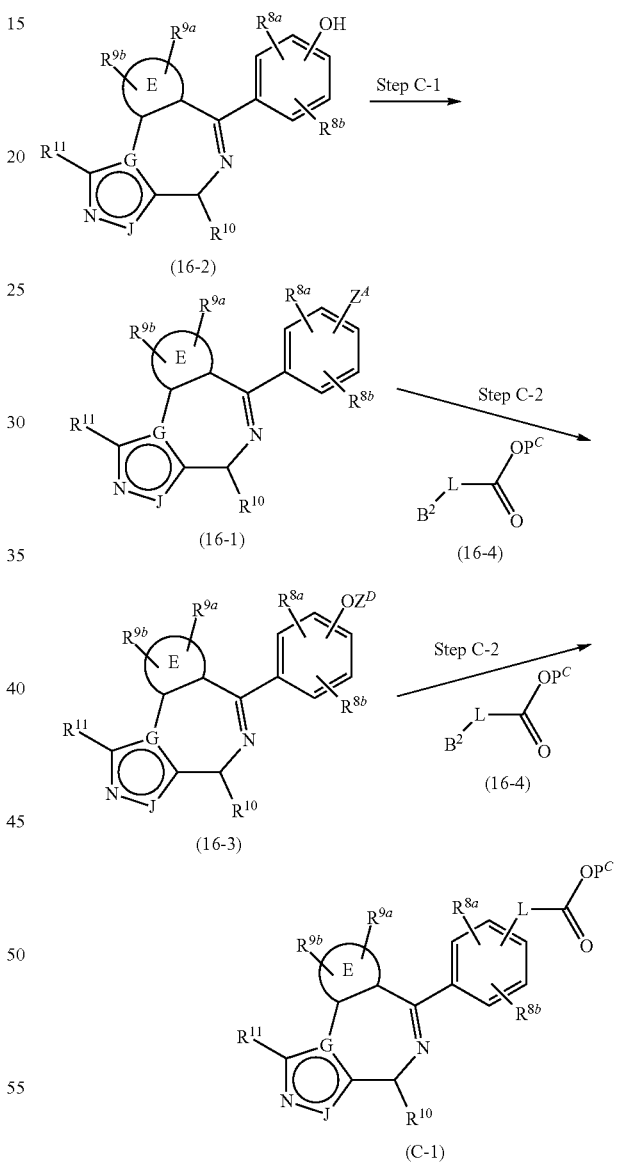

wherein $Z^A$ is a halogen atom, $Z^D$ is a hydroxyl group-activating group, $B^2$ is a hydrogen atom, amine, olefin, acetylene, thiol, alcohol, boronic acid or boronic acid ester optionally having substituent(s), and other symbols are as defined above.

In the formula, the halogen atom for $Z^A$ is a chlorine atom, a bromine atom or an iodine atom, and the hydroxyl group-activating group for $Z^D$ is a sulfonyl group such as trifluoromethanesulfonyl, toluenesulfonyl and the like. In the formula, the boronic acid ester optionally having substituent(s) for $B^2$ is pinacolatoboron, neopentylglycolatoboron or the like.

Step C-1

In this step, the hydroxyl group of compound (16-2) is converted to an activating group $OZ^D$. The reaction preferably proceeds in the presence of a base in a suitable solvent at about −50 to 50° C., particularly 0° C. to room temperature. As the activating reagent, an activated sulfonic acid derivative such as trifluoromethanesulfonic acid anhydride, 1-(trifluoromethanesulfonyl)imidazole or toluenesulfonyl chloride is used. This reaction can also be performed by using sulfonic acid and a condensing agent in combination. Examples of the base include triethylamine, pyridine, lutidine and the like. Examples of the solvent include dichloromethane, 1,2-dichloroethane, chloroform, pyridine, toluene and the like.

Step C-2

Compound (C-1) can be obtained by reacting compound (16-1) or compound (16-3) with compound (16-4).

Compound (C-1) is obtained by a coupling reaction of compound (16-1) or compound (16-3) and amine, olefin, acetylene, thiol or alcohol represented by $P^COC(O)$-L-$B^2$ (wherein L and Pc are as defined above), an arylboronic acid derivative represented by L-B(OH)$_2$ or an ester thereof (wherein L is as defined above). The palladium catalyst, phosphine ligand, reagent in which a palladium catalyst and a phosphine ligand form a complex, base and solvent to be used are the same as those in Step B-1.

When L is aryl having 6-12 carbon atoms, heteroaryl containing 5-12 ring-constituting atoms, olefin or acetylene, compound (C-1) can also be obtained by a coupling reaction of an organic metal salt (e.g., tin, zinc, copper and the like) for L or an alkylmetal derivative (e.g., alkylaluminum derivative, alkyltin derivative, alkylborane derivative and the like) for L or the like, and compound (16-1) or compound (16-3).

(2) An intermediate of a compound represented by the formula (I), namely, the following compound (C-1) can also be produced by the following method.

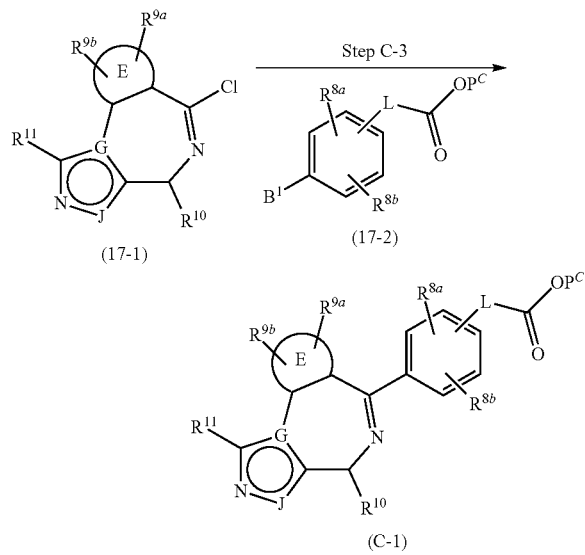

wherein each symbol is as defined above.

Compound (C-1) can be obtained by a coupling reaction of compound (17-1) and boronic acid derivative (17-2). The reaction conditions are the same as those in the aforementioned Step B-1.

(3) The following step is suitable for producing a compound (C-1) wherein L can be introduced by a reaction with boronic acid (18-1) (e.g., L is unsubstituted or substituted aryl having 6-10 carbon atoms, unsubstituted or substituted heteroaryl having 1 to 5 hetero atoms selected from a nitrogen atom, an oxygen atom and a sulfur atom and containing 3 to 10 ring-constituting atoms, olefin, acetylene etc.).

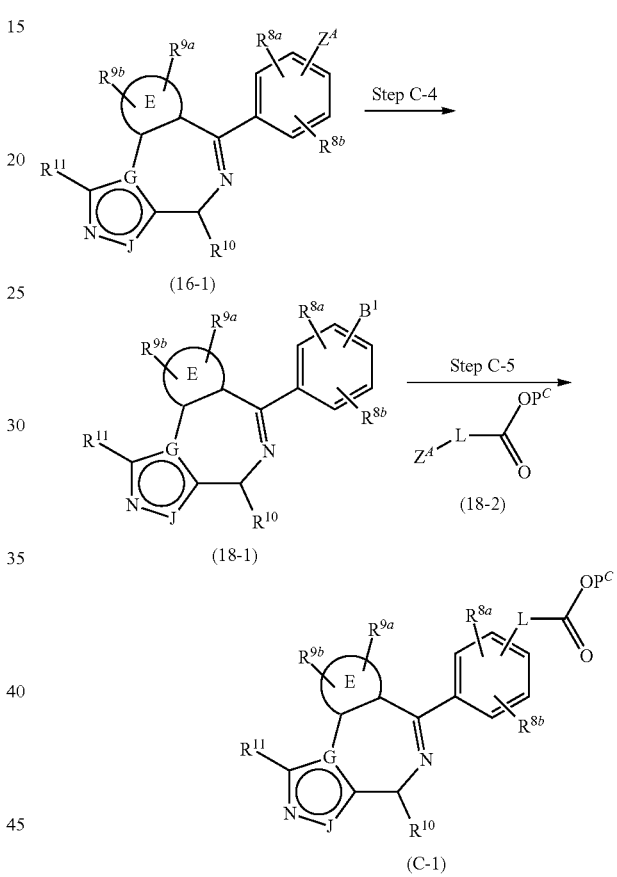

wherein each symbol is as defined above.

Step C-4

Boronic acid (18-1) is obtained by reacting compound (16-1) with a boronic acid derivative (e.g., bispinacolatodiboron, bisneopentylglycolatodiboron and the like). The reaction preferably proceeds in the presence of a palladium catalyst, a phosphine ligand and a base in a suitable solvent at 0° C. to under heating, particularly at room temperature to the boiling point of the solvent. As the palladium catalyst, phosphine ligand, base and solvent, those recited in Step B-1 can be used.

Step C-5

Compound (C-1) is obtained by reacting boronic acid (18-1) with compound (18-2). The reaction preferably proceeds in the presence of a palladium catalyst, a phosphine ligand and a base in a suitable solvent at 0° C. to under heating, particularly at room temperature to the boiling point of the solvent. As the palladium catalyst, phosphine ligand, base and solvent, those recited in Step B-1 can be used.

(4) An intermediate of a compound represented by the formula (I) wherein ring E is represented by the aforementioned formula (Ea), G is a nitrogen atom, J is a nitrogen atom, and $R^{9a}$ is a halogen atom, namely, the following compound (C-2) can also be produced by the following method.

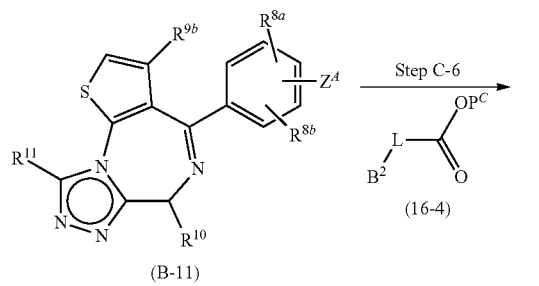

(B-11)

(16-4)

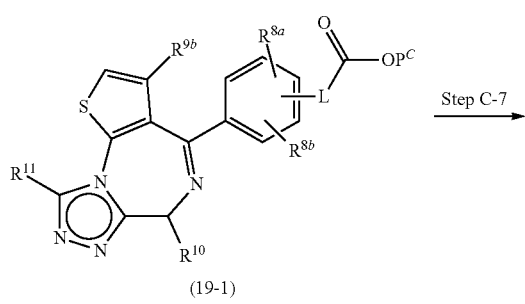

(19-1)

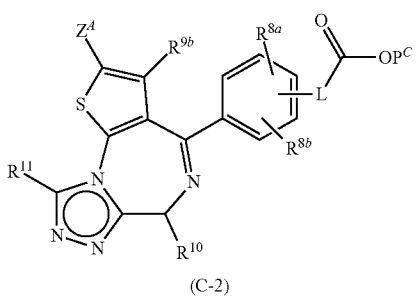

(C-2)

wherein each symbol is as defined above.

Step C-6

Compound (19-1) can be obtained by reacting compound (B-11) with compound (16-4). The reaction conditions are the same as those in Step C-2.

Step C-7

Compound (C-2) is obtained by reacting compound (19-1) with sulfuryl chloride, N-bromosuccinimide and the like in acetic acid or a mixture of acetic acid and chloroform at room temperature to 50° C.

(Method D)

(1) A compound represented by the formula (I) wherein T is —CO—NH—, and n is 2, namely, the following compound (D-1) can be produced by the following method.

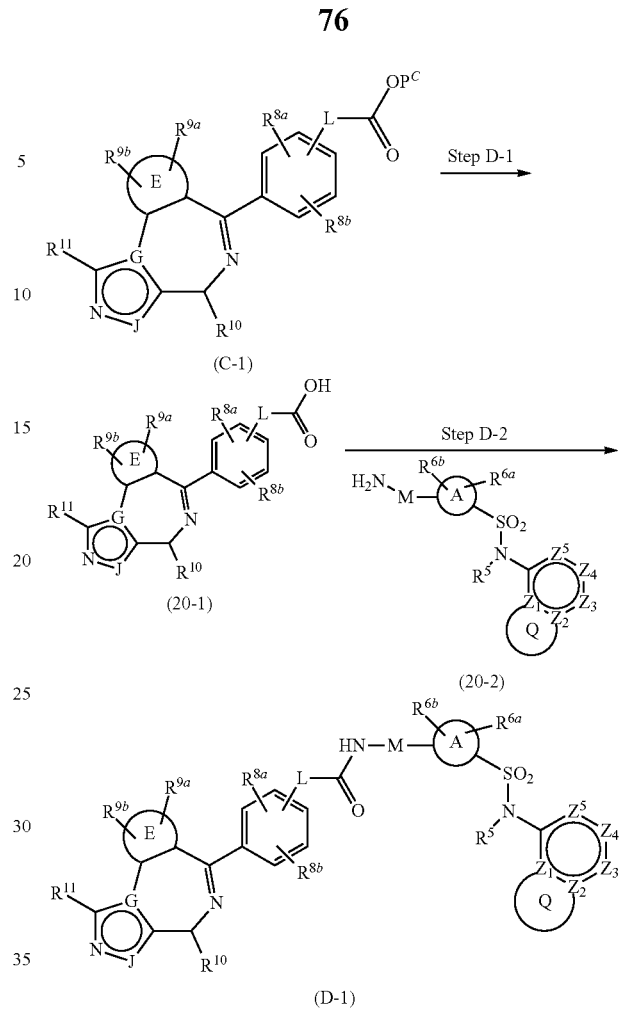

(C-1)

(20-1)

(20-2)

(D-1)

wherein each symbol is as defined above.

Step D-1

Compound (20-1) can be obtained by removing protecting group $P^C$ from compound (C-1). When $P^C$ is a hydrogen atom, this step can be omitted. The condition for removing protecting group $P^C$ is not particularly limited as long as it is used for deprotection of Pc. For example, when $P^C$ is methyl, a method using Lewis acid such as boron tribromide and the like in a methylene chloride solvent and a method using an inorganic base such as sodium hydroxide and the like in a mixed solvent of alcohol solvent and water can be mentioned. When it is ethyl, a method using an inorganic base such as sodium hydroxide and the like in a mixed solvent of alcohol solvent and water can be mentioned. When it is t-butyl, a method using an acid such as hydrochloric acid, trifluoroacetic acid and the like can be mentioned. When $P^C$ is benzyl or substituted benzyl, benzyloxymethyl or the like, a method using catalytic hydrogenation reaction can be mentioned.

Step D-2

Compound (D-1) can be obtained by a condensation reaction of carboxylic acid derivative (20-1) and amine derivative (20-2). The reaction conditions are the same as those in the aforementioned Step B-14.

(2) A compound represented by the formula (I) wherein T is —CO—NH— and n is 2, i.e., the following compound (D-1), can also be produced by, for example, the following production method.

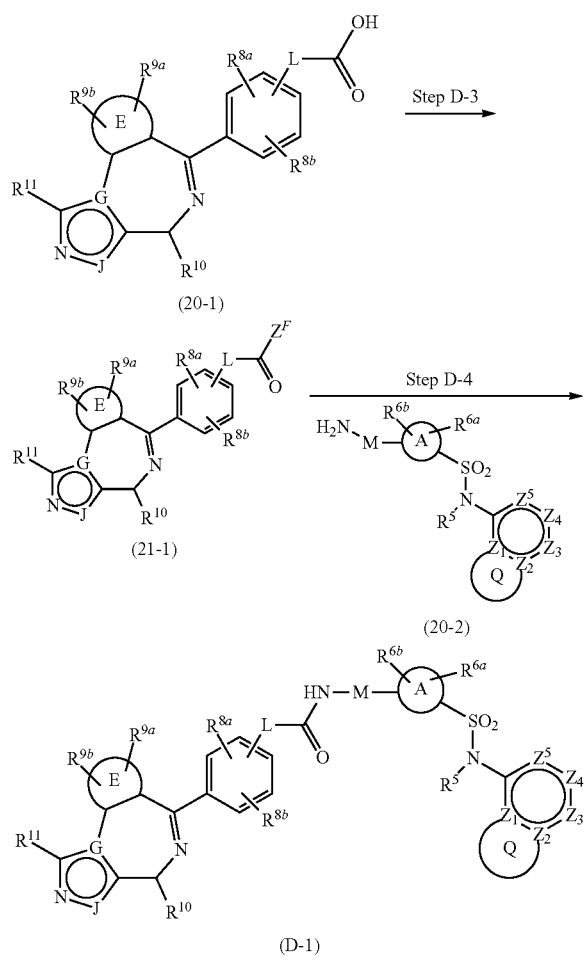

wherein $Z^F$ is a chlorine atom or a bromine atom, and other symbols are as defined above.

Step D-3

In this step, compound (20-1) is converted to acid halide (21-1). The reaction proceeds in an appropriate solvent generally at 0° C. to the refluxing temperature of the solvent for generally from 1 hr to 24 hr. Examples of the halogenating agent include thionyl chloride, oxalyl chloride, phenylphosphonyl dichloride and the like. Examples of the base include triethylamine, pyridine and the like. Examples of the solvent include dichloromethane, 1,2-dichloroethane, chloroform, pyridine, toluene and the like.

Step D-4

Compound (D-1) can be obtained by reacting acid halide (21-1) with amine derivative (20-2). The reaction proceeds using a base in a suitable solvent generally at 0° C. to the refluxing temperature of the solvent. While the reaction time varies depending on the starting material and solvent to be used and the reaction temperature and the like, it is generally from 30 min to 12 hr. Examples of the base include triethylamine, pyridine and the like. Examples of the solvent include dichloromethane, dichloroethane, chloroform, N-methylpyrrolidone, pyridine, toluene and the like.

(Method E)

(1) A compound represented by the formula (I) wherein T is —CO—NH—, and n is 2, namely, the following compound (D-1), can also be produced by the following method.

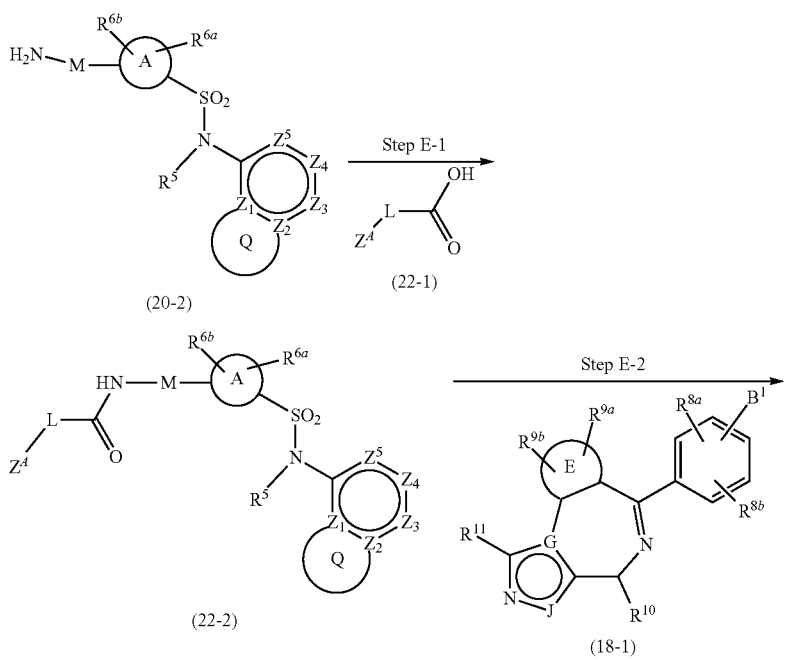

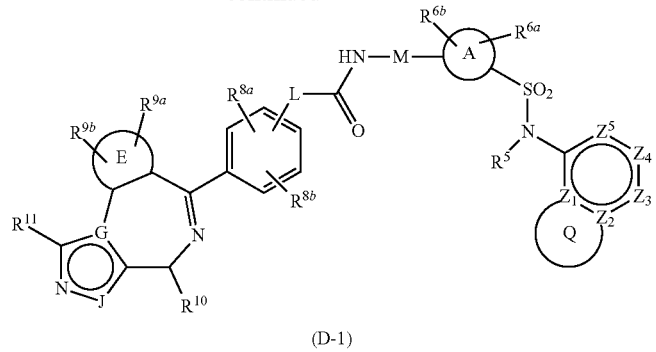

(D-1)

wherein each symbol is as defined above.

Step E-1

Compound (22-2) can be obtained by reacting amine (20-2) with carboxylic acid (22-1) represented by HOC(O)-L-$Z^A$ (wherein $Z^A$ is as defined above). The reaction conditions are the same as those in the aforementioned Step B-14.

Step E-2

In this step, compound (D-1) is obtained by reacting compound (22-2) with boronic acid or an ester derivative thereof (18-1). The reaction conditions are the same as those in Step B-1.

(2) A compound represented by the formula (I) wherein T is —CO—NH—, and n is 2, namely, the following compound (D-1) can also be produced by the following method.

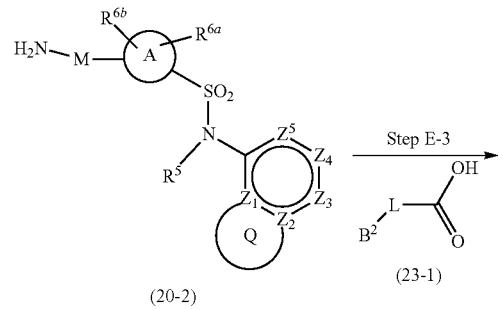

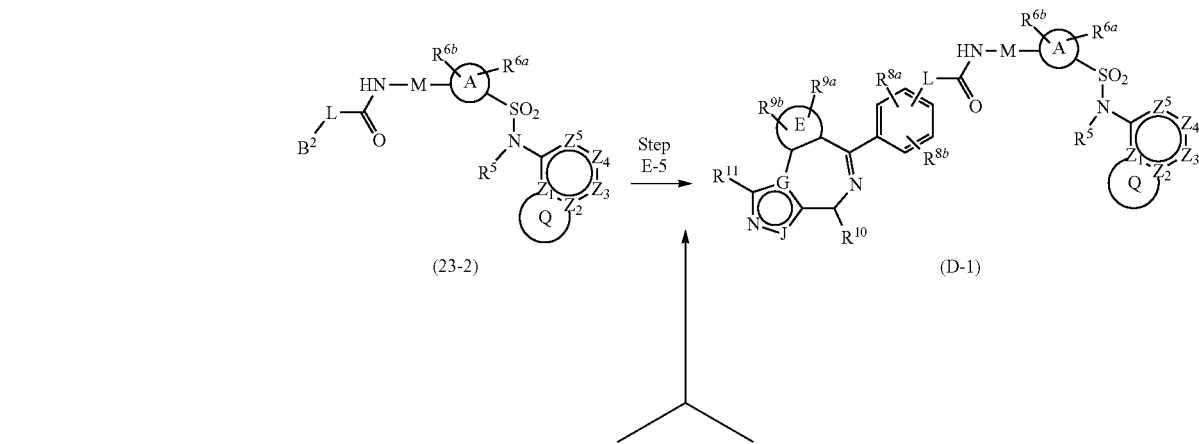

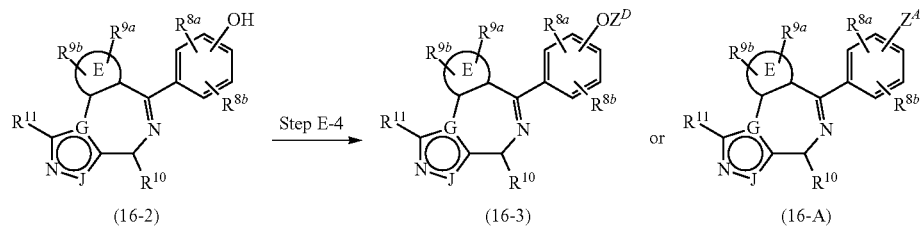

wherein each symbol is as defined above.

Step E-3

Compound (23-2) can be obtained by reacting amine derivative (20-2) with carboxylic acid derivative (23-1). The reaction conditions are the same as those in the aforementioned Step B-14. If there is a possibility of self-condensation, such as when $B^2$ is amine and the like, protection and deprotection steps can be added as appropriate.

Step E-4

In this step, a hydroxyl group of compound (16-2) is converted to activated group $OZ^D$. The reaction conditions are the same as those in the aforementioned Step C-1.

Step E-5

In this step, compound (D-1) is obtained by reacting compound (16-1) or compound (16-3) obtained in Step E-4 with compound (23-2). The reaction conditions are the same as those in the aforementioned Step C-2.

(3) A compound represented by the formula (I) wherein T is —CO—NH—, and n is 2, namely, the following compound (D-1) can also be produced by the following method.

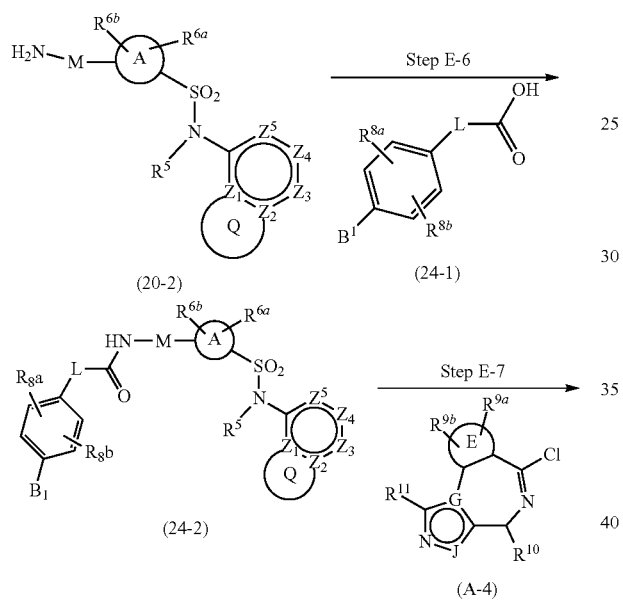

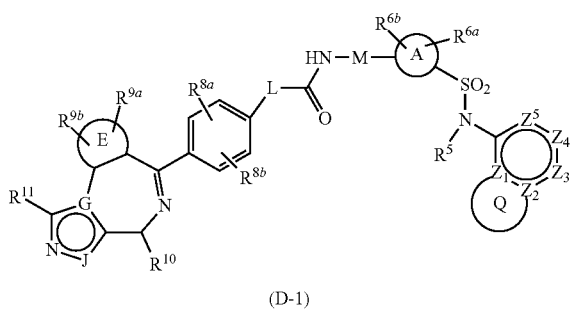

wherein each symbol is as defined above.

In the aforementioned method E (2), boronic acid derivative (24-2) is obtained using compound (24-1) instead of compound (23-1) which is reacted with iminochloride (A-4) to give compound (D-1).

The reaction conditions of Step E-6 are the same as those in Step B-14.

The reaction conditions of Step E-7 are the same as those in Step B-1.

(Method F)

(1) A compound represented by the formula (I) wherein T is —CO—NH—, and n is 2, namely, the following compound (D-1) can also be produced by the following method.

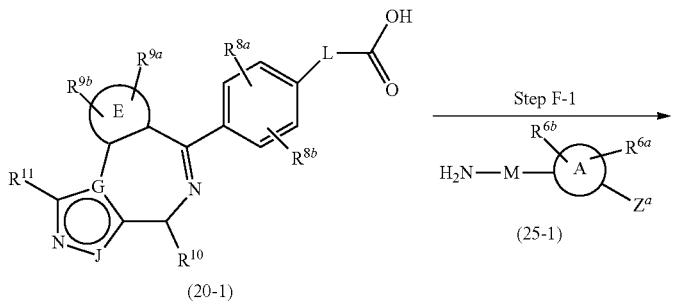

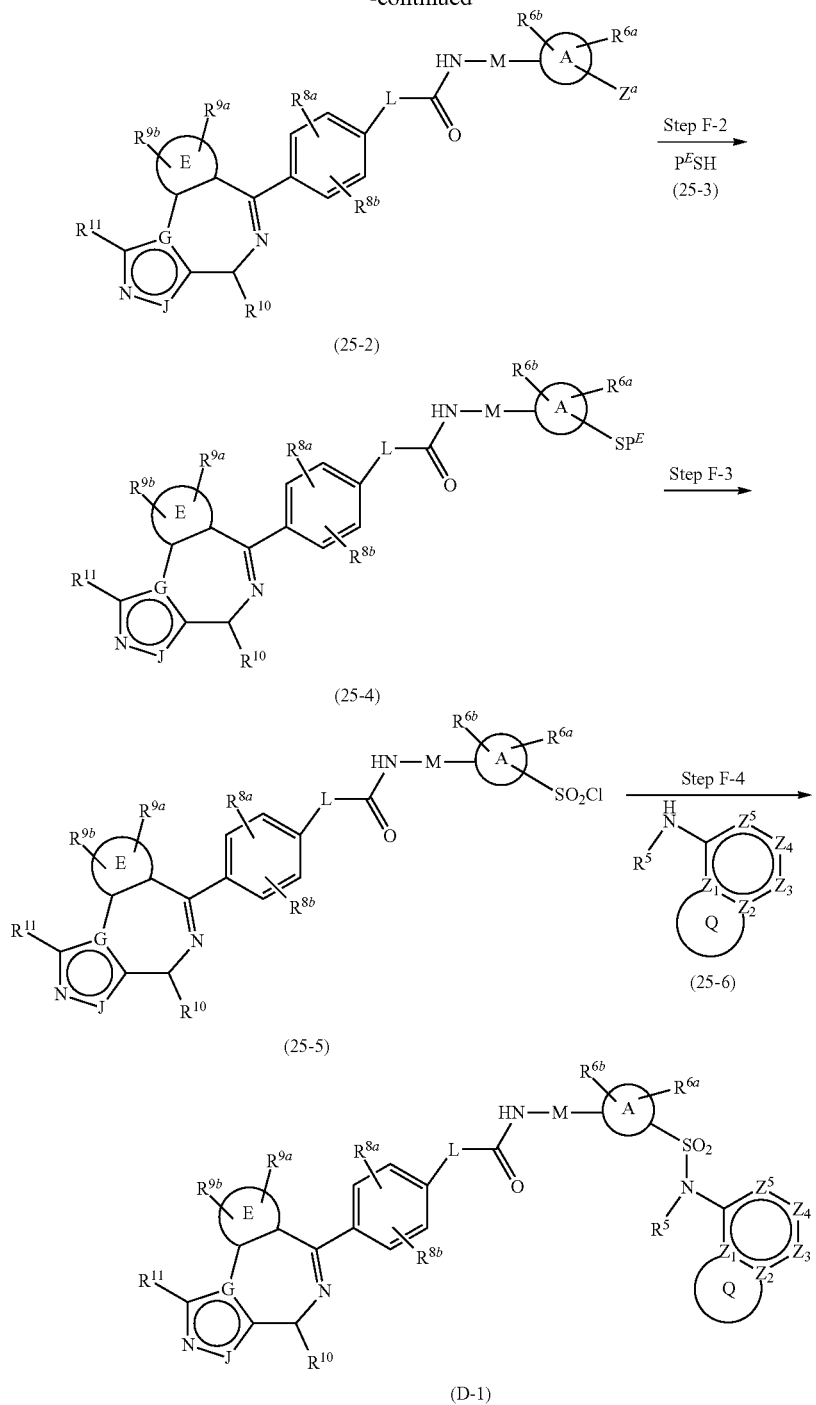

(25-2)

(25-4)

(25-5)

(D-1)

wherein $P^E$ is a protecting group, and other symbols are each as defined above.

The $P^E$ in the formula is not particularly limited as long as it protects a thiol group and compound (25-5) can be obtained. For example, a benzyl group and the like can be mentioned.

Step F-1

Compound (25-2) can be obtained by reacting carboxylic acid derivative (20-1) with amine derivative (25-1). The reaction conditions are the same as those in the aforementioned Step B-14.

Step F-2

Compound (25-4) can be obtained by reacting compound (25-2) with $P^E$SH (25-3). The reaction conditions are the same as those in the aforementioned Step C-2.

Step F-3

Compound (25-5) can be obtained by reacting compound (25-4) with N-chlorosuccinimide and the like in an acetonitrile-hydrochloric acid mixture, or in acetic acid at 0° C.-50° C.

Step F-4

Compound (D-1) is obtained by reacting sulfonyl chloride derivative (25-5) with amine derivative (25-6). The reaction proceeds using a base in an appropriate solvent at generally from 0° C. to the refluxing temperature of the solvent. While the reaction time varies depending on the starting material and solvent to be used and the reaction temperature, it is generally from 0.5 hr to 24 hr. Examples of the base include triethylamine, pyridine and the like. Examples of the solvent include tetrahydrofuran, dichloromethane, acetonitrile and the like.

(2) A compound represented by the aforementioned (20-2) wherein a fused ring moiety is 3-cyano-1H-indole, i.e., the following compound (F-1), can be produced, for example, by the following method.

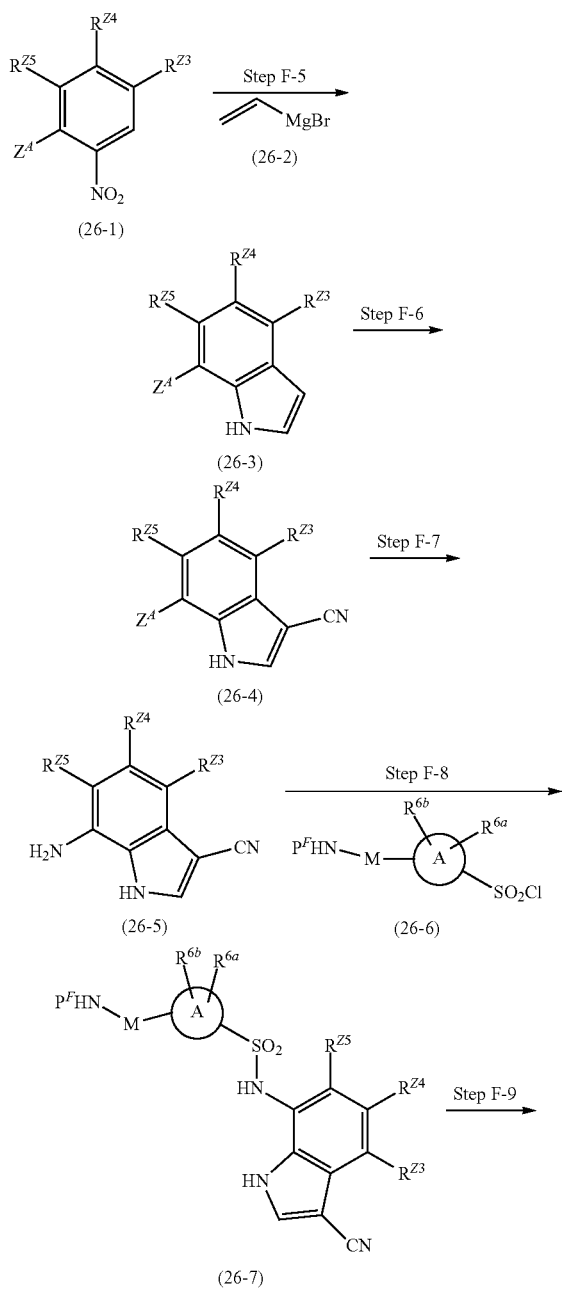

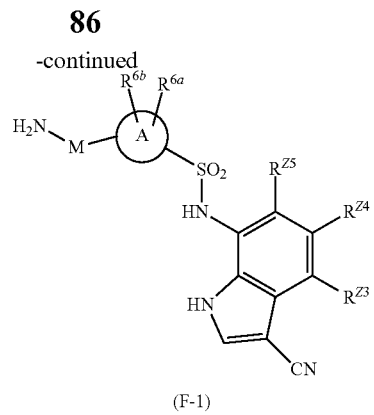

wherein $P^F$ is an amino-protecting group, and other symbols are as defined above.

$P^F$ in the formula is not particularly limited as long as it protects an amino group and compound (26-6) is obtained. For example, a t-butyloxycarbonyl group, a benzyloxycarbonyl group and the like can be mentioned.

Step F-5

Compound (26-3) can be obtained by reacting nitro compound (26-1) with vinylmagnesium bromide (26-2). The reaction proceeds in an appropriate solvent at generally from −78° C. to room temperature. While the reaction time varies depending on the starting material and solvent to be used and the reaction temperature, it is generally from 0.5 hr to 24 hr. Examples of the solvent include tetrahydrofuran.

Step F-6

Compound (26-4) can be obtained by, for example, formylation of indole derivative (26-3), successive production of oxime, and a dehydration reaction. Formylation reaction proceeds using a halogenating agent and DMF generally at room temperature to the refluxing temperature of the solvent. While the reaction time varies depending on the starting material and solvent to be used and the reaction temperature, it is generally from 1 hr to 24 hr. Examples of the halogenating agent include phosphoryl chloride, phenylphosphonyl dichloride and the like. Examples of the solvent include DMF, a dichlorobenzene-DMF mixed solution and the like. Compound (26-4) is obtained by adding hydroxylamine hydrochloride to the above-mentioned reaction solution and heating the mixture. The reaction proceeds generally at 40° C. to the refluxing temperature of the solvent. While the reaction time varies depending on the starting material and solvent to be used and the reaction temperature, it is generally from 0.5 hr to 24 hr.

Step F-7

Compound (26-5) can be obtained by a coupling reaction of compound (26-4) and benzophenone imine, and successive deprotection reaction. The reaction conditions of the coupling reaction are the same as those in Step C-2. As the reaction conditions of the deprotection, an acid such as hydrochloric acid and the like is reacted, or hydroxylamine or the like is reacted. The reaction proceeds generally at room temperature to the refluxing temperature of the solvent. While the reaction time varies depending on the starting material and solvent to be used and the reaction temperature, it is generally from 1 hr to 24 hr. Examples of the solvent include methanol, tetrahydrofuran, 1,4-dioxane, a mixed solution thereof and the like.

Step F-8

Compound (26-7) can be obtained by reacting sulfonyl chloride derivative (26-6) with amine derivative (26-5). The reaction conditions in step F-8 are the same as those in step F-4.

Step F-9

Compound (F-1) can be obtained by removing protecting group $P^F$ from compound (26-7). The deprotection condition is not particularly limited as long as it is used for deprotection of $P^F$. For example, when $P^F$ is a tert-butyloxycarbonyl group, deprotection can be performed using an acid. As the acid, inorganic acids such as hydrochloric acid and the like, trifluoroacetic acid and the like can be mentioned. As the reaction conditions, a reaction in an alcoholic solvent such as ethanol and the like, ether solvent such as tetrahydrofuran and the like, water or a mixed solvent thereof under ice-cooling to 80° C. for 10 min to about 12 hr can be mentioned. When $P^F$ is a benzyloxycarbonyl group, deprotection can be performed by reduction by catalytic hydrogenation. Examples of the catalyst include palladium carbon and the like. The reaction temperature is generally room temperature to the refluxing temperature of the solvent and the hydrogen pressure is 1 to 20 atm. While the reaction time varies depending on the starting material and solvent to be used, the reaction temperature, and the like, it is generally from 1 hr to 48 hr.

A compound represented by the formula (I), which is produced by the aforementioned method, can be purified to any purity by a conventionally used purification means, for example, concentration, extraction, chromatography, reprecipitation, recrystallization and the like. It can be converted to a pharmaceutically acceptable salt as necessary by treating with an acid or a base etc. in a suitable solvent (water, alcohol, ether etc.). Furthermore, the obtained compound of the present invention or a pharmaceutically acceptable salt thereof can be converted to hydrate or solvate by treating with water, water-containing solvent or other solvent.

The compound and a pharmaceutically acceptable salt thereof of the present invention include racemic compounds, stereoisomers, and mixture of these compounds, and includes isotope-labeled and radioactive-labeled compounds. Such isomers can be isolated by a standard separation technique including fractional crystallization and chiral column chromatography. In addition, the compound of the present invention has an asymmetric carbon atom. Therefore, it is includes enantiomer and diastereomer. A diastereomer mixture can be separated into each diastereomer based on their physical/chemical differences by a method well known in the art, for example, chromatography and/or fractional crystallization. Enantiomer can be separated by chiral column chromatography or by reacting an enantiomer compound with an appropriate optically active compound to give a diastereomer mixture, separating each diastereomer and converting each diastereomer to a corresponding enantiomer. The compound of the present invention may be any of such isomers including diastereomer, enantiomer and a mixture thereof.

The compound or a pharmaceutically acceptable salt thereof of the present invention has a cytotoxic action on cancer cells. Furthermore, it also has an action to induce degradation of BET protein in cancer cells and an inhibitory action on the binding of BET protein and acetylated histone. Therefore, the compound or a pharmaceutically acceptable salt thereof of the present invention can also be used as an anticancer drug, and further can be used as a BET protein degrader or a BET protein inhibitor. According to the present invention, a cancer treatment method using the compound or a pharmaceutically acceptable salt thereof of the present invention, a BET protein degradation inducing method and a BET protein inhibitory method can also be provided.

Furthermore, the compound or a pharmaceutically acceptable salt thereof of the present invention also has an action to induce degradation of BRD4 protein in cancer cells and an inhibitory action on the binding of BRD4 protein and acetylated histone. Therefore, the compound or a pharmaceutically acceptable salt thereof of the present invention can also be used as a BRD4 protein degrader or a BRD4 protein inhibitor. According to the present invention, a cancer treatment method using the compound or a pharmaceutically acceptable salt thereof of the present invention, a BRD4 protein degradation inducing method and a BRD4 protein inhibitory method can also be provided.

In the present invention, the type of cancer does not matter. Concrete examples thereof include oral cancer, pharyngeal cancer, laryngeal cancer, thyroid cancer, esophageal cancer, gastric cancer, duodenum cancer, small intestine cancer, colorectal cancer, anal cancer, liver cancer, biliary tract cancer, pancreatic cancer, gastrointestinal stromal tumor, lung cancer, skin cancer, breast cancer, uterine cancer, ovarian cancer, prostate cancer, testicular cancer, bladder cancer, kidney cancer, urothelial cancer, brain tumor, bone and soft tissue tumor, leukemia, malignant lymphoma, multiple myeloma, sarcoma (e.g., Ewing sarcoma, rhabdomyosarcoma, bone and soft tissue sarcoma) and the like.

In the medical field, colorectal cancer is sometimes called colon cancer or rectal cancer, liver cancer is sometimes called hepatocyte cancer, biliary tract cancer is sometimes called bile duct cancer or gallbladder cancer, pancreatic cancer is sometimes called pancreatic duct cancer or pancreatic endocrine tumor, lung cancer is sometimes called non-small cell lung cancer, small cell lung cancer, large cell lung cancer, malignant pleural mesothelioma or thymus tumor, skin cancer is sometimes called skin malignancy or skin lymphoma, uterine cancer is sometimes called cervix cancer, uterine body cancer or uterine sarcoma, kidney cancer is sometimes called renal cell cancer, urothelial cancer is sometimes called renal pelvis cancer or ureter cancer, and brain tumor is sometimes called glioma. In addition, breast cancer includes subtypes called triple-negative breast cancer, HER2 positive breast cancer, luminal A type breast cancer, luminal B type breast cancer and the like, prostate cancer includes subtypes called hormone dependency prostate cancer, hormone independent prostate cancer, castration-resistant prostate cancer and the like, leukemia includes subtypes called acute myeloid leukemia (AML), acute promyelocytic leukemia (APL), acute lymphoblastic leukemia (ALL), lymphoblastic lymphoma (LBL), chronic myeloid leukemia (CML), myeloproliferative neoplasm (MPN), chronic lymphocytic leukemia (CLL), small lymphocytic lymphoma (SLL), myelodysplastic syndrome (MDS) and the like, and malignant lymphoma includes subtypes called follicular lymphoma (FL), MALT lymphoma, marginal zone lymphoma, lymphoplasmacytic lymphoma (LPL), Waldenstrom's macroglobulinemia (WM), mantle cell lymphoma (MCL), diffuse large B-cell lymphoma (DLBCL, NOS), Burkitt lymphoma (BL), peripheral T-cell lymphoma (PTCL), adult T cell leukemia/lymphoma (ATL), extranodal NK/T-cell lymphoma, nasal type (ENKL), Hodgkin lymphoma (HL) and the like.

In one embodiment, the compound of the present invention or a pharmaceutically acceptable salt thereof may be useful for the treatment of acute myeloid leukemia, chronic myeloid leukemia, multiple myeloma, diffuse large B-cell lymphoma, adult T-cell leukemia/lymphoma, Burkitt lymphoma, prostate cancer, ovarian cancer, bladder cancer, breast cancer, uterus cervix cancer, uterine sarcoma, stomach cancer, lung cancer, colon cancer, glioma, pancreatic cancer, liver cancer, bile duct cancer, renal cell cancer and fibrosarcoma.

In another embodiment, the compound of the present invention or a pharmaceutically acceptable salt thereof may be useful for the treatment of acute myeloid leukemia, chronic myeloid leukemia, acute lymphocytic leukemia, diffuse large B-cell lymphoma, multiple myeloma, Burkitt lymphoma, glioma, stomach cancer, colon cancer, pancreatic cancer, liver cancer, prostate cancer, non-small cell lung cancer, breast cancer, ovarian cancer and uterine sarcoma.

In a still another embodiment, the compound of the present invention or a pharmaceutically acceptable salt thereof may be useful for the treatment of acute myeloid leukemia, diffuse large B-cell lymphoma, multiple myeloma, prostate cancer, non-small cell lung cancer, ovarian cancer and breast cancer.

In a yet another embodiment, the compound of the present invention or a pharmaceutically acceptable salt thereof may be useful for the treatment of acute myeloid leukemia, diffuse large B-cell lymphoma, multiple myeloma, prostate cancer, ovarian cancer and breast cancer.

In the present specification, the anticancer drug is a concept including carcinostatic agent, antitumor agent and the like. It has the effect of damaging, killing or weakening cancer cells and tumor cells, and reducing or eliminating or preventing an increase in the clump of cells that grew abnormally for the purpose of treating cancer. In addition, treatment means an act of administering the compound of the present invention or a pharmaceutical acceptable salt thereof or a pharmaceutical composition containing same to an individual who has developed an illness, disease or symptom. Therefore, an act of administration to an individual who has developed an illness, disease or symptom, for the prevention of aggravation of the symptom and the like, and for the prevention of recurrence is one embodiment of the treatment.

When the compound of the present invention is used as a medicament, the compound of the present invention is mixed with a pharmaceutically acceptable additive (excipient, binder, disintegrant, corrigent, flavor, emulsifier, diluent, solubilizing agents and the like) to give a pharmaceutical composition which can be orally or parenterally administered. A pharmaceutical composition can be formulated by a general method.

While the subject to which the compound or pharmaceutical composition of the present invention is to be administered is not particularly limited, mammal is preferable. Examples of the mammal include primates (e.g., human, monkey, chimpanzee), rodents (e.g., mouse, rat, guinea pig), pets (e.g., dog, cat, rabbit), working animals or domestic animals (e.g., bovine, horse, swine, sheep, goat), and human is preferable.

In the present specification, parenteral includes subcutaneous injection, intravenous injection, intramuscular injection, intraperitoneal injection, drip or topical administration (intraarticular administration, transdermal administration, transocular administration, transpulmonary or bronchial administration, transnasal administration, transrectal administration and the like) and the like.

The dose of the compound of the present invention is determined according to the age, body weight, general health condition, sex, diet, administration time, administration method, clearance rate, and the level of symptom for which patients are undergoing treatments at that time, or further in consideration of other factors. While the daily dose of the compound of the present invention varies depending on the condition and body weight of patient, the kind of the compound, administration route and the like, it is parenterally administered at, for example, about 0.001 to 100 mg/patient/day by subcutaneous, intravenous, intramuscular, intraarticular, transdermal, transocular, transpulmonary or bronchial, transnasal or rectal administration, or about 0.01 to 1000 mg/patient/day by oral administration.

EXAMPLE

The present invention is explained in detail in the following by referring to Reference Examples, Examples and Experimental Examples, which are not to be construed as limitative.

Reference Example 1

(1-1) methyl [(6S)-4-(4-chlorophenyl)-2,3,9-trimethyl-6H-thieno[3,2-f][1,2,4]triazolo[4,3-a][1,4]diazepin-6-yl]acetate (Reference Example Compound 1)

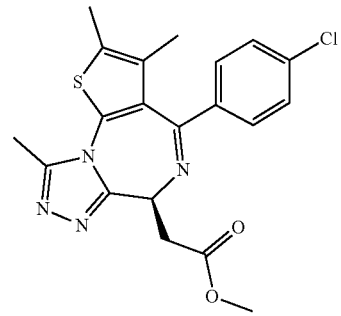 [SMILES: COC(=O)C[C@@H]1N=C(c2ccc(Cl)cc2)c2c(sc(C)c2C)-n2c(C)nnc21]

To a suspension of (6S)-4-(4-chlorophenyl)-2,3,9-trimethyl-6H-thieno[3,2-f][1,2,4]triazolo[4,3-a][1,4]diazepine-6-acetic acid (300 g) in methanol (1.5 L) was added dropwise (10-25° C.) under ice-cooling thionyl chloride (320 g) over 1 hr, and the mixture was stirred at room temperature for 4 hr. After completion of the reaction, the solvent was evaporated under reduced pressure, chloroform (1.5 L) and water (1 L) were added for partitioning, and the mixture was further extracted with chloroform (500 mL). The organic layer was washed with saturated aqueous sodium hydrogen carbonate (500 mL), dried over anhydrous sodium sulfate, and the solvent was evaporated under reduced pressure (azeotropically distilled twice with methanol). The residue was washed with methanol/water (300 mL/300 mL) to give the title compound (250 g).

MS(ESI) m/z: 415.2[M+H]$^+$

Reference Example 2

(2-1) 3-(4-bromophenyl)-3-oxopropanenitrile (Reference Example Compound 2-1)

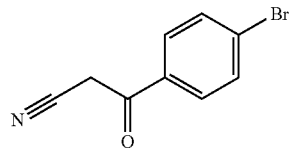 [SMILES: N#CCC(=O)c1ccc(Br)cc1]

At room temperature, to a suspension of sodium methoxide (12.4 g) in dimethyl sulfoxide (23 mL) was added acetonitrile (12.3 g), and the mixture was stirred at room temperature for 2 hr. A solution of ethyl 4-bromobenzoate (22.9 g) in dimethyl sulfoxide (23 mL) was slowly added, and the mixture was stirred at 45° C. for 3 hr. The reaction solution was cooled under ice-cooling, water and concentrated hydrochloric acid were added and the mixture was stirred for 0.5 hr. The precipitate was collected by filtration and the obtained residue was dried to give the title compound (22.4 g) as a pale-brown solid. ¹H NMR (400 MHz, DMSO-d6) δ4.75 (brs, 2H), 7.87-7.70 (m, 4H)

(2-2) (2-amino-4,5-dimethylthiophen-3-yl) (4-bromophenyl)methanone (Reference Example Compound 2-2)

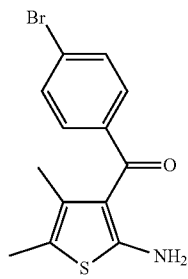 [SMILES: Cc1sc(N)c(C(=O)c2ccc(Br)cc2)c1C]

A mixture of Reference Example compound 2-1 (25.0 g), ethyl methyl ketone (8.0 g), sulfur (3.6 g), morpholine (9.7 mL) and ethanol (325 mL) was stirred at 70° C. for 7 hr. After evaporation of the solvent, ethyl acetate was added. The organic layer was washed with 1N hydrochloric acid, 1N aqueous sodium hydroxide solution and saturated brine, dried over anhydrous sodium sulfate and filtered. The filtrate was concentrated under reduced pressure. To the obtained solid was added ethanol, and the mixture was stirred at room temperature for 2 hr. The precipitate was collected by filtration to give the title compound (13.5 g) as a yellow solid.
MS(ESI) m/z: 310.2, 312.1[M+H]⁺

(2-3) (3S)-5-(4-bromophenyl)-3,6,7-trimethyl-1,3-dihydro-2H-thieno[2,3-e][1,4]diazepine-2-one (Reference Example Compound 2-3)

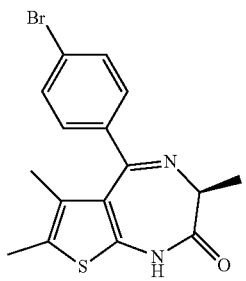

Under ice-cooling, to Reference Example compound 2-2 (43.0 g) were added (2S)-2-(t-butoxycarbonylamino)propanoic acid (27.6 g) and pyridine (200 mL), and phenylphosphonyl dichloride (29.7 g) was slowly added dropwise, and the mixture was stirred under ice-cooling for 1 hr. After evaporation of the solvent, ethyl acetate was added, and the organic layer was washed with saturated aqueous sodium hydrogen carbonate and water, dried over anhydrous sodium sulfate and filtered. The filtrate was concentrated under reduced pressure. To a solution of the obtained residue in dichloromethane (70 mL) was added trifluoroacetic acid (53 mL), and the mixture was stirred at room temperature for 2 hr. Trifluoroacetic acid (53 mL) was added and the mixture was stirred at room temperature for 2 hr. The reaction solution was concentrated and azeotropically distilled with toluene. To the obtained mixture was added saturated aqueous sodium hydrogen carbonate, and the mixture was extracted with ethyl acetate. The organic layer was dried over anhydrous sodium sulfate and filtered. The filtrate was concentrated under reduced pressure. To a suspension of the obtained residue in 2-propanol (200 mL) was added acetic acid (12 mL), and the mixture was stirred at 90° C. for 1 hr. To the reaction mixture was added saturated aqueous sodium hydrogen carbonate and the mixture was extracted with ethyl acetate. The organic layer was washed with saturated aqueous sodium hydrogen carbonate, dried over anhydrous sodium sulfate and filtered. The filtrate was concentrated under reduced pressure. To the obtained residue was added ethyl acetate (43 mL) and the mixture was stirred at 45° C. for 1 hr. The insoluble material was collected by filtration. The obtained solid was dried under reduced pressure to give the title compound (25.7 g) as a yellow solid. MS(ESI) m/z: 363.2, 365.2[M+H]⁺

(2-4) (6S)-4-(4-bromophenyl)-2,3,6,9-tetramethyl-6H-thieno[3,2-f][1,2,4]triazolo[4,3-a][1,4]diazepine (Reference Example Compound 2)

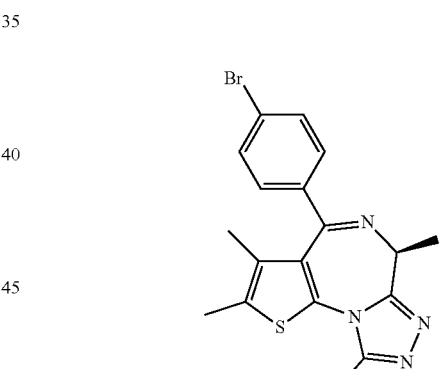

Under ice-cooling, to a solution of Reference Example compound 2-3 (9.6 g) in tetrahydrofuran (65 mL) was added sodium hydride (60%, 1.1 g) and the mixture was stirred for 0.5 hr. Diethylphosphonyl chloride (5.5 g) was added and the mixture was stirred at room temperature for 0.25 hr. Acetohydrazide (2.9 g) and n-butanol (10 mL) were added and the mixture was stirred at 70° C. for 0.5 hr. To the reaction mixture was added saturated aqueous sodium hydrogen carbonate, and the mixture was extracted with ethyl acetate. The organic layer was washed with saturated brine, dried over anhydrous sodium sulfate, filtered, and the filtrate was concentrated under reduced pressure. The obtained residue was purified by NH silica gel column chromatography (n-hexane:ethyl acetate) to give the title compound (8.9 g) as a yellow powder.
MS(ESI) m/z: 401.1, 403.1[M+H]⁺

Reference Example 3

(3-1) methyl {(6S)-2,3,9-trimethyl-4-[4-(4,4,5,5-tetramethyl-1,3,2-dioxaboronan-2-yl)phenyl]-6H-thieno[3,2-f][1,2,4]triazolo[4,3-a][1,4]diazepin-6-yl}acetate (Reference Example Compound 3)

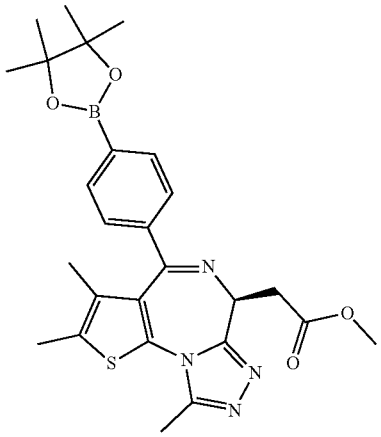

Under an argon stream, Reference Example compound 1 (5.00 g), bis(pinacolato)diboron (4.59 g), potassium acetate (2.37 g) and dichlorobis(tricyclohexylphosphine)palladium (445 mg) were heated under reflux in a tetrahydrofuran solvent for 25 hr. Furthermore, dichlorobis(tricyclohexylphosphine)palladium (445 mg), bis(pinacolato)diboron (1.53 g) were added and the mixture was heated under reflux for 7 hr. Bis(pinacolato)diboron (1.53 g), potassium acetate (1.18 g) and dichlorobis(tricyclohexylphosphine)palladium (445 mg) were added and the mixture was heated under reflux for 16 hr. After cooling to room temperature, the reaction mixture was filtered through celite using ethyl acetate. The filtrate was washed twice with saturated brine, and the organic layer was concentrated under reduced pressure. The residue was purified by silica gel column chromatography (chloroform/methanol=100:0-97:3) and then by silica gel column chromatography (ethyl acetate/methanol=100:0-95:5) to give the title compound (5.27 g) as a pale-yellow solid. MS(ESI) m/z: 507.2[M+H]$^+$

Reference Example 4

(4-1) t-butyl 4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylate (Reference Example Compound 4-1)

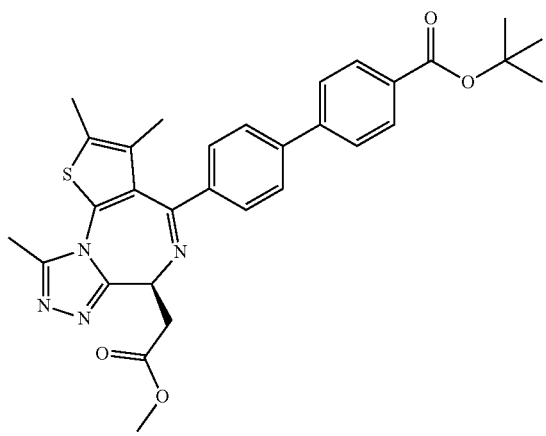 [SMILES: COC(=O)C[C@@H]1N=C(c2ccc(-c3ccc(C(=O)OC(C)(C)C)cc3)cc2)c2c(sc(C)c2C)-n2c(C)nnc21]

A mixture of Reference Example compound 1 (5.00 g), t-butyl 4-(4,4,5,5-tetramethyl-1,3,2-dioxaborolan-2-yl)benzoate (4.03 g), potassium fluoride (2.10 g), 2-dicyclohexylphosphino-2'-6'-dimethoxybiphenyl (hereinafter to be indicated as S-phos, 495 mg), palladium acetate (271 mg), tetrahydrofuran (40.2 mL) and water (0.78 mL) was stirred with heating under reflux for 40 hr. Furthermore, (4-t-butoxycarbonylphenyl)boronic acid (803 mg), S-phos (247 mg), palladium acetate (135 mg), water (0.78 mL) were added and the mixture was stirred for 20 hr. To the reaction mixture was added ethyl acetate, the insoluble material in the reaction mixture was filtered off through diatomaceous earth, and the filtrate was concentrated under reduced pressure. To the residue were added chloroform, water to extract the organic layer, and the aqueous layer was extracted again with chloroform. The organic layer was collected, dried over anhydrous sodium sulfate, and the solvent was evaporated under reduced pressure. The residue was purified by silica gel column chromatography (chloroform:methanol=98:2-95:5). It was further purified by silica gel column chromatography (chloroform:methanol=100:0-95:5) to give the title compound (6.55 g) as a crudely purified yellow solid. MS(ESI) m/z: 557.3[M+H]$^+$ (4-2) 4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Reference Example Compound 4)

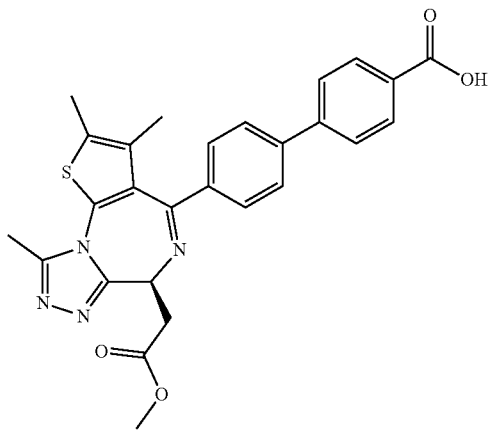 [SMILES: COC(=O)C[C@@H]1N=C(c2ccc(-c3ccc(C(=O)O)cc3)cc2)c2c(sc(C)c2C)-n2c(C)nnc21]

Reference Example compound 4-1 (7.05 g) was dissolved in chloroform (8.0 mL), trifluoroacetic acid (8.0 mL) was added at room temperature, and the mixture was stirred at room temperature for 7 hr. The reaction mixture was concentrated under reduced pressure, and toluene azeotropic distillation was performed twice. The mixture was dissolved in ethyl acetate, cooled to 0° C., and set to pH=8 by adding saturated aqueous sodium hydrogen carbonate by small portions. The organic layer was separated and washed with ethyl acetate. 1N hydrochloric acid was slowly added to the aqueous layer to pH=5, and the mixture was extracted twice with chloroform. The organic layer was concentrated under reduced pressure to give a pale-yellow solid (6.29 g). MS(ESI) m/z: 501.2[M+H]$^+$

Reference Example 5

(5-1) N-(3-cyano-4-methyl-1H-indol-7-yl)-4-formyl-benzene-1-sulfonamide (Reference Example Compound 5-1)

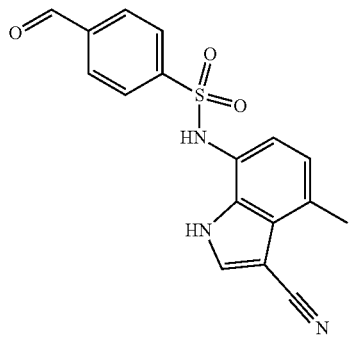 [SMILES: Cc1ccc(NS(=O)(=O)c2ccc(C=O)cc2)c2[nH]cc(C#N)c12]

To a solution of Reference Example compound 9 (100 mg) and 4-formylbenzenesulfonyl chloride (132 mg) in tetrahydrofuran (6.0 mL) was added pyridine (0.29 mL) at room temperature, and the mixture was stirred at the same temperature for 16 hr. 4-Formylbenzenesulfonyl chloride (48 mg) was added, and the mixture was stirred at room temperature for 1 hr. The reaction mixture was acidified by adding 1N hydrochloric acid, and extracted twice with ethyl acetate. The organic layer was dried over anhydrous magnesium sulfate and filtered, and the solvent was evaporated under reduced pressure. The obtained residue was purified by silica gel column chromatography (hexane:ethyl acetate=100:0-40:60), the obtained purified product was solidified by adding chloroform, and concentrated under reduced pressure to give the title compound (126 mg) as a yellow powder. MS(ESI) m/z: 340.1[M+H]$^+$

(5-2) 4-(azidomethyl)-N-(3-cyano-4-methyl-1H-indol-7-yl)benzene-1-sulfonamide (Reference Example Compound 5-2)

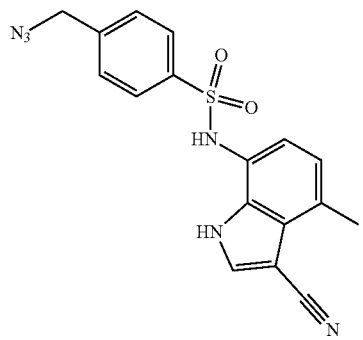 [SMILES: Cc1ccc(NS(=O)(=O)c2ccc(CN=[N+]=[N-])cc2)c2[nH]cc(C#N)c12]

To a solution of Reference Example compound 5-1 (730 mg) in methanol (21.0 mL) was added sodium borohydride (163 mg) at room temperature, and the mixture was stirred at the same temperature for 20 min. The reaction mixture was partitioned by adding 1N hydrochloric acid-water-saturated brine and ethyl acetate-acetone. The aqueous layer was extracted once with ethyl acetate. The combined organic layer was dried over anhydrous magnesium sulfate and filtered, and the solvent was evaporated under reduced pressure. The obtained residue was dissolved in tetrahydrofuran (30.0 mL), 1,8-diazabicyclo[5.4.0]-7-undecene (0.49 mL) and 2-azido-1,3-dimethylimidazolinium hexafluorophosphate (736 mg) were added at room temperature, and the mixture was stirred at the same temperature for 15 hr. 1,8-Diazabicyclo[5.4.0]-7-undecene (0.486 mL) and 2-azido-1,3-dimethylimidazolinium hexafluorophosphate (736 mg) were added at room temperature, and the mixture was stirred at the same temperature for 4 hr. 1N Hydrochloric acid was added to the reaction mixture and the mixture was extracted twice with ethyl acetate. The organic layer was dried over anhydrous magnesium sulfate and filtered, and the solvent was evaporated under reduced pressure. The obtained residue was purified by silica gel column chromatography (hexane:ethyl acetate=100:0-60:40), and the obtained purified product was solidified by adding chloroform and concentrated under reduced pressure to give the title compound (355 mg) as a pale-yellow powder. MS(ESI) m/z: 365.3[M–H]$^-$

(5-3) 4-(aminomethyl)-N-(3-cyano-4-methyl-1H-indol-7-yl)benzene-1-sulfonamide (Reference Example Compound 5)

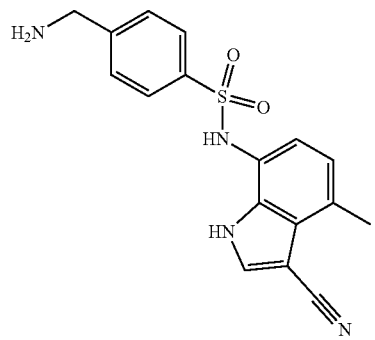 [SMILES: Cc1ccc(NS(=O)(=O)c2ccc(CN)cc2)c2[nH]cc(C#N)c12]

To a mixture of Reference Example compound 5-2 (350 mg) and triphenylphosphine (326 mg) were added tetrahydrofuran (10.0 mL) and water (1.0 mL), and the mixture was stirred at 50° C. for 3 hr. The reaction mixture was concentrated under reduced pressure, chloroform was added to the obtained residue, and the precipitate was collected by filtration to give the title compound (300 mg) as a white powder.

MS(ESI) m/z: 341.1[M+H]$^+$

Reference Example 6

(6-1) 4-[(3-cyano-4-methyl-1H-indol-7-yl)sulfamoyl]benzoic acid (Reference Example Compound 6)

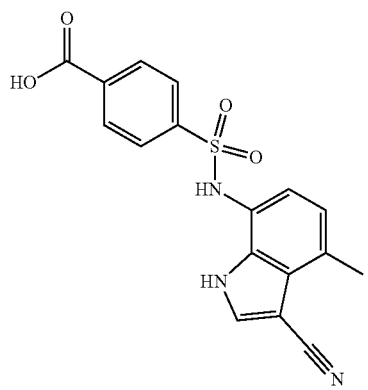 [SMILES: Cc1ccc(NS(=O)(=O)c2ccc(C(=O)O)cc2)c2[nH]cc(C#N)c12]

To a mixture of Reference Example compound 9 (1.00 g) and tetrahydrofuran (30.0 mL) was added, under ice-cooling, 4-chlorosulfonylbenzoic acid (1.42 g), and the mixture was stirred at room temperature for 24 hr. To the reaction mixture was added 1N hydrochloric acid, and the mixture was extracted with ethyl acetate. The organic layer was dried over anhydrous sodium sulfate and filtered, and the solvent was evaporated under reduced pressure. To the obtained residue was added diethyl ether, and the precipitate was collected by filtration to give the title compound (1.81 g) as a brown solid.
MS(ESI) m/z: 354.1[M−H]−

Reference Example 7

(7-1) 7-bromo-4-methyl-1H-indole (Reference Example Compound 7)

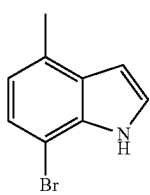

To a solution (35.0 mL) of 1-bromo-4-methyl-2-nitrobenzene (1.08 g) in tetrahydrofuran was added at −40° C. 1M vinylmagnesium bromide/tetrahydrofuran solution (15.0 mL). The mixture was stirred at the same temperature for 40 min. To the reaction mixture were added saturated aqueous ammonium chloride solution and water for partitioning. The aqueous layer was extracted twice with ethyl acetate. The combined organic layer was washed with saturated brine, dried over anhydrous sodium sulfate and filtered. The solvent was evaporated under reduced pressure. The obtained residue was purified by silica gel column chromatography (hexane:ethyl acetate=98:2-95:5) to give the title compound (600 mg) as a yellow oil. $^1$H NMR (400 MHz, CDCl$_3$) δ ppm 2.52 (3H, d, J=0.77 Hz), 6.63 (1H, dd, J=3.28, 2.25 Hz), 6.80 (1H, dq, J=7.71, 0.81 Hz), 7.22-7.27 (2H, m), 8.32 (1H, brs)

Reference Example 8

(8-1) 7-bromo-4-methyl-1H-indole-3-carbonitrile (Reference Example Compound 8)

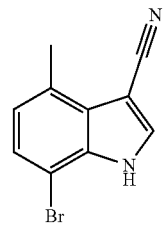

To a solution (1.35 mL) of Reference Example compound 7 (284 mg) in N,N-dimethylformamide was added at room temperature phenylphosphonyl dichloride (0.23 mL). After stirring at room temperature for 0.5 hr, phenylphosphonyl dichloride (0.04 mL) was added, and the mixture was further stirred at the same temperature for 0.5 hr. To the reaction mixture was added at room temperature hydroxylamine hydrochloride (188 mg), and the mixture was stirred with heating at 60° C. for 1 hr and at 100° C. for 2 hr. The reaction mixture was diluted with ethyl acetate, washed twice with saturated aqueous sodium hydrogen carbonate and once with saturated brine, dried over anhydrous sodium sulfate and filtered. The solvent was evaporated under reduced pressure. The obtained residue was purified by silica gel column chromatography (chloroform:methanol=98:2) to give the title compound (220 mg) as a pale-brown solid. $^1$H NMR (400 MHz, CDCl$_3$) δ ppm 2.75 (3H, d, J=0.6 Hz), 6.92 (1H, dq, J=7.6, 1.8 Hz), 7.36 (1H, d, J=7.7 Hz), 7.78 (1H, d, J=2.8 Hz), 8.73 (1H, brs)

Reference Example 9

(9-1) 7-amino-4-methyl-1H-indole-3-carbonitrile (Reference Example Compound 9)

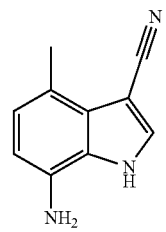

To a mixture of Reference Example compound 8 (215 mg), benzophenone imine (240 mg), [1,3-bis(2,6-di-3-pentylphenyl)imidazol-2-ylidene](3-chloropyridyl)dichloropalladium(II) (Pd-PEPPSI-IPent catalyst, 22 mg), tetrahydrofuran (2.3 mL) was added at room temperature 1.3M lithium bis(trimethylsilyl)amide/tetrahydrofuran solution (2.5 mL), and the mixture was stirred under a nitrogen atmosphere under microwave irradiation at 120° C. for 0.5 hr. After allowing to cool to room temperature, water was added to the reaction mixture, and the mixture was extracted twice with ethyl acetate. The organic layers were combined, washed with saturated brine, dried over sodium sulfate, and filtered. The solvent was evaporated under reduced pressure. The obtained residue was dissolved in tetrahydrofuran (2.3 mL)-methanol (2.3 mL), hydroxylamine hydrochloride (159 mg) and sodium acetate (225 mg) were added at room temperature, and the mixture was stirred at the same temperature for 4 hr. To the reaction mixture was added saturated aqueous sodium hydrogen carbonate, and the mixture was extracted twice with ethyl acetate. The organic layers were combined, washed with saturated brine, dried over anhydrous sodium sulfate, and filtered. The solvent was evaporated under reduced pressure. The obtained residue was purified by silica gel column chromatography (chloroform:methanol=98:2) to give the title compound (139 mg) as a pale-brown solid.

MS(ESI) m/z: 172.1[M+H]$^+$

Reference Example 10

(10-1) methyl [(6S)-4-(4'-{[(4-bromophenyl)methyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Reference Example Compound 10-1)

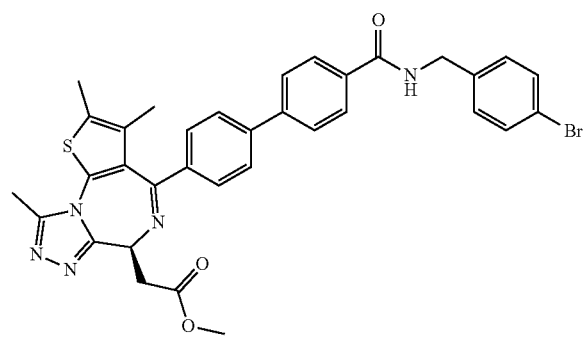 [SMILES: COC(=O)C[C@@H]1N=C(c2ccc(-c3ccc(C(=O)NCc4ccc(Br)cc4)cc3)cc2)c2c(sc(C)c2C)-n2c(C)nnc21]

To a solution of Reference Example compound 4 (500 mg) and 4-bromobenzylamine (223 mg) in N,N-dimethylformamide (5.0 mL) were added at room temperature N,N-diisopropylethylamine (0.52 mL) and HATU (456 mg), and the mixture was stirred at the same temperature for 1 hr. The reaction mixture was diluted with ethyl acetate, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-90:10) to give the title compound (643 mg) as a pale-yellow powder.

MS(ESI) m/z: 668.3, 670.3[M+H]$^+$ (10-2) methyl {(6S)-4-[4'-({[4-(benzylsulfanyl)phenyl]methyl}carbamoyl) [1,1'-biphenyl]-4-yl]-2,3,9-trimethyl-6H-thieno[3,2-f][1,2,4]triazolo[4,3-a][1,4]diazepin-6-yl}acetate (Reference Example Compound 10-2)

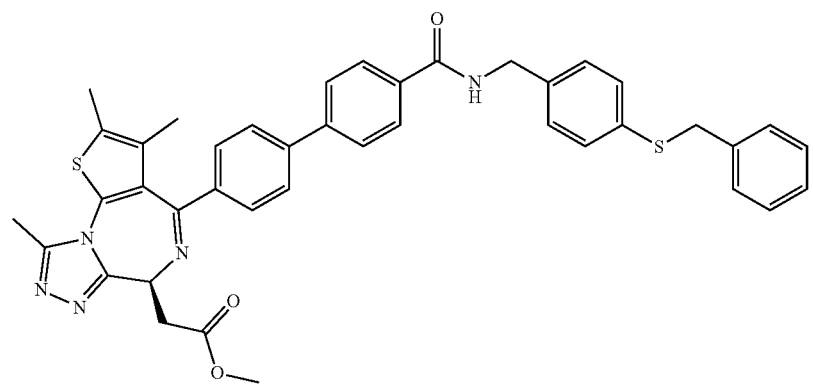 [SMILES: COC(=O)C[C@@H]1N=C(c2ccc(-c3ccc(C(=O)NCc4ccc(SCc5ccccc5)cc4)cc3)cc2)c2c(sc(C)c2C)-n2c(C)nnc21]

A mixture of Reference Example compound 10-1 (635 mg), benzylmercaptan (0.14 mL), N,N-diisopropylethylamine (0.50 mL), 4,5-bis(diphenylphosphino)-9,9-dimethylxanthene (Xantphos, 110 mg), tris(dibenzylideneacetone)dipalladium (87 mg), toluene (9.0 mL) and tetrahydrofuran (3.0 mL) was stirred under a nitrogen atmosphere under microwave irradiation at 150° C. for 0.5 hr. After allowing to cool to room temperature, the reaction mixture was directly purified by NH silica gel column chromatography (hexane:ethyl acetate=50:50-0:100) to give the title compound (613 mg) as a pale-yellow powder.

MS(ESI) m/z: 712.4[M+H]$^+$ (10-3) methyl {(6S)-4-[4'-({[4-(chlorosulfonyl)phenyl]methyl}carbamoyl) [1,1'-biphenyl]-4-yl]-2,3,9-trimethyl-6H-thieno[3,2-f][1,2,4]triazolo[4,3-a][1,4]diazepin-6-yl}acetate (Reference Example Compound 10)

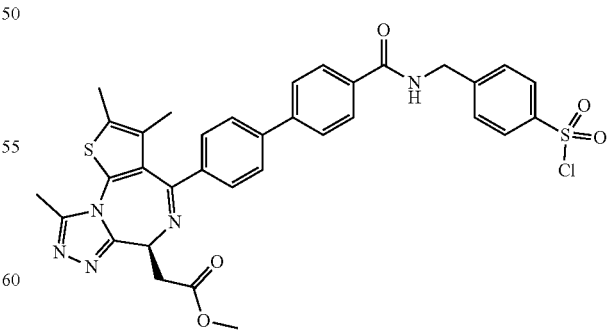

To a solution of Reference Example compound 10-2 (594 mg) in acetonitrile (12.0 mL)-2N hydrochloric acid (2.4 mL) was added under ice-cooling N-chlorosuccinimide (390 mg), and the mixture was stirred at the same temperature for 1.5 hr. To the reaction mixture was added N-chlorosuccinimide (23 mg), and the mixture was stirred at the same temperature for 0.5 hr. To the reaction mixture was added saturated brine-water (1:1), and the mixture was extracted twice with ethyl acetate. The combined organic layer was washed with saturated brine, dried over anhydrous sodium sulfate and filtered. The solvent was evaporated under reduced pressure. The obtained residue was purified by silica gel column chromatography (chloroform:methanol=98:2) to give the title compound (570 mg) as a pale-yellow powder. MS(ESI) m/z: 670.4[M−Cl+H$_2$O]+; 1H NMR (400 MHz, CDCl$_3$) δ ppm 1.75 (3H, d, J=0.64 Hz), 2.41-2.46 (3H, m), 2.70 (3H, s), 3.66 (2H, dd, J=7.06, 3.72 Hz), 3.79 (3H, s), 4.44 (1H, d, J=5.65 Hz), 4.67 (1H, dd, J=7.77, 6.36 Hz), 4.80 (2H, d, J=6.04 Hz), 7.55-7.63 (6H, m), 7.68 (2H, m, J=8.61 Hz), 7.90 (2H, m, J=8.61 Hz), 8.02 (2H, d, J=7.74 Hz)

Reference Example 11

(11-1) t-butyl (2-{4-[(3-cyano-4-methyl-1H-indol-7-yl) sulfamoyl]phenyl}ethyl) carbamate (Reference Example Compound 11-1)

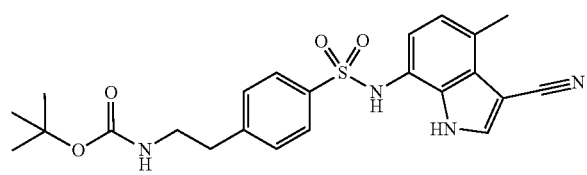 [SMILES: Cc1ccc(NS(=O)(=O)c2ccc(CCNC(=O)OC(C)(C)C)cc2)c2[nH]cc(C#N)c12]

s A mixed solution of Reference Example compound 9 (120 mg), t-butyl N-2-[4-(chlorosulfonyl)phenyl]ethylcarbamate (250 mg), pyridine (0.28 mL) and tetrahydrofuran (5.0 mL) was stirred at room temperature for 3 hr. The reaction mixture was diluted with ethyl acetate, washed twice with 1N hydrochloric acid and once with saturated brine, dried over anhydrous sodium sulfate and filtered. The solvent was evaporated under reduced pressure. The obtained residue was suspended and washed with hexane and collected by filtration to give the title compound (301 mg) as a pale-yellow solid. MS(ESI) m/z: 455.4[M+H]$^+$ (11-2) 4-(2-aminoethyl)-N-(3-cyano-4-methyl-1H-indol-7-yl)benzene-1-sulfonamide hydrochloride (Reference Example Compound 11)

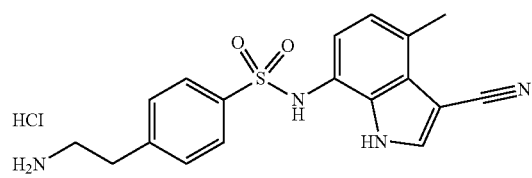 [SMILES: "HCI" ; Cc1ccc(NS(=O)(=O)c2ccc(CCN)cc2)c2[nH]cc(C#N)c12]

To Example compound 11-1 (301 mg) was added 4M hydrogen chloride/1,4-dioxane solution (3.0 mL) at room temperature. After stirring at the same temperature for 1 hr, the reaction mixture was concentrated under reduced pressure. The residue was suspended and washed with diethyl ether and collected by filtration to give the title compound (260 mg) as a milk-white solid. MS(ESI) m/z: 355.1[M+H]$^+$ Reference Example 12

(12-1) t-butyl 3-fluoro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylate (Reference Example Compound 12-1)

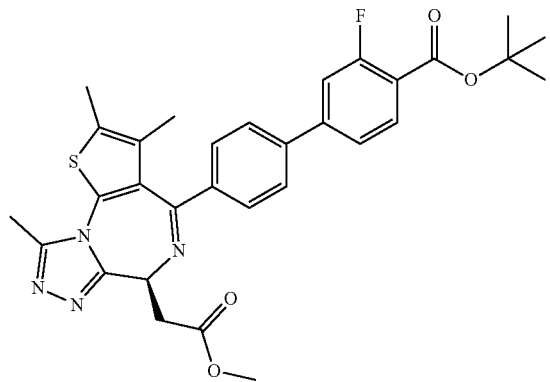 [SMILES: COC(=O)C[C@@H]1N=C(c2ccc(-c3ccc(C(=O)OC(C)(C)C)c(F)c3)cc2)c2c(sc(C)c2C)-n2c(C)nnc21]

Reference Example compound 3 (300 mg) was dissolved in tetrahydrofuran (3.0 mL), t-butyl 4-bromo-2-fluorobenzoate (196 mg), tetrakis(triphenylphosphine)palladium(0) (69 mg), potassium phosphate (377 mg) and water (0.038 mL) were added, and the mixture was stirred under a nitrogen atmosphere under microwave irradiation at 90° C. for 0.5 hr. The reaction mixture was diluted with ethyl acetate, and insoluble materials were filtered off through diatomaceous earth. The filtrate was concentrated under reduced pressure, and the residue was purified by silica gel column chromatography (chloroform:methanol=100:0-98:2, precolumn: NH silica gel) to give the title compound (346 mg) as a white crudely-purified powder. MS(ESI) m/z: 575.4[M+H]$^+$ (12-2) 3-fluoro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Reference Example Compound 12)

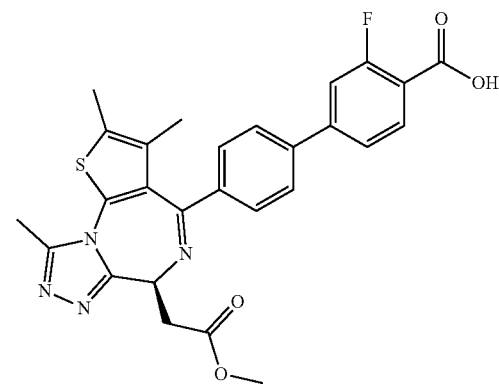

Reference Example compound 12-1 (240 mg) was dissolved in dichloromethane (2.0 mL), trifluoroacetic acid (2.0 mL) was added at room temperature, and the mixture was stirred at the same temperature for 1 hr. The reaction mixture was concentrated under reduced pressure, and the residue was dissolved in ethyl acetate, and extracted twice with saturated aqueous sodium hydrogen carbonate. The aqueous layers were combined, and 2N hydrochloric acid was added by small portions under ice-cooling to pH=4. The mixture was extracted twice with chloroform. The combined organic layer was washed with saturated brine, dried over anhydrous sodium sulfate and filtered, and the solvent was evaporated under reduced pressure to give the title compound (205 mg) as a white powder.

MS(ESI) m/z: 519.1[M+H]$^+$

Reference Example 13

(13-1) 3-chloro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Reference Example Compound 13)

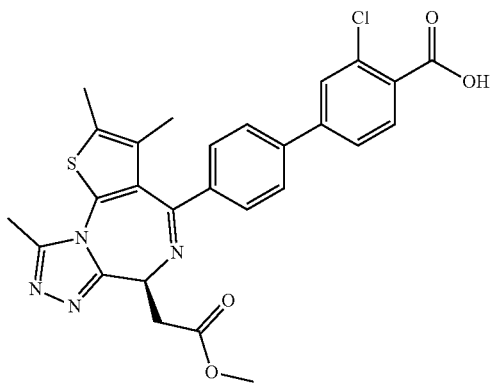 [SMILES: COC(=O)C[C@@H]1N=C(c2ccc(-c3ccc(C(=O)O)c(F)c3)cc2)c2c(sc(C)c2C)-n2c(C)nnc21]

Reference Example compound 3 (117 mg) was dissolved in tetrahydrofuran (1.0 mL), 4-bromo-2-chlorobenzoic acid (48 mg), 2-dicyclohexylphosphino-2',4',6'-triisopropylbiphenyl (X-Phos, 10 mg), X-Phos aminobiphenylpalladium chloride precatalyst (16 mg), cesium fluoride (93 mg) and water (0.25 mL) were added, and the mixture was stirred under a nitrogen atmosphere under microwave irradiation at 120° C. for 1 hr. The reaction mixture was diluted with ethyl acetate, and extracted twice with saturated aqueous sodium hydrogen carbonate. The aqueous layers were combined, and 2N hydrochloric acid was added by small portions under ice-cooling to pH=1. The aqueous layer was extracted twice with ethyl acetate. The combined organic layer was washed with saturated brine, dried over anhydrous sodium sulfate and filtered, and the solvent was evaporated under reduced pressure to give the title compound (73 mg) as a white powder. MS(ESI) m/z: 535.1, 537.1[M+H]$^+$ Reference Example 14

(14-1) 4-bromo-N-(3-cyano-4-methyl-1H-indol-7-yl)benzene-1-sulfonamide (Reference Example Compound 14)

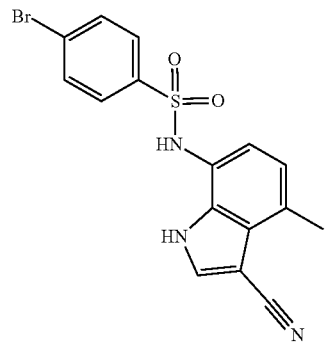 [SMILES: Cc1ccc(NS(=O)(=O)c2ccc(Br)cc2)c2[nH]cc(C#N)c12]

To a solution (12.0 mL) of Reference Example compound 9 (622 mg) and pyridine (2.92 mL) in tetrahydrofuran was added at room temperature 4-bromobenzenesulfonyl chloride (929 mg), and the mixture was stirred at the same temperature for 3 hr. The reaction mixture was diluted with ethyl acetate, washed once with saturated brine-water (1:1) and washed once with saturated brine, dried over anhydrous sodium sulfate and filtered. The solvent was evaporated under reduced pressure. The obtained residue was suspended and washed with chloroform, and collected by filtration to give the title compound (1061 mg) as a beige powder. MS(ESI) m/z: 390.2, 392.1[M+H]$^+$ Reference Example 15

(15-1) 7-amino-4-bromo-1H-indole-3-carbonitrile (Reference Example Compound 15)

To N,N-dimethylformamide (11.0 mL) was added phenylphosphonyl dichloride (1.27 mL), and the mixture was stirred at 70° C. for 10 min. N-(4-Bromo-1H-indol-7-yl)-2,2,2-trifluoroacetamide (929 mg) and N,N-dimethylformamide (11.0 mL) were added and the mixture was stirred at 70° C. for 1 hr. Then, hydroxylamine hydrochloride (2.42 g) was added, and the mixture was stirred at 100° C. for 2 hr. Further, ethylenediamine (2.02 mL) and methanol (22.0 mL) were added, and the mixture was stirred at 70° C. for 1 hr. After cooling to room temperature, methanol was evaporated under reduced pressure, and the obtained residue was partitioned by adding ethyl acetate, saturated aqueous sodium hydrogen carbonate and saturated brine. The organic layer was washed twice with a mixture of saturated aqueous sodium hydrogen carbonate and saturated brine, once with water, and once with saturated brine, dried over anhydrous sodium sulfate and filtered. The solvent was evaporated under reduced pressure. The obtained residue was suspended and washed with ethyl acetate, collected by filtration and dried under reduced pressure to give the title compound (260 mg) as a brown powder. The solvent was evaporated under reduced pressure from the filtrate and the obtained residue was purified by silica gel column chromatography (hexane:ethyl acetate=50:50-75:25) to give the target compound (104 mg) as a brown solid. MS(ESI) m/z: 236.0, 237.9[M+H]⁺

Reference Example 16

(16-1) 7-bromo-4-ethyl-1H-indole-3-carbonitrile (Reference Example Compound 16-1)

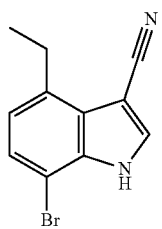

To a solution (17.4 mL) of 7-bromo-4-ethyl-1H-indole (3.90 g) in N,N-dimethylformamide was added under ice-cooling phenylphosphonyl dichloride (3.64 mL), and the mixture was stirred at room temperature for 30 min and at 70° C. for 40 min. Hydroxylamine hydrochloride (2.42 g) was added and the mixture was stirred at 70° C. for 30 min and at 80° C. for 30 min. After cooling to room temperature, the reaction mixture was diluted with ethyl acetate, ice-cooled, and saturated aqueous sodium hydrogen carbonate was added with stirring. The mixture was extracted twice with ethyl acetate, the extracts were combined, and washed twice with a mixed solution of saturated brine and saturated aqueous sodium hydrogen carbonate and once with saturated brine, dried over anhydrous sodium sulfate and filtered. The solvent was evaporated under reduced pressure. The obtained residue was purified by silica gel column chromatography (hexane:ethyl acetate=90:10-70:30), toluene was added to the residue and the mixture was concentrated under reduced pressure. This was repeated twice to give the title compound (3.12 g) as a pale-yellow solid.
MS(ESI) m/z: 246.9, 248.9[M−H]⁻

(16-2) 7-amino-4-ethyl-1H-indole-3-carbonitrile (Reference Example Compound 16)

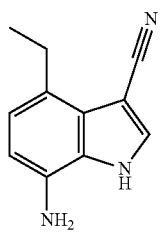

To a mixture of Reference Example compound 16-1 (2.12 g), benzophenone imine (2.16 g), and [1,3-bis(2,6-di-3-pentylphenyl)imidazol-2-ylidene](3-chloropyridyl)dichloropalladium(II) (Pd-PEPPSI-IPent catalyst, 202 mg) was added 1.3M lithium bis(trimethylsilyl)amide/tetrahydrofuran solution (23.0 mL) at room temperature, and the mixture was stirred under a nitrogen atmosphere under microwave irradiation at 120° C. for 1 hr. After allowing to cool to room temperature, water was added to the reaction mixture and the mixture was extracted twice with ethyl acetate. The organic layers were combined, washed with saturated brine, dried over anhydrous sodium sulfate, and filtered. The solvent was evaporated under reduced pressure. The obtained residue was dissolved in tetrahydrofuran (11.0 mL)-methanol (11.0 mL), hydroxylamine hydrochloride (1.48 g) and sodium acetate (2.09 g) were added at room temperature, and the mixture was stirred at the same temperature for 16 hr. To the reaction mixture was added saturated aqueous sodium hydrogen carbonate and the mixture was extracted twice with ethyl acetate. The organic layers were combined, washed once with a mixed solution of saturated brine and water and once with saturated brine, dried over anhydrous sodium sulfate, and filtered. The solvent was evaporated under reduced pressure. The obtained residue was purified by silica gel column chromatography (chloroform:methanol=100:0-98:2) to give the title compound (954 mg) as a pale-brown solid.
MS(ESI) m/z: 186.1[M+H]⁺

Reference Example 17

(17-1) t-butyl [(1R)-1-(4-bromophenyl)ethyl]carbamate (Reference Example Compound 17-1)

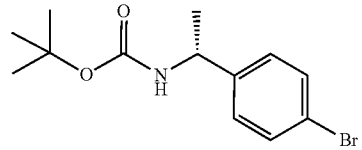 [SMILES: C[C@@H](NC(=O)OC(C)(C)C)c1ccc(Br)cc1]

To a solution (45.0 mL) of (R)-1-(4-bromophenyl)ethanamine (3.00 g) and trimethylamine (2.50 mL) in dichloromethane was added at room temperature di-t-butyl carbonate (3.60 g), and the mixture was stirred at room temperature for 14 hr. To the reaction mixture was added 1N hydrochloric acid for partitioning. The aqueous layer was extracted once with chloroform. The combined organic layer was dried over anhydrous sodium sulfate and filtered. The solvent was evaporated under reduced pressure. The obtained residue was suspended and washed with hexane, and collected by filtration to give the title compound (4.36 g) as a white solid.
MS(ESI) m/z: 300.2, 302.1[M+H]⁺

(17-2) t-butyl {(1R)-1-[4-(benzylsulfanyl)phenyl]ethyl}carbamate (Reference Example Compound 17-2)

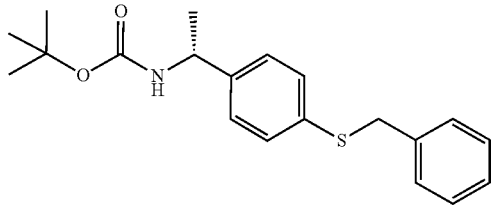 [SMILES: C[C@@H](NC(=O)OC(C)(C)C)c1ccc(SCc2ccccc2)cc1]

A mixture of Reference Example compound 17-1 (4.34 g), benzylmercaptan (2.04 mL), N,N-diisopropylethylamine (3.75 mL), 4,5-bis(diphenylphosphino)-9,9-dimethylxanthene (Xantphos, 1.67 g), tris(dibenzylideneacetone)dipalladium (1.32 g) and toluene (10.0 mL) was stirred under a nitrogen atmosphere under microwave irradiation at 150° C. for 0.5 hr. To the reaction mixture was added ethyl acetate, insoluble materials were filtered off through diatomaceous earth, and the filtrate was concentrated under reduced pressure. The residue was purified by silica gel column chromatography (hexane:ethyl acetate=90:10-80:20) to give the title compound (4.91 g) as a pale-yellow solid. MS(ESI) m/z: 344.3[M+H]$^+$

(17-3) t-butyl {(1R)-1-[4-(chlorosulfonyl)phenyl]ethyl}carbamate (Reference Example Compound 17-3)

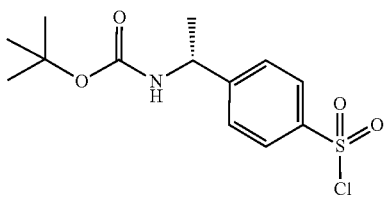 [SMILES: C[C@@H](NC(=O)OC(C)(C)C)c1ccc(S(=O)(=O)Cl)cc1]

To a solution of Reference Example compound 17-2 (2.72 g) in acetonitrile (50.0 mL)-2N hydrochloric acid (10.0 mL) was added, under ice-cooling, N-chlorosuccinimide (4.30 g), and the mixture was stirred at the same temperature for 2 hr. To the reaction mixture was added water, and the mixture was extracted twice with ethyl acetate. The combined organic layer was washed with saturated brine, dried over anhydrous sodium sulfate and filtered. The solvent was evaporated under reduced pressure. The obtained residue was purified by silica gel column chromatography (hexane:ethyl acetate=90:10-75:25) to give the title compound (2.21 g) as a white solid. $^1$H NMR (400 MHz, CDCl$_3$) δ ppm 1.32-1.51 (12H, m), 4.87 (2H, brs), 7.48-7.60 (2H, m), 7.93-8.06 (2H, m)

(17-4) t-butyl [(1R)-1-{4-[(3-cyano-4-methyl-1H-indol-7-yl)sulfamoyl]phenyl}ethyl]carbamate (Reference Example Compound 17-4)

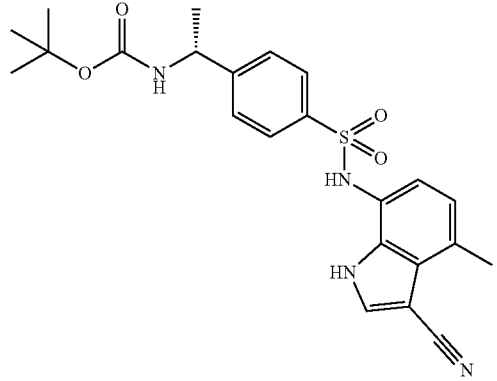 [SMILES: Cc1ccc(NS(=O)(=O)c2ccc([C@@H](C)NC(=O)OC(C)(C)C)cc2)c2[nH]cc(C#N)c12]

To a solution of Reference Example compound 17-3 (2.20 g) in tetrahydrofuran (66.0 mL) were added, at room temperature, Reference Example compound 9 (1.18 g) and pyridine (2.77 mL), and the mixture was stirred at the same temperature for 2 hr. The reaction mixture was diluted with ethyl acetate, washed twice with 1N hydrochloric acid and once with saturated brine, dried over anhydrous sodium sulfate and filtered. The solvent was evaporated under reduced pressure. The residue was suspended and washed with chloroform and filtered to give the title compound (1.67 g) as a pale-brown solid. The filtrate was concentrated under reduced pressure, and the residue was purified by silica gel column chromatography (chloroform:methanol=98:2) to give the title compound (0.84 g) as a pale-brown solid. MS(ESI) m/z: 455.3[M+H]$^+$

(17-5) 4-[(1R)-1-aminoethyl]-N-(3-cyano-4-methyl-1H-indol-7-yl)benzene-1-sulfonamide hydrochloride (Reference Example Compound 17)

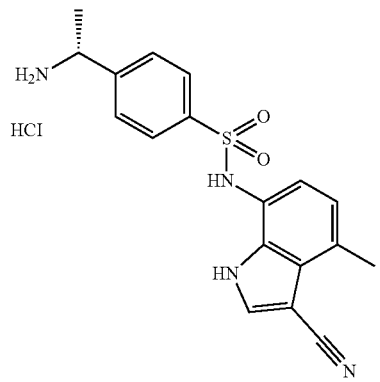 [SMILES: "HCI" ; Cc1ccc(NS(=O)(=O)c2ccc([C@@H](C)N)cc2)c2[nH]cc(C#N)c12]

To Example compound 17-4 (2.47 g) was added 4M hydrogen chloride/1,4-dioxane solution (25.0 mL) at room temperature. After stirring at the same temperature for 3 hr, the reaction mixture was diluted with diethyl ether, and the solid was suspended and washed, and collected by filtration to give the title compound (2.27 g) as a milk-white solid. MS(ESI) m/z: 355.2[M+H]$^+$

Reference Example 18

(18-1) t-butyl 2-fluoro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylate (Reference Example Compound 18-1)

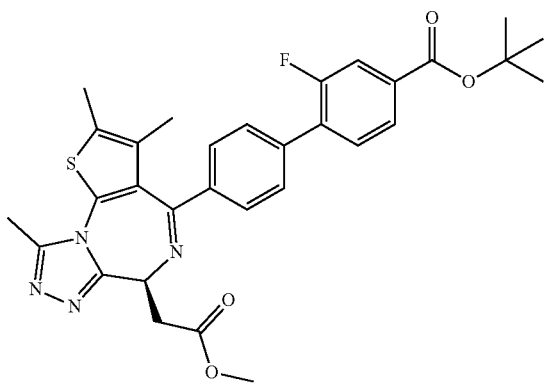 [SMILES: COC(=O)C[C@@H]1N=C(c2ccc(-c3ccc(C(=O)OC(C)(C)C)cc3F)cc2)c2c(sc(C)c2C)-n2c(C)nnc21]

Reference Example compound 3 (300 mg) was dissolved in tetrahydrofuran (3.0 mL), t-butyl 4-bromo-3-fluorobenzoate (180 mg), tetrakis(triphenylphosphine)palladium(0) (69 mg), potassium phosphate (378 mg) and water (0.039 mL) were added, and the mixture was stirred under a nitrogen atmosphere under microwave irradiation at 90° C. for 0.5 hr. The reaction mixture was diluted with ethyl acetate, and insoluble materials were filtered off through diatomaceous earth. The filtrate was concentrated under reduced pressure, and the residue was purified by NH silica gel column chromatography (hexane:ethyl acetate=50:50-0:100) to give the title compound (300 mg) as a white powder. MS(ESI) m/z: 575.3[M+H]$^+$ (18-2) 2-fluoro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Reference Example Compound 18)

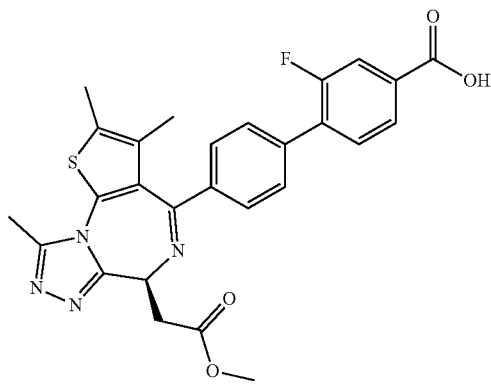

Reference Example compound 18-1 (290 mg) was dissolved in dichloromethane (2.0 mL), trifluoroacetic acid (2.0 mL) was added at room temperature, and the mixture was stirred at the same temperature for 1 hr. The reaction mixture was concentrated under reduced pressure, and the residue was dissolved in ethyl acetate and extracted twice with saturated aqueous sodium hydrogen carbonate. The aqueous layers were combined, and 2N hydrochloric acid was added by small portions under ice-cooling to pH=4. The mixture was extracted twice with chloroform. The combined organic layer was washed with saturated brine, dried over anhydrous sodium sulfate and filtered, and the solvent was evaporated under reduced pressure to give the title compound (246 mg) as a white powder.

MS(ESI) m/z: 519.3[M+H]$^+$

Reference Example 19

(19-1) 2-chloro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Reference Example Compound 19)

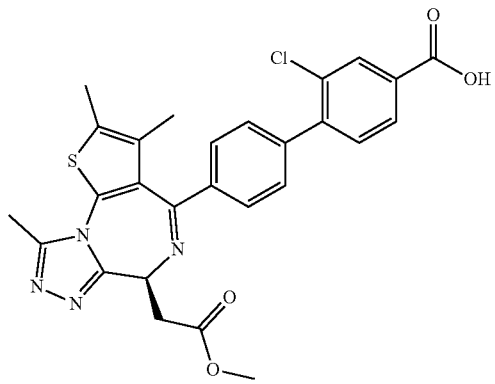 [SMILES: COC(=O)C[C@@H]1N=C(c2ccc(-c3ccc(C(=O)O)cc3Cl)cc2)c2c(sc(C)c2C)-n2c(C)nnc21]

Reference Example compound 3 (364 mg) was dissolved in tetrahydrofuran (3.2 mL), 4-bromo-3-chlorobenzoic acid (150 mg), 2-dicyclohexylphosphino-2',4',6'-triisopropylbiphenyl (X-Phos, 30 mg), X-Phos aminobiphenylpalladium chloride precatalyst (50 mg), cesium fluoride (290 mg) and water (0.80 mL) were added, and the mixture was stirred under a nitrogen atmosphere under microwave irradiation at 120° C. for 0.5 hr. The reaction mixture was diluted with ethyl acetate, and extracted twice with saturated aqueous sodium hydrogen carbonate. The aqueous layers were combined, and 2N hydrochloric acid was added under ice-cooling by small portions to pH=1. The aqueous layer was extracted twice with ethyl acetate. The combined organic layer was washed with saturated brine, dried over anhydrous sodium sulfate and filtered, and the solvent was evaporated under reduced pressure to give the title compound (247 mg) as a pale-yellow powder. MS(ESI) m/z: 535.3, 537.3[M+H]$^+$ Reference Example 20

(20-1) 4'-[(6S)-6-(2-methoxy-2-oxoethyl)-2,3,9-trimethyl-6H-thieno[3,2-f][1,2,4]triazolo[4,3-a][1,4]diazepin-4-yl]-3-methyl[1,1'-biphenyl]-4-carboxylic acid (Reference Example Compound 20)

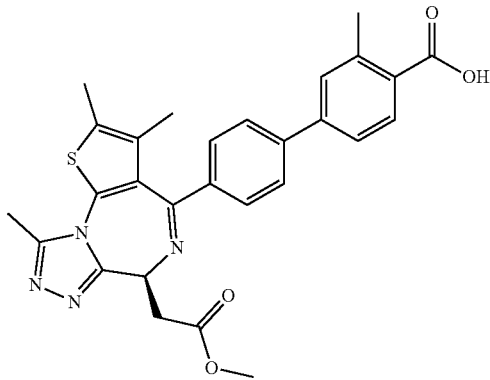 [SMILES: COC(=O)C[C@@H]1N=C(c2ccc(-c3ccc(C(=O)O)c(C)c3)cc2)c2c(sc(C)c2C)-n2c(C)nnc21]

Reference Example compound 3 (231 mg) was dissolved in tetrahydrofuran (2.0 mL), 4-bromo-2-methylbenzoic acid (87 mg), 2-dicyclohexylphosphino-2',4',6'-triisopropylbiphenyl (X-Phos, 19 mg), X-Phos aminobiphenylpalladium chloride precatalyst (32 mg), cesium fluoride (185 mg) and water (0.50 mL) were added, and the mixture was stirred at under a nitrogen atmosphere under microwave irradiation at 120° C. for 0.5 hr. The reaction mixture was diluted with ethyl acetate and extracted twice with saturated aqueous sodium hydrogen carbonate. The aqueous layers were combined, and 2N hydrochloric acid was added by small portions under ice-cooling to pH=1. The aqueous layer was extracted twice with ethyl acetate, the combined organic layer was washed with saturated brine, dried over anhydrous sodium sulfate and filtered, and the solvent was evaporated under reduced pressure to give the title compound (229 mg) as a white crudely-purified powder. MS(ESI) m/z: 515.3[M+H]$^+$ Reference Example 21

(21-1) t-butyl ({4-[(3-cyano-4-ethyl-1H-indol-7-yl)sulfamoyl]phenyl}methyl)carbamate (Reference Example Compound 21-1)

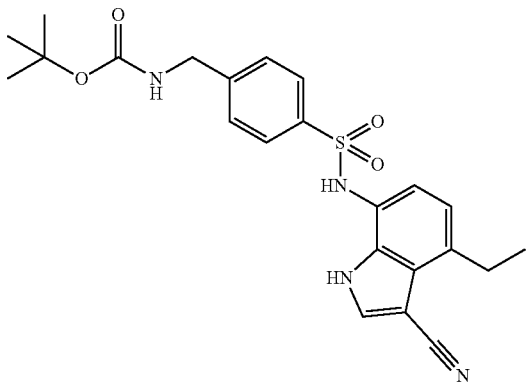 [SMILES: CCc1ccc(NS(=O)(=O)c2ccc(CNC(=O)OC(C)(C)C)cc2)c2[nH]cc(C#N)c12]

To a solution of Reference Example compound 16 (347 mg) in tetrahydrofuran (9.4 mL) were added, at room temperature, t-butyl N-[(4-chlorosulfonylphenyl)methyl]carbamate (630 mg) and pyridine (0.76 mL), and the mixture was stirred at the same temperature for 1 hr. The reaction mixture was diluted with ethyl acetate, washed twice with 1N hydrochloric acid and once with saturated brine, dried over anhydrous sodium sulfate and filtered. The solvent was evaporated under reduced pressure. The obtained residue was suspended and washed with diethyl ether-hexane (1:1), and collected by filtration to give the title compound (730 mg) as a as a beige solid.

MS(ESI) m/z: 453.3[M−H]$^-$ (21-2) 4-(aminomethyl)-N-(3-cyano-4-ethyl-1H-indol-7-yl)benzene-1-sulfonamide hydrochloride (Reference Example Compound 21)

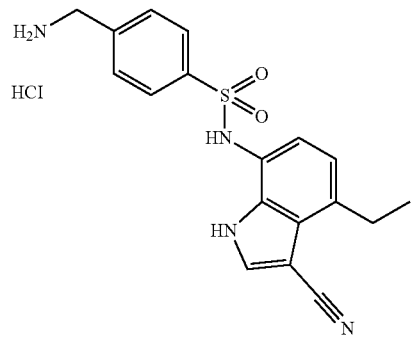 [SMILES: "HCI" ; CCc1ccc(NS(=O)(=O)c2ccc(CN)cc2)c2[nH]cc(C#N)c12]

To Reference Example compound 21-1 (720 mg) was added 4M hydrogen chloride/1,4-dioxane solution (7.2 mL) at room temperature. After stirring at the same temperature for 16 hr, the reaction mixture was diluted with diethyl ether, and the solid was suspended and washed, and collected by filtration to give the title compound (653 mg) as a beige solid.

MS(ESI) m/z: 355.0[M+H]$^+$

Reference Example 22

(22-1) t-butyl [(1R)-1-{4-[(3-cyano-4-ethyl-1H-indol-7-yl)sulfamoyl]phenyl}ethyl]carbamate (Reference Example compound 22-1)

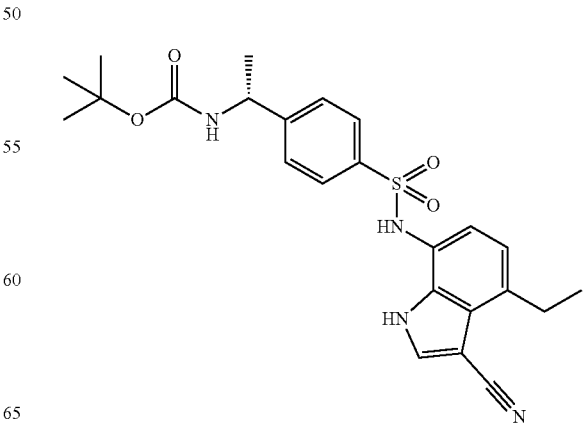

To a solution of Reference Example compound 16 (300 mg) in tetrahydrofuran (8.0 mL) were added, at room temperature, Reference Example compound 17-3 (570 mg) and pyridine (0.65 mL), and the mixture was stirred at the same temperature for 1 hr. The reaction mixture was diluted with ethyl acetate, washed twice with 1N hydrochloric acid and once with saturated brine, dried over anhydrous sodium sulfate and filtered. The solvent was evaporated under reduced pressure. The obtained residue was suspended and washed with hexane-chloroform (15:1), and collected by filtration to give the title compound (710 mg) as a pale-brown solid. MS(ESI) m/z: 467.3[M−H]⁻

(22-2) 4-[(1R)-1-aminoethyl]-N-(3-cyano-4-ethyl-1H-indol-7-yl)benzene-1-sulfonamide hydrochloride (Reference Example Compound 22)

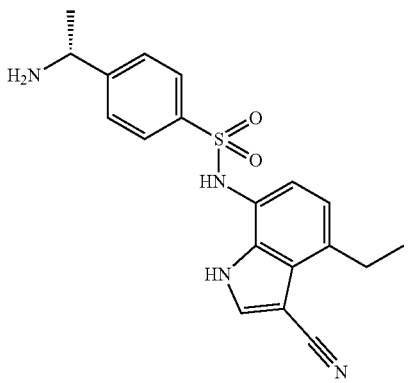 [SMILES: CCc1ccc(NS(=O)(=O)c2ccc([C@@H](C)N)cc2)c2[nH]cc(C#N)c12]

To Reference Example compound 22-1 (701 mg) was added 4M hydrogen chloride/1,4-dioxane solution (7.0 mL) at room temperature. After stirring at the same temperature for 16 hr, the reaction mixture was diluted with diethyl ether, and the solid was collected by filtration to give the title compound (653 mg) as a beige solid. MS(ESI) m/z: 369.1 [M+H]⁺

Reference Example 23

(23-1) t-butyl (2-{4-[(3-cyano-4-ethyl-1H-indol-7-yl)sulfamoyl]phenyl}ethyl)carbamate (Reference Example Compound 23-1)

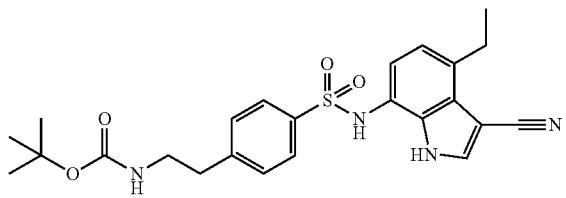 [SMILES: CCc1ccc(NS(=O)(=O)c2ccc(CCNC(=O)OC(C)(C)C)cc2)c2[nH]cc(C#N)c12]

To a solution of Reference Example compound 16 (300 mg) in tetrahydrofuran (8.0 mL) were added, at room temperature, t-butyl N-2-[4-(chlorosulfonyl)phenyl]ethylcarbamate (570 mg) and pyridine (0.65 mL), and the mixture was stirred at the same temperature for 1 hr. The reaction mixture was diluted with ethyl acetate, washed twice with 1N hydrochloric acid and once with saturated brine, dried over anhydrous sodium sulfate and filtered. The solvent was evaporated under reduced pressure. The obtained residue was suspended and washed with diethyl ether-hexane (1:1) and collected by filtration to give the title compound (710 mg) as a beige solid. MS(ESI) m/z: 467.3[M−H]⁻

(23-2) 4-(2-aminoethyl)-N-(3-cyano-4-ethyl-1H-indol-7-yl)benzene-1-sulfonamide hydrochloride (Reference Example Compound 23)

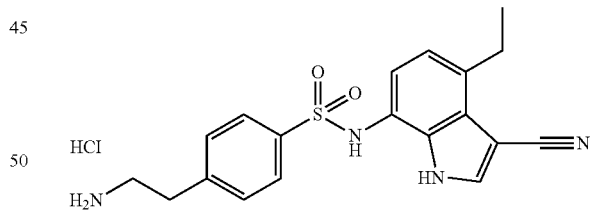

To Reference Example compound 23-1 (702 mg) was added 4M hydrogen chloride/1,4-dioxane solution (7.0 mL) at room temperature. After stirring at the same temperature for 16 hr, the reaction mixture was diluted with diethyl ether, and the solid was suspended and washed, and collected by filtration to give the title compound (610 mg) as a beige solid.

MS(ESI) m/z: 369.1[M+H]⁺

Example 1

(1-1) methyl [(6S)-4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 1)

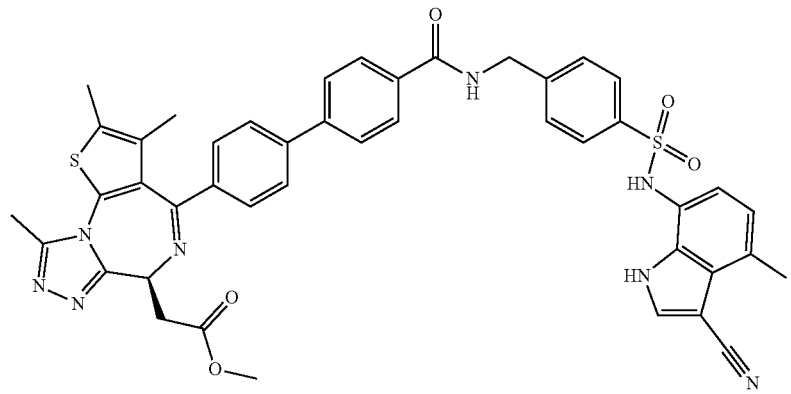

To a solution of Reference Example compound 4 (50 mg), Reference Example compound 5 (38 mg) and triethylamine (0.042 mL) in N,N-dimethylformamide (2.0 mL) was added HATU (46 mg) at room temperature, and the mixture was stirred at the same temperature for 5 hr. Under ice-cooling, water was added to the reaction mixture, and the mixture was extracted twice with chloroform. The combined organic layer was washed twice with water, dried over anhydrous sodium sulfate and filtered. The solvent was evaporated under reduced pressure. The obtained residue was purified by preparative HPLC (10 mM aqueous ammonium carbonate solution-acetonitrile) to give the title compound (49 mg) as a pale-yellow powder.

MS(ESI) m/z: 823.5[M+H]$^+$

Example 2

(2-1) methyl [(6S)-4-{4'-[({4-[(3-cyano-4-methyl-1H-indol-7-yl) sulfamoyl]phenyl}methyl) carbamoyl]-3'-fluoro[1,1'-biphenyl]-4-yl}-2,3,9-trimethyl-6H-thieno[3,2-f][1,2,4]triazolo[4,3-a][1,4]diazepin-6-yl]acetate (Example Compound 2)

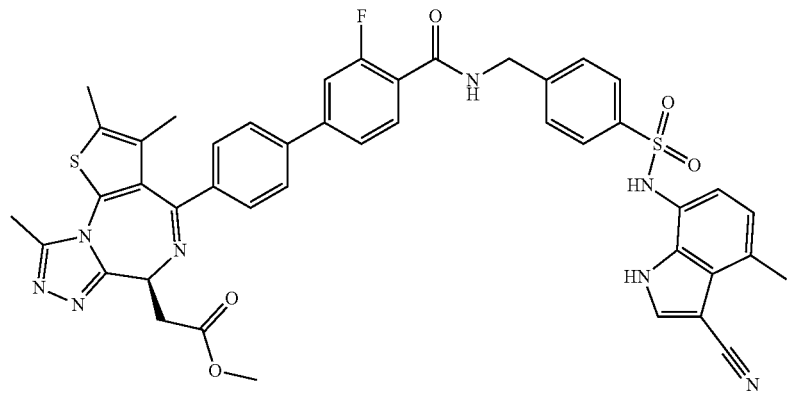

A mixture of Reference Example compound 12 (78 mg), Reference Example compound 5 (56 mg), N,N-diisopropylethylamine (0.052 mL), HATU (86 mg) was stirred in N,N-dimethylformamide (3.0 mL) at room temperature for 2 hr. To the reaction mixture was added water, the mixture was stirred and the resulting solid was collected by filtration and purified by silica gel column chromatography (chloroform:methanol=100:0-95:5) to give the title compound (86 mg) as a white solid.

MS(ESI) m/z: 841.6[M+H]$^+$

Example 3

(3-1) methyl [(6S)-4-{3'-chloro-4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 3)

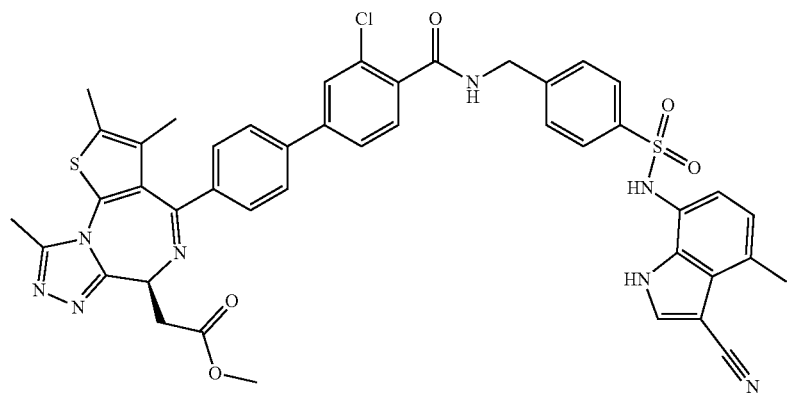

A mixture of Reference Example compound 13 (80 mg), Reference Example compound 5 (56 mg), N,N-diisopropylethylamine (0.052 mL) and HATU (86 mg) was stirred in N,N-dimethylformamide (3 mL) at room temperature for 2 hr. To the reaction mixture was added water, the mixture was stirred, and the resulting solid was collected by filtration, and purified by silica gel column chromatography (chloroform:methanol=100:0-95:5) to give the title compound (115 mg) as a pale-yellow solid. MS(ESI) m/z: 857.6, 859.6[M+H]$^+$

Example 4

(4-1) t-butyl (3R)-1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyrrolidine-3-carboxylate (Example Compound 4-1)

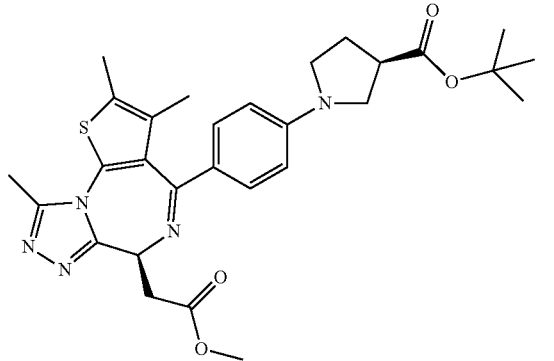 [SMILES: COC(=O)C[C@@H]1N=C(c2ccc(N3CC[C@@H](C(=O)OC(C)(C)C)C3)cc2)c2c(sc(C)c2C)-n2c(C)nnc21]

Under a nitrogen stream, Reference Example compound 1 (200 mg), t-butyl pyrrolidine-3-carboxylate (99 mg), (2-dicyclohexylphosphino-2',6'-diisopropoxy-1,1'-biphenyl)[2-(2'-amino-1,1'-biphenyl)]palladium(II) methanesulfonate (40 mg), potassium phosphate (256 mg), water (0.043 mL) were heated under reflux for 100 min in a tetrahydrofuran (1.0 mL) solvent. The reaction mixture was allowed to cool, diluted with ethyl acetate and washed with water, saturated brine. After drying over anhydrous sodium sulfate, the mixture was filtered through activated carbon, washed with methanol, tetrahydrofuran, and the filtrate was concentrated under reduced pressure. The residue was purified by silica gel column chromatography (chloroform:methanol=100:0-95:5) to give the title compound (266 mg) as a pale-yellow powder. MS(ESI) m/z: 550.3[M+H]+

(4-2) (3R)-1-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyrrolidine-3-carboxylic acid (Example Compound 4-2)

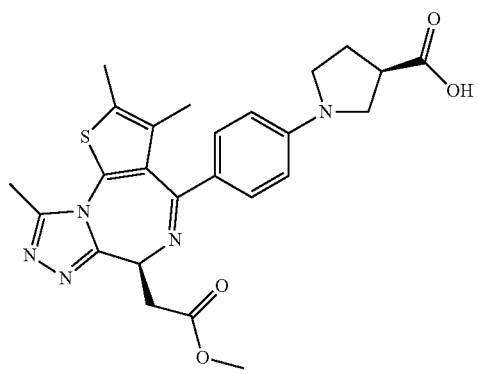 [SMILES: COC(=O)C[C@@H]1N=C(c2ccc(N3CC[C@@H](C(=O)O)C3)cc2)c2c(sc(C)c2C)-n2c(C)nnc21]

To a solution of Example compound 4-1 (266 mg) in dichloromethane (1.0 mL) was added trifluoroacetic acid (1.0 mL), and the mixture was stirred at room temperature for 3 hr. The reaction mixture was concentrated under reduced pressure, and the residue was azeotropically distilled 3 times with chloroform-toluene. The residue was dissolved in ethyl acetate, and, N,N-diisopropylethylamine (0.30 mL) was added by small portions with stirring. Hexane (2.5 mL) was added dropwise, and the mixture was stirred at room temperature for 1 hr, and the resulting solid was filtered and washed with ethyl acetate-hexane mixture (2:1) to give the title compound (181 mg) as a yellow powder. MS(ESI) m/z: 494.3[M+H]+

(4-3) methyl [(6S)-4-(4-{(3R)-3-[({4-[(3-cyano-4-methyl-1H-indol-7-yl)sulfamoyl]phenyl}methyl)carbamoyl]pyrrolidin-1-yl}phenyl)-2,3,9-trimethyl-6H-thieno[3,2-f][1,2,4]triazolo[4,3-a][1,4]diazepin-6-yl]acetate (Example Compound 4)

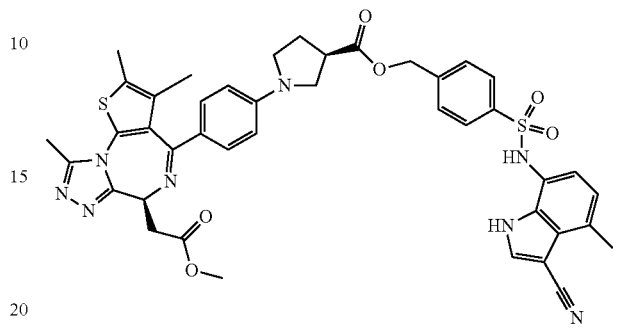

By reaction and treatment in the same manner as in (2-1) except that Example compound 4-2 (74 mg) was used instead of Reference Example compound 12 in Example 2, the title compound (111 mg) was obtained as a yellow powder.
MS(ESI) m/z: 816.3[M+H]+

Example 5

(5-1) methyl {(6S)-4-[4-(3-hydroxyprop-1-yn-1-yl)phenyl]-2,3,9-trimethyl-6H-thieno[3,2-f][1,2,4]triazolo[4,3-a][1,4]diazepin-6-yl}acetate (Example Compound 5-1)

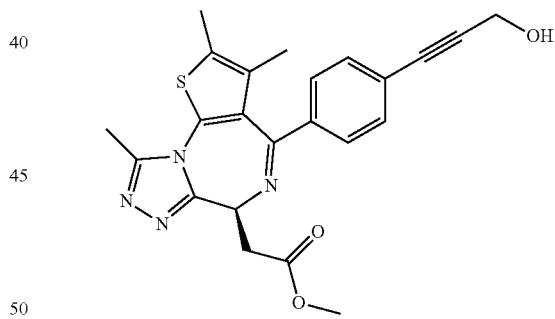

A mixture of Reference Example compound 1 (100 mg), propargyl alcohol (27 mg), 2-dicyclohexylphosphino-2',4',6'-triisopropylbiphenyl (X-Phos, 12 mg), X-Phos aminobiphenylpalladium chloride precatalyst (21 mg), potassium phosphate (102 mg) and tetrahydrofuran (1.2 mL) was stirred under a nitrogen atmosphere under microwave irradiation at 90° C. for 1 hr. The reaction mixture was diluted with ethyl acetate, washed twice with saturated brine-water (1:1) and once with saturated brine, dried over anhydrous sodium sulfate and filtered. The solvent was evaporated under reduced pressure. The residue was purified by silica gel column chromatography (chloroform:methanol=98:2-90:10, precolumn: NH silica gel) to give the title compound (63 mg) as a pale-yellow viscous compound. MS(ESI) m/z: 435.3[M+H]+

(5-2) methyl {(6S)-2,3,9-trimethyl-4-[4-(3-oxoprop-1-yn-1-yl)phenyl]-6H-thieno[3,2-f][1,2,4]triazolo[4,3-a][1,4]diazepin-6-yl}acetate (Example Compound 5-2)

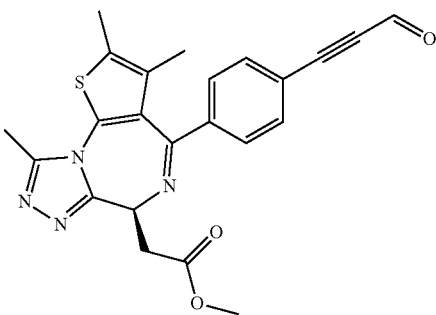 [SMILES: COC(=O)C[C@@H]1N=C(c2ccc(C#CC=O)cc2)c2c(sc(C)c2C)-n2c(C)nnc21]

To Example compound 5-1 (60 mg) in dichloromethane (1.2 mL) was added 1,1,1-triacetoxy-1,1-dihydro-1,2-benziodoxol-3-(1H)-one (Dess-Martin reagent, 71 mg), and the mixture was stirred at room temperature for 30 min. To the reaction mixture were added saturated aqueous sodium hydrogen carbonate and saturated aqueous sodium thiosulfate solution, and the mixture was extracted twice with ethyl acetate. The combined organic layer was washed twice with saturated aqueous sodium hydrogen carbonate, dried over anhydrous sodium sulfate and filtered. The solvent was evaporated under reduced pressure. The obtained residue was purified by silica gel column chromatography (chloroform:methanol=98:2-90:10) to give the title compound (59 mg) as a pale-yellow viscous compound.

MS(ESI) m/z: 433.3[M+H]+

(5-3) methyl [(6S)-4-(4-{3-[({4-[(3-cyano-4-methyl-1H-indol-7-yl)sulfamoyl]phenyl}methyl)amino]-3-oxoprop-1-yn-1-yl}phenyl)-2,3,9-trimethyl-6H-thieno[3,2-f][1,2,4]triazolo[4,3-a][1,4]diazepin-6-yl]acetate (Example Compound 5)

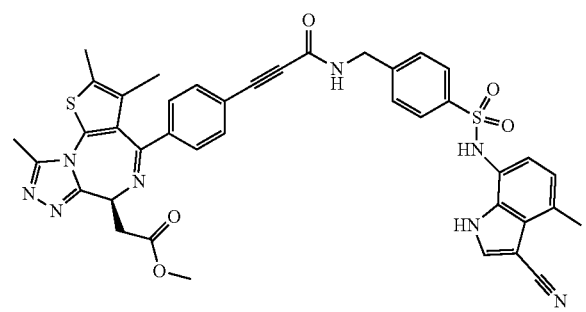

To a solution of Example compound 5-2 (57 mg), 2-methyl-but-2-ene (0.021 mL) in acetonitrile (3.0 mL) was added a solution of 80% sodium chlorite (18 mg) and sodium dihydrogen phosphate (19 mg) in water (1.0 mL), and the mixture was stirred at room temperature for 30 min. To the reaction mixture were added 2-methyl-but-2-ene (0.021 mL), 80% sodium chlorite (18 mg) and sodium dihydrogen phosphate (19 mg) at room temperature, and the mixture was stirred at the same temperature for 30 min more. The reaction mixture was concentrated under reduced pressure, ethanol was added and the mixture was concentrated again under reduced pressure. To the obtained residue were added, at room temperature, Reference Example compound 5 (47 mg), N,N-diisopropylethylamine (0.11 mL) and N,N-dimethylformamide (2.0 mL), and HATU (57 mg) was added lastly. The mixture was stirred at the same temperature for 16 hr. The reaction mixture was diluted with ethyl acetate, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-90:10) to give the title compound (17 mg) as a beige powder.

MS(ESI) m/z: 771.4[M+H]+

Example 6

(6-1) methyl {(6S)-4-[4-(3-aminoprop-1-yn-1-yl)phenyl]-2,3,9-trimethyl-6H-thieno[3,2-f][1,2,4]triazolo[4,3-a][1,4]diazepin-6-yl}acetate (Example Compound 6-1)

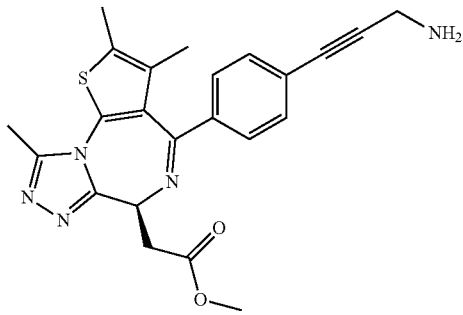 [SMILES: COC(=O)C[C@@H]1N=C(c2ccc(C#CCN)cc2)c2c(sc(C)c2C)-n2c(C)nnc21]

A mixture of Reference Example compound 1 (25 mg), propargylamine (0.019 mL), 2-dicyclohexylphosphino-2',4',6'-triisopropylbiphenyl (X-Phos, 3 mg), X-Phos aminobiphenylpalladium chloride precatalyst (5 mg), potassium phosphate (64 mg) and tetrahydrofuran (0.3 mL) was stirred under a nitrogen atmosphere under microwave irradiation at 90° C. for 2 hr. The reaction mixture was diluted with ethyl acetate, washed twice with water and once with saturated brine, dried over anhydrous sodium sulfate and filtered. The solvent was evaporated under reduced pressure. The residue was purified by silica gel column chromatography (chloroform:methanol=95:5-90:10) to give the title compound (15 mg) as a beige powder.

MS(ESI) m/z: 434.3[M+H]+

(6-2) methyl {(6S)-4-[4-(3-{4-[(3-cyano-4-methyl-1H-indol-7-yl)sulfamoyl]benzamide}prop-1-yn-1-yl)phenyl]-2,3,9-trimethyl-6H-thieno[3,2-f][1,2,4]triazolo[4,3-a][1,4]diazepin-6-yl}acetate (Example Compound 6)

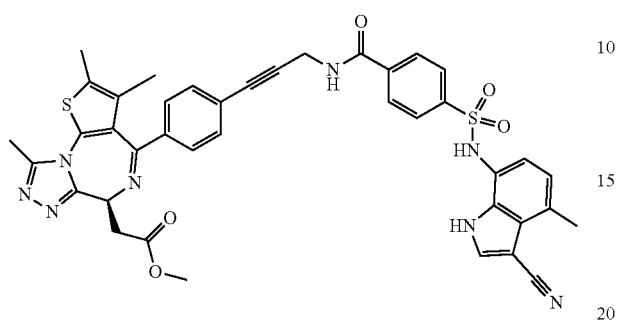

To a solution of Example compound 6-1 (14 mg), Reference Example compound 6 (13 mg) in N,N-dimethylformamide (0.4 mL) were added, at room temperature, N,N-diisopropylethylamine (0.11 mL) and HATU (15 mg), and the mixture was stirred at the same temperature for 1 hr. The reaction mixture was diluted with ethyl acetate, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-90:10) to give the title compound (20 mg) as a white powder.

MS(ESI) m/z: 771.4[M+H]$^+$

Example 7

(7-1) 7-bromo-3-chloro-1H-indole (Example Compound 7-1)

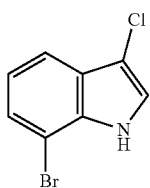 [SMILES: Clc1c[nH]c2c(Br)cccc12]

To a solution of 7-bromo-1H-indole (500 mg) in N,N-dimethylformamide (5.0 mL) was added, at room temperature, N-chlorosuccinimide (358 mg), and the mixture was stirred at the same temperature for 2 hr. To the reaction mixture were added saturated aqueous sodium hydrogen carbonate and saturated aqueous sodium thiosulfate solution, and the mixture was extracted with ethyl acetate. The organic layer was washed with saturated brine, dried over anhydrous sodium sulfate and filtered. The solvent was evaporated under reduced pressure. The obtained residue was purified by silica gel column chromatography (hexane:ethyl acetate=95:5-90:10) to give the title compound (577 mg) as a pale-yellow solid. $^1$H NMR (400 MHz, CDCl$_3$) δ ppm 7.09 (1H, t, J=7.77 Hz), 7.24-7.27 (1H, m), 7.41 (1H, dd, J=7.71, 0.64 Hz), 7.59 (1H, dt, J=7.96, 0.77 Hz), 8.25 (1H, brs)

(7-2) 3-chloro-1H-indole-7-amine (Example Compound 7-2)

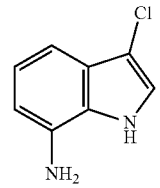 [SMILES: Nc1cccc2c(Cl)c[nH]c12]

By reaction and treatment in the same manner as in Reference Example 9 except that Example compound 7-1 (570 mg) was used instead of Reference Example compound 8, the title compound (163 mg) was obtained as a pale-brown solid.

MS(ESI) m/z: 167.0, 169.0[M+H]$^+$

(7-3) methyl [(6S)-4-{4'-[({4-[(3-chloro-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 7)

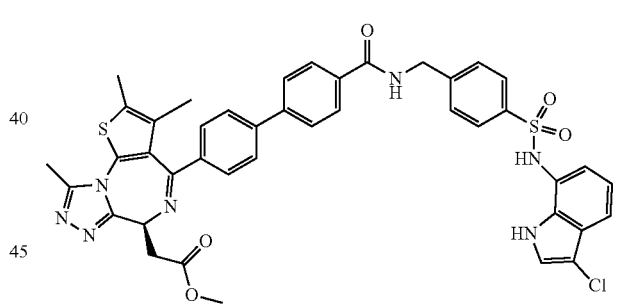

To a solution of Example compound 7-2 (18 mg) and Reference Example compound 10 (50 mg) in tetrahydrofuran (2.0 mL) was added, at room temperature, pyridine (0.060 mL), and the mixture was stirred at the same temperature for 16 hr. The reaction mixture was diluted with ethyl acetate, washed once with 1N hydrochloric acid and once with saturated brine, dried over anhydrous sodium sulfate and filtered. The solvent was evaporated under reduced pressure. The obtained residue was purified by silica gel column chromatography (chloroform:methanol=98:2-90:10) to give the title compound (37 mg) as a white solid.

MS(ESI) m/z: 818.4, 820.4[M+H]$^+$

Example 8

(8-1) 7-bromo-3-chloro-4-methyl-1H-indole (Example Compound 8-1)

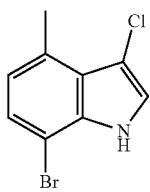

By reaction and treatment in the same manner as in (7-1) except that 7-bromo-4-methyl-1H-indole (200 mg) was used instead of 7-bromo-1H-indole in Example 7, the title compound (212 mg) was obtained as a yellow oil. $^1$H NMR (400 MHz, CDCl$_3$) δ ppm 2.75 (3H, d, J=0.64 Hz), 6.77 (1H, d, J=7.87 Hz), 7.20 (1H, d, J=2.70 Hz), 7.24 (1H, d, J=7.71 Hz), 8.22 (1H, brd, J=1.67 Hz)

(8-2) 3-chloro-4-methyl-1H-indole-7-amine (Example Compound 8-2)

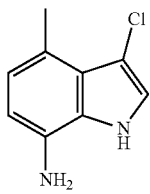

By reaction and treatment in the same manner as in Reference Example 9 except that Example compound 8-1 (205 mg) was used instead of Reference Example compound 8, the title compound (56 mg) was obtained as a pale-brown solid. MS (ESI) m/z: 181.0, 183.0[M+H]$^+$

(8-3) methyl [(6S)-4-{4'-[({4-[(3-chloro-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 8)

By reaction and treatment in the same manner as in (7-3) except that Example compound 8-2 (20 mg) was used instead of Example compound 7-2 and using Reference Example compound 10 (50 mg) in Example 7, the title compound (44 mg) was obtained as a gray powder. MS(ESI) m/z: 832.4, 834.4[M+H]$^+$

Example 9

(9-1) 7-bromo-1H-indole-3-carbonitrile (Example Compound 9-1)

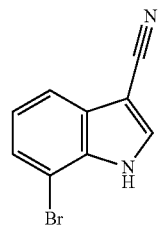 [SMILES: N#Cc1c[nH]c2c(Br)cccc12]

By reaction and treatment in the same manner as in Reference Example 8 except that 7-bromo-1H-indole (500 mg) was used instead of Reference Example compound 7, the title compound (548 mg) was obtained as a pale-brown solid. 1H NMR (400 MHz, CDCl$_3$) δ ppm 7.20 (1H, t, J=7.83 Hz), 7.50 (1H, dd, J=7.71, 0.77 Hz), 7.73 (1H, d, J=7.96 Hz), 7.80 (1H, d, J=2.95 Hz), 8.84 (1H, brs)

(9-2) 7-amino-1H-indole-3-carbonitrile (Example Compound 9-2)

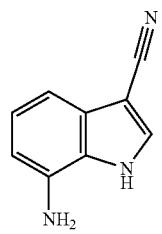 [SMILES: N#Cc1c[nH]c2c(N)cccc12]

By reaction and treatment in the same manner as in Reference Example 9 except that Example compound 9-1

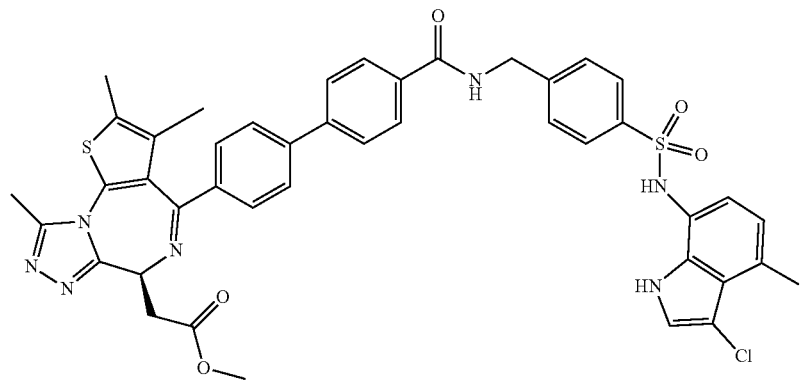

(542 mg) was used instead of Reference Example compound 8, the title compound (322 mg) was obtained as a pale-brown solid. 1H NMR (400 MHz, DMSO-d6) δ ppm 5.33 (2H, s), 6.47 (1H, dd, J=7.58, 0.90 Hz), 6.81 (1H, dd, J=7.96, 0.90 Hz), 6.94 (1H, t, J=7.77 Hz), 8.13 (1H, s), 11.73 (1H, brs)

(9-3) methyl [(6S)-4-{4'-[({4-[(3-cyano-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 9)

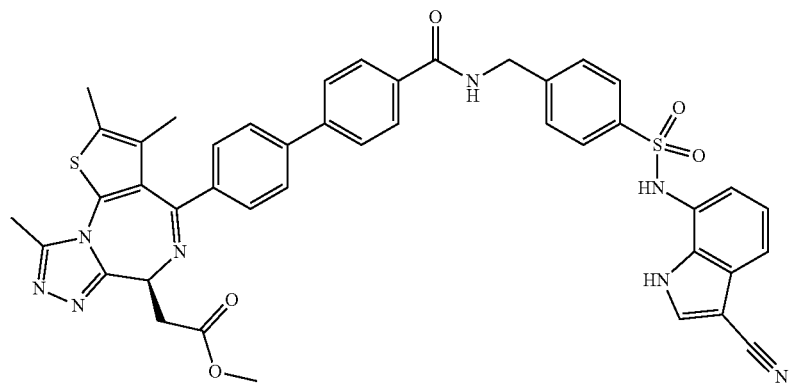 [SMILES: COC(=O)C[C@@H]1N=C(c2ccc(-c3ccc(C(=O)NCc4ccc(S(=O)(=O)Nc5cccc6c(C#N)c[nH]c56)cc4)cc3)cc2)c2c(sc(C)c2C)-n2c(C)nnc21]

By reaction and treatment in the same manner as in (7-3) except that Example compound 9-2 (15 mg) was used instead of Example compound 7-2 in Example 7, the title compound (40 mg) was obtained as a beige powder. MS(ESI) m/z: 809.4[M+H]$^+$ Example 10

(10-1) 4-methyl-1H-indole-7-amine (Example Compound 10-1)

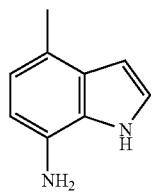

By reaction and treatment in the same manner as in Reference Example 9 except that Reference Example compound 7 (92 mg) was used instead of Reference Example compound 8, the title compound (29 mg) was obtained as a pale-brown solid.

MS(ESI) m/z: 147.1[M+H]$^+$ (10-2) methyl [(6S)-2,3,9-trimethyl-4-{4'-[({4-[(4-methyl-1H-indol-7-yl)sulfamoyl]phenyl}methyl)carbamoyl][1,1'-biphenyl]-4-yl}-6H-thieno[3,2-f][1,2,4]triazolo[4,3-a][1,4]diazepin-6-yl]acetate (Example Compound 10)

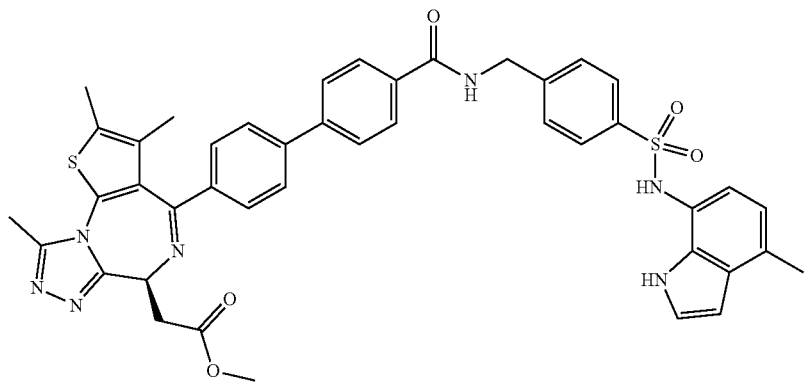

By reaction and treatment in the same manner as in (7-3) except that Example compound 10-1 (28 mg) was used instead of Example compound 7-2 and using Reference Example compound 10 (120 mg) in Example 7, the title compound (107 mg) was obtained as a beige powder. MS(ESI) m/z: 798.5[M+H]$^+$ Example 11

(11-1) methyl [(6S)-4-{4'-[(2-{4-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 11)

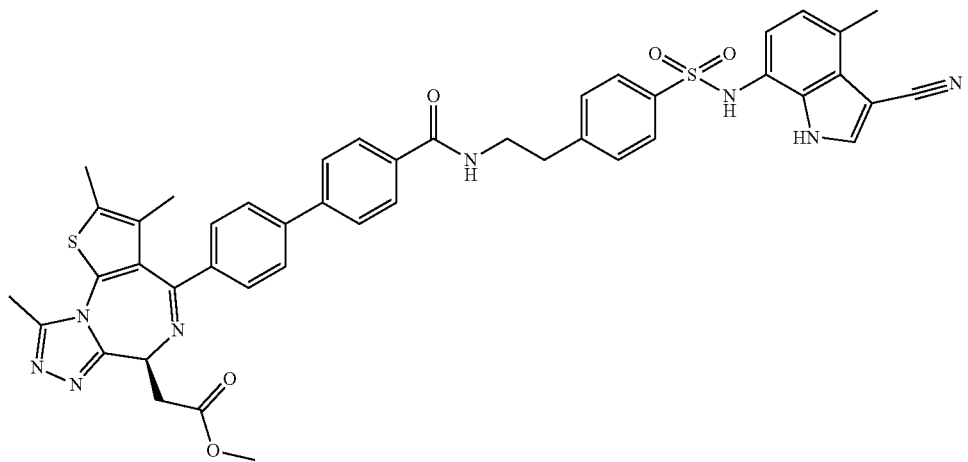 [SMILES: COC(=O)C[C@@H]1N=C(c2ccc(-c3ccc(C(=O)NCCc4ccc(S(=O)(=O)Nc5ccc(C)c6c(C#N)c[nH]c56)cc4)cc3)cc2)c2c(sc(C)c2C)-n2c(C)nnc21]

A mixture of Reference Example compound 4 (75 mg), Reference Example compound 11 (65 mg), N,N-diisopropylethylamine (0.078 mL), HATU (86 mg) was stirred in N,N-dimethylformamide (3.0 mL) at room temperature for 2 hr. To the reaction mixture was added water, the mixture was stirred, and the resulting solid was collected by filtration. The solid was purified by silica gel column chromatography (chloroform:methanol=100:0-95:5) to give the title compound (115 mg) as a pale-yellow solid. MS(ESI) m/z: 837.4[M+H]$^+$

Example 12

(12-1) methyl 3-[(3-cyano-4-methyl-1H-indol-7-yl)sulfamoyl]benzoate (Example Compound 12-1)

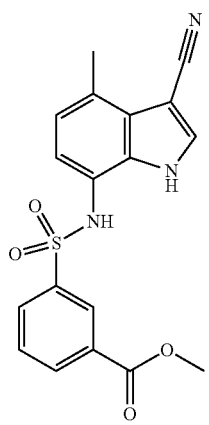 [SMILES: COC(=O)c1cccc(S(=O)(=O)Nc2ccc(C)c3c(C#N)c[nH]c23)c1]

Reference Example compound 9 (200 mg), methyl 3-(chlorosulfonyl)benzoate (302 mg), triethylamine (0.33 mL) were stirred in chloroform (5.0 mL) at room temperature for 7 hr. To the reaction mixture was added water, and the mixture was stirred, the aqueous layer was removed by PhaseSeparator, and the organic layer was concentrated under reduced pressure. The residue was purified by silica gel column chromatography (hexane:ethyl acetate=70:30-30:70), and silica gel column chromatography (chloroform:methanol=100:0-95:5) to give the title compound (190 mg) as a pale-yellow solid.
MS(ESI) m/z: 370.3[M+H]$^+$

(12-2) N-(3-cyano-4-methyl-1H-indol-7-yl)-3-(hydroxymethyl)benzene-1-sulfonamide (Example Compound 12-2)

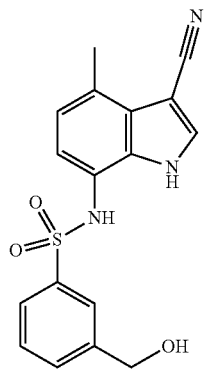 [SMILES: Cc1ccc(NS(=O)(=O)c2cccc(CO)c2)c2[nH]cc(C#N)c12]

A solution of Example compound 12-1 (190 mg) in tetrahydrofuran (5.0 mL) was cooled to 0° C., 2M lithium borohydride/tetrahydrofuran solution (0.77 mL) and methanol (0.063 mL) were added, and the mixture was stirred for 4 hr while allowing to naturally warm to room temperature. 2M Lithium borohydride/tetrahydrofuran solution (0.77 mL) was added, and the mixture was stirred at room temperature for 3 hr. To the reaction mixture was added 1N hydrochloric acid by small portions, and the mixture was stirred, then chloroform was added and the mixture was stirred. The aqueous layer was removed by PhaseSeparator, and the organic layer was concentrated under reduced pressure. The residue was purified by silica gel column chromatography (chloroform:methanol=100:0-95:5) to give the title compound (124 mg) as a white solid.
MS(ESI) m/z: 342.1[M+H]$^+$

(12-3) 3-(azidomethyl)-N-(3-cyano-4-methyl-1H-indol-7-yl)benzene-1-sulfonamide (Example Compound 12-3)

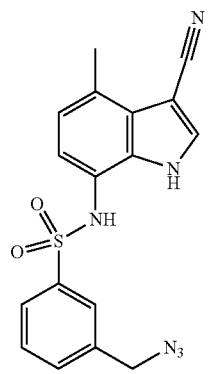 [SMILES: Cc1ccc(NS(=O)(=O)c2cccc(CN=[N+]=[N-])c2)c2[nH]cc(C#N)c12]

To a solution of Example compound 12-2 (124 mg) in tetrahydrofuran (5.0 mL) were added 2-azido-1,3-dimethylimidazolinium hexafluorophosphate (207 mg), and 1,8-diazabicyclo[5.4.0]-7-undecene (111 mg), and the mixture was stirred at room temperature for 4 hr. To the reaction mixture were added 1N hydrochloric acid and ethyl acetate and the mixture was stirred. The organic layer was separated, washed twice with brine, and concentrated under reduced pressure. The residue was purified by silica gel column chromatography (hexane:ethyl acetate=80:20-50:50) to give the title compound (69 mg) as a white solid.
MS(ESI) m/z: 367.1[M+H]$^+$

(12-4) 3-(aminomethyl)-N-(3-cyano-4-methyl-1H-indol-7-yl)benzene-1-sulfonamide (Example Compound 12-4)

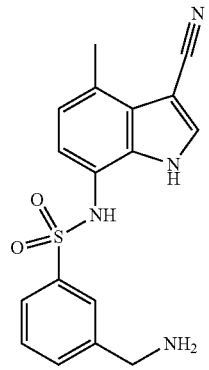

Example compound 12-3 (69 mg), triphenylphosphine (64 mg) and water (0.5 mL) were stirred in tetrahydrofuran (5.0 mL) at 50° C. for 6 hr. The reaction mixture was concentrated under reduced pressure, and the resulting solid was suspended and washed with chloroform. The solid was collected by filtration, and dried to give the title compound (60 mg) as a white solid.
MS(ESI) m/z: 341.1[M+H]$^+$ (12-5) methyl [(6S)-4-{4'-[({3-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 12)

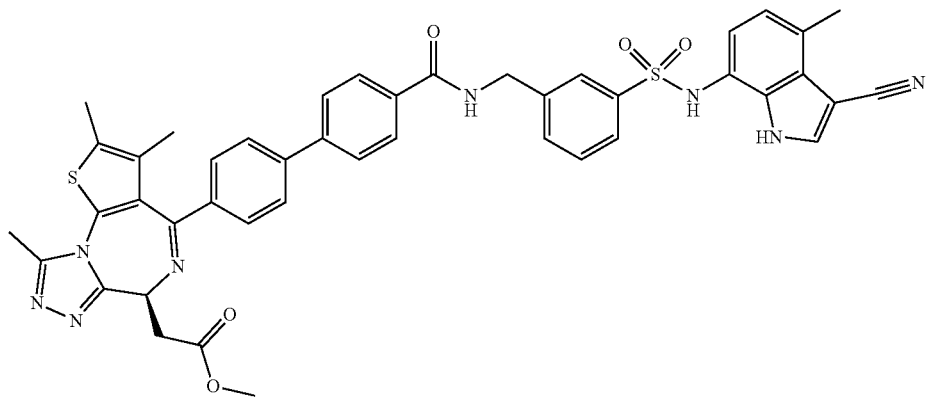 [SMILES: COC(=O)C[C@@H]1N=C(c2ccc(-c3ccc(C(=O)NCc4cccc(S(=O)(=O)Nc5ccc(C)c6c(C#N)c[nH]c56)c4)cc3)cc2)c2c(sc(C)c2C)-n2c(C)nnc21]

By reaction and treatment in the same manner as in (11-1) except that Example compound 12-4 was used instead of Reference Example compound 11 in Example 11, the title compound was obtained as a white solid. MS(ESI) m/z: 823.4[M+H]$^+$ Example 13

(13-1) 7-bromo-6-methyl-1H-indole (Example Compound 13-1)

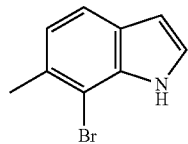

By reaction and treatment in the same manner as in Reference Example 7 except that 2-bromo-3-nitrotoluene (2160 mg) was used instead of 1-bromo-4-methyl-2-nitrobenzene, the title compound (1108 mg) was obtained as a white solid. $^1$H NMR (400 MHz, CDCl$_3$) δ ppm 2.52 (3H, s), 6.58 (1H, dd, J=3.21, 2.18 Hz), 7.00 (1H, d, J=7.96 Hz), 7.19 (1H, dd, J=3.08, 2.44 Hz), 7.46 (1H, d, J=7.96 Hz), 8.27 (1H, brs)

(13-2) 7-bromo-6-methyl-1H-indole-3-carbonitrile (Example Compound 13-2)

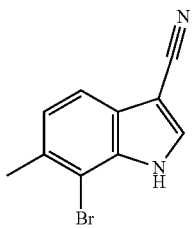

By reaction and treatment in the same manner as in Reference Example 8 except that Example compound 13-1 (500 mg) was used instead of Reference Example compound 7, the title compound (461 mg) was obtained as a beige solid. $^1$H NMR (400 MHz, CDCl$_3$) δ ppm 2.54 (3H, s), 7.19 (1H, d, J=8.1 Hz), 7.61 (1H, d, J=8.1 Hz), 7.72 (1H, d, J=2.8 Hz), 8.72 (1H, brs)

(13-3) 7-amino-6-methyl-1H-indole-3-carbonitrile (Example Compound 13-3)

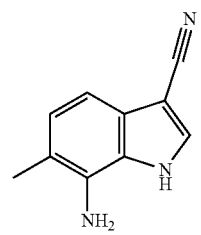

By reaction and treatment in the same manner as in Reference Example 9 except that Example compound 13-2 (455 mg) was used instead of Reference Example compound 8, the title compound (146 mg) was obtained as a white solid.

MS(ESI) m/z: 172.1[M+H]$^+$ (13-4) methyl [(6S)-4-{4'-[({4-[(3-cyano-6-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 13)

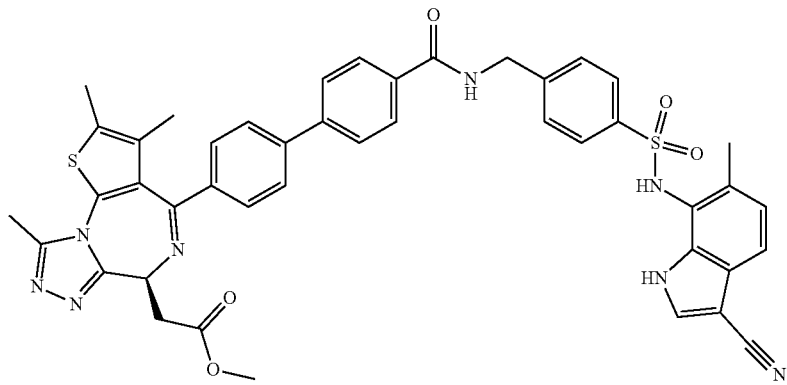 [SMILES: COC(=O)C[C@@H]1N=C(c2ccc(-c3ccc(C(=O)NCc4ccc(S(=O)(=O)Nc5c(C)ccc6c(C#N)c[nH]c56)cc4)cc3)cc2)c2c(sc(C)c2C)-n2c(C)nnc21]

By reaction and treatment in the same manner as in Example 7 except that Example compound 13-3 (17 mg) was used instead of Example compound 7-2 and using Reference Example compound 10 (60 mg), the title compound (34 mg) was obtained as a white powder. MS(ESI) m/z: 823.5[M+H]$^+$ Example 14

(14-1) methyl [(6S)-4-{4'-[({4-[(4-chloro-3-cyano-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 14)

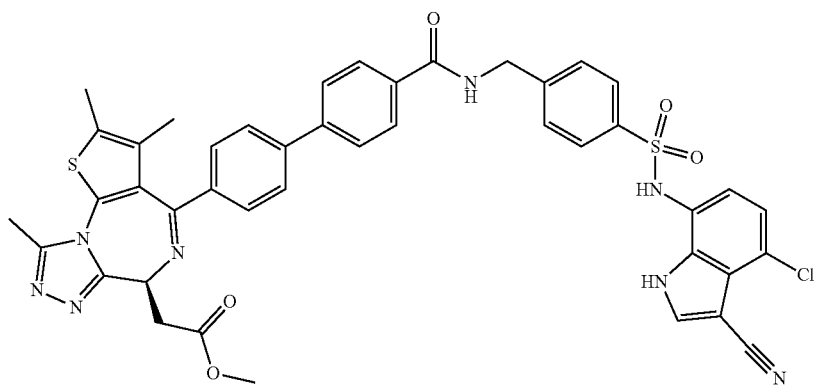 [SMILES: COC(=O)C[C@@H]1N=C(c2ccc(-c3ccc(C(=O)NCc4ccc(S(=O)(=O)Nc5ccc(Cl)c6c(C#N)c[nH]c56)cc4)cc3)cc2)c2c(sc(C)c2C)-n2c(C)nnc21]

By reaction and treatment in the same manner as in (13-1)-(13-4) except that 1-bromo-4-chloro-2-nitrobenzene was used instead of 2-bromo-3-nitrotoluene in Example 13, the title compound was obtained as a white solid.

MS(ESI) m/z: 843.4, 845.5[M+H]$^+$

Example 15

(15-1) methyl [(6S)-4-{4'-[({4-[(3-cyano-4-methoxy-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl] acetate (Example Compound 15)

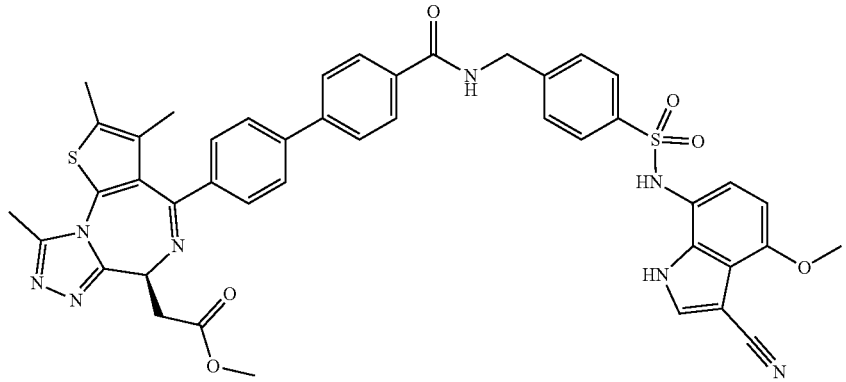

By reaction and treatment in the same manner as in (13-1)-(13-4) except that 4-bromo-3-nitroanisole was used instead of 2-bromo-3-nitrotoluene in Example 13, the title compound was obtained as a purple solid. MS(ESI) m/z: 839.5[M+H]$^+$

Example 16

(16-1) methyl [(6S)-4-{4'-[({4-[(2,3-dimethyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 16)

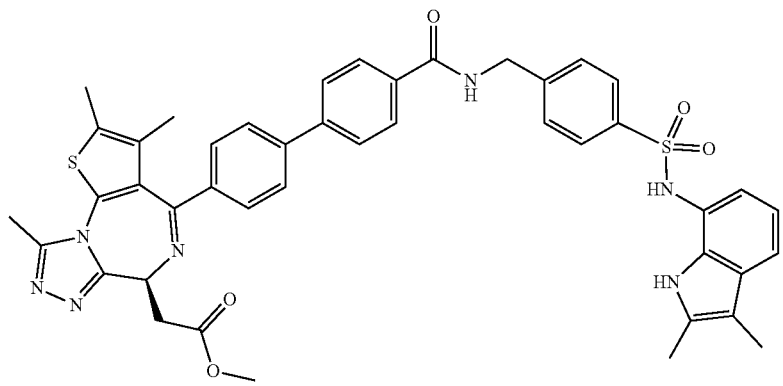 [SMILES: COC(=O)C[C@@H]1N=C(c2ccc(-c3ccc(C(=O)NCc4ccc(S(=O)(=O)Nc5cccc6c(C)c(C)[nH]c56)cc4)cc3)cc2)c2c(sc(C)c2C)-n2c(C)nnc21]

By reaction and treatment in the same manner as in (7-3) except that 2,3-dimethyl-1H-indole-7-amine (17 mg) was used instead of Example compound 7-2 and using Reference Example compound 10 (50 mg) in Example 7, the title compound (22 mg) was obtained as a brown solid. MS(ESI) m/z: 812.5[M+H]$^+$

Example 17

(17-1) methyl [(6S)-4-{4'-[({4-[(3-cyano-4-fluoro-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 17)

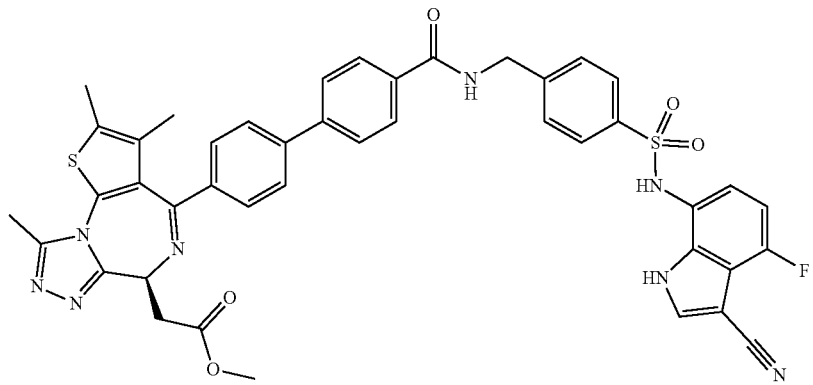 [SMILES: COC(=O)C[C@@H]1N=C(c2ccc(-c3ccc(C(=O)NCc4ccc(S(=O)(=O)Nc5ccc(F)c6c(C#N)c[nH]c56)cc4)cc3)cc2)c2c(sc(C)c2C)-n2c(C)nnc21]

By reaction and treatment in the same manner as in (13-1)-(13-4) except that 1-bromo-4-fluoro-2-nitrobenzene was used instead of 2-bromo-3-nitrotoluene in Example 13, the title compound was obtained as a beige powder.
MS(ESI) m/z: 827.5[M+H]$^+$

Example 18

(18-1) methyl [(6S)-4-(4'-{[(4-{[3-cyano-4-(trifluoromethyl)-1H-indol-7-yl]sulfamoyl}phenyl)methyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 18)

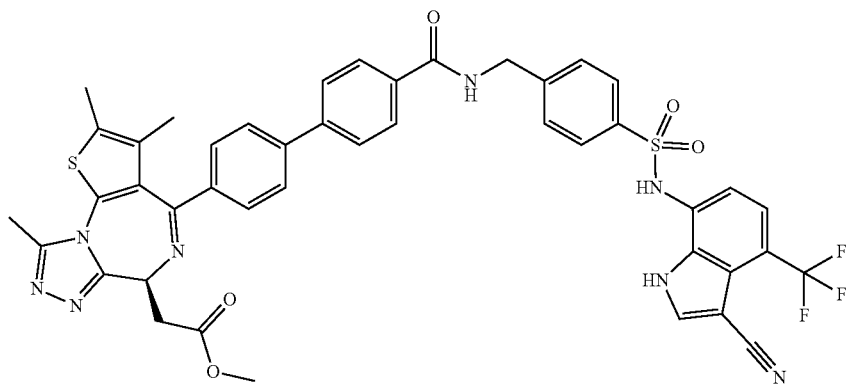 [SMILES: COC(=O)C[C@@H]1N=C(c2ccc(-c3ccc(C(=O)NCc4ccc(S(=O)(=O)Nc5ccc(C(F)(F)F)c6c(C#N)c[nH]c56)cc4)cc3)cc2)c2c(sc(C)c2C)-n2c(C)nnc21]

By reaction and treatment in the same manner as in (13-1)-(13-4) except that 1-bromo-2-nitro-4-trifluoromethylbenzene was used instead of 2-bromo-3-nitrotoluene in Example 13, the title compound was obtained as a white powder.
MS(ESI) m/z: 877.5[M+H]$^+$

Example 19

(19-1) methyl [(6S)-4-{4'-[({4-[(3-cyano-5-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 19)

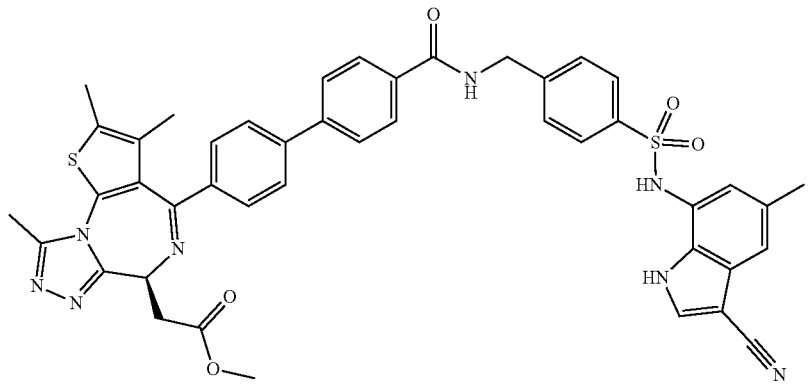

By reaction and treatment in the same manner as in (13-1)-(13-4) except that 3-bromo-4-nitrotoluene was used instead of 2-bromo-3-nitrotoluene in Example 13, the title compound was obtained as a white powder. MS(ESI) m/z: 823.5[M+H]$^+$

Example 20

(20-1) methyl 5-[(3-cyano-4-methyl-1H-indol-7-yl)sulfamoyl]pyridine-2-carboxylate (Example Compound 20-1)

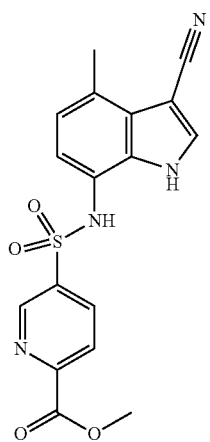 [SMILES: COC(=O)c1ccc(S(=O)(=O)Nc2ccc(C)c3c(C#N)c[nH]c23)cn1]

Reference Example compound 9 (300 mg), methyl 5-(chlorosulfonyl)pyridine-2-carboxylate (454 mg), pyridine (0.71 mL) were stirred in tetrahydrofuran (5.0 mL) at room temperature for 4 hr. To the reaction mixture were added ethyl acetate and 1N hydrochloric acid, and the mixture was stirred, and the resulting solid was collected by filtration. To the solid were added saturated aqueous sodium hydrogen carbonate, and tetrahydrofuran, and the mixture was stirred and chloroform was added. The aqueous layer was removed by PhaseSeparator, and the organic layer was concentrated under reduced pressure. The residue was suspended and washed with diethyl ether and collected by filtration to give the title compound (210 mg) as a yellow solid. MS(ESI) m/z: 371.1[M+H]$^+$ (20-2) 6-(azidomethyl)-N-(3-cyano-4-methyl-1H-indol-7-yl)pyridine-3-sulfonamide (Example Compound 20-2)

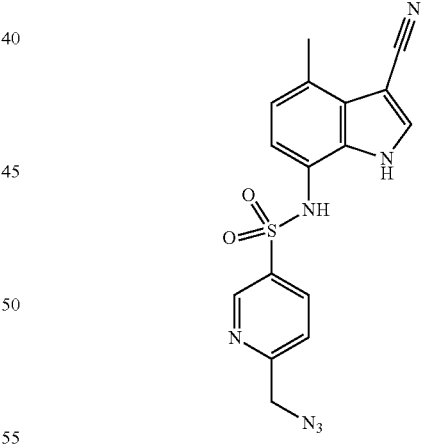

Under a nitrogen stream, to a suspension of Example compound 20-1 (210 mg) in tetrahydrofuran (5.0 mL) was added 2M lithium borohydride/tetrahydrofuran solution (1.14 mL) and the mixture was stirred at room temperature for 5 hr. To the reaction mixture was added saturated aqueous ammonium chloride solution, and the mixture was stirred, then chloroform was added and the mixture was stirred. The aqueous layer was removed by PhaseSeparator, and the organic layer was concentrated under reduced pressure. The residue was purified by silica gel column chromatography (chloroform:methanol=100:0-95:5) to give a white solid (75 mg). The solid, 2-azido-1,3-dimethylimidazolinium hexafluorophosphate (125 mg), and 1,8-diazabicyclo[5.4.0]-7-undecene (0.066 mL) were stirred in tetrahydrofuran (5.0 mL) at room temperature for 2 hr. To the reaction mixture were added saturated aqueous ammonium chloride solution and chloroform and the mixture was stirred. The aqueous layer was removed by PhaseSeparator, and the organic layer was concentrated under reduced pressure. The residue was purified by silica gel column chromatography (hexane:ethyl acetate=70:30-30:70) to give the title compound (63 mg) as a white solid. MS(ESI) m/z: 368.2[M+H]$^+$ (20-3) 6-(aminomethyl)-N-(3-cyano-4-methyl-1H-indol-7-yl)pyridine-3-sulfonamide (Example Compound 20-3)

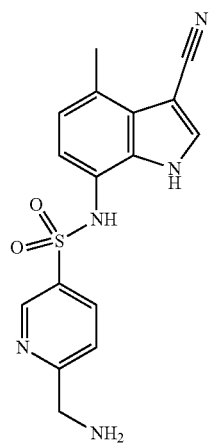 [SMILES: Cc1ccc(NS(=O)(=O)c2ccc(CN)nc2)c2[nH]cc(C#N)c12]

By reaction and treatment in the same manner as in (12-4) except that Example compound 20-2 (63 mg) was used instead of Example compound 12-3 in Example 12, the title compound (24 mg) was obtained as a white solid. MS(ESI) m/z: 342.1[M+H]$^+$ (20-4) methyl [(6S)-4-{4'-[({5-[(3-cyano-4-methyl-1H-indol-7-yl)sulfamoyl]pyridin-2-yl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 20)

By reaction and treatment in the same manner as in (11-1) except that Example compound 20-3 was used instead of Reference Example compound 11 in Example 11, the title compound was obtained as a pale-yellow solid. MS(ESI) m/z: 824.3[M+H]$^+$ Example 21

(21-1) t-butyl 4-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-3,6-dihydropyridine-1(2H)-carboxylate (Example Compound 21-1)

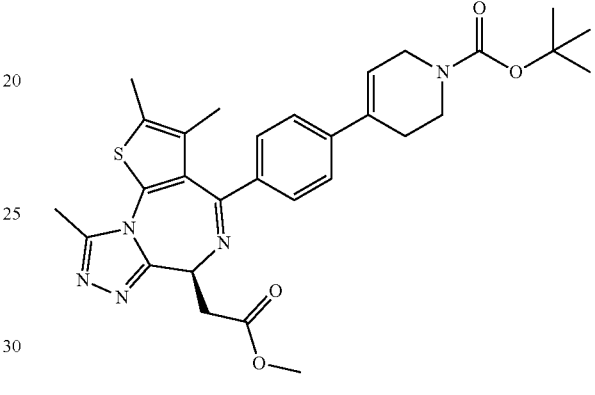

Under an argon stream, Reference Example compound 1 (500 mg), N-(t-butoxycarbonyl)-1,2,3,6-tetrahydropyridine-4-boronic acid pinacol ester (447 mg), palladium acetate (7.1 mg), S-phos (99 mg), potassium fluoride (210 mg) and water (0.078 mL) were heated under reflux in tetrahydrofuran (5.0 mL) solvent for 7 hr. Using ethyl acetate, the reaction mixture was filtered through diatomaceous earth, and the filtrate was concentrated under reduced pressure. The residue was purified by NH silica gel column chromatography (hexane:ethyl acetate=70:30-20:80) to give the title compound (680 mg) as a pale-yellow solid.

MS(ESI) m/z: 562.5[M+H]$^+$

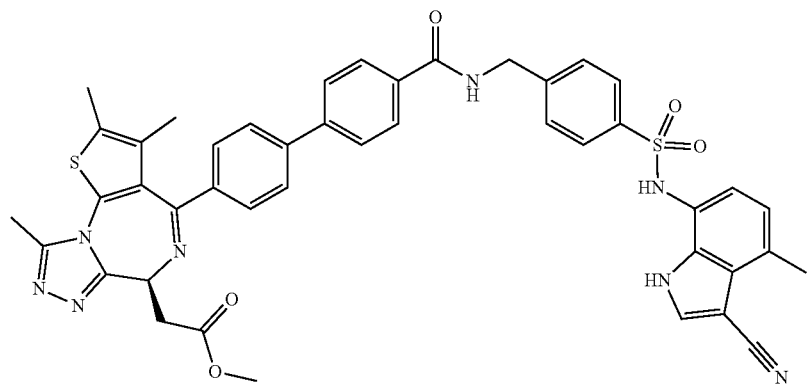

(21-2) methyl {(6S)-2,3,9-trimethyl-4-[4-(1,2,3,6-tetrahydropyridin-4-yl)phenyl]-6H-thieno[3,2-f][1,2,4]triazolo[4,3-a][1,4]diazepin-6-yl}acetate hydrochloride (Example Compound 21-2)

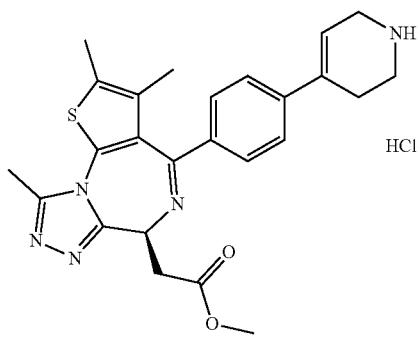 [SMILES: COC(=O)C[C@@H]1N=C(c2ccc(C3=CCNCC3)cc2)c2c(sc(C)c2C)-n2c(C)nnc21 ; Cl]

To a solution of Example compound 21-1 (217 mg) in methanol (0.5 mL) was added 4M hydrogen chloride/1,4-dioxane solution (2.0 mL), and the mixture was stirred at room temperature for 1 hr. The reaction mixture was concentrated under reduced pressure, and the residue was suspended and washed with diisopropyl ether, collected by filtration and dried to give the title compound (198 mg) as a yellow solid.

MS(ESI) m/z: 462.2[M+H]$^+$ (21-3) methyl [(6S)-4-(4-{1-[({4-[(3-cyano-4-methyl-1H-indol-7-yl)sulfamoyl]phenyl}methyl)carbamoyl]-1,2,3,6-tetrahydropyridin-4-yl}phenyl)-2,3,9-trimethyl-6H-thieno[3,2-f][1,2,4]triazolo[4,3-a][1,4]diazepin-6-yl]acetate (Example Compound 21)

To a solution of triphosgene (22 mg) in tetrahydrofuran (3.0 mL) were added Reference Example compound 5 (68 mg) and N,N-diisopropylethylamine (0.11 mL), and the mixture was stirred at room temperature for 15 min. Then, Example compound 21-2 (100 mg) and N,N-dimethylformamide (0.5 mL) were added, and the mixture was stirred at room temperature for 2 hr. To the reaction mixture was added water, and the mixture was stirred, extracted 3 times with ethyl acetate, and the organic layer was concentrated under reduced pressure. The residue was purified by silica gel column chromatography (chloroform:methanol=100:0-95:5), and suspended and washed with diethyl ether, collected by filtration and dried to give the title compound (60 mg) as a milk-white powder.

MS(ESI) m/z: 828.4[M+H]$^+$

Example 22

(22-1) 7-bromo-1H-indole-4-carbonitrile (Example Compound 22-1)

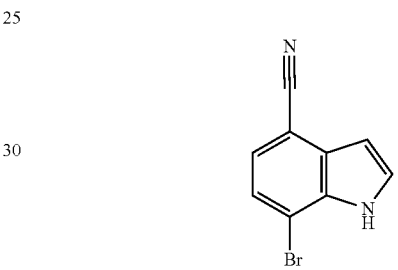

By reaction and treatment in the same manner as in Reference Example 7 except that 4-bromo-3-benzonitrile (2270 mg) was used instead of 1-bromo-4-methyl-2-nitrobenzene, the title compound (540 mg) was obtained as a pale-yellow solid. $^1$H NMR (400 MHz, CDCl$_3$) δ ppm 6.86 (1H, dd, J=3.21, 2.18 Hz), 7.36 (1H, d, J=8.35 Hz), 7.41 (1H, d, J=7.83 Hz), 7.46 (1H, t, J=3.21 Hz), 8.65 (1H, brs)

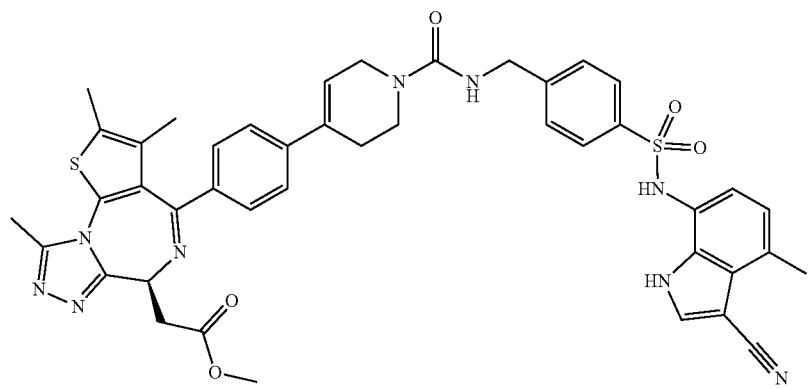

(22-2) 7-amino-1H-indole-4-carbonitrile (Example Compound 22-2)

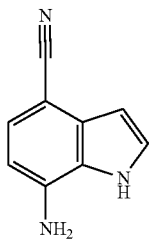

By reaction and treatment in the same manner as in Reference Example 9 except that Example compound 22-1 (100 mg) was used instead of Reference Example compound 8, the title compound (53 mg) was obtained as a pale-yellow solid. $^1$H NMR (400 MHz, DMSO-d6) δ ppm 6.06 (2H, s), 6.34-6.41 (2H, m), 7.22 (1H, d, J=7.96 Hz), 7.49 (1H, t, J=2.83 Hz), 11.15 (1H, brs)

(22-3) methyl [(6S)-4-{4'-[({4-[(4-cyano-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 22)

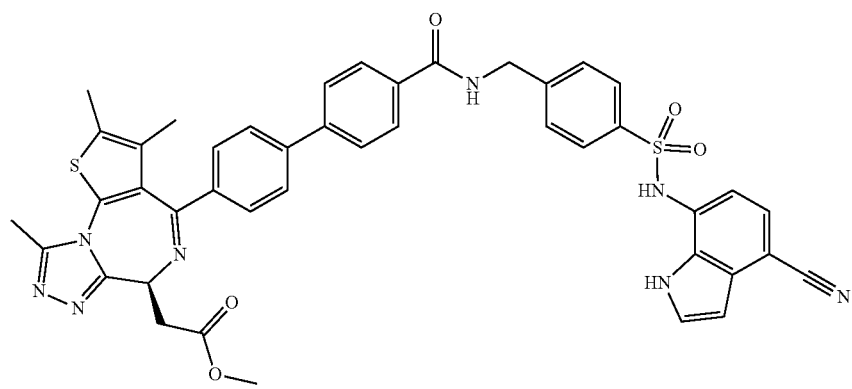 [SMILES: COC(=O)C[C@@H]1N=C(c2ccc(-c3ccc(C(=O)NCc4ccc(S(=O)(=O)Nc5ccc(C#N)c6cc[nH]c56)cc4)cc3)cc2)c2c(sc(C)c2C)-n2c(C)nnc21]

By reaction and treatment in the same manner as in (7-3) except that Example compound 22-2 (29 mg) was used instead of Example compound 7-2 and using Reference Example compound 10 (80 mg) in Example 7, the title compound (26 mg) was obtained as a white powder. MS(ESI) m/z: 809.4[M+H]$^+$ Example 23

(23-1) 7-bromo-1H-indole-3,4-dicarbonitrile (Example Compound 23-1)

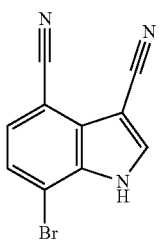 [SMILES: N#Cc1ccc(Br)c2[nH]cc(C#N)c12]

By reaction and treatment in the same manner as in Reference Example 8 except that Example compound 22-1 (100 mg) was used instead of Reference Example compound 7, the title compound (48 mg) was obtained as a pale-yellow solid.

MS(ESI) m/z: 246.0, 248.0[M+H]$^+$

By reaction and treatment in the same manner as in (7-3) except that Example compound 23-2 (9.4 mg) was used instead of Example compound 7-2 and using Reference Example compound 10 (72 mg) in Example 7, the title compound (15 mg) was obtained as a pale-yellow powder.

MS(ESI) m/z: 834.5[M+H]$^+$

Example 24

(23-2) 7-amino-1H-indole-3,4-dicarbonitrile (Example Compound 23-2)

(24-1) N-(3-{4-[(3-cyano-4-methyl-1H-indol-7-yl)sulfamoyl]phenyl}propyl)-2,2,2-trifluoroacetamide (Example Compound 24-1)

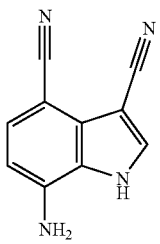 [SMILES: N#Cc1ccc(N)c2[nH]cc(C#N)c12]

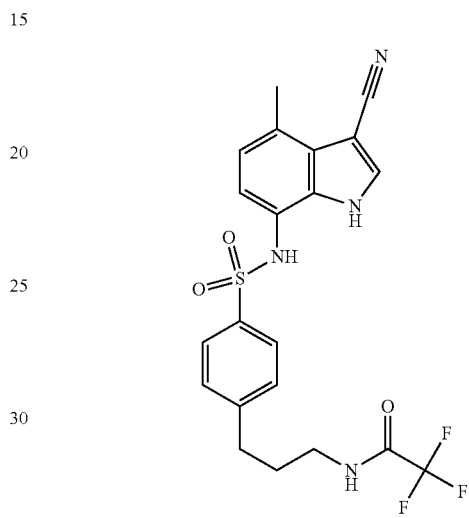

By reaction and treatment in the same manner as in Reference Example 9 except that Example compound 23-1 (45 mg) was used instead of Reference Example compound 8, the title compound (10 mg) was obtained as a pale-yellow solid.

MS(ESI) m/z: 183.1[M+H]$^+$ (23-3) methyl [(6S)-4-{4'-[({4-[(3,4-dicyano-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 23)

By reaction and treatment in the same manner as in (20-1) except that 4-[3-(trifluoroacetamido)propyl]benzenesulfonyl chloride was used instead of methyl 5-(chlorosulfonyl)pyridine-2-carboxylate in Example 20, the title compound was obtained as a brown powder. MS(ESI) m/z: 465.2[M+H]$^+$

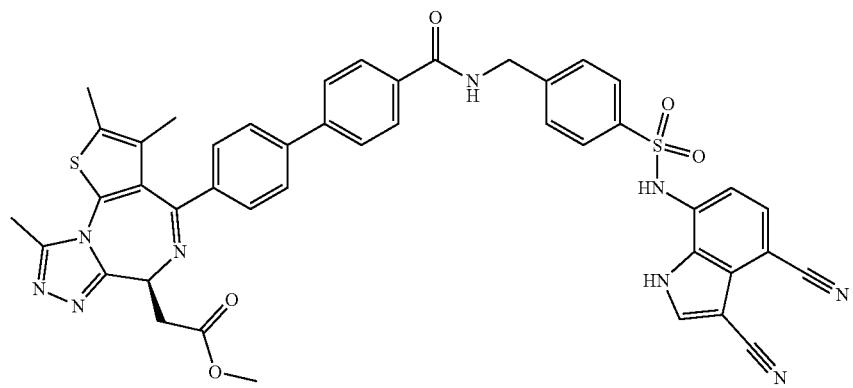 [SMILES: COC(=O)C[C@@H]1N=C(c2ccc(-c3ccc(C(=O)NCc4ccc(S(=O)(=O)Nc5ccc(C#N)c6c(C#N)c[nH]c56)cc4)cc3)cc2)c2c(sc(C)c2C)-n2c(C)nnc21]

151

(24-2) 4-(3-aminopropyl)-N-(3-cyano-4-methyl-1H-indol-7-yl)benzene-1-sulfonamide (Example Compound 24-2)

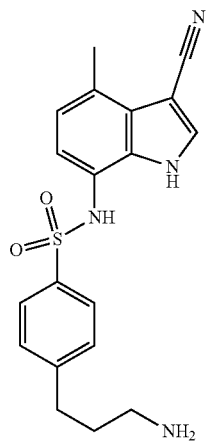 [SMILES: Cc1ccc(NS(=O)(=O)c2ccc(CCCN)cc2)c2[nH]cc(C#N)c12]

Example compound 24-1 (610 mg), potassium carbonate (545 mg), water (0.8 mL) were stirred in methanol (8.0 mL) at room temperature for 2 hr. Methanol was evaporated under reduced pressure, water was added and the mixture was stirred. 1N Hydrochloric acid (5 mL) was added and the mixture was stirred, and the resulting solid was collected by filtration. The solid was suspended and washed with water, and dried to give a gray solid. To the solid were added potassium carbonate (273 mg), water (0.5 mL), and methanol (5.0 mL), and the mixture was heated under reflux for 6 hr. Methanol was evaporated under reduced pressure, water was added and the mixture was stirred. 1N Hydrochloric acid was added, the mixture was stirred, and the resulting solid was collected by filtration. The solid was suspended and washed with water, collected by filtration, and dried to give the title compound (453 mg) as a gray solid.
MS(ESI) m/z: 369.2[M+H]$^+$ (24-3) methyl [(6S)-4-{4'-[(3-{4-[(3-cyano-4-methyl-1H-indol-7-yl)sulfamoyl]phenyl}propyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 24)

152

By reaction and treatment in the same manner as in (11-1) except that Example compound 24-2 was used instead of Reference Example compound 11 in Example 11, the title compound was obtained as a beige solid. MS(ESI) m/z: 851.7[M+H]$^+$ Example 25

(25-1) methyl {(6S)-4-[4'-({[4-(chlorosulfonyl)-3-fluorophenyl]methyl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 25-1)

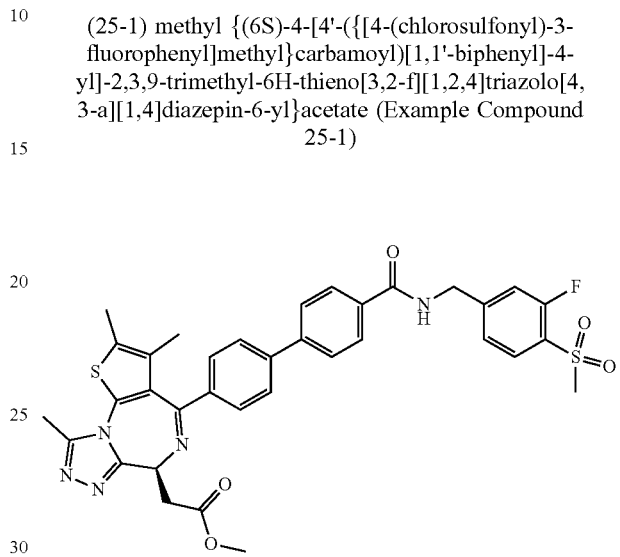

By reaction and treatment in the same manner as in (10-1)-(10-3) except that 4-bromo-3-fluorophenylmethanamine hydrochloride was used instead of 4-bromobenzylamine in Reference Example 10, the title compound was obtained as a pale-yellow powder. MS(ESI) m/z: 688.4[M−Cl+H$_2$O]$^+$

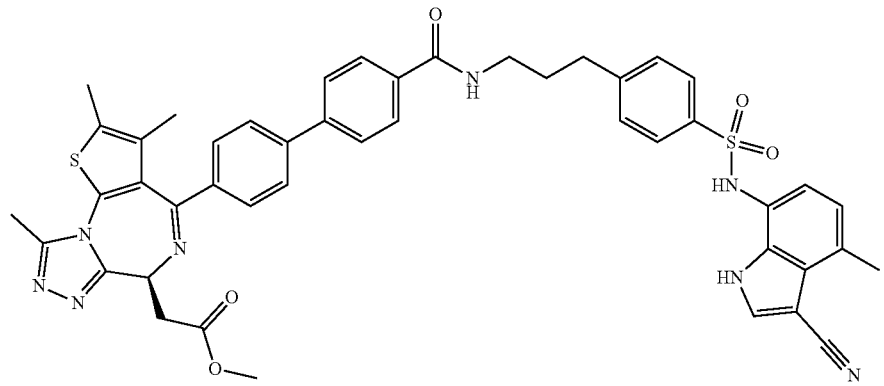

(25-2) methyl [(6S)-4-{4'-[({4-[(3-cyano-4-methyl-1H-indol-7-yl)sulfamoyl]-3-fluorophenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 25)

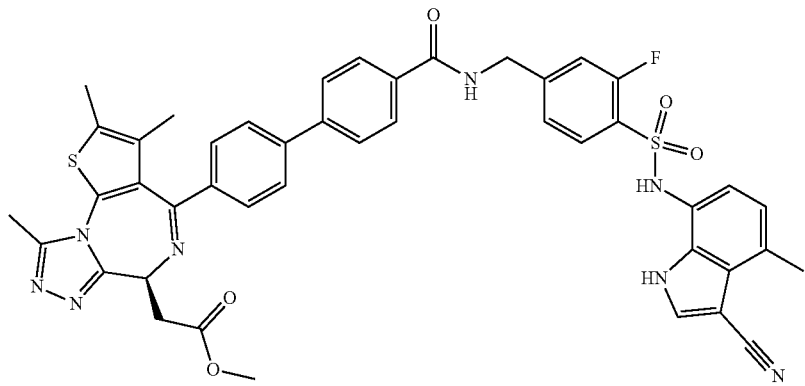

By reaction and treatment in the same manner as in (7-3) except that Reference Example compound 9 (26 mg) was used instead of Example compound 7-2, and Example compound 25-1 (97 mg) instead of Example compound 10 in Example 7, the title compound (69 mg) was obtained as a beige powder.

MS(ESI) m/z: 841.5[M+H]$^+$

Example 26

(26-1) methyl [(6S)-4-(4'-{[(1R)-1-(4-bromophenyl)ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 26-1)

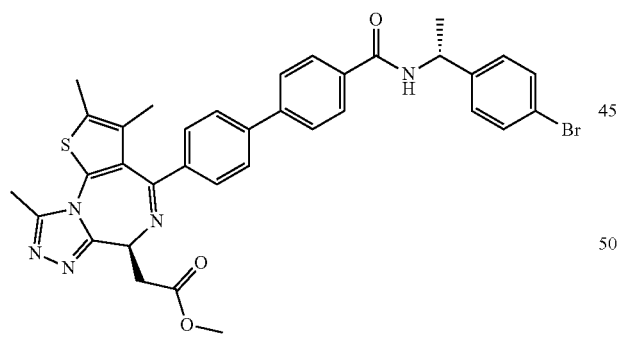

A mixed solution of Reference Example compound 4 (100 mg), (1R)-1-(4-bromophenyl)ethanamine (48 mg), N,N-diisopropylethylamine (0.10 mL), HATU (91 mg) in N,N-dimethylformamide (2.0 mL) was stirred at room temperature for 16 hr. The reaction mixture was diluted with ethyl acetate, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-90:10) to give the title compound (156 mg) as a pale-yellow crudely-purified powder. MS(ESI) m/z: 682.4, 684.4[M+H]$^+$ (26-2) methyl {(6S)-4-[4'-({(1R)-1-[4-(benzylsulfa-nyl)phenyl]ethyl}carbamoyl)[1,1'-biphenyl]-4-yl]-2,3,9-trimethyl-6H-thieno[3,2-f][1,2,4]triazolo[4,3-a][1,4]diazepin-6-yl}acetate (Example Compound 26-2)

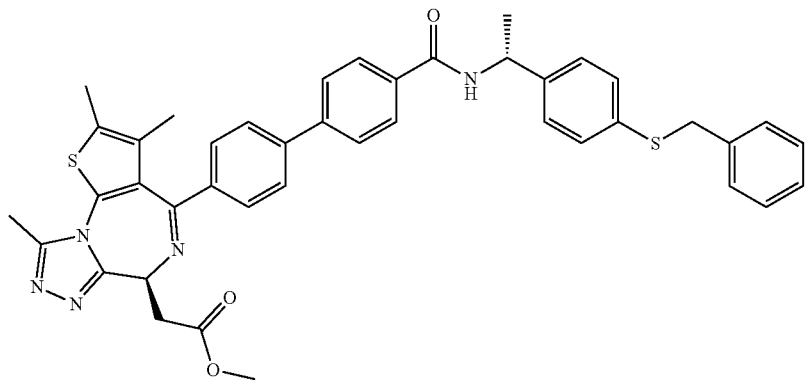 [SMILES: COC(=O)C[C@@H]1N=C(c2ccc(-c3ccc(C(=O)N[C@H](C)c4ccc(SCc5ccccc5)cc4)cc3)cc2)c2c(sc(C)c2C)-n2c(C)nnc21]

A mixture of Example compound 26-1 (133 mg), benzylmercaptan (0.028 mL), N,N-diisopropylethylamine (0.10 mL), 4,5-bis(diphenylphosphino)-9,9-dimethylxanthene (Xantphos, 23 mg), tris (dibenzylideneacetone) dipalladium (18 mg), toluene (2.0 mL) and tetrahydrofuran (0.70 mL) was stirred under a nitrogen atmosphere under microwave irradiation at 150° C. for 0.5 hr. After allowing to cool to room temperature, the reaction mixture was directly purified by NH silica gel column chromatography (hexane:ethyl acetate=50:50-0:100) to give the title compound (126 mg) as a pale-yellow powder.

MS(ESI) m/z: 726.5[M+H]$^+$ (26-3) methyl [(6S)-4-(4'-{[(1R)-1-{4-[(3-cyano-4-methyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 26)

To a solution of Example compound 26-2 (124 mg) in acetonitrile (2.5 mL)-2N hydrochloric acid (0.50 mL) was added, under ice-cooling, N-chlorosuccinimide (80 mg), and the mixture was stirred at the same temperature for 2 hr. To the reaction mixture was added saturated brine-water (1:1), and the mixture was extracted twice with ethyl acetate. The combined organic layer was washed with saturated brine, dried over anhydrous sodium sulfate and filtered. The solvent was evaporated under reduced pressure. To a solution of the obtained residue and Reference Example compound 9 (33 mg) in tetrahydrofuran (5.0 mL) was added pyridine (0.14 mL) at room temperature, and the mixture was stirred at the same temperature for 16 hr. To the reaction mixture was added saturated brine-water (1:1), and the mixture was extracted once with chloroform-methanol and twice with chloroform. The combined organic layer was dried over anhydrous sodium sulfate and filtered. The solvent was evaporated under reduced pressure. The obtained residue was purified by NH silica gel column chromatography (chloroform:methanol=90:10-50:50), and again purified by silica gel column chromatography (chloroform:methanol=98:2-90:10) to give the title compound as a crudely purified product. The total amount of the crudely purified product was purified by preparative HPLC (10 mM aqueous ammonium carbonate solution-acetonitrile) to give the title compound (16 mg) as a white powder. MS(ESI) m/z: 837.5[M+H]$^+$

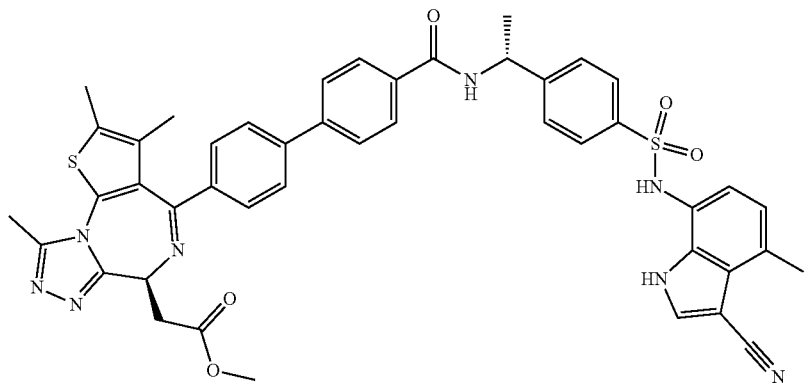

Example 27

(27-1) methyl [(6S)-4-{4'-[({4-[(3-cyano-4-methyl-1H-indol-7-yl)sulfamoyl]-2-fluorophenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 27)

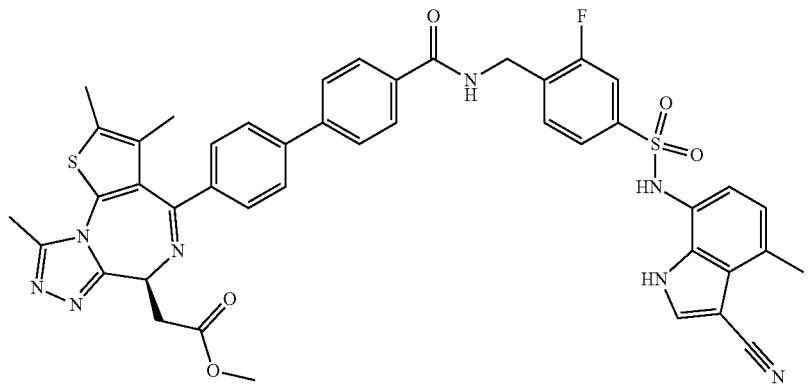

By reaction and treatment in the same manner as in (25-1)-(25-2) except that 4-bromo-2-fluorophenylmethanamine hydrochloride was used instead of 4-bromo-3-fluorophenylmethanamine hydrochloride in Example 25, the title compound was obtained as a beige powder.
MS(ESI) m/z: 841.5[M+H]$^+$ Example 28

(28-1) methyl [(6S)-4-{4'-[(1-{4-[(3-cyano-4-methyl-1H-indol-7-yl)sulfamoyl]phenyl}-2-hydroxyethyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 28)

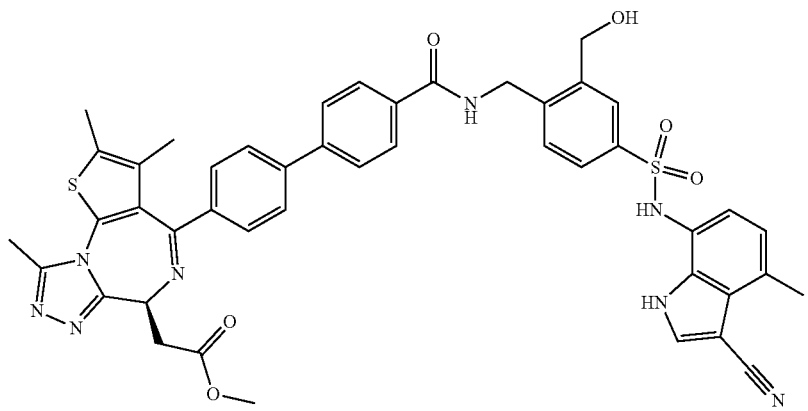

By reaction and treatment in the same manner as in (25-1)-(25-2) except that 2-amino-2-(4-bromophenyl)ethanol was used instead of 4-bromo-3-fluorophenylmethanamine hydrochloride, the title compound was obtained as a white powder.
MS(ESI) m/z: 853.5[M+H]$^+$

Example 29

(29-1) 3,4-dimethyl-1H-indol-7-amine (Example Compound 29-1)

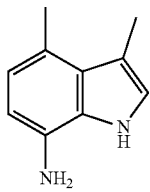

Under a nitrogen stream, 7-bromo-3,4-dimethyl-1H-indole (443 mg), benzophenone imine (501 mg), 1.3M lithium bis(trimethylsilyl)amide/tetrahydrofuran solution (5.3 mL), [1,3-bis(2,6-di-3-pentylphenyl)imidazol-2-ylidene](3-chloropyridyl)dichloropalladium(II) (Pd-PEPPSI-IPent catalyst, 47 mg) were heated under reflux for 7 hr in tetrahydrofuran (3.0 mL). To the reaction mixture were added saturated aqueous ammonium chloride solution and chloroform and the mixture was stirred. The aqueous layer was removed by PhaseSeparator, and the organic layer was concentrated under reduced pressure. The residue, hydroxylamine hydrochloride (344 mg) and sodium acetate (487 mg) were stirred in a methanol (3.0 mL)-tetrahydrofuran (3.0 mL) mixed solvent at room temperature for 3 hr. The reaction mixture was concentrated under reduced pressure, saturated sodium bicarbonate water and chloroform were added and the mixture was stirred. The aqueous layer was removed by PhaseSeparator, and the organic layer was concentrated under reduced pressure. The residue was purified by silica gel column chromatography (chloroform:methanol=100:0-95:5) to give the title compound (279 mg) as a gray solid.
MS(ESI) m/z: 161.2[M+H]$^+$ (29-2) methyl [(6S)-4-{4'-[({4-[(3,4-dimethyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 29)

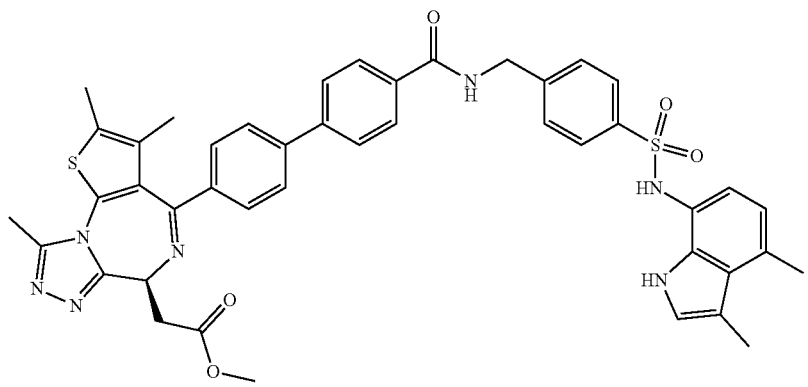

Example compound 29-1 (19 mg), Reference Example compound 10 (70 mg), pyridine (0.041 mL) were stirred in tetrahydrofuran (3.0 mL) at room temperature for 5 hr. The reaction mixture was concentrated under reduced pressure, and azeotropically distilled with toluene. The residue was purified by silica gel column chromatography (chloroform:methanol=100:0-95:5), and silica gel column chromatography (ethyl acetate:methanol=100:0-95:5) to give the title compound (57 mg) as a pale-yellow solid. MS(ESI) m/z: 812.7[M+H]$^+$

Example 30

(30-1) methyl {(6S)-4-[4'-(4-{4-[(3-cyano-4-methyl-1H-indol-7-yl)sulfamoyl]phenyl}piperidine-1-carbonyl)[1,1'-biphenyl]-4-yl]-2,3,9-trimethyl-6H-thieno[3,2-f][1,2,4]triazolo[4,3-a][1,4]diazepin-6-yl}acetate (Example Compound 30)

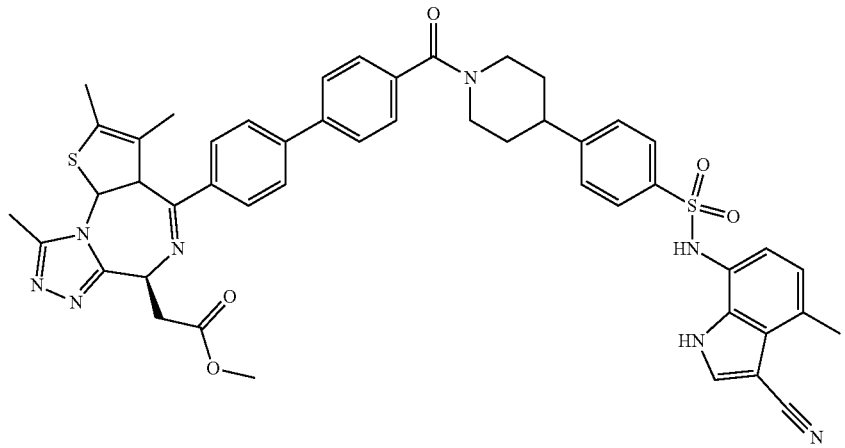

By reaction and treatment in the same manner as in (25-1)-(25-2) except that 4-(4-bromophenyl)piperidine hydrochloride was used instead of 4-bromo-3-fluorophenyl-methanamine hydrochloride in Example 25, the title compound was obtained as a white powder. MS(ESI) m/z: 877.6[M+H]$^+$

Example 31

(31-1) t-butyl (3-{4-[(3-cyano-4-methyl-1H-indol-7-yl)sulfamoyl]phenyl}prop-2-yn-1-yl) carbamate (Example Compound 31-1)

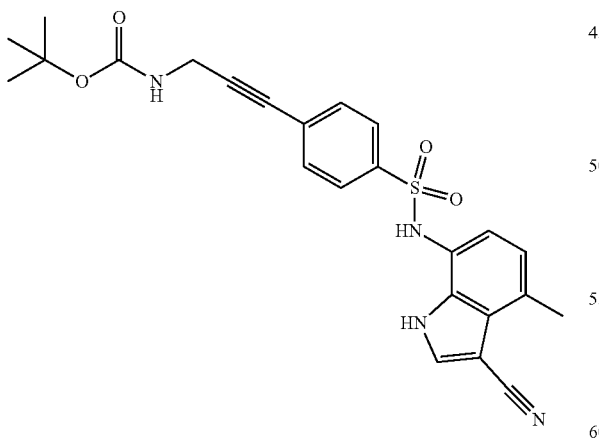

A mixture of Reference Example compound 14 (300 mg), N-(t-butoxycarbonyl)propargylamine (239 mg), 2-dicyclohexylphosphino-2',4',6'-triisopropylbiphenyl (X-Phos, 37 mg), X-Phos aminobiphenylpalladium chloride precatalyst (61 mg), potassium phosphate (490 mg) and tetrahydrofuran (4.0 mL) was stirred under a nitrogen atmosphere under microwave irradiation at 120° C. for 1 hr. To the reaction mixture was added saturated brine-water (1:1), and the mixture was extracted twice with ethyl acetate. The combined organic layer was washed with saturated brine, dried over anhydrous sodium sulfate and filtered. The solvent was evaporated under reduced pressure. The residue was purified by silica gel column chromatography (chloroform:methanol=98:2-95:5) and purified again by NH silica gel column chromatography (chloroform:methanol=95:5-50:50) to give the title compound (209 mg) as a pale-yellow powder. MS(ESI) m/z: 465.3[M+H]$^+$ (31-2) 4-(3-aminoprop-1-yn-1-yl)-N-(3-cyano-4-methyl-1H-indol-7-yl)benzene-1-sulfonamide hydrochloride (Example Compound 31-2)

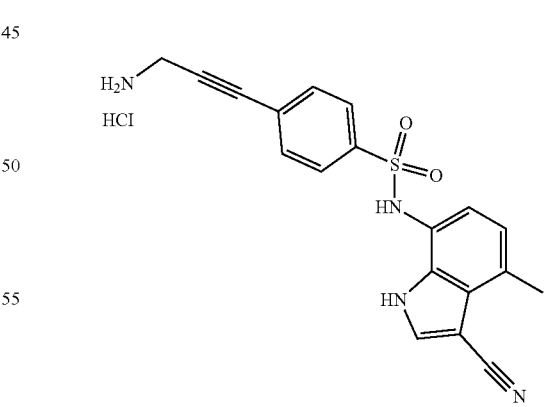

To Example compound 31-1 (205 mg) was added 4M hydrogen chloride/1,4-dioxane solution (6.0 mL) at room temperature. After stirring at the same temperature for 1.5 hr, the reaction mixture was concentrated under reduced pressure. The residue was suspended and washed with diethyl ether, and collected by filtration to give the title compound (150 mg) as a brown solid.

MS(ESI) m/z: 365.2[M+H]$^+$ (31-3) methyl [(6S)-4-{4'-[(3-{4-[(3-cyano-4-methyl-1H-indol-7-yl)sulfamoyl]phenyl}prop-2-yn-1-yl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 31)

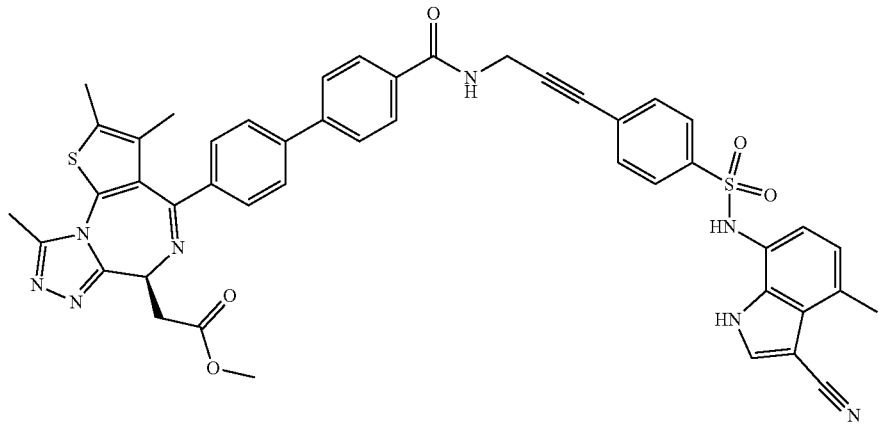

To a solution of Example compound 31-2 (65 mg), Reference Example compound 4 (80 mg) in N,N-dimethylformamide (1.6 mL) was added, at room temperature, N,N-diisopropylethylamine (0.083 mL) and HATU (73 mg), and the mixture was stirred at the same temperature for 1 hr. The reaction mixture was diluted with methanol and added to ethyl acetate and saturated brine-water (1:1). A small amount of insoluble material was filtered off, and the filtrate was partitioned. The organic layer was washed twice with saturated brine-water (1:1), washed once with saturated brine, dried over anhydrous sodium sulfate and filtered. The solvent was evaporated under reduced pressure. The obtained residue was purified by NH silica gel column chromatography (chloroform:methanol=95:5-50:50, precolumn: silica gel) to give the title compound (103 mg) as a white powder. MS(ESI) m/z: 847.5[M+H]$^+$ Example 31

(32-1) methyl 4'-[(6S)-2,3,6,9-tetramethyl-6H-thieno[3,2-f][1,2,4]triazolo[4,3-a][1,4]diazepin-4-yl][1,1'-biphenyl]-4-carboxylate (Example Compound 32-1)

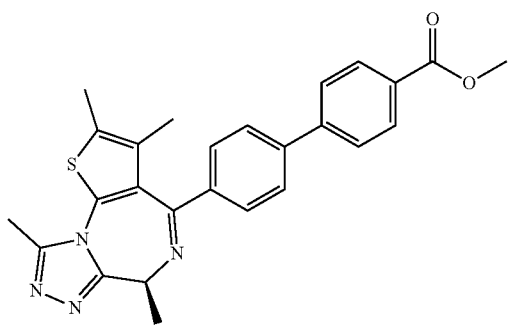

Reference Example compound 2 (150 mg), 4-(methoxycarbonyl)phenylboronic acid (81 mg), 2-dicyclohexylphosphino-2',4',6'-triisopropylbiphenyl aminobiphenyl palladium chloride precatalyst (15 mg), sodium carbonate (79 mg), 1,4-dioxane (3.0 mL) and water (1.0 mL) were mixed and stirred under microwave irradiation at 100° C. for 20 min. Water was added to the reaction mixture and the mixture was extracted with ethyl acetate. The organic layer was washed with saturated brine, dried over anhydrous sodium sulfate and filtered. The filtrate was concentrated under reduced pressure. The residue was purified by NH silica gel column chromatography (hexane:ethyl acetate=80:20-0:100) to give the title compound (161 mg) as a white powder. MS(ESI) m/z: 457.3[M+H]$^+$ (32-2) N-({4-[(3-cyano-4-methyl-1H-indol-7-yl)sulfamoyl]phenyl}methyl)-4'-[(6S)-2,3,6,9-tetramethyl-6H-thieno[3,2-f][1,2,4]triazolo[4,3-a][1,4]diazepin-4-yl][1,1'-biphenyl]-4-carboxamide (Example Compound 32)

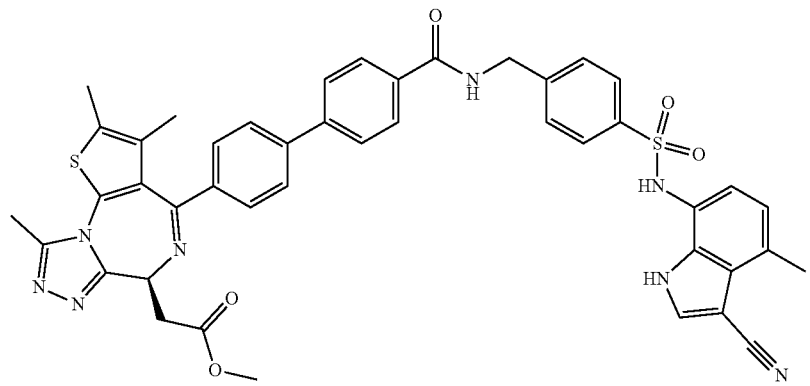

To a solution of Example compound 32-1 (73 mg) in methanol (3.0 mL) was added 1N aqueous sodium hydroxide solution (0.32 mL), and the mixture was stirred at room temperature for 9 hr. To the reaction mixture was added 1N hydrochloric acid and the mixture was stirred and concentrated under reduced pressure. The obtained solid, Reference Example compound 5 (60 mg), N,N-diisopropylethylamine (0.082 mL) and HATU (72 mg) were stirred in N,N-dimethylformamide (3.0 mL) at room temperature for 1 hr. To the reaction mixture was added water, the mixture was stirred, and the resulting solid was collected by filtration. The solid was purified by silica gel column chromatography (chloroform:methanol=100:0-95:5) to give the title compound (100 mg) as a white solid.
MS(ESI) m/z: 765.6[M+H]$^+$ Example 33

(33-1) methyl 7-bromo-1H-indole-4-carboxylate (Example Compound 33-1)

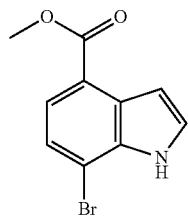

To a solution (30.0 mL) of methyl 4-bromo-3-nitrobenzoate (2600 mg) in tetrahydrofuran was added, at −78° C., 1M vinylmagnesium bromide/tetrahydrofuran solution (25.0 mL) over min. After stirring at the same temperature for 1 hr, to the reaction mixture were added saturated aqueous ammonium chloride solution and water, and the mixture was heated to room temperature. After partitioning, the aqueous layer was extracted once with ethyl acetate. The combined organic layer was washed with saturated brine, dried over anhydrous sodium sulfate and filtered. The solvent was evaporated under reduced pressure. The obtained residue was purified by silica gel column chromatography (hexane:ethyl acetate=90:10) to give the title compound (1223 mg) as a white solid.

MS(ESI) m/z: 254.1, 256.0[M+H]$^+$ (33-2) methyl 7-bromo-3-cyano-1H-indole-4-carboxylate (Example Compound 33-2)

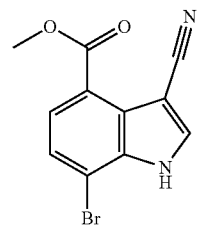 [SMILES: COC(=O)c1ccc(Br)c2[nH]cc(C#N)c12]

To a solution (4.0 mL) of Example compound 33-1 (1000 mg) in N,N-dimethylformamide was added phenylphosphonyl dichloride (1.0 mL) at room temperature. After stirring at 100° C. for 20 min, N,N-dimethylformamide (4.0 mL) was added, and the mixture was stirred at 100° C. for 40 min more. Hydroxylamine hydrochloride (547 mg) was added and the mixture was stirred with heating at 100° C. for 2 hr and at 140° C. for 0.5 hr. After allowing to cool to room temperature, the reaction mixture was diluted with ethyl acetate, washed 3 times with saturated aqueous sodium hydrogen carbonate and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (703 mg) as a crudely purified brown solid.

MS(ESI) m/z: 279.2, 281.2[M+H]⁺

(33-3) 7-bromo-4-(hydroxymethyl)-1H-indole-3-carbonitrile (Example Compound 33-3)

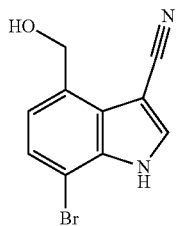 [SMILES: N#Cc1c[nH]c2c(Br)ccc(CO)c12]

To a suspension of Example compound 33-2 (391 mg) in tetrahydrofuran (16.0 mL) was added dropwise, under ice-cooling, 2.5M lithium aluminum hydride/tetrahydrofuran solution (1.70 mL). After stirring at the same temperature for 10 min, 1N hydrochloric acid was added, and the mixture was extracted twice with ethyl acetate. The combined organic layer was washed with saturated brine, dried over anhydrous sodium sulfate and filtered. The solvent was evaporated under reduced pressure. The obtained residue was suspended and washed with chloroform and collected by filtration to give the title compound (221 mg) as a gray solid. MS(ESI) m/z: 233.0, 235.0[M-OH]⁺; ¹H NMR (400 MHz, DMSO-d6) δ ppm 4.94 (2H, d, J=5.27 Hz), 5.33 (1H, t, J=5.33 Hz), 7.10-7.27 (1H, m), 7.48 (1H, d, J=7.83 Hz), 8.31 (1H, s), 12.44 (1H, brs)

(33-4) 7-[(diphenylmethyliden)amino]-4-(hydroxymethyl)-1H-indole-3-carbonitrile (Example Compound 33-4)

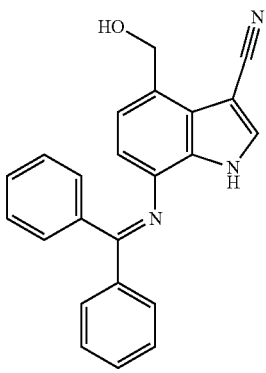 [SMILES: N#Cc1c[nH]c2c(N=C(c3ccccc3)c3ccccc3)ccc(CO)c12]

To a mixture of Example compound 33-3 (267 mg), benzophenone imine (270 mg), [1,3-bis(2,6-di-3-pentylphenyl)imidazol-2-ylidene](3-chloropyridyl)dichloropalladium (II) (Pd-PEPPSI-IPent catalyst, 26 mg) and tetrahydrofuran (7.0 mL) was added 1.3M lithium bis(trimethylsilyl)amide/tetrahydrofuran solution (2.9 mL) at room temperature, and the mixture was stirred under a nitrogen atmosphere under microwave irradiation at 140° C. for 0.5 hr. Pd-PEPPSI-IPent catalyst (85 mg) and 1.3M lithium bis(trimethylsilyl)amide/tetrahydrofuran solution (2.9 mL) were added, and the mixture was stirred under a nitrogen atmosphere under microwave irradiation at 160° C. for 0.5 hr. After allowing to cool to room temperature, water was added to the reaction mixture and the mixture was extracted twice with ethyl acetate. The organic layers were combined, washed with saturated brine, dried over anhydrous sodium sulfate, and filtered. The solvent was evaporated under reduced pressure. The obtained residue was purified by silica gel column chromatography (chloroform:methanol=98:2), and purified again by NH silica gel column chromatography (chloroform:methanol=98:2) to give the title compound (59 mg) as a pale-yellow solid. MS(ESI) m/z: 352.2[M+H]⁺

(33-5) 7-amino-4-(hydroxymethyl)-1H-indole-3-carbonitrile (Example Compound 33-5)

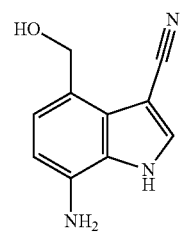 [SMILES: N#Cc1c[nH]c2c(N)ccc(CO)c12]

Example compound 33-4 (57 mg) was dissolved in tetrahydrofuran (1.0 mL)-methanol (1.0 mL), hydroxylamine hydrochloride (28 mg) and sodium acetate (40 mg) were added at room temperature, and the mixture was stirred at the same temperature for 2 hr. To the reaction mixture was added saturated aqueous sodium hydrogen carbonate and the mixture was extracted twice with ethyl acetate. The organic layers were combined, washed with saturated brine, dried over anhydrous sodium sulfate, and filtered. The solvent was evaporated under reduced pressure. The obtained residue was purified by NH silica gel column chromatography (chloroform:methanol=98:2-80:20) to give the title compound (14 mg) as a pale-brown solid.

MS(ESI) m/z: 170.1[M-OH]⁺, ¹H NMR (400 MHz, DMSO-d6) δ ppm 4.74-4.83 (3H, m), 5.22 (2H, s), 6.42 (1H, d, J=7.7 Hz), 6.91 (1H, d, J=7.7 Hz), 8.12 (1H, s), 11.75 (1H, brs)

(33-6) methyl [(6S)-4-(4'-{[(4-{[3-cyano-4-(hydroxymethyl)-1H-indol-7-yl]sulfamoyl}phenyl)methyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 33)

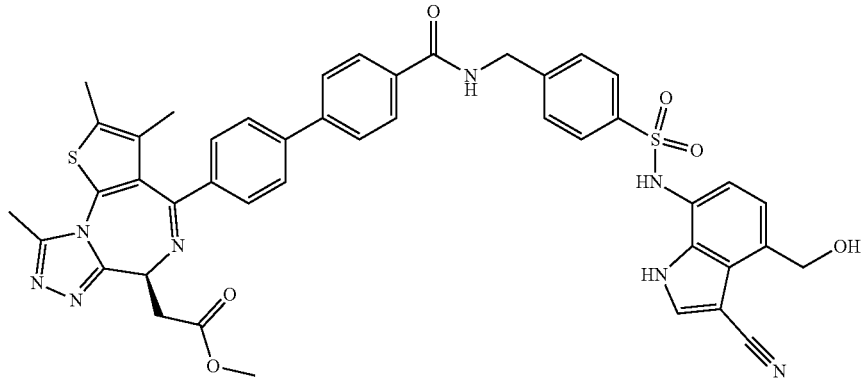 [SMILES: COC(=O)C[C@@H]1N=C(c2ccc(-c3ccc(C(=O)NCc4ccc(S(=O)(=O)Nc5ccc(CO)c6c(C#N)c[nH]c56)cc4)cc3)cc2)c2c(sc(C)c2C)-n2c(C)nnc21]

To a solution of Example compound 33-5 (13 mg) and Reference Example compound 10 (73 mg) in tetrahydrofuran (1.0 mL) was added, at room temperature, pyridine (0.17 mL), and the mixture was stirred at the same temperature for 14 hr. The reaction mixture was diluted with ethyl acetate-methanol, washed once with saturated brine-water (1:1) and once with saturated brine, dried over anhydrous sodium sulfate and filtered. The solvent was evaporated under reduced pressure. The obtained residue was purified twice by silica gel column chromatography (chloroform:methanol=98:2-90:10) to give the title compound (29 mg) as a beige powder.
MS(ESI) m/z: 839.5[M+H]$^+$ Example 34

(34-1) [(6S)-4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetic acid (Example Compound 34)

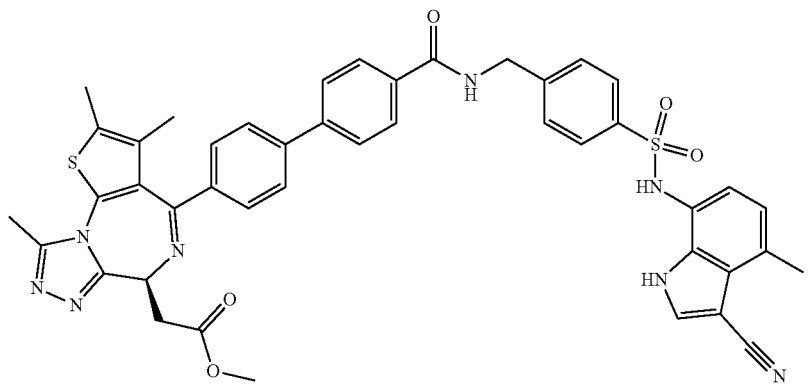

To a mixed solution of Example compound 1 (295 mg) in tetrahydrofuran (2.0 mL)-methanol (2.0 mL) was added 2N aqueous lithium hydroxide solution (0.72 mL), and the mixture was stirred at room temperature for 2 hr. 1N Hydrochloric acid was added and the mixture was stirred, and concentrated under reduced pressure. The residue was suspended and washed with water, and collected by filtration and dried to give the title compound (258 mg) as a yellow powder. MS(ESI) m/z: 809.4[M+H]$^+$ Example 35

(35-1) t-butyl 5-(4,4,5,5-tetramethyl-1,3,2-dioxaboronan-2-yl)-1-benzofuran-2-carboxylate (Example Compound 35-1)

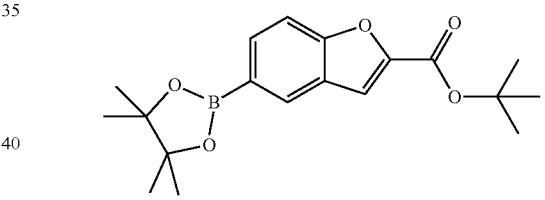

To a mixture of t-butyl 5-bromo-1-benzofuran-2-carboxylate (1.50 g), bis(pinacolato)diboron (1.41 g), 1,1'-(diphenylphosphino)ferrocene-palladium(II) dichloromethane complex (206 mg) and potassium acetate (991 mg) was added 1,4-dioxane (17 mL). After nitrogen substitution, the mixture was stirred with heating under microwave irradiation at 130° C. for 30 min. To the reaction mixture were added water, ethyl acetate and activated carbon, the insoluble material was filtered off through diatomaceous earth, and the filtration residue was washed with ethyl acetate. The filtrate was partitioned, and the organic layer was washed with saturated brine, dried over anhydrous sodium sulfate and filtered. The solvent was evaporated under reduced pressure. The residue was purified by silica gel column chromatography (hexane:ethyl acetate=100:0-90:10) to give the title compound (1.38 g) as a pale-yellow solid. 1H NMR (400 MHz, CDCl$_3$) δ ppm 1.37 (12H, s), 1.63 (9H, s), 7.40 (1H, d, J=1.0 Hz), 7.56 (1H, d, J=8.7 Hz), 7.87 (1H, dd, J=1.3, 8.5 Hz), 8.15 (1H, s)

(35-2) t-butyl 5-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}-1-benzofuran-2-carboxylate (Example Compound 35-2)

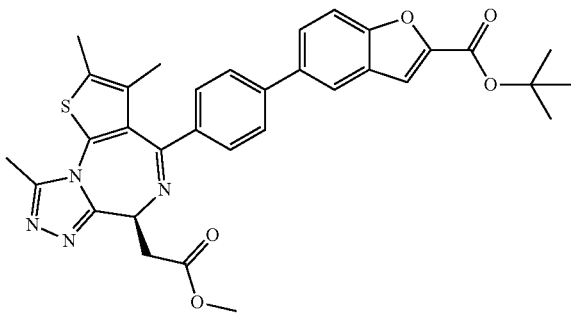 [SMILES: COC(=O)C[C@@H]1N=C(c2ccc(-c3ccc4oc(C(=O)OC(C)(C)C)cc4c3)cc2)c2c(sc(C)c2C)-n2c(C)nnc21]

A mixture of Reference Example compound 1 (80 mg), Example compound 35-1 (73 mg), 2-dicyclohexylphosphino-2',4',6'-triisopropylbiphenyl (X-Phos, 9 mg), X-Phos aminobiphenylpalladium chloride precatalyst (15 mg), potassium phosphate (123 mg), water (0.013 mL) and tetrahydrofuran (1.0 mL) was stirred under a nitrogen atmosphere under microwave irradiation at 90° C. for 0.5 hr. The reaction mixture was diluted with ethyl acetate, washed once with water and once with saturated brine, dried over anhydrous sodium sulfate and filtered. The solvent was evaporated under reduced pressure. The residue was purified by NH silica gel column chromatography (hexane:ethyl acetate=50:50-0:100) to give the title compound (115 mg) as a white powder. MS(ESI) m/z: 597.5[M+H]$^+$ (35-3) methyl [(6S)-4-(4-{2-[({4-[(3-cyano-4-methyl-1H-indol-7-yl)sulfamoyl]phenyl}methyl)carbamoyl]-1-benzofuran-5-yl}phenyl)-2,3,9-trimethyl-6H-thieno[3,2-f][1,2,4]triazolo[4,3-a][1,4]diazepin-6-yl]acetate (Example Compound 35)

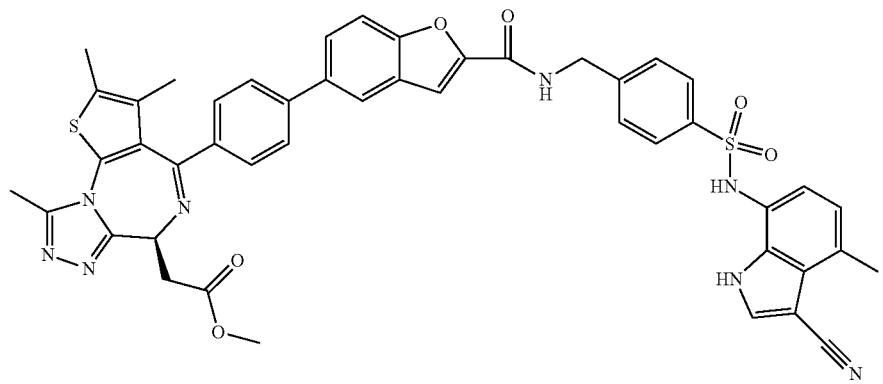

To a solution of Example compound 35-2 (111 mg) in dichloromethane (1.0 mL) was added trifluoroacetic acid (1.0 mL), and the mixture was stirred at room temperature for 1 hr. The reaction mixture was concentrated, toluene was added and the solvent was evaporated. The obtained residue was dissolved in N,N-dimethylformamide (2.0 mL), Reference Example compound 5 (64 mg), N,N-diisopropylethylamine (0.32 mL) and HATU (85 mg) were added at room temperature, and the mixture was stirred at the same temperature for 1 hr. The reaction mixture was diluted with ethyl acetate, added to saturated aqueous sodium hydrogen carbonate, and the resulting precipitate (A) was collected by filtration. The filtrate was partitioned. The aqueous layer was extracted once with ethyl acetate. The combined organic layer (B) was washed twice with saturated brine-water (1:1) and once with saturated brine. The filtered residue (A) was dissolved in chloroform, combined with the organic layer (B), and the mixture was dried over anhydrous sodium sulfate and filtered. The solvent was evaporated under reduced pressure. The obtained residue was purified by silica gel column chromatography (chloroform:methanol=98:2-95:5) to give the title compound (104 mg) as a white powder. MS(ESI) m/z: 863.5[M+H]$^+$

Example 36

(36-1) methyl [4-(4-chlorophenyl)-2,3,9-trimethyl-6H-thieno[3,2-f][1,2,4]triazolo[4,3-a][1,4]diazepin-6-yl]carbamate (Example Compound 36-1)

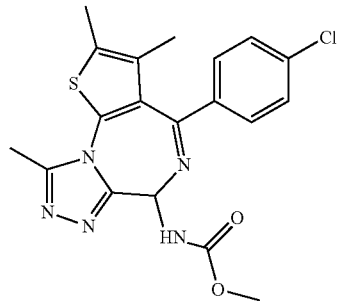 [SMILES: COC(=O)NC1N=C(c2ccc(Cl)cc2)c2c(sc(C)c2C)-n2c(C)nnc21]

To a solution of 6-amino-4-(4-chlorophenyl)-2,3,9-trimethyl-6H-thieno[3,2-f][1,2,4]triazolo[4,3-a][1,4]diazepine (200 mg) (described in JP-A-7-17941, Starting Material Preparation Example 1) in dichloromethane (6.0 mL) were added under ice-cooling methyl chloroformate (0.048 mL) and N,N-diisopropylethylamine (0.15 mL), and the mixture was stirred at the same temperature for 0.5 hr. Water was added to the reaction mixture, and the mixture was extracted twice with chloroform, and the extract was dried over anhydrous sodium sulfate and filtered. The solvent was evaporated under reduced pressure. The residue was purified by silica gel column chromatography (chloroform:methanol=100:0-97:3) to give the title compound (233 mg) as a pale-orange powder.

MS(ESI) m/z: 416.3[M+H]$^+$

(36-2) t-butyl 4'-{6-[(methoxycarbonyl)amino]-2,3,9-trimethyl-6H-thieno[3,2-f][1,2,4]triazolo[4,3-a][1,4]diazepin-4-yl}[1,1'-biphenyl]-4-carboxylate (Example Compound 36-2)

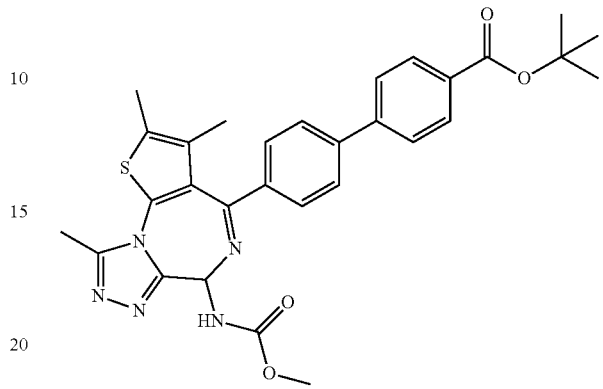

A mixture of Example compound 36-1 (30 mg), t-butyl 4-(4,4,5,5-tetramethyl-1,3,2-dioxaborolan-2-yl)benzoate (25 mg), 2-dicyclohexylphosphino-2',4',6'-triisopropylbiphenyl (X-Phos, 4 mg), X-Phos aminobiphenylpalladium chloride precatalyst (6 mg), potassium phosphate (46 mg), water (0.005 mL) and tetrahydrofuran (0.36 mL) was stirred under a nitrogen atmosphere under microwave irradiation at 90° C. for 0.5 hr. The reaction mixture was diluted with ethyl acetate, washed once with water and once with saturated brine, dried over anhydrous sodium sulfate and filtered. The solvent was evaporated under reduced pressure. The residue was purified by NH silica gel column chromatography (hexane:ethyl acetate=50:50-0:100) to give the title compound (39 mg) as a white powder.

MS(ESI) m/z: 558.4[M+H]$^+$

(36-3) methyl (4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl) carbamate (Example Compound 36)

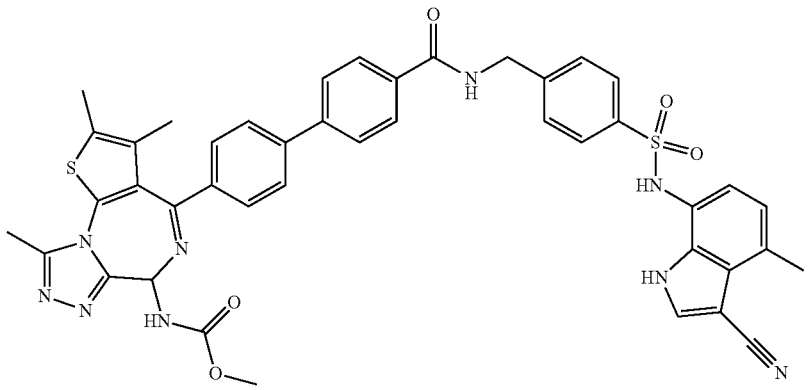

To a solution of Example compound 36-2 (37 mg) in dichloromethane (1.0 mL) was added trifluoroacetic acid (1.0 mL), and the mixture was stirred at room temperature for 1 hr. The reaction mixture was concentrated, toluene was added and the solvent was evaporated. The obtained residue was dissolved in N,N-dimethylformamide (0.67 mL), Reference Example compound (25 mg), N,N-diisopropylethylamine (0.12 mL) and HATU (31 mg) were added at room temperature, and the mixture was stirred at the same temperature for 15 hr. The reaction mixture was diluted with ethyl acetate, washed once with saturated aqueous sodium hydrogen carbonate, twice with saturated brine-water (1:1), and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (43 mg) as a white powder.

MS(ESI) m/z: 824.5[M+H]$^+$

Example 37

(37-1) N-({4-[(3-cyano-4-methyl-1H-indol-7-yl)sulfamoyl]phenyl}methyl)-4'-[(6S)-6-{2-[(2-hydroxyethyl)amino]-2-oxoethyl}-2,3,9-trimethyl-6H-thieno[3,2-f][1,2,4]triazolo[4,3-a][1,4]diazepin-4-yl][1,1'-biphenyl]-4-carboxamide (Example Compound 37)

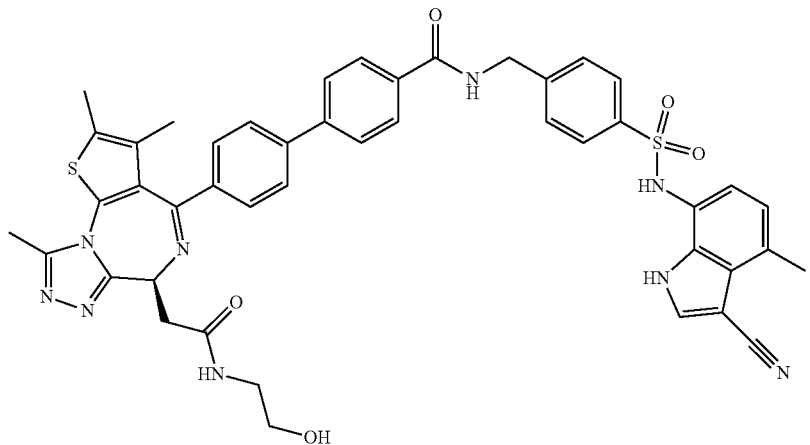

Example compound 34 (100 mg), 2-aminoethanol (12 mg), N,N-diisopropylethylamine (0.064 mL) and HATU (56 mg) were stirred in N,N-dimethylformamide (3.0 mL) at room temperature for 2 hr. To the reaction mixture was added water and the mixture was stirred and extracted twice with ethyl acetate. The combined organic layer was washed twice with water, and concentrated under reduced pressure. The residue was purified by silica gel column chromatography (chloroform:methanol=100:0-80:20) to give the title compound (97 mg) as a white solid.

MS(ESI) m/z: 852.5[M+H]$^+$

Example 38

(38-1) N-({4-[(3-cyano-4-methyl-1H-indol-7-yl)sulfamoyl]phenyl}methyl)-4'-{(6S)-6-[2-(dimethylamino)-2-oxoethyl]-2,3,9-trimethyl-6H-thieno[3,2-f][1,2,4]triazolo[4,3-a][1,4]diazepin-4-yl}[1,1'-biphenyl]-4-carboxamide (Example Compound 38)

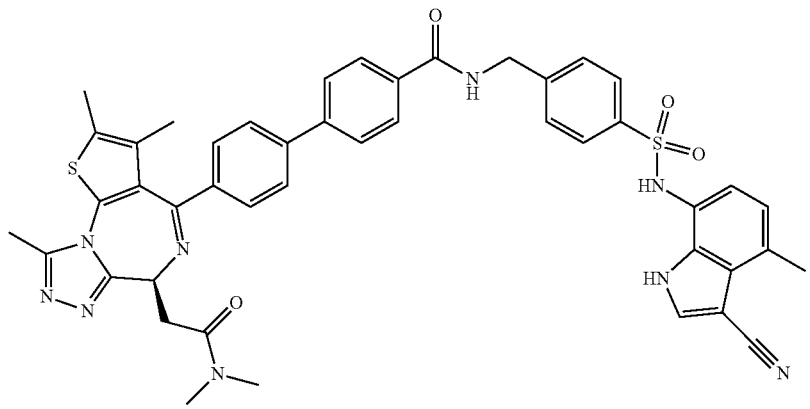

By reaction and treatment in the same manner as in (37-1) except that dimethylamine hydrochloride was used instead of 2-aminoethanol in Example 37, the title compound was obtained as a milk-white solid. MS(ESI) m/z: 836.5[M+H]$^+$ Example 39

(39-1) methyl [(6S)-4-{4'-[(2-{4-[(3-cyano-4-methyl-1H-indol-7-yl)sulfamoyl]phenoxy}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 39)

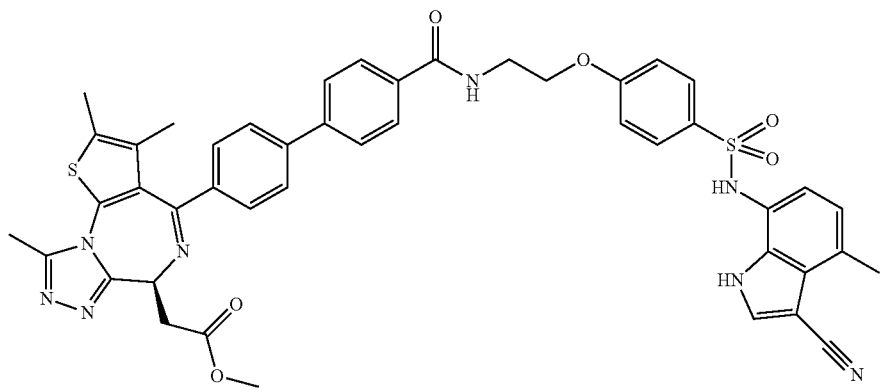

By reaction and treatment in the same manner as in (25-1)-(25-2) except that 2-(4-bromophenoxy)ethanamine was used instead of 4-bromo-3-fluorophenylmethanamine hydrochloride in Example 25, the title compound was obtained as a beige powder.

MS(ESI) m/z: 853.5[M+H]$^+$

Example 40

(40-1) methyl [(6S)-4-{4'-[(2-{4-[(3-cyano-4-methyl-1H-indol-7-yl)sulfamoyl]phenyl}ethyl)carbamoyl]-3'-fluoro[1,1'-biphenyl]-4-yl}-2,3,9-trimethyl-6H-thieno[3,2-f][1,2,4]triazolo[4,3-a][1,4]diazepin-6-yl]acetate (Example Compound 40)

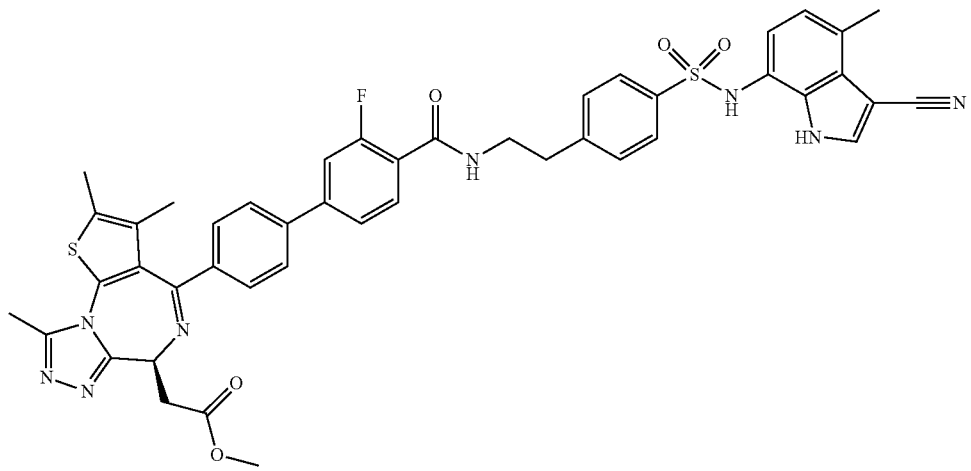 [SMILES: COC(=O)C[C@@H]1N=C(c2ccc(-c3ccc(C(=O)NCCc4ccc(S(=O)(=O)Nc5ccc(C)c6c(C#N)c[nH]c56)cc4)c(F)c3)cc2)c2c(sc(C)c2C)-n2c(C)nnc21]

To a solution of Reference Example compound 12 (63 mg), Reference Example compound 11 (53 mg) in N,N-dimethylformamide (1.3 mL) were added, at room temperature, N,N-diisopropylethylamine (0.063 mL) and HATU (56 mg), and the mixture was stirred at the same temperature for 1.5 hr. To the reaction mixture was added water, and the precipitate was collected by filtration and washed with water. The filtered residue was dissolved in chloroform, dried over anhydrous sodium sulfate and filtered. The solvent was evaporated under reduced pressure. The obtained residue was purified by silica gel column chromatography (chloroform:methanol=98:2-95:5), the title compound (61 mg) was obtained as a pale-yellow powder.

MS(ESI) m/z: 855.5[M+H]$^+$

Example 41

(41-1) methyl [(6S)-4-{3'-chloro-4'-[(2-{4-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 41)

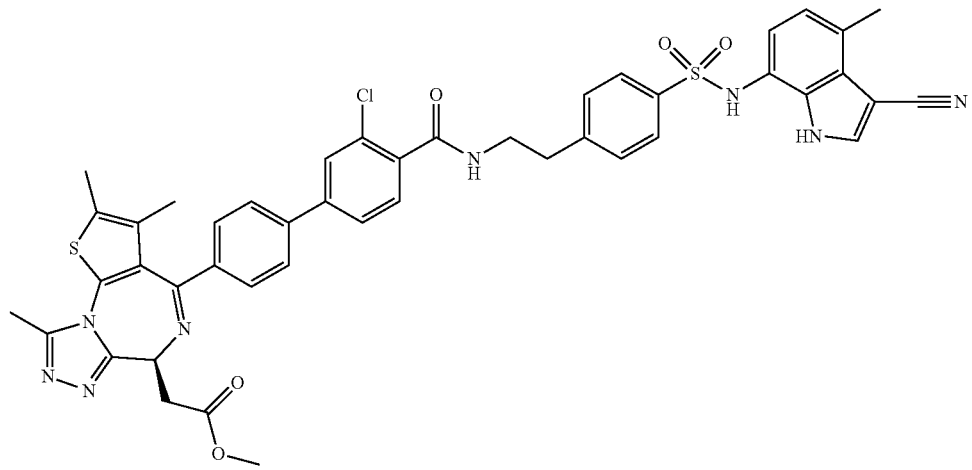 [SMILES: COC(=O)C[C@@H]1N=C(c2ccc(-c3ccc(C(=O)NCCc4ccc(S(=O)(=O)Nc5ccc(C)c6c(C#N)c[nH]c56)cc4)c(Cl)c3)cc2)c2c(sc(C)c2C)-n2c(C)nnc21]

By reaction and treatment in the same manner as in Example 40 except that Reference Example compound 13 (80 mg) was used instead of Reference Example compound 12, the title compound (115 mg) was obtained as a white powder.

MS(ESI) m/z: 871.5[M+H]$^+$

Example 42

(42-1) methyl [(6S)-4-{4'-[({4-[(4-bromo-3-cyano-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 42)

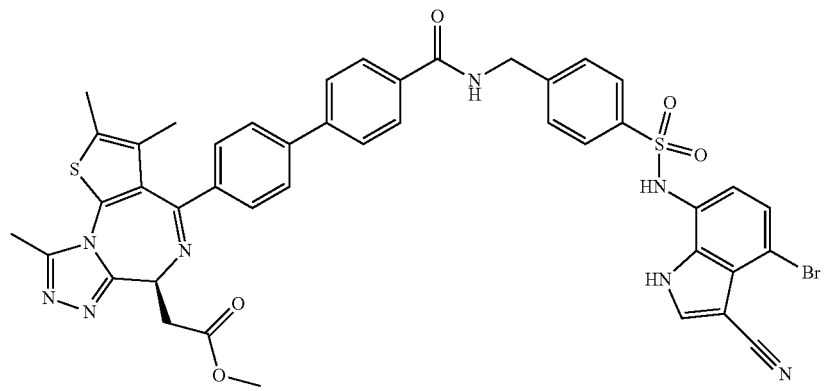 [SMILES: COC(=O)C[C@@H]1N=C(c2ccc(-c3ccc(C(=O)NCc4ccc(S(=O)(=O)Nc5ccc(Br)c6c(C#N)c[nH]c56)cc4)cc3)cc2)c2c(sc(C)c2C)-n2c(C)nnc21]

By reaction and treatment in the same manner as in (7-3) except that Reference Example compound 15 (24 mg) was used instead of Example compound 7-2 in Example 7, the title compound (56 mg) was obtained as a pale-yellow solid.

MS(ESI) m/z: 887.3, 889.3[M+H]$^+$

Example 43

(43-1) methyl [(6S)-4-{4'-[({4-[(3-cyano-4-ethyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 43)

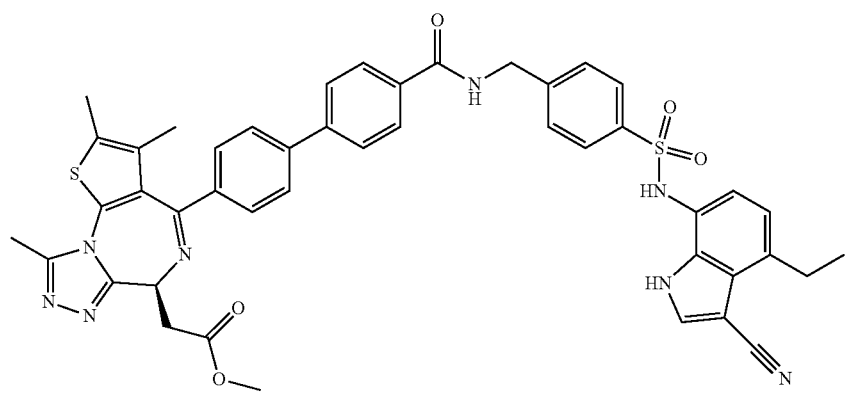 [SMILES: CCc1ccc(NS(=O)(=O)c2ccc(CNC(=O)c3ccc(-c4ccc(C5=N[C@@H](CC(=O)OC)c6nnc(C)n6-c6sc(C)c(C)c65)cc4)cc3)cc2)c2[nH]cc(C#N)c12]

A mixture of Reference Example compound 16 (14 mg), pyridine (0.059 mL), tetrahydrofuran (2.0 mL) and Reference Example compound 10 (50 mg) was stirred at room temperature for 24 hr. The reaction mixture was diluted and dissolved in a tetrahydrofuran-ethyl acetate (1:1) mixture and a small amount of methanol. The organic layer was washed once with a mixture of saturated brine and 1N hydrochloric acid water, once with saturated brine, once with saturated aqueous sodium hydrogen carbonate, and once with saturated brine, dried over anhydrous sodium sulfate and filtered. The solvent was evaporated under reduced pressure. The obtained residue was purified by preparative HPLC (10 mM aqueous ammonium carbonate solution-acetonitrile) to give the title compound (42 mg) as a pale-yellow solid. MS(ESI) m/z: 837.5[M+H]$^+$ Example 44

(44-1) 7-amino-4-cyclopropyl-1H-indole-3-carbonitrile (Example Compound 44-1)

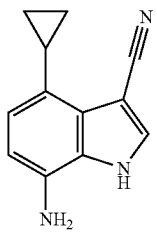 [SMILES: N#Cc1c[nH]c2c(N)ccc(C3CC3)c12]

To a solution of Reference Example compound 15 (90 mg), mesyl[(tri-t-butylphosphine)-2-(2-aminobiphenyl)]palladium(II) in tetrahydrofuran (1.9 mL) was added, under a nitrogen atmosphere and ice-cooling, 0.5M cyclopropylzinc bromide/tetrahydrofuran solution (4.6 mL), and the mixture was stirred at room temperature for 50 min. To the reaction mixture was added, under ice-cooling, saturated aqueous ammonium chloride solution. After stirring at room temperature for 1 hr, ethyl acetate and water were added for partitioning. The organic layer was washed once with saturated aqueous sodium hydrogen carbonate and once with saturated brine, dried over anhydrous sodium sulfate and filtered. The solvent was evaporated under reduced pressure. The obtained residue was purified by silica gel column chromatography (hexane:ethyl acetate=50:50-20:80), and then preparative HPLC (10 mM aqueous ammonium carbonate solution-acetonitrile) to give the title compound (26 mg) as a white solid.
MS(ESI) m/z: 198.1[M+H]$^+$ (44-2) methyl [(6S)-4-{4'-[({4-[(3-cyano-4-cyclopropyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 44)

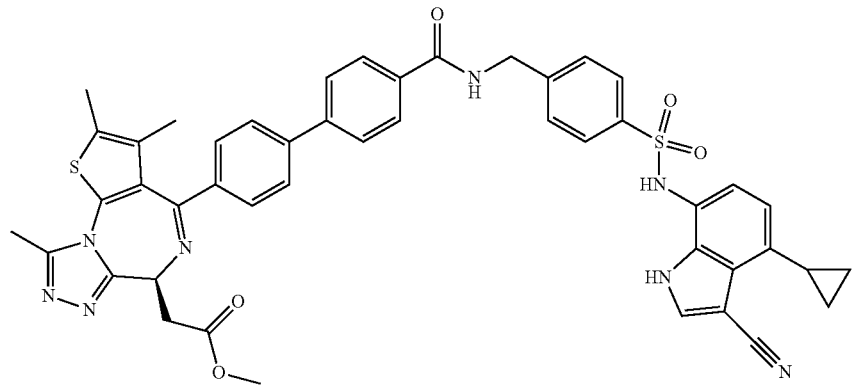 [SMILES: COC(=O)C[C@@H]1N=C(c2ccc(-c3ccc(C(=O)NCc4ccc(S(=O)(=O)Nc5ccc(C6CC6)c6c(C#N)c[nH]c56)cc4)cc3)cc2)c2c(sc(C)c2C)-n2c(C)nnc21]

By reaction and treatment in the same manner as in (7-3) except that Example compound 44-1 (18 mg) was used instead of Example compound 7-2 in Example 7, the title compound (47 mg) was obtained as a pale-yellow solid. MS(ESI) m/z: 849.5[M+H]$^+$

Example 45

(45-1) methyl [(6S)-4-{4'-[({4-[(3-cyano-4-methyl-1H-indol-7-yl) sulfamoyl]phenyl}methyl) carbamoyl]-2'-fluoro[1,1'-biphenyl]-4-yl}-2,3,9-trimethyl-6H-thieno[3,2-f][1,2,4]triazolo[4,3-a][1, 4]diazepin-6-yl]acetate (Example Compound 45)

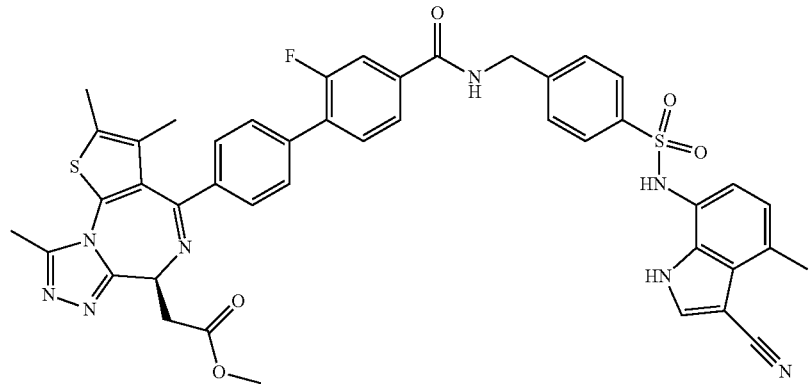

To a solution of Reference Example compound 18-1 (85 mg) in dichloromethane (1.0 mL) was added trifluoroacetic acid (1.0 mL), and the mixture was stirred at room temperature for 1 hr. The reaction mixture was concentrated, toluene was added and the solvent was evaporated. The obtained residue was dissolved in N,N-dimethylformamide (1.5 mL), Reference Example compound 5 (56 mg), N,N-diisopropylethylamine (0.26 mL) and HATU (68 mg) were added at room temperature, and the mixture was stirred at the same temperature for 16 hr. To the reaction mixture was added water, and the precipitate was collected by filtration and washed with water. The filtered residue was dissolved in chloroform, dried over anhydrous sodium sulfate and filtered. The solvent was evaporated under reduced pressure. The obtained residue was purified by silica gel column chromatography (chloroform:methanol=98:2-95:5), the title compound (87 mg) was obtained as a white powder.

MS(ESI) m/z: 841.5[M+H]$^+$

Example 46

(46-1) methyl [(6S)-4-{4'-[(2-{4-[(3-cyano-4-methyl-1H-indol-7-yl)sulfamoyl]phenyl}ethyl)carbamoyl]-2'-fluoro[1,1'-biphenyl]-4-yl}-2,3,9-trimethyl-6H-thieno[3,2-f][1,2,4]triazolo[4,3-a][1,4]diazepin-6-yl]acetate (Example Compound 46)

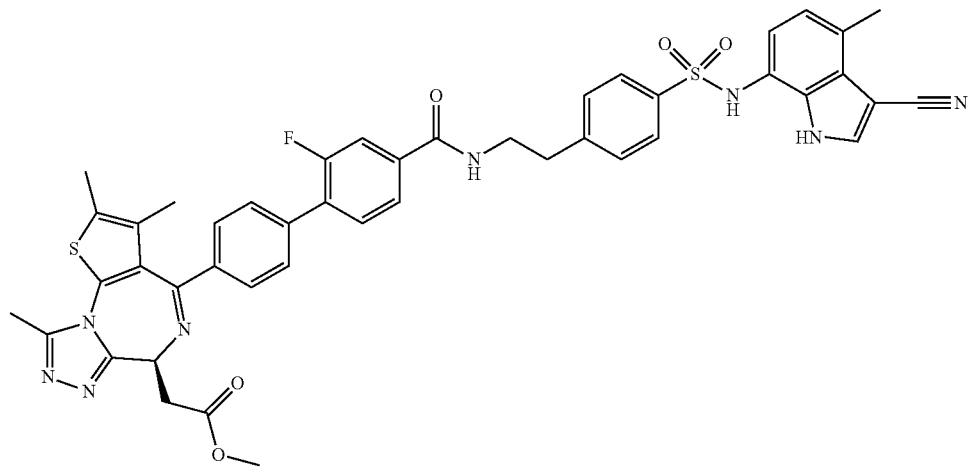 [SMILES: COC(=O)C[C@@H]1N=C(c2ccc(-c3ccc(C(=O)NCCc4ccc(S(=O)(=O)Nc5ccc(C)c6c(C#N)c[nH]c56)cc4)cc3F)cc2)c2c(sc(C)c2C)-n2c(C)nnc21]

To a solution of Reference Example compound 18-1 (85 mg) in dichloromethane (1.0 mL) was added trifluoroacetic acid (1.0 mL), and the mixture was stirred at room temperature for 1 hr. The reaction mixture was concentrated, toluene was added and the solvent was evaporated. The obtained residue was dissolved in N,N-dimethylformamide (1.5 mL), Reference Example compound 11 (64 mg), N,N-diisopropylethylamine (0.26 mL) and HATU (68 mg) were added at room temperature, and the mixture was stirred at the same temperature for 16 hr. To the reaction mixture was added water, and the precipitate was collected by filtration and washed with water. The filtered residue was dissolved in chloroform, dried over anhydrous sodium sulfate and filtered. The solvent was evaporated under reduced pressure. The obtained residue was purified by silica gel column chromatography (chloroform:methanol=98:2-95:5), the title compound (65 mg) was obtained as a white powder.

MS(ESI) m/z: 855.5[M+H]$^+$

Example 47

(47-1) t-butyl 2-chloro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylate (Example Compound 47-1)

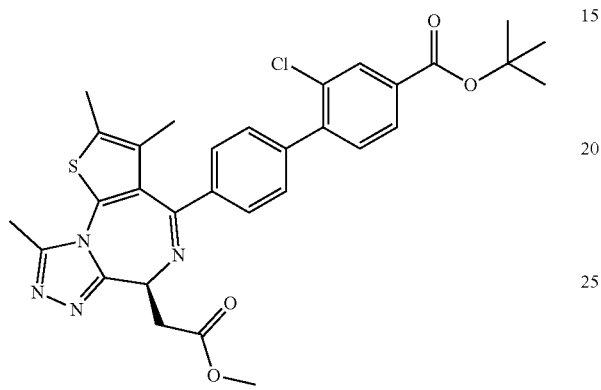

By reaction and treatment in the same manner as in Reference Example 18 using Reference Example compound 3 (300 mg) except that t-butyl 4-bromo-3-chlorobenzoate (207 mg) was used instead of t-butyl 4-bromo-3-fluorobenzoate, the title compound (374 mg) was obtained as a white crudely-purified powder. MS(ESI) m/z: 591.4, 593.4[M+H]$^+$ (47-2) methyl [(6S)-4-{2'-chloro-4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 47)

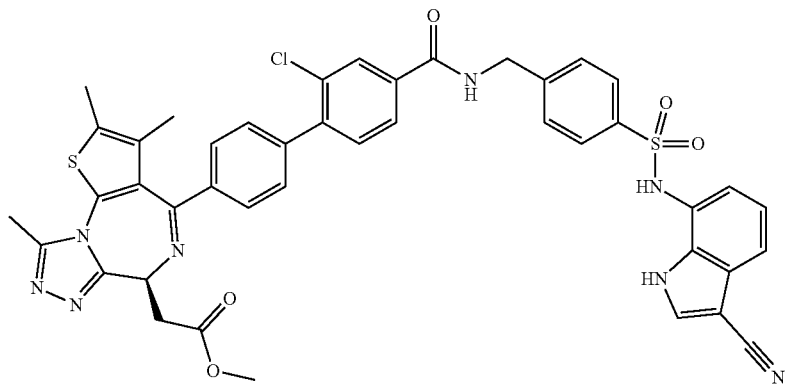 [SMILES: COC(=O)C[C@@H]1N=C(c2ccc(-c3ccc(C(=O)NCc4ccc(S(=O)(=O)Nc5cccc6c(C#N)c[nH]c56)cc4)cc3Cl)cc2)c2c(sc(C)c2C)-n2c(C)nnc21]

By reaction and treatment in the same manner as in Example 45 except that Example compound 47-1 (180 mg) was used instead of Reference Example compound 18-1, the title compound (221 mg) was obtained as a beige powder.

MS(ESI) m/z: 857.5, 859.5[M+H]$^+$

Example 48

(48-1) methyl [(6S)-4-{2'-chloro-4'-[(2-{4-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 48)

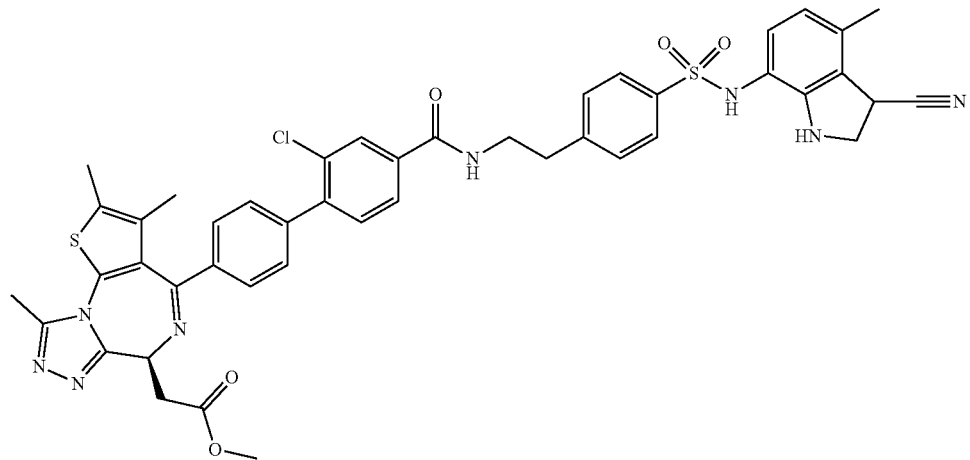 [SMILES: COC(=O)C[C@@H]1N=C(c2ccc(-c3ccc(C(=O)NCCc4ccc(S(=O)(=O)Nc5ccc(C)c6c5NCC6C#N)cc4)cc3Cl)cc2)c2c(sc(C)c2C)-n2c(C)nnc21]

By reaction and treatment in the same manner as in Example 46 except that Example compound 47-1 (180 mg) was used instead of Reference Example compound 18-1, the title compound (189 mg) was obtained as a beige powder.
MS(ESI) m/z: 871.5, 873.5[M+H]$^+$

Example 49

(49-1) methyl [(6S)-4-(4-{2-[({4-[(3-cyano-4-methyl-1H-indol-7-yl)sulfamoyl]phenyl}methyl)carbamoyl]-1,3-benzoxazol-5-yl}phenyl)-2,3,9-trimethyl-6H-thieno[3,2-f][1,2,4]triazolo[4,3-a][1,4]diazepin-6-yl]acetate (Example Compound 49)

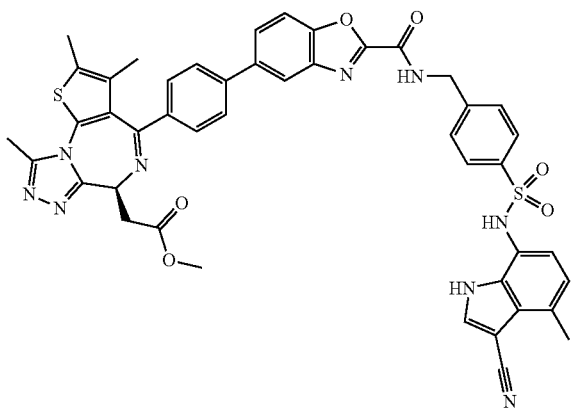

Reference Example compound 3 (200 mg), methyl 5-bromo-benzoxazole-2-carboxylate (121 mg), palladium acetate (9 mg), S-phos (32 mg), potassium fluoride (69 mg) and water (0.026 mL) were stirred in tetrahydrofuran (5.0 mL) under a nitrogen atmosphere under microwave irradiation at 100° C. for 1 hr. The mixture was filtered using ethyl acetate, and the filtrate was concentrated under reduced pressure to give an orange viscous compound. The obtained viscous compound, Reference Example compound 5 (134 mg), 1H-1,2,4-triazole (6 mg) and triethylamine (0.055 mL) were heated under reflux in tetrahydrofuran (5.0 mL) for 6 hr. The reaction mixture was concentrated under reduced pressure, and the residue was purified by silica gel column chromatography (chloroform:methanol=100:0-95:5) to give the title compound (190 mg) as a milk-white solid.
MS(ESI) m/z: 864.4[M+H]$^+$

Example 50

(50-1) t-butyl 4'-[(6S)-6-(2-methoxy-2-oxoethyl)-2,3,9-trimethyl-6H-thieno[3,2-f][1,2,4]triazolo[4,3-a][1,4]diazepin-4-yl]-3-methyl[1,1'-biphenyl]-4-carboxylate (Example compound

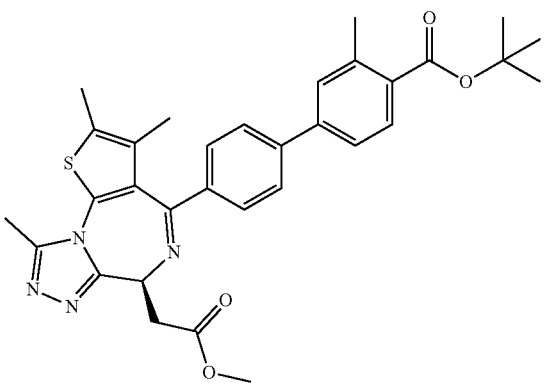 [SMILES: COC(=O)C[C@@H]1N=C(c2ccc(-c3ccc(C(=O)OC(C)(C)C)c(C)c3)cc2)c2c(sc(C)c2C)-n2c(C)nnc21]

Reference Example compound 3 (100 mg) was dissolved in tetrahydrofuran (2.0 mL), t-butyl 4-bromo-2-methylbenzoate (65 mg), tetrakis (triphenylphosphine)palladium(0) (23 mg), potassium phosphate (126 mg) and water (0.013 mL) were added, and the mixture was stirred under a nitrogen atmosphere under microwave irradiation at 90° C. for 0.5 hr. The reaction mixture was diluted with ethyl acetate, and insoluble materials were filtered off through diatomaceous earth. The filtrate was concentrated under reduced pressure, and the residue was purified by NH silica gel column chromatography (hexane:ethyl acetate=50:50-0:100) to give the title compound (117 mg) as a white crudely-purified powder. MS(ESI) m/z: 571.3[M+H]$^+$ (50-2) methyl [(6S)-4-{4'-[({4-[(3-cyano-4-methyl-1H-indol-7-yl)sulfamoyl]phenyl}methyl)carbamoyl]-3'-methyl[1,1'-biphenyl]-4-yl}-2,3,9-trimethyl-6H-thieno[3,2-f][1,2,4]triazolo[4,3-a][1,4]diazepin-6-yl]acetate (Example Compound 50)

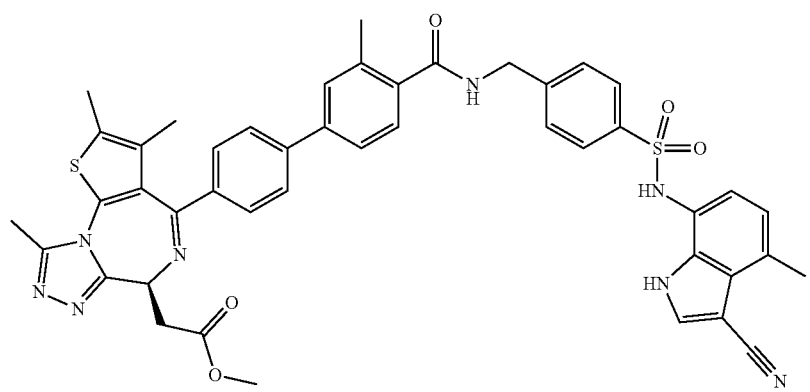

To a solution of Example compound 50-1 (113 mg) in dichloromethane (2.0 mL) was added trifluoroacetic acid (2.0 mL), and the mixture was stirred at room temperature for 1 hr. The reaction mixture was concentrated, toluene was added and the solvent was evaporated. The obtained residue was dissolved in N,N-dimethylformamide (2.0 mL), Reference Example compound 5 (74 mg), N,N-diisopropylethylamine (0.34 mL) and HATU (90 mg) were added at room temperature, and the mixture was stirred at the same temperature for 1 hr. To the reaction mixture was added water, and the precipitate was collected by filtration and washed with water. The filtered residue was dissolved in chloroform, dried over anhydrous sodium sulfate and filtered. The solvent was evaporated under reduced pressure. The obtained residue was purified by silica gel column chromatography (chloroform:methanol=98:2-95:5) to give the title compound (121 mg) as a white powder.

MS(ESI) m/z: 837.5[M+H]$^+$

Example 51

(51-1) methyl [(6S)-4-{4'-[({4-[(3-cyano-4-methyl-1H-indol-7-yl)sulfamoyl]phenyl}methyl)carbamoyl]-3'-(trifluoromethyl) [1,1'-biphenyl]-4-yl}-2,3,9-trimethyl-6H-thieno[3,2-f][1,2,4]triazolo[4,3-a][1,4]diazepin-6-yl]acetate (Example Compound 51)

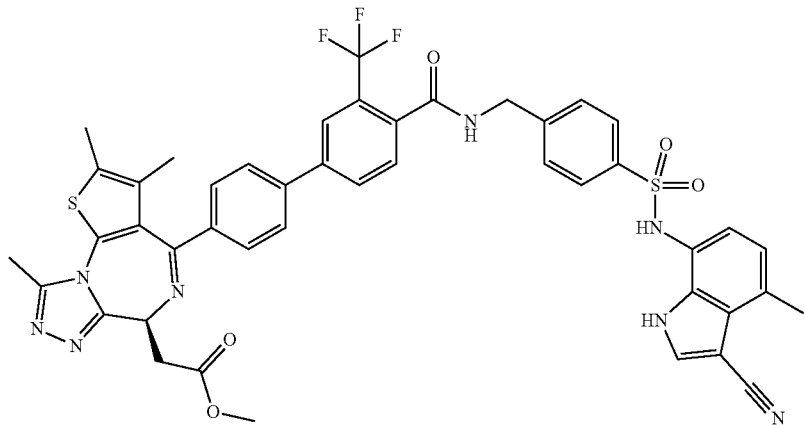

By reaction and treatment in the same manner as in (50-1)-(50-2) except that t-butyl 4-bromo-2-trifluoromethylbenzoate was used instead of t-butyl 4-bromo-2-methylbenzoate in Example 50, the title compound was obtained as a white powder.

MS(ESI) m/z: 891.5[M+H]$^+$

Example 52

(52-1) methyl [(6S)-4-{4'-[({4-[(3-cyano-4-methyl-1H-indol-7-yl)sulfamoyl]phenyl}methyl)carbamoyl]-3'-methoxy[1,1'-biphenyl]-4-yl}-2,3,9-trimethyl-6H-thieno[3,2-f][1,2,4]triazolo[4,3-a][1,4]diazepin-6-yl]acetate (Example Compound 52)

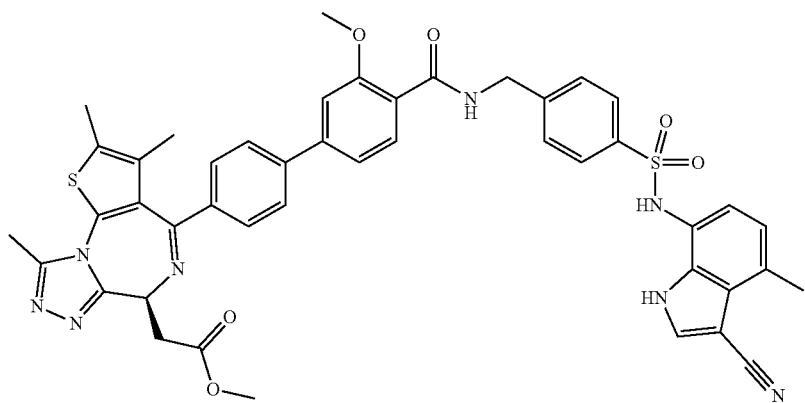

By reaction and treatment in the same manner as in (50-1)-(50-2) except that t-butyl 4-bromo-2-methoxybenzoate was used instead of t-butyl 4-bromo-2-methylbenzoate in Example 50, the title compound was obtained as a white powder.

MS(ESI) m/z: 853.5[M+H]$^+$

Example 53

(53-1) t-butyl 5-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyridine-2-carboxylate (Example Compound 53-1)

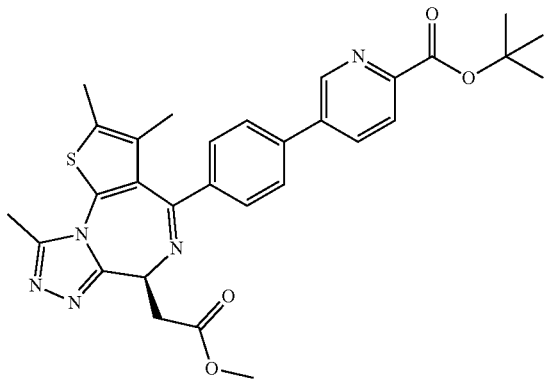 [SMILES: COC(=O)C[C@@H]1N=C(c2ccc(-c3ccc(C(=O)OC(C)(C)C)nc3)cc2)c2c(sc(C)c2C)-n2c(C)nnc21]

Example compound 3 (100 mg), t-butyl 5-bromopyridine-2-carboxylate (77 mg), tetrakis (triphenylphosphine)palladium(0) (23 mg), potassium phosphate (126 mg) and water (0.014 mL) were stirred in tetrahydrofuran (4.0 mL) under a nitrogen atmosphere under microwave irradiation at 100° C. for 0.5 hr. The reaction mixture was filtered and the filtrate was concentrated, and the residue was purified by silica gel column chromatography (chloroform:methanol=100:0-95:5) to give the title compound (109 mg) as a colorless viscous compound.

MS(ESI) m/z: 558.5[M+H]$^+$ (53-2) methyl [(6S)-4-(4-{6-[({4-[(3-cyano-4-methyl-1H-indol-7-yl)sulfamoyl]phenyl}methyl)carbamoyl]pyridin-3-yl}phenyl)-2,3,9-trimethyl-6H-thieno[3,2-f][1,2,4]triazolo[4,3-a][1,4]diazepin-6-yl]acetate (Example Compound 53)

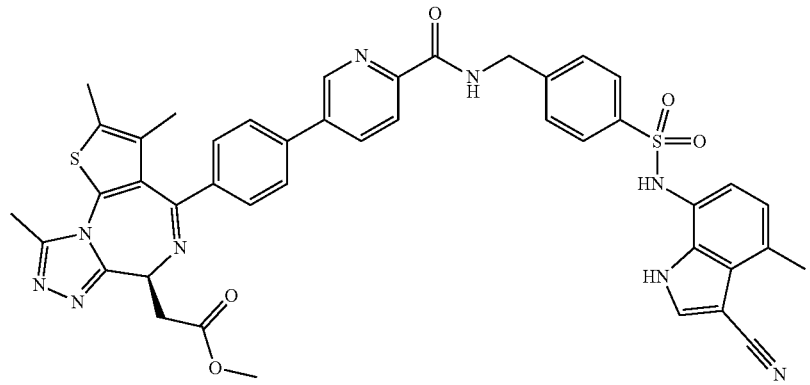

To a solution of Example compound 53-1 (109 mg) in chloroform (1.0 mL) was added trifluoroacetic acid (1.0 mL), and the mixture was stirred at room temperature for 2 hr. The reaction mixture was concentrated under reduced pressure, and azeotropically distilled twice with toluene. The residue, Reference Example compound 5 (73 mg), N,N-diisopropylethylamine (0.17 mL) and HATU (89 mg) were stirred in N,N-dimethylformamide (3.0 mL) at room temperature for 2 hr. To the reaction mixture was added water and the mixture was stirred and extracted twice with ethyl acetate. The combined organic layer was washed twice with water and concentrated under reduced pressure. The residue was purified by silica gel column chromatography (chloroform:methanol=100:0-95:5) to give the title compound (104 mg) as a milk-white solid.

MS(ESI) m/z: 824.7[M+H]$^+$

Example 54

(54-1) methyl [(6S)-4-(4-{5-[({4-[(3-cyano-4-methyl-1H-indol-7-yl)sulfamoyl]phenyl}methyl)carbamoyl]pyridin-2-yl}phenyl)-2,3,9-trimethyl-6H-thieno[3,2-f][1,2,4]triazolo[4,3-a][1,4]diazepin-6-yl]acetate (Example Compound 54)

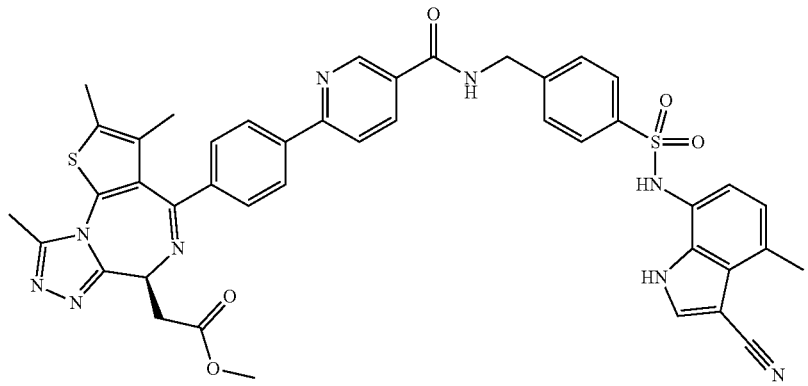

By reaction and treatment in the same manner as in (53-1)-(53-2) except that t-butyl 6-bromopyridine-3-carboxylate was used instead of t-butyl 5-bromopyridine-2-carboxylate in Example 53, the title compound was obtained as a milk-white solid. MS(ESI) m/z: 824.7[M+H]$^+$

Example 55

(55-1) t-butyl 4'-[(6S)-2-(hydroxymethyl)-6-(2-methoxy-2-oxoethyl)-3,9-dimethyl-6H-thieno[3,2-f][1,2,4]triazolo[4,3-a][1, 4]diazepin-4-yl][1,1'-biphenyl]-4-carboxylate (Example Compound 55-1)

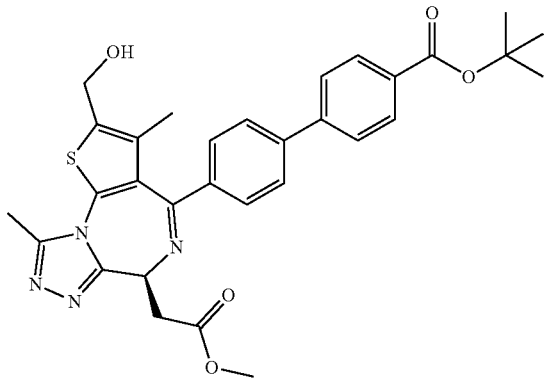 [SMILES: COC(=O)C[C@@H]1N=C(c2ccc(-c3ccc(C(=O)OC(C)(C)C)cc3)cc2)c2c(sc(CO)c2C)-n2c(C)nnc21]

A mixture of methyl [(6S)-4-(4-chlorophenyl)-2-(hydroxymethyl)-3,9-dimethyl-6H-thieno[3,2-f][1,2,4]triazolo[4,3-a][1,4]diazepin-6-yl]acetate (500 mg) described in WO 2006/129623, (4-t-butoxycarbonylphenyl)boronic acid (386 mg), potassium phosphate (616 mg), tetrahydrofuran (5.0 mL), water (0.52 mL), 2-dicyclohexylphosphino-2'-6'-dimethoxybiphenyl aminobiphenyl palladium chloride precatalyst (42 mg), S-phos (24 mg) was stirred with heating under reflux for 3 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by NH silica gel column chromatography (ethyl acetate:methanol=99:1-90:10) to give the title compound (610 mg) as a milky white solid.

MS(ESI) m/z: 573.2[M+H]$^+$ (55-2) methyl [(6S)-4-{4'-[({4-[(3-cyano-4-methyl-1H-indol-7-yl)sulfamoyl]phenyl}methyl)carbamoyl][1,1'-biphenyl]-4-yl}-2-(hydroxymethyl)-3,9-dimethyl-6H-thieno[3,2-f][1,2,4]triazolo[4,3-a][1,4]diazepin-6-yl]acetate (Example Compound 55)

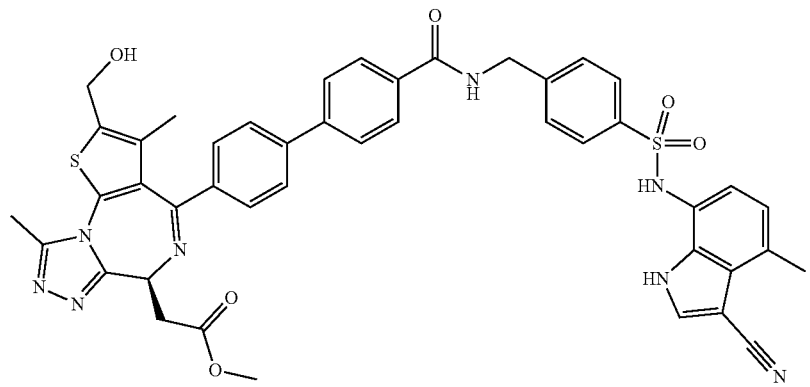

To a solution of Example compound 55-1 (80 mg) in dichloromethane (1.0 mL) was added trifluoroacetic acid (1.0 mL), and the mixture was stirred at room temperature for 5 hr. The reaction mixture was concentrated under reduced pressure. The obtained residue and Reference Example compound 5 (57 mg) were dissolved in N,N-dimethylformamide (3.0 mL), N,N-diisopropylethylamine (0.073 mL) was added at room temperature, HATU (69 mg) was added under ice-cooling, and the mixture was stirred at room temperature for 7 hr. The reaction solution was diluted with a mixture of ethyl acetate-tetrahydrofuran (1:1), and 1N hydrochloric acid and saturated brine were added for partitioning. The organic layer was washed once with saturated brine, once with saturated aqueous sodium hydrogen carbonate, and once with saturated brine, dried over anhydrous sodium sulfate and filtered. The solvent was evaporated under reduced pressure. The obtained residue was purified by silica gel column chromatography (ethyl acetate:methanol=100:0-85:15) to give the title compound (51 mg) as a pale-yellow solid. MS(ESI) m/z: 839.4[M+H]+

Example 56

(56-1) methyl {(6S)-2,3,9-trimethyl-4-[4-(1,2,3,4-tetrahydroisoquinolin-6-yl)phenyl]-6H-thieno[3,2-f][1,2,4]triazolo[4,3-a][1,4]diazepin-6-yl}acetate (Example Compound 56-1)

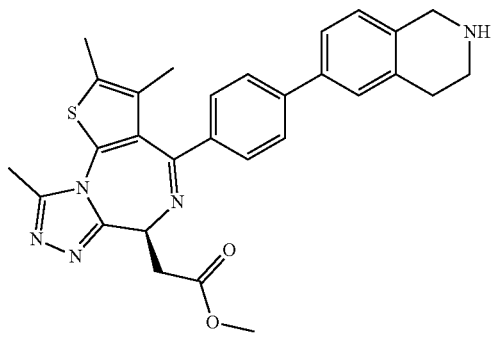 [SMILES: COC(=O)C[C@@H]1N=C(c2ccc(-c3ccc4c(c3)CCNC4)cc2)c2c(sc(C)c2C)-n2c(C)nnc21]

A mixture of Reference Example compound 1 (200 mg), t-butyl 6-(4,4,5,5-tetramethyl-1,3,2-dioxaborolan-2-yl)-3,4-dihydroisoquinoline-2 (1H)-carboxylate (208 mg), X-Phos aminobiphenylpalladium chloride precatalyst (38 mg), X-Phos (23 mg), potassium phosphate (307 mg), water (0.031 mL) and tetrahydrofuran (2.4 mL) was stirred under microwave irradiation at 90° C. for 0.5 hr. To the reaction mixture were added ethyl acetate and saturated brine, insoluble materials were filtered off, and the filtrate was partitioned. The organic layer was washed once with saturated brine, dried over anhydrous sodium sulfate and filtered. The solvent was evaporated under reduced pressure. The obtained residue was dissolved in chloroform (1.0 mL), trifluoroacetic acid (1.0 mL) was added at room temperature, and the mixture was stirred at the same temperature for 6 hr. The solvent was evaporated under reduced pressure and the residue was azeotropically concentrated with toluene. The obtained residue was purified by NH silica gel column chromatography (ethyl acetate:methanol=100:0-96:4) to give the title compound (244 mg) as a pale-yellow powder. MS(ESI) m/z: 512.3[M+H]+

(56-2) methyl [(6S)-4-{2-({4-[(3-cyano-4-methyl-1H-indol-7-yl)sulfamoyl]phenyl}methyl)-1,2,3,4-tetrahydroisoquinolin-6-yl]phenyl}-2,3,9-trimethyl-6H-thieno[3,2-f][1,2,4]triazolo[4,3-a][1,4]diazepin-6-yl]acetate (Example Compound 56)

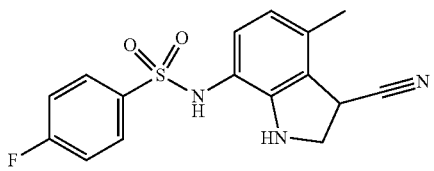 [SMILES: Cc1ccc(NS(=O)(=O)c2ccc(F)cc2)c2c1C(C#N)CN2]

To a mixture of Example compound 56-1 (60 mg), Reference Example compound 5-1 (44 mg) and chloroform (2.0 mL) was added sodium triacetoxyborohydride (50 mg) at room temperature, and the mixture was stirred at the same temperature for 22 hr. Furthermore, sodium triacetoxyborohydride (50 mg) was added at room temperature, and the mixture was stirred at the same temperature for 8 hr. To the reaction mixture was added saturated aqueous sodium hydrogen carbonate, and the mixture was stirred at room temperature for 30 min. Saturated brine was added, and the mixture was extracted 3 times with chloroform. The extract was dried over anhydrous sodium sulfate and filtered. The solvent was evaporated under reduced pressure. The residue was purified by preparative HPLC (10 mM aqueous ammonium carbonate solution-acetonitrile) to give the title compound (74 mg) as a pale-yellow solid.

MS(ESI) m/z: 835.5[M+H]+

Example 57

(57-1) N-(3-cyano-4-methyl-1H-indol-7-yl)-4-fluorobenzene-1-sulfonamide (Example Compound 57-1)

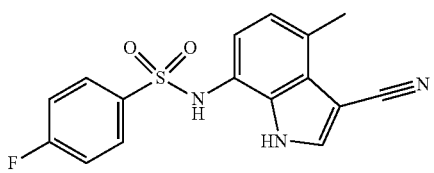 [SMILES: Cc1ccc(NS(=O)(=O)c2ccc(F)cc2)c2[nH]cc(C#N)c12]

To a mixture of Reference Example compound 9 (300 mg), pyridine (0.71 mL), and tetrahydrofuran (3.0 mL) was added 4-fluorobenzenesulfonyl chloride (375 mg) at room temperature, and the mixture was stirred at the same temperature for 1.5 hr. The reaction mixture was diluted with ethyl acetate, and partitioned by adding saturated brine and 1N hydrochloric acid. The organic layer was washed twice with saturated brine, dried over anhydrous sodium sulfate and filtered. The solvent was evaporated under reduced pressure to give the title compound (580 mg) as a brown solid. MS(ESI) m/z: 328.1[M-H]−

(57-2) 4-[(2-aminoethyl)amino]-N-(3-cyano-4-methyl-1H-indol-7-yl)benzene-1-sulfonamide (Example Compound 57-2)

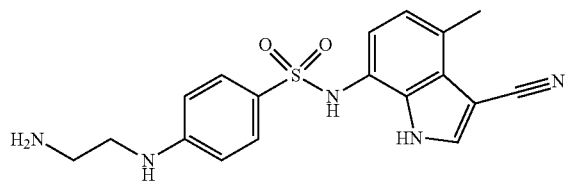 [SMILES: Cc1ccc(NS(=O)(=O)c2ccc(NCCN)cc2)c2[nH]cc(C#N)c12]

A mixture of Example compound 57-1 (200 mg), ethylenediamine (0.61 mL) and tetrahydrofuran (1.0 mL) was stirred with heating under microwave irradiation at 150° C. for 0.5 hr. To the reaction mixture was added saturated brine, and the mixture was extracted 3 times with an ethyl acetate-tetrahydrofuran (1:1) mixture. The extracts were combined, washed once with a small amount of saturated brine, dried over anhydrous sodium sulfate and filtered. The solvent was evaporated under reduced pressure. The obtained residue was suspended and washed with ethyl acetate, and collected by filtration to give the title compound (180 mg) as a brown powder. MS(ESI) m/z: 370.2[M+H]$^+$ (57-3) methyl [(6S)-4-{4'-[(2-{4-[(3-cyano-4-methyl-1H-indol-7-yl)sulfamoyl]anilino}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 57)

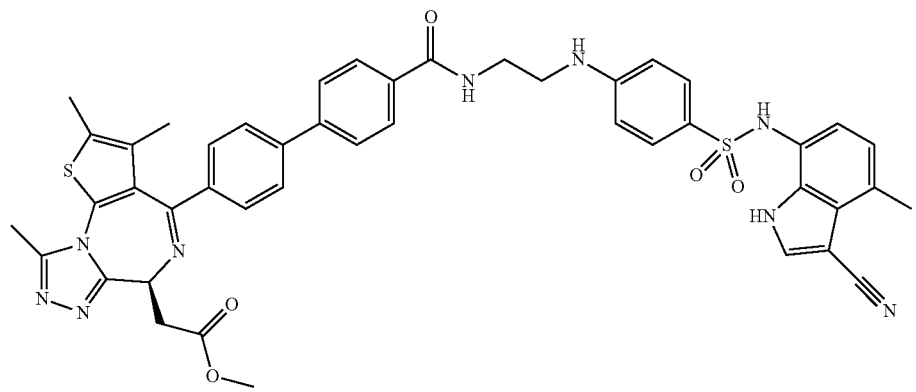

To a mixture of Example compound 57-2 (41 mg), Reference Example compound 4 (50 mg), N,N-diisopropylethylamine (0.043 mL) and N,N-dimethylformamide (1.0 mL) was added HATU (49 mg) under ice-cooling, and the mixture was stirred at the same temperature for 5 min and at room temperature for 3 hr. The reaction mixture was diluted with an ethyl acetate-tetrahydrofuran (1:1) mixture, washed once with saturated aqueous sodium hydrogen carbonate and once with saturated brine, dried over anhydrous sodium sulfate and filtered. The solvent was evaporated under reduced pressure. The residue was suspended and washed with acetonitrile-water, collected by filtration, and washed with water to give the title compound (45 mg) as a pink powder. MS(ESI) m/z: 852.5[M+H]$^+$ Example 58

(58-1) 3-[4-(benzylsulfanyl)phenyl]propan-1-ol (Example Compound 58-1)

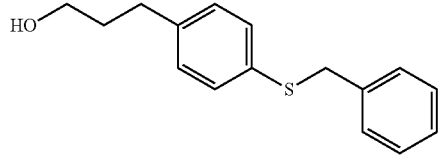 [SMILES: OCCCc1ccc(SCc2ccccc2)cc1]

A mixture of 3-(4-bromophenyl)propan-1-ol (1000 mg), benzylmercaptan (0.55 mL), N,N-diisopropylethylamine (2.41 mL), 4,5-bis(diphenylphosphino)-9,9-dimethylxanthene (Xantphos, 269 mg), tris(dibenzylideneacetone)dipalladium (213 mg) and toluene (15.0 mL) was stirred under a nitrogen atmosphere at 100° C. for hr. After allowing to cool to room temperature, the reaction mixture was directly purified by silica gel column chromatography (hexane:ethyl acetate=60:40-20:80, precolumn: NH silica gel) to give the title compound (681 mg) as a red solid. 1H NMR (400 MHz, CDCl$_3$) δ ppm 1.23 (1H, t, J=5.3 Hz), 1.81-1.91 (2H, m), 2.62-2.71 (2H, m), 3.61-3.70 (2H, m), 4.08 (2H, s), 7.05-7.11 (2H, m), 7.19-7.31 (7H, m)

(58-2) 2-(4-{3-[4-(benzylsulfanyl)phenyl]propoxy}phenyl)-4,4,5,5-tetramethyl-1,3,2-dioxaborolane (Example Compound 58-2)

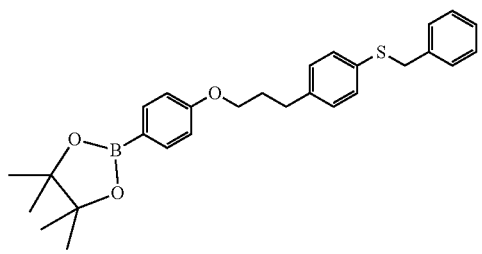 [SMILES: CC1(C)OB(c2ccc(OCCCc3ccc(SCc4ccccc4)cc3)cc2)OC1(C)C]

To a solution of 4-(4,4,5,5-tetramethyl-1,3,2-dioxaborolan-2-yl)phenol (200 mg) and Example compound 58-1 (281 mg) in toluene (3.0 mL) was added cyanomethylenetrimethylphosphorane (157 mg) at room temperature, and the mixture was stirred under a nitrogen atmosphere under microwave irradiation at 150° C. for 0.5 hr. The reaction mixture was diluted with ethyl acetate, washed once with saturated brine-water (1:1) and once with saturated brine, dried over anhydrous sodium sulfate and filtered. The solvent was evaporated under reduced pressure. The obtained residue was purified by silica gel column chromatography (hexane:ethyl acetate=95:5) to give the title compound (338 mg) as a colorless viscous compound. 1H NMR (400 MHz, CDCl$_3$) δ ppm 1.33 (12H, s), 2.00-2.12 (2H, m), 2.76 (2H, t, J=7.6 Hz), 3.96 (2H, t, J=6.2 Hz), 4.08 (2H, s), 6.87 (2H, d, J=8.7 Hz), 7.09 (2H, d, J=8.3 Hz), 7.22 (3H, d, J=8.3 Hz), 7.25-7.28 (4H, m), 7.74 (2H, d, J=8.7 Hz)

(58-3) methyl [(6S)-4-(4'-{3-[4-(benzylsulfanyl)phenyl]propoxy}[1,1'-biphenyl]-4-yl)-2,3,9-trimethyl-6H-thieno[3,2-f][1,2,4]triazolo[4,3-a][1,4]diazepin-6-yl]acetate (Example Compound 58-3)

column chromatography (hexane:ethyl acetate=50:50-0:100) to give the title compound (147 mg) as a pale-yellow powder.

MS(ESI) m/z: 713.5[M+H]$^+$ (58-4) methyl [(6S)-4-(4'-{3-[4-(chlorosulfonyl)phenyl]propoxy}[1,1'-biphenyl]-4-yl)-2,3,9-trimethyl-6H-thieno[3,2-f][1,2,4]triazolo[4,3-a][1,4]diazepin-6-yl]acetate (Example Compound 58-4)

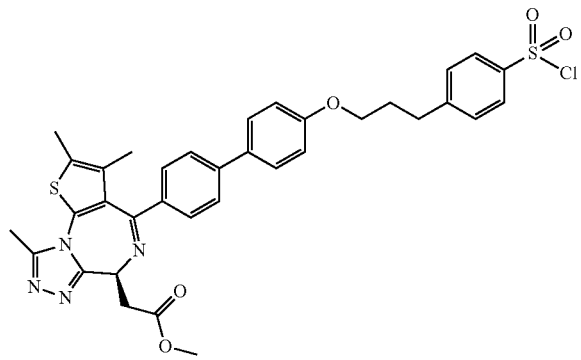

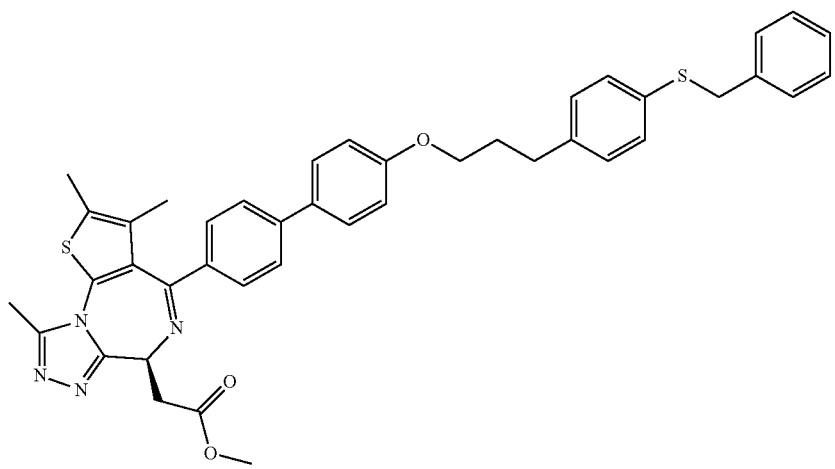 [SMILES: COC(=O)C[C@@H]1N=C(c2ccc(-c3ccc(OCCCc4ccc(SCc5ccccc5)cc4)cc3)cc2)c2c(sc(C)c2C)-n2c(C)nnc21]

A mixture of Reference Example compound 1 (100 mg), Example compound 58-2 (122 mg), 2-dicyclohexylphosphino-2',4',6'-triisopropylbiphenyl (X-Phos, 12 mg), X-Phos aminobiphenylpalladium(II) methanesulfonate precatalyst (21 mg), potassium phosphate (154 mg), water (0.016 mL) and tetrahydrofuran (1.2 mL) was stirred under a nitrogen atmosphere under microwave irradiation at 90° C. for 0.5 hr. Example compound 58-2 (67 mg), X-Phos (12 mg), X-Phos aminobiphenylpalladium(II) methanesulfonate precatalyst (21 mg) were added, and the mixture was stirred under a nitrogen atmosphere under microwave irradiation at 90° C. for 1 hr. The reaction mixture was diluted with ethyl acetate, and insoluble materials were filtered off through diatomaceous earth. The filtrate was concentrated under reduced pressure, and the residue was purified by NH silica gel To a solution of Example compound 58-3 (141 mg) in acetonitrile (3.0 mL)-2N hydrochloric acid (0.60 mL) was added, under ice-cooling, N-chlorosuccinimide (93 mg), and the mixture was stirred at the same temperature for 1.5 hr. N-Chlorosuccinimide (6 mg) was added, and the mixture was stirred at the same temperature for 0.5 hr. The reaction mixture was diluted with ethyl acetate, washed successively with saturated brine-water (1:1) and saturated brine, dried over anhydrous sodium sulfate and filtered. The solvent was evaporated under reduced pressure. The obtained residue was purified by silica gel column chromatography (chloroform:methanol=98:2) to give the title compound (134 mg) as a pale-yellow powder. MS (ESI) m/z: 671.4 [M−Cl+H$_2$O]$^+$ (58-5) methyl {(6S)-4-[4'-(3-{4-[(3-cyano-4-methyl-1H-indol-7-yl)sulfamoyl]phenyl}propoxy) [1,1'-biphenyl]-4-yl]-2,3,9-trimethyl-6H-thieno[3,2-f][1,2,4]triazolo[4,3-a][1,4]diazepin-6-yl}acetate (Example Compound 58)

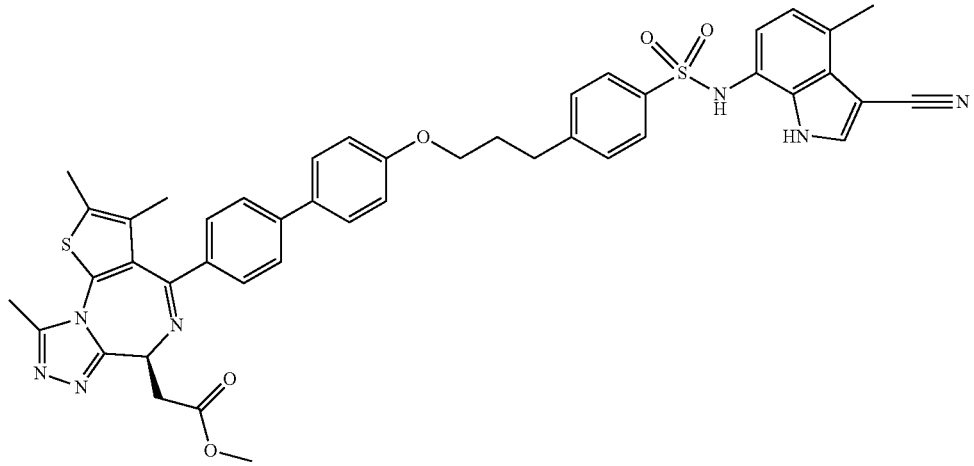 [SMILES: COC(=O)C[C@@H]1N=C(c2ccc(-c3ccc(OCCCc4ccc(S(=O)(=O)Nc5ccc(C)c6c(C#N)c[nH]c56)cc4)cc3)cc2)c2c(sc(C)c2C)-n2c(C)nnc21]

To a solution of Example compound 58-4 (130 mg) and Reference Example compound 9 (39 mg) in tetrahydrofuran (2.6 mL) was added pyridine (0.15 mL) at room temperature, and the mixture was stirred at the same temperature for 1.5 hr. The reaction mixture was concentrated under reduced pressure, and the residue was dissolved in chloroform, washed once with 1N hydrochloric acid and once with saturated brine, dried over anhydrous sodium sulfate and filtered. The solvent was evaporated under reduced pressure. The obtained residue was purified by NH silica gel column chromatography (chloroform:methanol=95:5-50:50) and purified again by silica gel column chromatography (chloroform:methanol=98:2-95:5) to give the title compound (52 mg) as a pale-brown powder.
MS(ESI) m/z: 824.5[M+H]$^+$ Example 59

(59-1) t-butyl 5-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}thiophene-2-carboxylate (Example Compound 59-1)

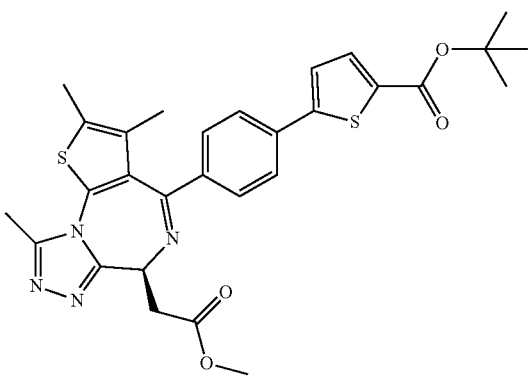 [SMILES: COC(=O)C[C@@H]1N=C(c2ccc(-c3ccc(C(=O)OC(C)(C)C)s3)cc2)c2c(sc(C)c2C)-n2c(C)nnc21]

Example compound 3 (100 mg), t-butyl 5-bromothiophene-2-carboxylate (78 mg), tetrakis (triphenylphosphine) palladium(0) (23 mg), potassium phosphate (126 mg) and water (0.014 mL) were stirred in tetrahydrofuran (4.0 mL) under a nitrogen atmosphere under microwave irradiation at 100° C. for 0.5 hr. The reaction mixture was filtered and the filtrate was concentrated, and the residue was purified by silica gel column chromatography (chloroform:methanol=100:0-95:5) to give the title compound (89 mg) as a pale-yellow solid. MS(ESI) m/z: 563.2[M+H]$^+$ (59-2) methyl [(6S)-4-(4-{5-[({4-[(3-cyano-4-methyl-1H-indol-7-yl)sulfamoyl]phenyl}methyl)carbamoyl]thiophen-2-yl}phenyl)-2,3,9-trimethyl-6H-thieno[3,2-f][1,2,4]triazolo[4,3-a][1, 4]diazepin-6-yl]acetate (Example Compound 59)

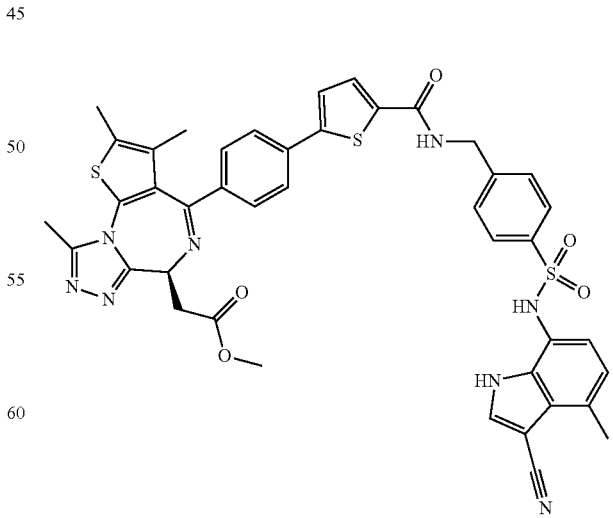

To a solution of Example compound 59-1 (89 mg) in chloroform (1.0 mL) was added trifluoroacetic acid (1.0 mL), and the mixture was stirred at room temperature for 2 hr. The reaction mixture was concentrated under reduced pressure and azeotropically distilled twice with toluene. The residue and Reference Example compound 5 (59 mg), N,N-diisopropylethylamine (0.14 mL) and HATU (72 mg) were stirred in N,N-dimethylformamide (3.0 mL) at room temperature for 2 hr. To the reaction mixture was added water and the mixture was stirred and extracted twice with ethyl acetate. The combined organic layer was washed twice with water and concentrated under reduced pressure. The residue was purified by silica gel column chromatography (chloroform:methanol=100:0-95:5) to give the title compound (117 mg) as a beige solid.

MS(ESI) m/z: 829.6[M+H]$^+$

Example 60

(60-1) methyl [(6S)-4-{4'-[({trans-3-[(3-cyano-4-methyl-1H-indol-7-yl)sulfamoyl]cyclobutyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example compound 60)

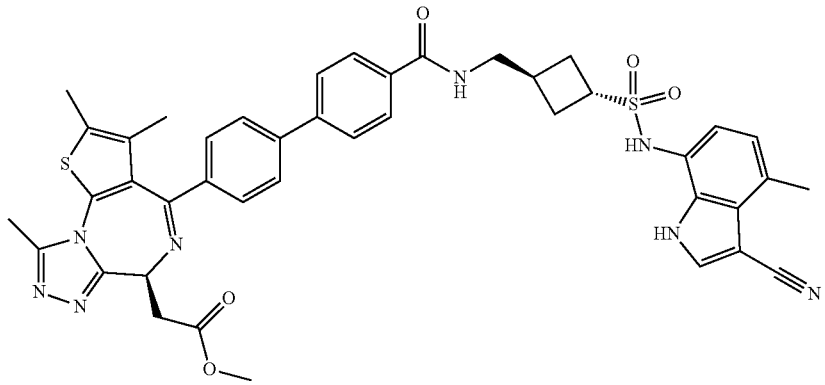 [SMILES: COC(=O)C[C@@H]1N=C(c2ccc(-c3ccc(C(=O)NC[C@H]4C[C@H](S(=O)(=O)Nc5ccc(C)c6c(C#N)c[nH]c56)C4)cc3)cc2)c2c(sc(C)c2C)-n2c(C)nnc21]

By reaction and treatment in the same manner as in (20-1)-(20-4) except that methyl trans-3-(chlorosulfonyl)cyclobutane-1-carboxylate was used instead of methyl 5-(chlorosulfonyl)pyridine-2-carboxylate in Example 20, the title compound was obtained as a beige solid.

MS(ESI) m/z: 801.7[M+H]$^+$

Example 61

(61-1) methyl [(6S)-4-(4-{2-[({4-[(3-cyano-4-methyl-1H-indol-7-yl)sulfamoyl]phenyl}methyl)carbamoyl]-1-benzothiophen-5-yl}phenyl)-2,3,9-trimethyl-6H-thieno[3,2-f][1,2,4]triazolo[4,3-a][1,4]diazepin-6-yl]acetate (Example Compound 61)

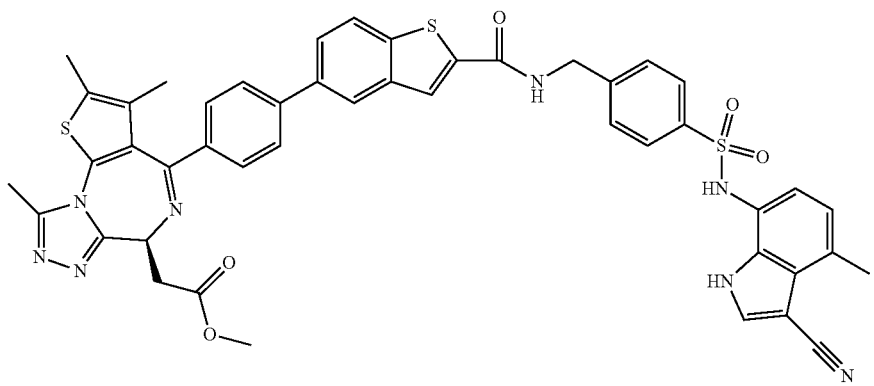

By reaction and treatment in the same manner as in (50-1)-(50-2) except that t-butyl 5-bromobenzothiophene-2-carboxylate was used instead of t-butyl 4-bromo-2-methylbenzoate in Example 50, the title compound was obtained as a white powder. MS(ESI) m/z: 879.5[M+H]$^+$

Example 62

(62-1) methyl [(6S)-4-(4-{2-[({4-[(3-cyano-4-methyl-1H-indol-7-yl)sulfamoyl]phenyl}methyl)carbamoyl]-1-benzothiophen-6-yl}phenyl)-2,3,9-trimethyl-6H-thieno[3,2-f][1,2,4]triazolo[4,3-a][1,4]diazepin-6-yl]acetate (Example Compound 62)

lbiphenyl (X-Phos, 11 mg), X-Phos aminobiphenylpalladium chloride precatalyst (18 mg), potassium phosphate (140 mg), water (0.015 mL) and tetrahydrofuran (1.5 mL) was stirred under a nitrogen atmosphere under microwave irradiation at 90° C. for 0.5 hr. The reaction mixture was diluted with ethyl acetate, and insoluble materials were filtered off through diatomaceous earth. The filtrate was concentrated under reduced pressure, and the residue was purified by silica gel column chromatography (chloroform:methanol=98:2) to give the title compound (107 mg) as a pale-yellow powder. MS(ESI) m/z: 633.5[M+H]$^+$

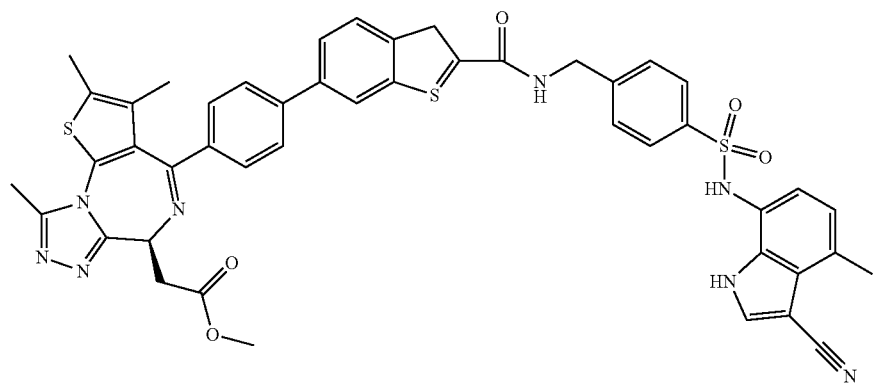

By reaction and treatment in the same manner as in (50-1)-(50-2) except that t-butyl 6-bromobenzothiophene-2-carboxylate was used instead of t-butyl 4-bromo-2-methylbenzoate in Example 50, the title compound was obtained as a white powder. MS(ESI) m/z: 879.5[M+H]$^+$

Example 63

(63-1) benzyl 4'-[(6S)-6-(2-t-butoxy-2-oxoethyl)-2,3,9-trimethyl-6H-thieno[3,2-f][1,2,4]triazolo[4,3-a][1,4]diazepin-4-yl][1,1'-biphenyl]-4-carboxylate (Example Compound 63-1)

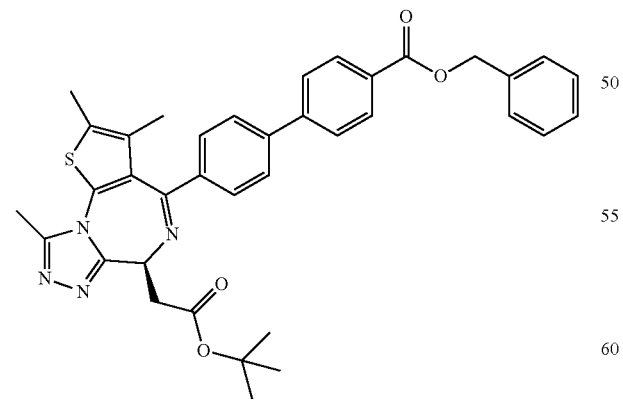

A mixture of t-butyl [(6S)-4-(4-chlorophenyl)-2,3,9-trimethyl-6H-thieno[3,2-f][1,2,4]triazolo[4,3-a][1,4]diazepin-6-yl]acetate (100 mg), (4-benzyloxycarbonylphenyl)boronic acid (68 mg), 2-dicyclohexylphosphino-2',4',6'-triisopropy- (63-2) 4'-[(6S)-6-(2-t-butoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Example Compound 63-2)

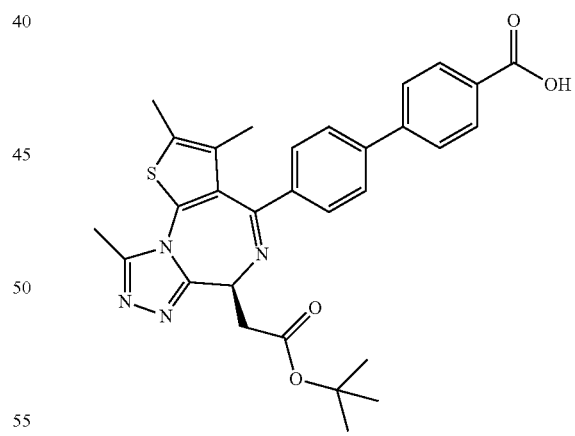

Example compound 63-1 (103 mg) was dissolved in methanol (5.0 mL), and 10% palladium hydroxide carbon (46 mg) was added. The reaction container was substituted with hydrogen, and the mixture was stirred at room temperature for 1 hr. The reaction container was substituted with nitrogen, and the reaction mixture was filtered, and the solvent was concentrated under reduced pressure to give a crudely purified title compound (89 mg) as a pale-yellow powder. MS(ESI) m/z: 543.4[M+H]$^+$ (63-3) t-butyl [(6S)-4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate
(Example Compound 63)

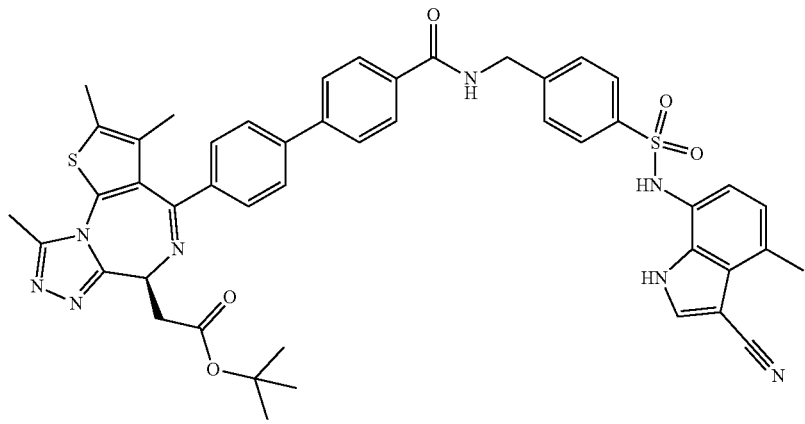

To a solution of Example compound 63-2 (43 mg) and Reference Example compound 5 (30 mg) in N,N-dimethylformamide (1.0 mL) were added N,N-diisopropylethylamine (0.027 mL) and HATU (37 mg) at room temperature, and the mixture was stirred at the same temperature for 3 hr. The reaction mixture was diluted with ethyl acetate, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (38 mg) as a beige powder. MS(ESI) m/z: 865.5[M+H]$^+$ Example 64

(64-1) t-butyl [(6S)-4-{4'-[(2-{4-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 64)

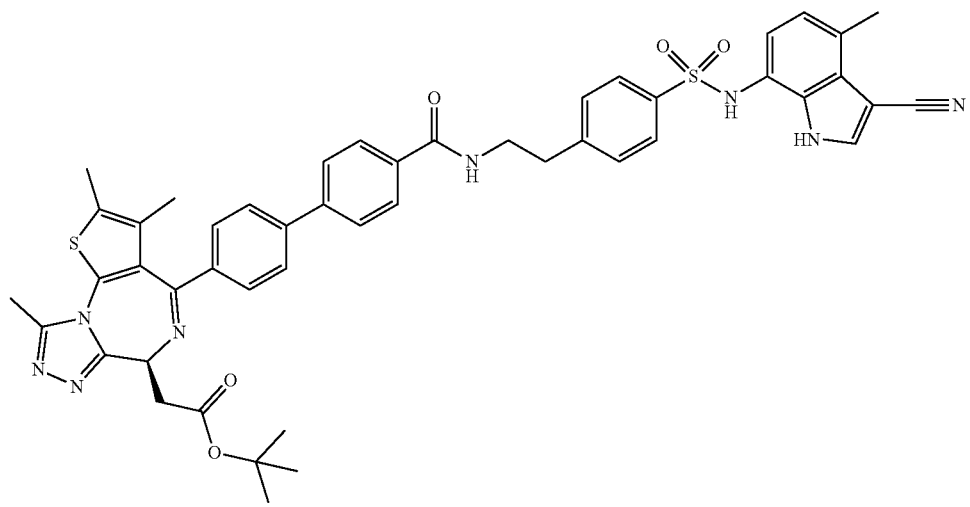 [SMILES: Cc1sc2c(c1C)C(c1ccc(-c3ccc(C(=O)NCCc4ccc(S(=O)(=O)Nc5ccc(C)c6c(C#N)c[nH]c56)cc4)cc3)cc1)=N[C@@H](CC(=O)OC(C)(C)C)c1nnc(C)n1-2]

To a solution of Example compound 63-2 (43 mg), Reference Example compound 11 (34 mg) in N,N-dimethylformamide (1.0 mL) were added N,N-diisopropylethylamine (0.041 mL) and HATU (37 mg) at room temperature, and the mixture was stirred at the same temperature for 3 hr. The reaction mixture was diluted with ethyl acetate, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (49 mg) as a white powder.

MS(ESI) m/z: 879.6[M+H]$^+$

Example 65

(65-1) t-butyl 5-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyrazine-2-carboxylate (Example Compound 65-1)

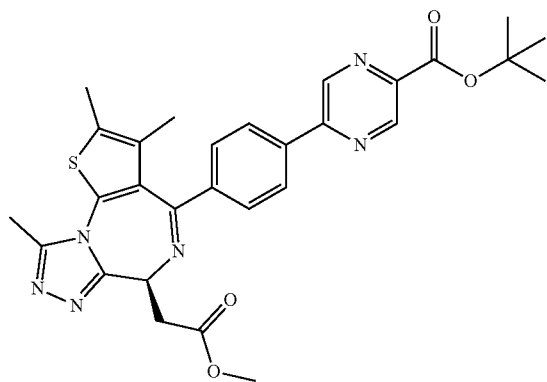 [SMILES: COC(=O)C[C@@H]1N=C(c2ccc(-c3cnc(C(=O)OC(C)(C)C)cn3)cc2)c2c(sc(C)c2C)-n2c(C)nnc21]

Example compound 3 (100 mg), t-butyl 5-bromopyrazine-2-carboxylate (77 mg), tetrakis(triphenylphosphine)palladium(0) (23 mg), potassium phosphate (126 mg) and water (0.014 mL) were stirred in tetrahydrofuran (4.0 mL) under a nitrogen atmosphere under microwave irradiation at 100° C. for 0.5 hr. The reaction mixture was filtered and the filtrate was concentrated, and the residue was purified by silica gel column chromatography (chloroform:methanol=100:0-95:5) to give the title compound (97 mg) as a pale-yellow solid. MS(ESI) m/z: 559.3[M+H]$^+$ (65-2) methyl [(6S)-4-(4-{5-[({4-[(3-cyano-4-methyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1,4]diazepin-6-yl]acetate (Example Compound 65)

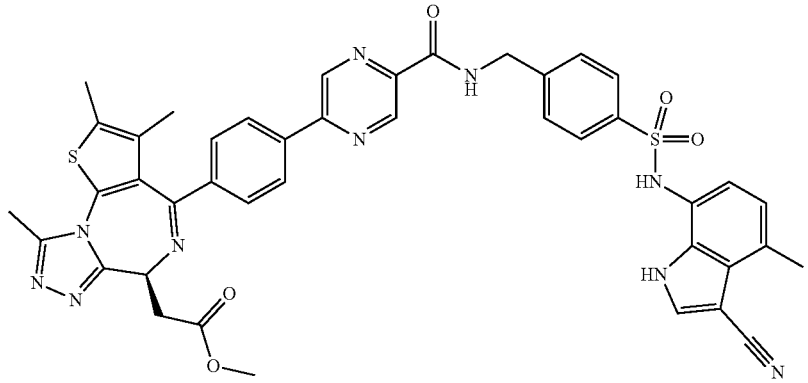

To a solution of Example compound 65-1 (97 mg) in chloroform (1.0 mL) was added trifluoroacetic acid (1.0 mL), and the mixture was stirred at room temperature for 2 hr. The reaction mixture was concentrated under reduced pressure and azeotropically distilled twice with toluene. The residue and Reference Example compound 5 (65 mg), N,N-diisopropylethylamine (0.15 mL) and HATU (79 mg) were stirred in N,N-dimethylformamide (3.0 mL) at room temperature for 1 hr. To the reaction mixture was added water and the mixture was stirred and extracted twice with ethyl acetate. The combined organic layer was washed twice with water and concentrated under reduced pressure. The residue was purified by silica gel column chromatography (chloroform:methanol=100:0-95:5) to give the title compound (111 mg) as a beige solid.

MS(ESI) m/z: 825.4[M+H]$^+$

Example 66

(66-1) methyl [(6S)-4-(4-{2-[({4-[(3-cyano-4-methyl-1H-indol-7-yl)sulfamoyl]phenyl}methyl)carbamoyl]-1-benzofuran-6-yl}phenyl)-2,3,9-trimethyl-6H-thieno[3,2-f][1,2,4]triazolo[4,3-a][1,4]diazepin-6-yl]acetate (Example Compound 66)

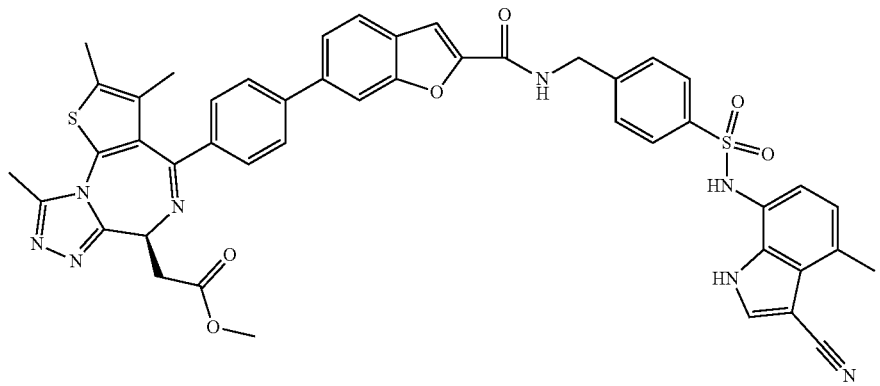

By reaction and treatment in the same manner as in (50-1)-(50-2) except that t-butyl 6-bromobenzofuran-2-carboxylate was used instead of t-butyl 4-bromo-2-methylbenzoate in Example 50, the title compound was obtained as a white powder.

MS(ESI) m/z: 863.5[M+H]$^+$

Example 67

(67-1) [4-(benzylsulfanyl)phenyl]methanol (Example Compound 67-1)

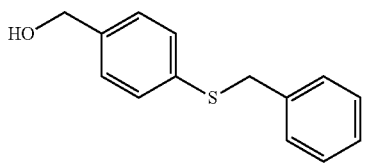 [SMILES: OCc1ccc(SCc2ccccc2)cc1]

A mixture of (4-bromophenyl)methanol (2000 mg), benzylmercaptan (1.51 mL), N,N-diisopropylethylamine (2.78 mL), 4,5-bis(diphenylphosphino)-9,9-dimethylxanthene (Xantphos, 1237 mg), tris(dibenzylideneacetone)dipalladium (980 mg) and toluene (10.0 mL) was stirred under a nitrogen atmosphere under microwave irradiation at 150° C. for 0.5 hr. After allowing to cool to room temperature, insoluble material was filtered off, and the filtered residue was washed with ethyl acetate. The filtrate was concentrated under reduced pressure, and the residue was purified by NH silica gel column chromatography (hexane:ethyl acetate=90:10-50:50, precolumn:NH silica gel) to give the title compound (2141 mg) as a pale-yellow solid. $^1$H NMR (400 MHz, CDCl$_3$) δ ppm 1.61 (1H, t, J=5.91 Hz), 4.11 (2H, s), 4.65 (2H, d, J=5.91 Hz), 7.17-7.35 (9H, m)

(67-2) 1-(benzylsulfanyl)-4-(chloromethyl)benzene (Example Compound 67-2)

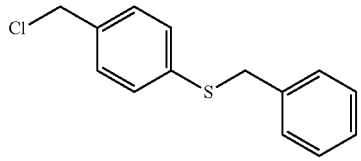 [SMILES: ClCc1ccc(SCc2ccccc2)cc1]

To a suspension of Example compound 67-1 (556 mg) in toluene (5.6 mL) was added thionyl chloride (0.21 mL) at room temperature, and the mixture was stirred at the same temperature for 0.5 hr. The reaction mixture was diluted with ethyl acetate, washed twice with saturated brine, dried over anhydrous sodium sulfate and filtered. The solvent was evaporated under reduced pressure to give the title compound (592 mg) as a crudely purified pale-brown solid. $^1$H NMR (400 MHz, CDCl$_3$) δ ppm 4.13 (2H, s), 4.54 (2H, s), 7.18-7.35 (9H, m)

(67-3) 2-{[4-(benzylsulfanyl)phenyl]methyl}-6-bromo-3,4-dihydroisoquinolin-1 (2H)-one (Example Compound 67-3)

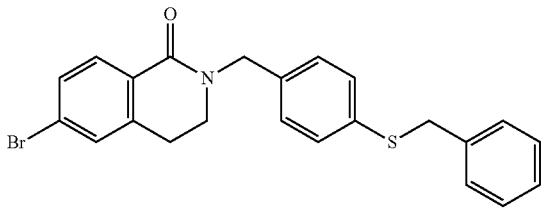 [SMILES: O=C1c2ccc(Br)cc2CCN1Cc1ccc(SCc2ccccc2)cc1]

To a solution of 6-bromo-3,4-dihydro-2H-isoquinolin-1-one (500 mg) in N,N-dimethylformamide (5.0 mL) was added sodium hydride (115 mg, 60%, dispersed in liquid paraffin) at room temperature and the mixture was stirred for 10 min. A solution of Example compound 67-2 (585 mg) in N,N-dimethylformamide (5.0 mL) was added, and the mixture was stirred at the same temperature for 2 hr. To the reaction mixture was partitioned between 1N hydrochloric acid and ethyl acetate. The organic layer was washed twice with saturated brine-water (1:1) and once with saturated brine, dried over anhydrous sodium sulfate, and filtered. The solvent was evaporated under reduced pressure. The residue was purified by silica gel column chromatography (hexane: ethyl acetate=90:10-80:20) to give the title compound (717 mg) as a pale-yellow solid.

MS(ESI) m/z: 438.2, 440.2[M+H]⁺

(67-4) methyl {(6S)-4-[4-(2-{[4-(benzylsulfanyl) phenyl]methyl}-1-oxo-1,2,3,4-tetrahydroisoquinolin-6-yl)phenyl]-2,3,9-trimethyl-6H-thieno[3,2-f][1,2,4] triazolo[4,3-a][1,4]diazepin-6-yl}acetate (Example Compound 67-4)

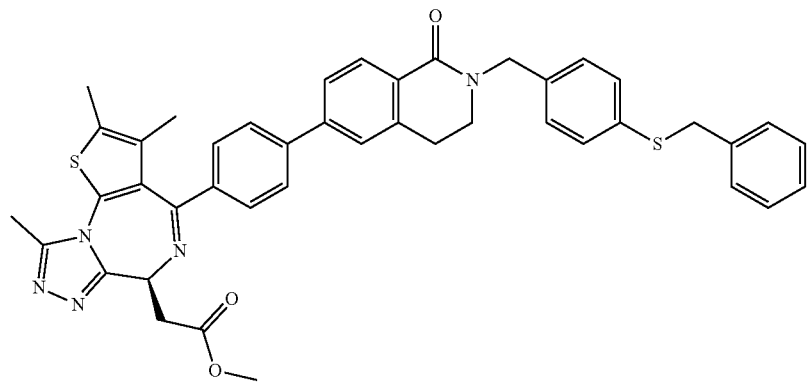 [SMILES: COC(=O)C[C@@H]1N=C(c2ccc(-c3ccc4c(c3)CCN(Cc3ccc(SCc5ccccc5)cc3)C4=O)cc2)c2c(sc(C)c2C)-n2c(C)nnc21]

Reference Example compound 3 (100 mg) was dissolved in tetrahydrofuran (1.3 mL), Example compound 67-3 (104 mg), tetrakis (triphenylphosphine)palladium(0) (23 mg), potassium phosphate (126 mg) and water (0.013 mL) were added, and the mixture was stirred under a nitrogen atmosphere under microwave irradiation at 90° C. for 0.5 hr. The reaction mixture was diluted with ethyl acetate, and insoluble materials were filtered off through diatomaceous earth. The filtrate was concentrated under reduced pressure, and the residue was purified by NH silica gel column chromatography (hexane:ethyl acetate=50:50-0:100) to give the title compound (151 mg) as a white crudely-purified powder. MS(ESI) m/z: 738.5[M+H]⁺

(67-5) methyl [(6S)-4-{4'-[{[4-(chlorosulfinyl)phenyl]methyl}(ethyl)carbamoyl]-3'-methyl[1,1'-biphenyl]-4-yl}-2,3,9-trimethyl-6H-thieno[3,2-f][1,2,4] triazolo[4,3-a][1,4]diazepin-6-yl]acetate (Example Compound 67-5)

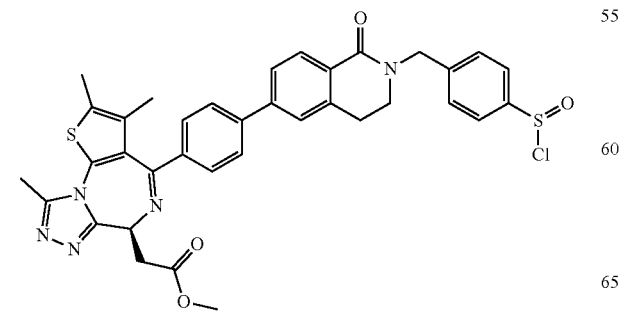

To a suspension of Example compound 67-4 (145 mg) in acetonitrile (3.0 mL)-2N hydrochloric acid (0.60 mL) was added N-chlorosuccinimide (92 mg) under ice-cooling, and the mixture was stirred at the same temperature for 1.5 hr. N-Chlorosuccinimide (8 mg) was added, and the mixture was stirred at the same temperature for 0.5 hr. The reaction mixture was diluted with ethyl acetate, washed successively with saturated brine-water (1:1) and saturated brine, dried over anhydrous sodium sulfate and filtered. The solvent was evaporated under reduced pressure. The obtained residue was purified by silica gel column chromatography (chloroform:methanol=98:2) to give the title compound (80 mg) as a white powder.

MS(ESI) m/z: 696.4[M-Cl+H$_2$O]+; 1H NMR (400 MHz, CDCl$_3$) δ ppm 1.74 (3H, d, J=0.6 Hz), 2.43 (3H, d, J=0.6 Hz), 2.69 (3H, s), 3.08 (2H, t, J=6.7 Hz), 3.59 (2H, t, J=6.6 Hz), 3.67 (2H, dd, J=7.1, 4.1 Hz), 3.79 (3H, s), 4.66 (1H, dd, J=7.8, 6.4 Hz), 4.91 (2H, s), 7.41 (1H, d, J=1.3 Hz), 7.51-7.64 (7H, m), 7.96-8.07 (2H, m), 8.20 (1H, d, J=8.2 Hz)

(67-6) methyl [(6S)-4-(4'-{[(4-{[(3-cyano-4-methyl-1H-indol-7-yl)amino]sulfinyl}phenyl)methyl](ethyl)carbamoyl}-3'-methyl[1,1'-biphenyl]-4-yl)-2,3,9-trimethyl-6H-thieno[3,2-f][1,2,4]triazolo[4,3-a][1,4]diazepin-6-yl]acetate (Example Compound 67)

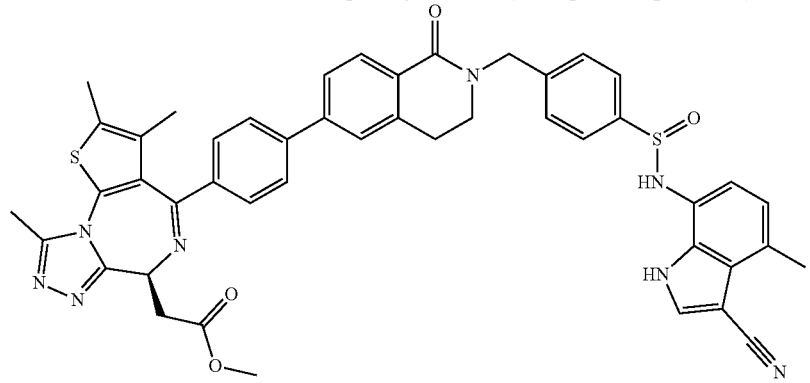

To a solution of Example compound 67-5 (77 mg) and Reference Example compound 9 (22 mg) in tetrahydrofuran (1.5 mL) was added pyridine (0.085 mL) at room temperature, and the mixture was stirred at the same temperature for 16 hr. To the reaction mixture was added chloroform, and the mixture was washed once with 1N hydrochloric acid and once with saturated brine. The aqueous layer was extracted once with chloroform, and the combined organic layer was dried over anhydrous sodium sulfate and filtered. The solvent was evaporated under reduced pressure. The obtained residue was purified by silica gel column chromatography (chloroform:methanol=98:2-95:5) to give the title compound (70 mg) as a beige solid.
MS(ESI) m/z: 849.5[M+H]$^+$ Example 68

(68-1) methyl [(6S)-4-(4'-{[2-(3-bromophenyl)ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 68-1)

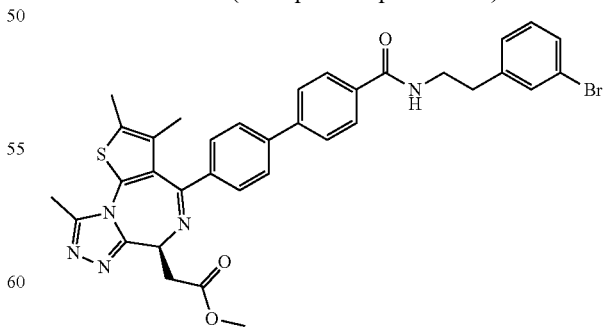

By reaction and treatment in the same manner as in (11-1) except that 3-bromophenethylamine was used instead of Reference Example compound 11 in Example 11, the title compound was obtained as a white solid. MS(ESI) m/z: 682.2, 684.2[M+H]$^+$ (68-2) methyl {(6S)-4-[4'-({2-[3-(benzylsulfanyl)
phenyl]ethyl}carbamoyl)[1,1'-biphenyl]-4-yl]-2,3,9-
trimethyl-6H-thieno[3,2-f][1,2,4]triazolo[4,3-a][1,4]
diazepin-6-yl}acetate (Example Compound 68-2)

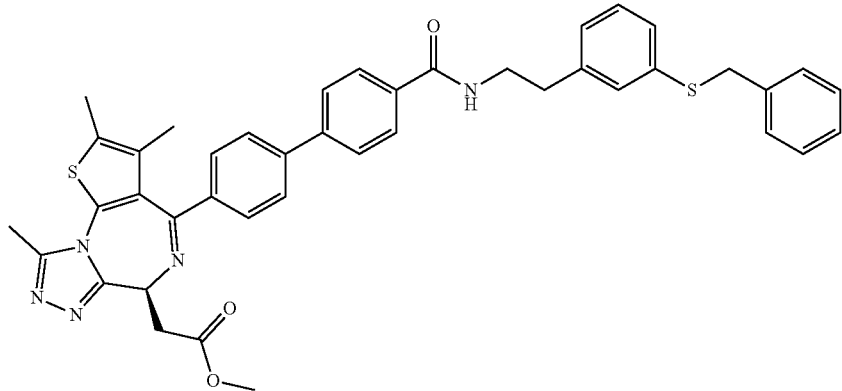 [SMILES: COC(=O)C[C@@H]1N=C(c2ccc(-c3ccc(C(=O)NCCc4cccc(SCc5ccccc5)c4)cc3)cc2)c2c(sc(C)c2C)-n2c(C)nnc21]

Under a nitrogen stream, Example compound 68-1 (183 mg), benzylmercaptan (0.038 mL), tris(dibenzylideneacetone)dipalladium (25 mg), 4,5-bis(diphenylphosphino)-9,9-dimethylxanthene (31 mg) and N,N-diisopropylethylamine (0.070 mL) were stirred in a toluene (3.0 mL)-tetrahydrofuran (1.5 mL) mixed solvent under microwave irradiation at 150° C. for 0.5 hr. Purification by silica gel column chromatography (chloroform:methanol=100:0-95:5) gave the title compound (193 mg) as a yellow solid.

MS(ESI) m/z: 726.4[M+H]$^+$ (68-3) methyl {(6S)-4-[4'-({2-[3-(chlorosulfonyl)
phenyl]ethyl}carbamoyl)[1,1'-biphenyl]-4-yl]-2,3,9-
trimethyl-6H-thieno[3,2-f][1,2,4]triazolo[4,3-a][1,4]
diazepin-6-yl}acetate (Example Compound 68-3)

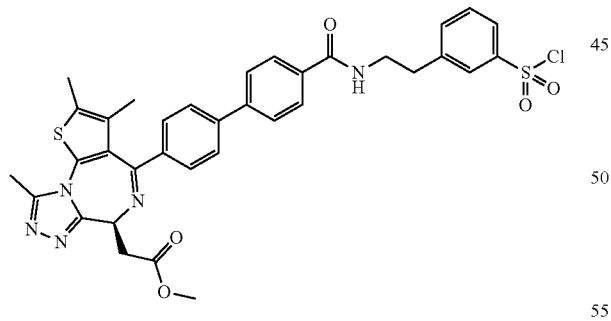

A mixed solution of Example compound 68-2 (193 mg) in acetonitrile (5.0 mL)-2N hydrochloric acid (1.0 mL) was cooled to 0° C., N-chlorosuccinimide (124 mg) was added, and the mixture was stirred at the same temperature for 3 hr. To the reaction mixture was added water and the mixture was stirred and extracted twice with ethyl acetate. The combined organic layer was washed with water and concentrated under reduced pressure. The residue was purified by silica gel column chromatography (chloroform:methanol=100:0-95:5) to give the title compound (183 mg) as a yellow solid. MS(ESI) m/z: 684.3[M-Cl+H$_2$O]+

(68-4) methyl [(6S)-4-{4'-[(2-{3-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 68)

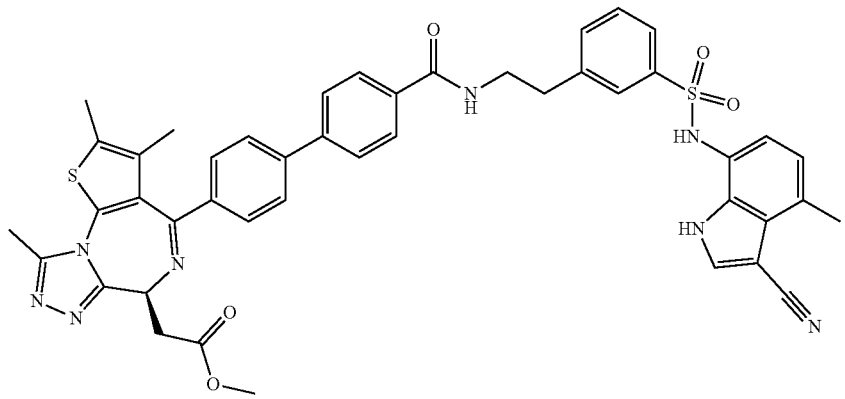

By reaction and treatment in the same manner as in (29-2) except that Example compound 68-3 was used instead of Reference Example compound 10, and Reference Example compound 9 was used instead of Example compound 29-1 in Example 29, the title compound was obtained as a beige solid. MS(ESI) m/z: 837.6[M+H]$^+$ Example 69

(69-1) methyl [(6S)-4-(4'-{[(1R)-1-{4-[(3-cyano-4-methyl-1H-indol-7-yl)sulfamoyl]phenyl}ethyl]carbamoyl}-3'-fluoro[1,1'-biphenyl]-4-yl)-2,3,9-trimethyl-6H-thieno[3,2-f][1,2,4]triazolo[4,3-a][1,4]diazepin-6-yl]acetate (Example Compound 69)

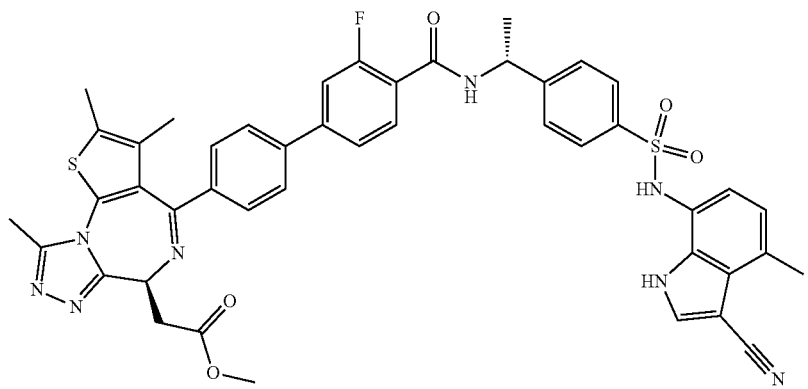

To a solution of Reference Example compound 12-1 (84 mg) in dichloromethane (2.0 mL) was added trifluoroacetic acid (2.0 mL), and the mixture was stirred at room temperature for 2 hr. The reaction mixture was concentrated, toluene was added and the solvent was evaporated. The obtained residue was dissolved in N,N-dimethylformamide (1.5 mL), Reference Example compound 17 (63 mg), N,N-diisopropylethylamine (0.25 mL) and HATU (67 mg) were added at room temperature, and the mixture was stirred at the same temperature for 16 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (77 mg) as a white powder. MS(ESI) m/z: 855.5[M+H]$^+$

Example 70

(70-1) methyl [(6S)-4-(3'-chloro-4'-{[(1R)-1-{4-[(3-cyano-4-methyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 70)

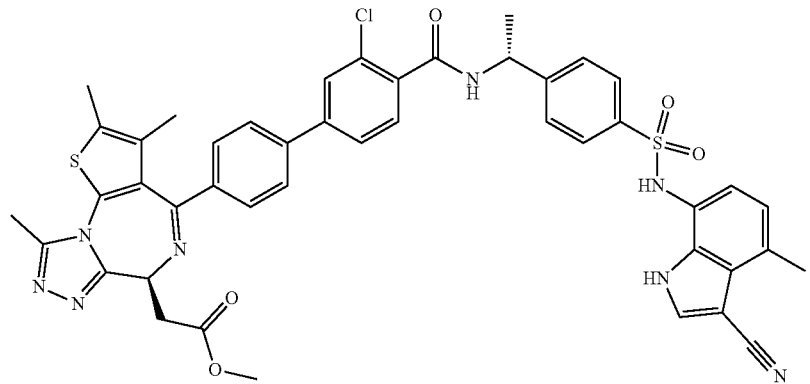

To a solution of Reference Example compound 13 (80 mg) in N,N-dimethylformamide (1.6 mL) were added Reference Example compound 17 (65 mg), N,N-diisopropylethylamine (0.078 mL) and HATU (69 mg) at room temperature, and the mixture was stirred at the same temperature for 16 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (53 mg) as a pale-brown powder. MS(ESI) m/z: 871.5, 873.5 [M+H]$^+$

Example 71

(71-1) 5-chloro-2-fluoro-4'-[(6S)-2,3,6,9-tetramethyl-6H-thieno[3,2-f][1,2,4]triazolo[4,3-a][1,4]diazepin-4-yl][1,1'-biphenyl]-4-carboxylic acid (Example Compound 71-1)

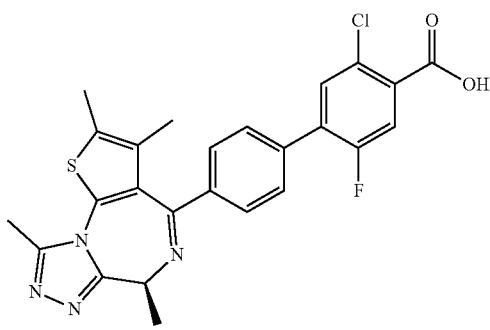 [SMILES: Cc1sc2c(c1C)C(c1ccc(-c3cc(Cl)c(C(=O)O)cc3F)cc1)=N[C@@H](C)c1nnc(C)n1-2]

A mixture of Reference Example compound 2 (370 mg), t-butyl 2-chloro-5-fluoro-4-(4,4,5,5-tetramethyl-1,3,2-dioxaborolan-2-yl)benzoate (330 mg), potassium phosphate (587 mg), 1,4-dioxane (5.0 mL), water (1.1 mL), 2-dicyclohexylphosphino-2'-6'-dimethoxybiphenyl aminobiphenyl palladium chloride precatalyst (66 mg) and S-phos (38 mg) was stirred with heating at 75° C. for 4 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by NH silica gel column chromatography (hexane:ethyl acetate=85:15-45:55). The obtained compound was dissolved in dichloromethane (4.0 mL), trifluoroacetic acid (1.5 mL) was added, and the mixture was stirred at room temperature for 2.5 hr. The reaction mixture was concentrated under reduced pressure, and the residue was dissolved in 1 M aqueous sodium carbonate solution and washed with toluene. The aqueous layer was acidified with 2N hydrochloric acid and the resulting precipitate was collected by filtration to give the title compound (310 mg) as a white solid.

MS(ESI) m/z: 495.3, 497.3[M+H]$^+$ (71-2) 5-chloro-N-({4-[(3-cyano-4-methyl-1H-in-dol-7-yl)sulfamoyl]phenyl}methyl)-2-fluoro-4'-[(6S)-2,3,6,9-tetramethyl-6H-thieno[3,2-f][1,2,4]triazolo[4,3-a][1, 4]diazepin-4-yl][1,1'-biphenyl]-4-carboxamide (Example Compound 71)

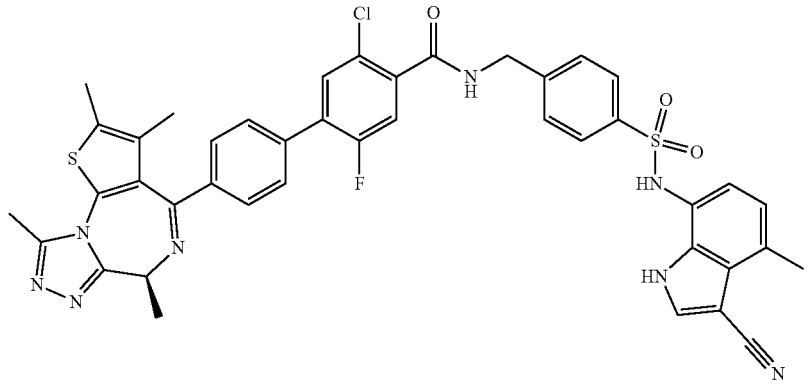

To a solution of Example compound 71-1 (50 mg) in N,N-dimethylformamide (1.0 mL) were added Reference Example compound 5 (38 mg), N,N-diisopropylethylamine (0.054 mL) and HATU (46 mg) at room temperature, and the mixture was stirred at the same temperature for 2 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (31 mg) as a white powder. MS(ESI) m/z: 817.3, 819.3[M+H]$^+$ Example 72

(72-1) 3-chloro-N-({4-[(3-cyano-4-methyl-1H-in-dol-7-yl)sulfamoyl]phenyl}methyl)-5-fluoro-4'-[(6S)-2,3,6,9-tetramethyl-6H-thieno[3,2-f][1,2,4]triazolo[4,3-a][1, 4]diazepin-4-yl][1,1'-biphenyl]-4-carboxamide (Example Compound 72)

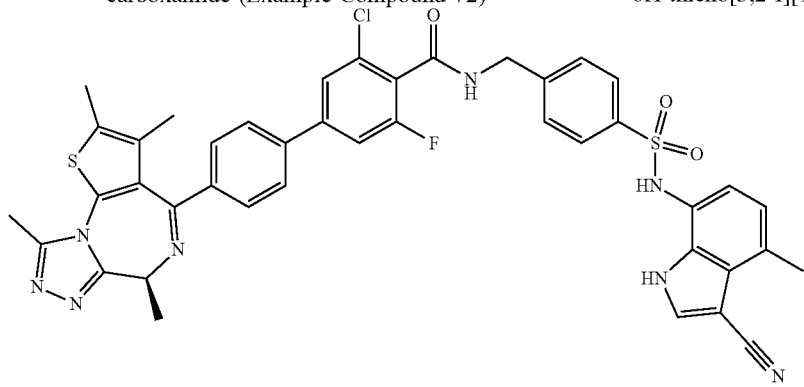

By reaction and treatment in the same manner as in (71-1)-(71-2) except that t-butyl 2-chloro-6-fluoro-4-(4,4,5,5-tetramethyl-1,3,2-dioxaborolan-2-yl)benzoate was used instead of t-butyl 2-chloro-5-fluoro-4-(4,4,5,5-tetramethyl-1,3,2-dioxaborolan-2-yl)benzoate in Example 71, the title compound was obtained as a white powder. MS(ESI) m/z: 817.3, 819.3[M+H]$^+$ Example 73

(73-1) [(6S)-4-(4-chlorophenyl)-2,3,9-trimethyl-6H-thieno[3,2-f][1,2,4]triazolo[4,3-a][1,4]diazepin-6-yl]acetonitrile (Example Compound 73-1)

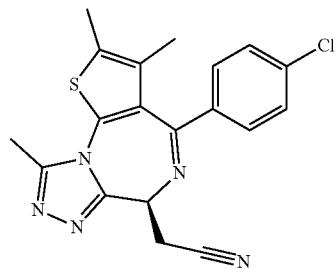 [SMILES: Cc1sc2c(c1C)C(c1ccc(Cl)cc1)=N[C@@H](CC#N)c1nnc(C)n1-2]

To a solution of (6S)-4-(4-chlorophenyl)-2,3,9-trimethyl-6H-thieno[3,2-f][1,2,4]triazolo[4,3-a][1,4]diazepine-6-acetic acid (500 mg) in N,N-dimethylformamide (6.0 mL) was added 28% aqueous ammonia (0.30 mL). 1-Hydroxy-7-azabenzotriazole (HOAt) (170 mg), 1-(3-dimethylaminopropyl)-3-ethylcarbodiimide hydrochloride (WSCI) (311 mg) were added, and the mixture was stirred at room temperature for 5 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was dissolved in tetrahydrofuran (18.0 mL) and N,N-diisopropylethylamine (0.85 mL). Trifluoroacetic anhydride (0.34 mL) was added and the mixture was stirred at room temperature for 3 hr. N,N-diisopropylethylamine (0.43 mL), trifluoroacetic anhydride (0.17 mL) were further added and the mixture was stirred at room temperature for 16 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by NH silica gel column chromatography (ethyl acetate) to give the title compound (255 mg) as a milky white powder. MS(ESI) m/z: 382.2, 384.2[M+H]$^+$ (73-2) t-butyl 4'-[(6S)-6-(cyanomethyl)-2,3,9-trimethyl-6H-thieno[3,2-f][1,2,4]triazolo[4,3-a][1,4]diazepin-4-yl][1,1'-biphenyl]-4-carboxylate (Example Compound 73-2)

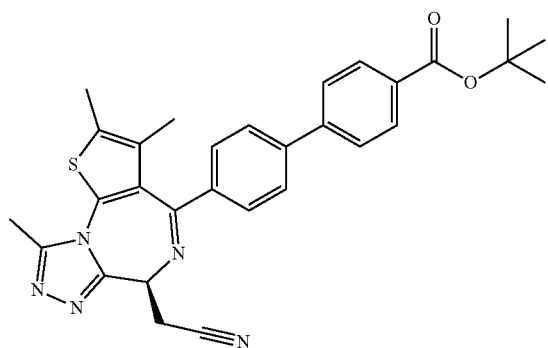 [SMILES: Cc1sc2c(c1C)C(c1ccc(-c3ccc(C(=O)OC(C)(C)C)cc3)cc1)=N[C@@H](CC#N)c1nnc(C)n1-2]

A mixture of Example compound 73-1 (114 mg), t-butyl 4-(4,4,5,5-tetramethyl-1,3,2-dioxaborolan-2-yl)benzoate (227 mg), potassium carbonate (124 mg), tetrahydrofuran (3.0 mL), water (0.80 mL), 2-dicyclohexylphosphino-2'-6'-dimethoxybiphenyl aminobiphenyl palladium chloride precatalyst (22 mg), S-phos (12 mg) was stirred with heating under reflux for 3 hr. Water was added to the reaction mixture and the mixture was extracted with ethyl acetate. The organic layer was washed with saturated brine, dried over anhydrous sodium sulfate, filtered, and the filtrate was concentrated under reduced pressure. The residue was purified by silica gel column chromatography (chloroform:methanol=99:1-90:10) to give the title compound (165 mg) as a gray powder. MS(ESI) m/z: 524.4[M+H]$^+$ (73-3) N-({4-[(3-cyano-4-methyl-1H-indol-7-yl)sulfamoyl]phenyl}methyl)-4'-[(6S)-6-(cyanomethyl)-2,3,9-trimethyl-6H-thieno[3,2-f][1,2,4]triazolo[4,3-a][1,4]diazepin-4-yl][1,1'-biphenyl]-4-carboxamide (Example Compound 73)

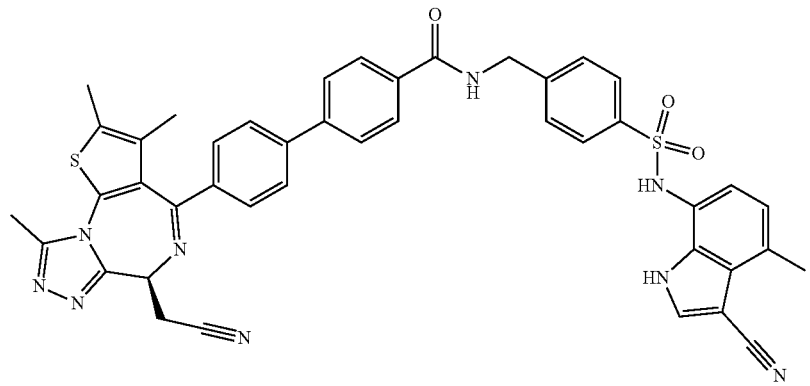

To a solution of Example compound 73-2 (50 mg) in dichloromethane (1.0 mL) was added trifluoroacetic acid (1.0 mL), and the mixture was stirred at room temperature for 1 hr. The reaction mixture was concentrated, toluene was added and the solvent was evaporated. The obtained residue was dissolved in N,N-dimethylformamide (1.0 mL), Reference Example compound 5 (36 mg), N,N-diisopropylethylamine (0.17 mL) and HATU (44 mg) were added at room temperature, and the mixture was stirred at the same temperature for 1 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (51 mg) as a white powder. MS(ESI) m/z: 790.3[M+H]$^+$ Example 74

(74-1) t-butyl 2,3-difluoro-4'-[(6S)-6-(2-methoxy-2-oxoethyl)-2,3,9-trimethyl-6H-thieno[3,2-f][1,2,4]triazolo[4,3-a][1, 4]diazepin-4-yl][1,1'-biphenyl]-4-carboxylate (Example compound 74-1)

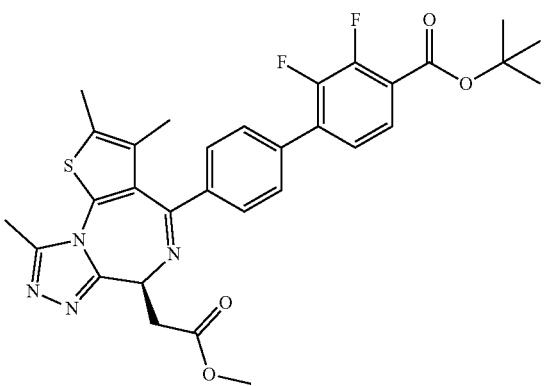 [SMILES: COC(=O)C[C@@H]1N=C(c2ccc(-c3ccc(C(=O)OC(C)(C)C)c(F)c3F)cc2)c2c(sc(C)c2C)-n2c(C)nnc21]

Reference Example compound 3 (100 mg) was dissolved in tetrahydrofuran (2.0 mL), t-butyl 4-bromo-2,3-difluorobenzoate (70 mg), tetrakis(triphenylphosphine)palladium (0) (23 mg), potassium phosphate (126 mg) and water (0.013 mL) were added, and the mixture was stirred under a nitrogen atmosphere under microwave irradiation at 90° C. for 0.5 hr. The reaction mixture was diluted with ethyl acetate, and insoluble materials were filtered off through diatomaceous earth. The filtrate was concentrated under reduced pressure, and the residue was purified by silica gel column chromatography (chloroform:methanol=100:0-98:2) to give the title compound (125 mg) as a white crudely-purified powder.

MS(ESI) m/z: 593.4[M+H]$^+$ (74-2) methyl [(6S)-4-{4'-[({4-[(3-cyano-4-methyl-1H-indol-7-yl)sulfamoyl]phenyl}methyl)carbamoyl]-2',3'-difluoro[1,1'-biphenyl]-4-yl}-2,3,9-trimethyl-6H-thieno[3,2-f][1,2,4]triazolo[4,3-a][1,4]diazepin-6-yl]acetate (Example Compound 74)

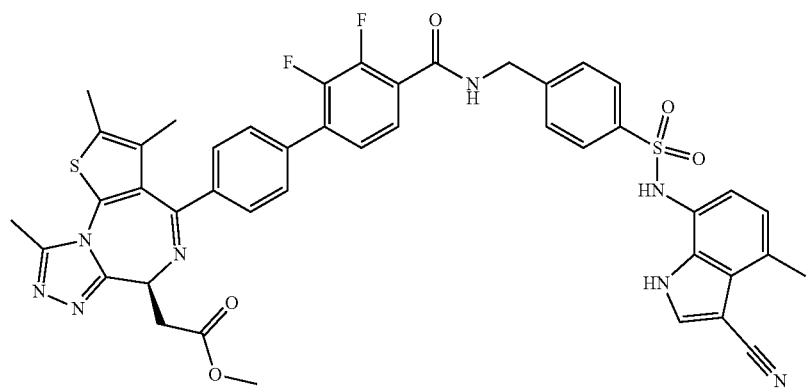

To a solution of Example compound 74-1 (117 mg) in dichloromethane (2.0 mL) was added trifluoroacetic acid (2.0 mL), and the mixture was stirred at room temperature for 1 hr. The reaction mixture was concentrated, toluene was added and the solvent was evaporated. The obtained residue was dissolved in N,N-dimethylformamide (2.0 mL), Reference Example compound 5 (74 mg), N,N-diisopropylethylamine (0.34 mL) and HATU (90 mg) were added at room temperature, and the mixture was stirred at the same temperature for 1 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (108 mg) as a beige powder. MS(ESI) m/z: 859.5[M+H]$^+$ Example 75

(75-1) 4'-[(6S)-6-(2-methoxy-2-oxoethyl)-2,3,9-trimethyl-6H-thieno[3,2-f][1,2,4]triazolo[4,3-a][1,4]diazepin-4-yl]-2-methyl[1,1'-biphenyl]-4-carboxylic acid (Example Compound 75-1)

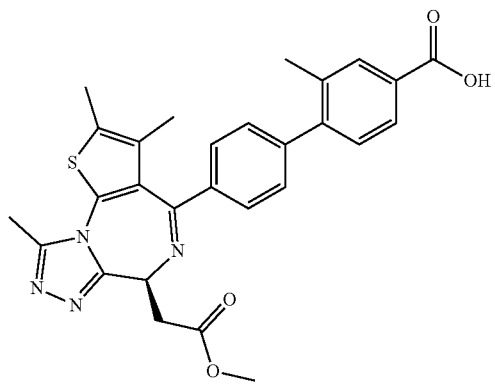 [SMILES: COC(=O)C[C@@H]1N=C(c2ccc(-c3ccc(C(=O)O)cc3C)cc2)c2c(sc(C)c2C)-n2c(C)nnc21]

Reference Example compound 3 (55 mg) was dissolved in tetrahydrofuran (0.8 mL). 4-Bromo-3-methylbenzoic acid (22 mg), 2-dicyclohexylphosphino-2',4',6'-triisopropylbiphenyl (X-Phos, 5 mg), X-Phos aminobiphenylpalladium chloride precatalyst (8 mg), cesium fluoride (46 mg) and water (0.2 mL) were added, and the mixture was stirred under a nitrogen atmosphere under microwave irradiation at 120° C. for 0.5 hr. The reaction mixture was diluted with ethyl acetate and extracted twice with saturated aqueous sodium hydrogen carbonate. The aqueous layers were combined, and 2N hydrochloric acid was added by small portions to pH=1 under ice-cooling. The aqueous layer was extracted twice with ethyl acetate, the combined organic layer was washed with saturated brine, dried over anhydrous sodium sulfate and filtered, and the solvent was evaporated under reduced pressure to give the title compound (52 mg) as a white powder. MS(ESI) m/z: 515.3[M+H]$^+$ (75-2) methyl [(6S)-4-{4'-[({4-[(3-cyano-4-methyl-1H-indol-7-yl)sulfamoyl]phenyl}methyl)carbamoyl]-2'-methyl[1,1'-biphenyl]-4-yl}-2,3,9-trimethyl-6H-thieno[3,2-f][1,2,4]triazolo[4,3-a][1, 4]diazepin-6-yl]acetate (Example Compound 75)

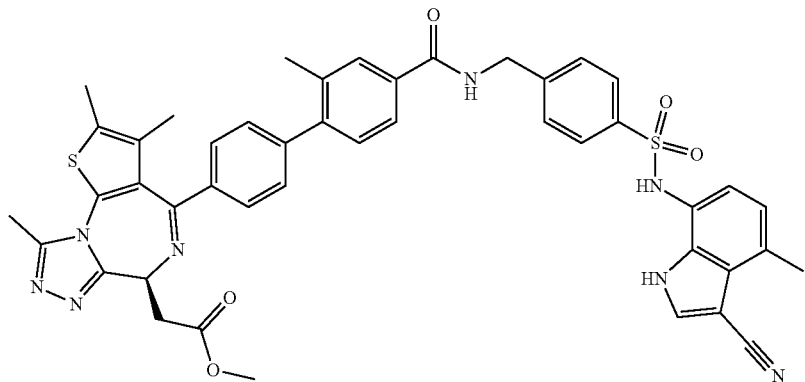

To a solution of Example compound 75-1 (50 mg) and Reference Example compound 5 (37 mg) in N,N-dimethylformamide (1.0 mL) were added, at room temperature, N,N-diisopropylethylamine (0.050 mL) and HATU (45 mg), and the mixture was stirred at the same temperature for 1 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (59 mg) as a beige powder.

MS(ESI) m/z: 837.4[M+H]$^+$

Example 76

(76-1) 4-bromo-2-cyano-N-({4-[(3-cyano-4-methyl-1H-indol-7-yl)sulfamoyl]phenyl}methyl)benzamide (Example Compound 76-1)

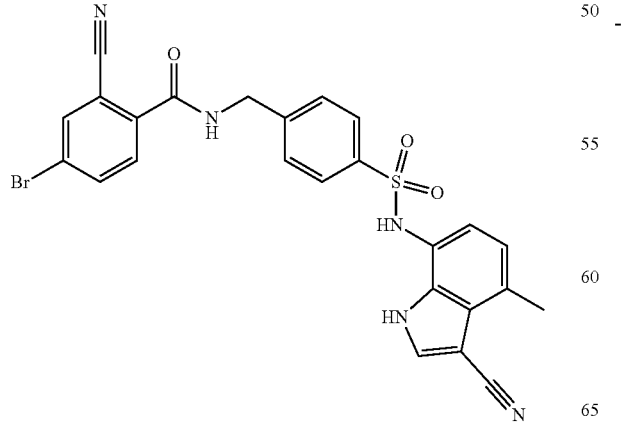

To a solution of 4-bromo-2-cyanobenzoic acid (100 mg) and Reference Example compound 5 (158 mg) in N,N-dimethylformamide (2.2 mL) were added N,N-diisopropylethylamine (0.23 mL) and HATU (202 mg) at room temperature, and the mixture was stirred at the same temperature for 2 days. The reaction mixture was diluted with ethyl acetate, washed twice with saturated aqueous sodium hydrogen carbonate and once with saturated brine-water (1:1), washed once with saturated brine, dried over anhydrous sodium sulfate and filtered. The solvent was evaporated under reduced pressure. The obtained residue was purified twice by silica gel column chromatography (chloroform:methanol=98:2) to give the title compound (29 mg) as a white solid.

MS(ESI) m/z: 548.1, 550.1[M+H]$^+$ (76-2) methyl [(6S)-4-{3'-cyano-4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 76)

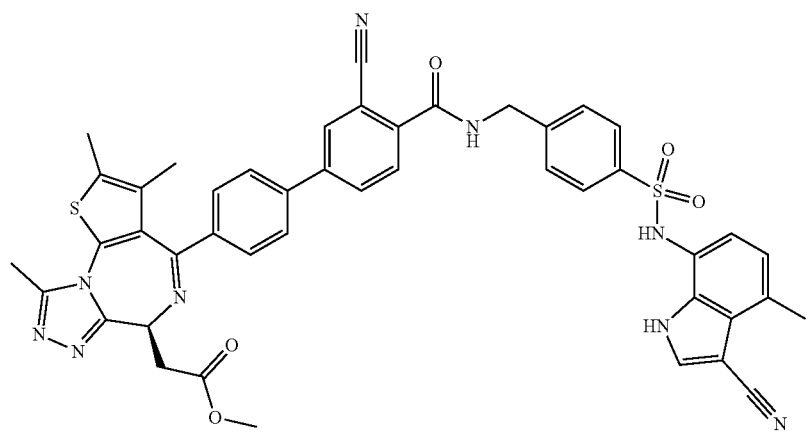

Reference Example compound 3 (25 mg) was dissolved in tetrahydrofuran (0.8 mL), Example compound 76-1 (24 mg), 2-dicyclohexylphosphino-2',4',6'-triisopropylbiphenyl (X-Phos, 2 mg), X-Phos aminobiphenylpalladium chloride precatalyst (4 mg), cesium fluoride (20 mg) and water (0.2 mL) were added, and the mixture was stirred under a nitrogen atmosphere under microwave irradiation at 120° C. for 0.5 hr. The reaction mixture was diluted with ethyl acetate, washed twice with saturated aqueous sodium hydrogen carbonate and once with saturated brine, dried over anhydrous sodium sulfate and filtered. The solvent was evaporated under reduced pressure. The obtained residue was purified twice by silica gel column chromatography (chloroform:methanol=98:2-95:5) to give the title compound (13 mg) as a white powder. MS(ESI) m/z: 848.4[M+H]$^+$

Example 77

(77-1) methyl [(6S)-4-(4-{6-[({4-[(3-cyano-4-methyl-1H-indol-7-yl)sulfamoyl]phenyl}methyl)carbamoyl]-5-fluoropyridin-3-yl}phenyl)-2,3,9-trimethyl-6H-thieno[3,2-f][1,2,4]triazolo[4,3-a][1,4]diazepin-6-yl]acetate (Example Compound 77)

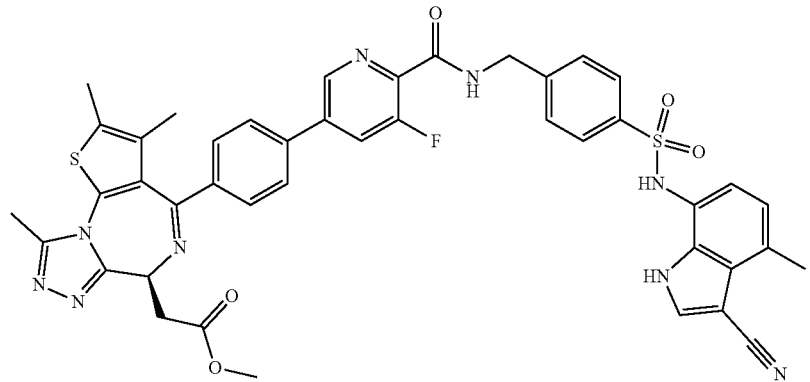

By reaction and treatment in the same manner as in (53-1)-(53-2) except that t-butyl 5-bromo-3-fluoropyridine-2-carboxylate was used instead of t-butyl 5-bromopyridine-2-carboxylate in Example 53, the title compound was obtained as a milk-white solid. MS(ESI) m/z: 842.3[M+H]$^+$

Example 78

(78-1) t-butyl 5-bromo-6-methylpyridine-2-carboxylate (Example Compound 78-1)

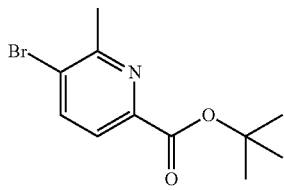

5-Bromo-6-methylpyridine-2-carboxylic acid (500 mg), di-t-butyl dicarbonate (1010 mg) and 4-dimethylaminopyridine (28 mg) were stirred in tetrahydrofuran (5.0 mL) at room temperature for 3 hr. The reaction mixture was concentrated under reduced pressure, and the residue was purified by silica gel column chromatography (hexane:ethyl acetate=95:5-70:30) to give the title compound (572 mg) as a colorless oil.

MS(ESI) m/z: 215.9, 217.9[M−tBu+2H]$^+$ (78-2) methyl [(6S)-4-(4-{6-[({4-[(3-cyano-4-methyl-1H-indol-7-yl)sulfamoyl]phenyl}methyl)carbamoyl]-2-methylpyridin-3-yl}phenyl)-2,3,9-trimethyl-6H-thieno[3,2-f][1,2,4]triazolo[4,3-a][1,4]diazepin-6-yl]acetate (Example Compound 78)

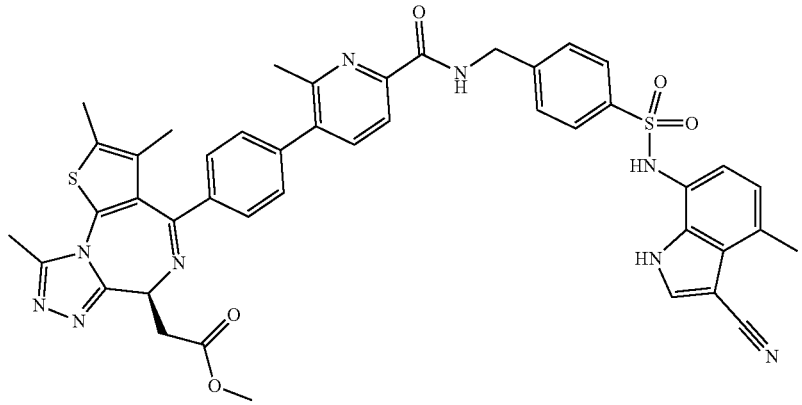

By reaction and treatment in the same manner as in (53-1)-(53-2) except that Example compound 78-1 was used instead of t-butyl 5-bromopyridine-2-carboxylate in Example 53, the title compound was obtained as a milk-white solid.

MS(ESI) m/z: 838.4[M+H]$^+$

Example 79

(79-1) methyl [(6S)-4-{4'-[({4-[(3-cyano-4-methyl-1H-indol-7-yl)sulfamoyl]phenyl}methyl)carbamoyl]-2'-(trifluoromethyl) [1,1'-biphenyl]-4-yl}-2,3,9-trimethyl-6H-thieno[3,2-f][1,2,4]triazolo[4,3-a][1,4]diazepin-6-yl]acetate (Example Compound 79)

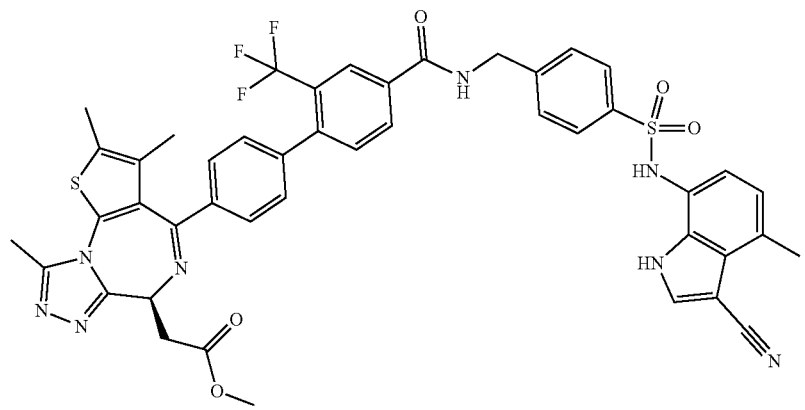

By reaction and treatment in the same manner as in (75-1)-(75-2) except that 4-bromo-3-(trifluoromethyl)benzoic acid was used instead of 4-bromo-3-methylbenzoic acid in Example 75, the title compound was obtained as a white powder.

MS(ESI) m/z: 891.4[M+H]$^+$

Example 80

(80-1) methyl [(6S)-4-{4'-[({4-[(3-cyano-4-methyl-1H-indol-7-yl)sulfamoyl]phenyl}methyl)carbamoyl]-2'-methoxy[1,1'-biphenyl]-4-yl}-2,3,9-trimethyl-6H-thieno[3,2-f][1,2,4]triazolo[4,3-a][1,4]diazepin-6-yl]acetate (Example Compound 80)

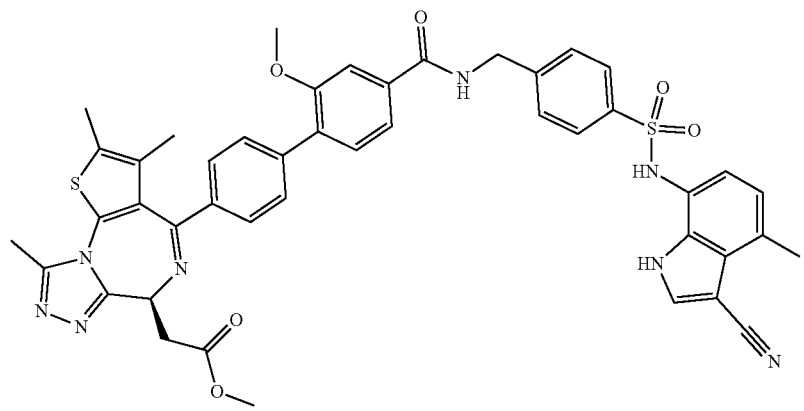

By reaction and treatment in the same manner as in (75-1)-(75-2) except that 4-bromo-3-methoxybenzoic acid was used instead of 4-bromo-3-methylbenzoic acid in Example 75, the title compound was obtained as a beige powder.

MS(ESI) m/z: 853.4[M+H]$^+$

Example 81

(81-1) methyl [(6S)-4-{2'-cyano-4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 81)

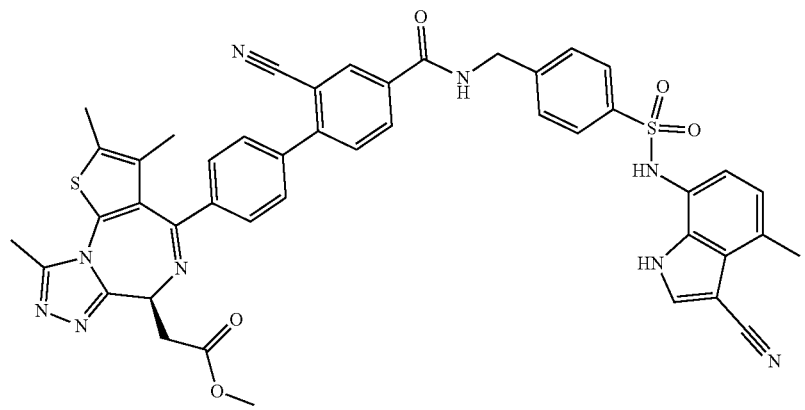

By reaction and treatment in the same manner as in (75-1)-(75-2) except that 4-bromo-3-cyanobenzoic acid was used instead of 4-bromo-3-methylbenzoic acid in Example 75, the title compound was obtained as a beige powder.

MS(ESI) m/z: 848.4[M+H]$^+$

Example 82

(82-1) 2,5-difluoro-4'-[(6S)-6-(2-methoxy-2-oxo-ethyl)-2,3,9-trimethyl-6H-thieno[3,2-f][1,2,4]triazolo[4,3-a][1,4]diazepin-4-yl][1,1'-biphenyl]-4-carboxylic acid (Example Compound 82-1)

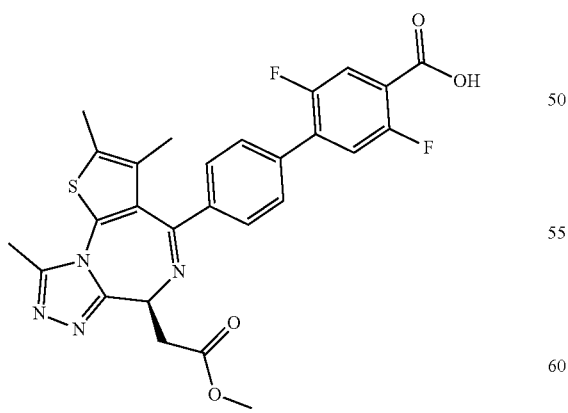

By reaction and treatment in the same manner as in (75-1) except that 4-bromo-2,5-difluorobenzoic acid (48 mg) was used instead of 4-bromo-3-methylbenzoic acid in Example 75, the title compound (116 mg) was obtained as a white crudely-purified powder. MS(ESI) m/z: 537.3[M+H]$^+$ (82-2) methyl [(6S)-4-{4'-[({4-[(3-cyano-4-methyl-1H-indol-7-yl)sulfamoyl]phenyl}methyl)carbamoyl]-2',5'-difluoro[1,1'-biphenyl]-4-yl}-2,3,9-trimethyl-6H-thieno[3,2-f][1,2,4]triazolo[4,3-a][1,4]diazepin-6-yl]acetate (Example Compound 82)

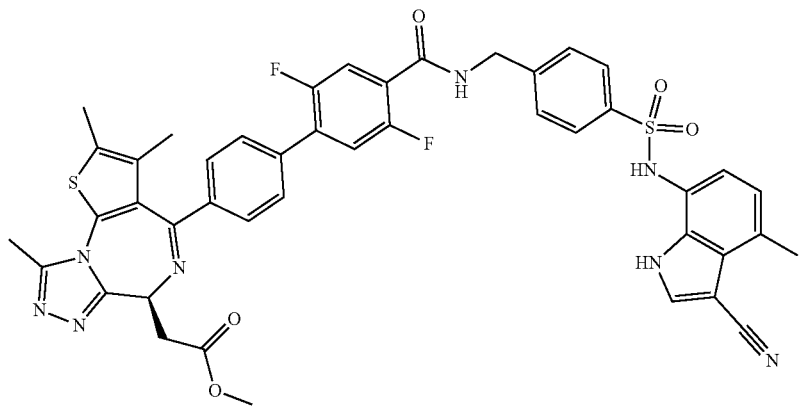

By reaction and treatment in the same manner as in (75-2) except that Example compound 82-1 (40 mg) was used instead of Example compound 75-1 in Example 75, the title compound (39 mg) was obtained as a beige powder.
MS(ESI) m/z: 859.4[M+H]$^+$ Example 83

(83-1) 2-fluoro-4'-[(6S)-6-(2-methoxy-2-oxoethyl)-2,3,9-trimethyl-6H-thieno[3,2-f][1,2,4]triazolo[4,3-a][1,4]diazepin-4-yl]-5-methyl[1,1'-biphenyl]-4-carboxylic acid (Example Compound 83-1)

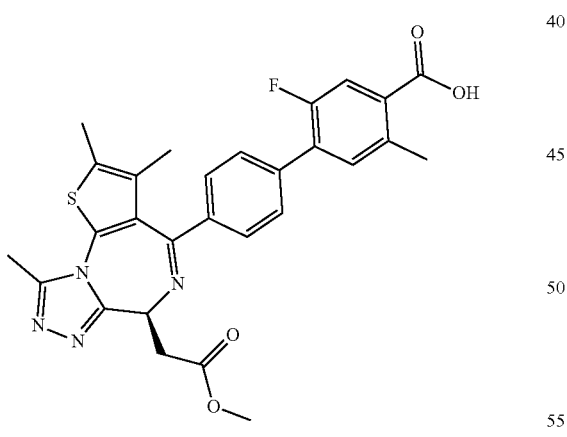

By reaction and treatment in the same manner as in (75-1) except that 4-bromo-5-fluoro-2-methylbenzoic acid (47 mg) was used instead of 4-bromo-3-methylbenzoic acid in Example 75, the title compound (96 mg) was obtained as a white powder.
MS(ESI) m/z: 533.3[M+H]$^+$ (83-2) methyl [(6S)-4-{4'-[({4-[(3-cyano-4-methyl-1H-indol-7-yl) sulfamoyl]phenyl}methyl) carbamoyl]-2'-fluoro-5'-methyl [1,1'-biphenyl]-4-yl}-2,3,9-trimethyl-6H-thieno[3,2-f][1,2,4]triazolo[4,3-a][1,4]diazepin-6-yl]acetate (Example Compound 83)

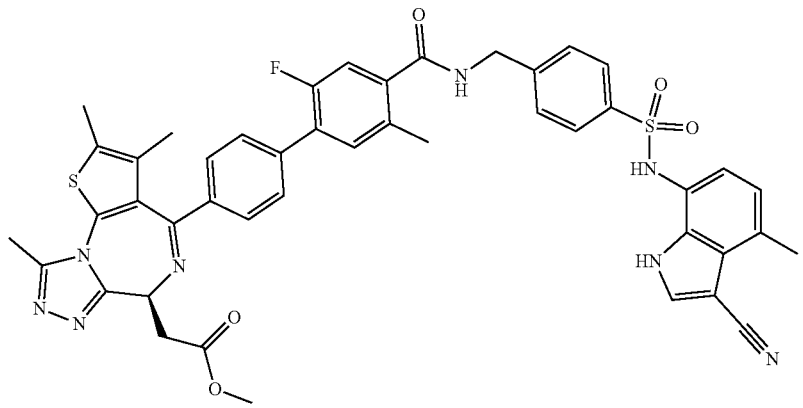

By reaction and treatment in the same manner as in (75-2) except that Example compound 83-1 (40 mg) was used instead of Example compound 75-1, the title compound (45 mg) was obtained as a beige powder. MS(ESI) m/z: 855.4 [M+H]$^+$ Example 84

(84-1) methyl [(6S)-4-(2'-chloro-4'-{[(1R)-1-{4-[(3-cyano-4-methyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 84)

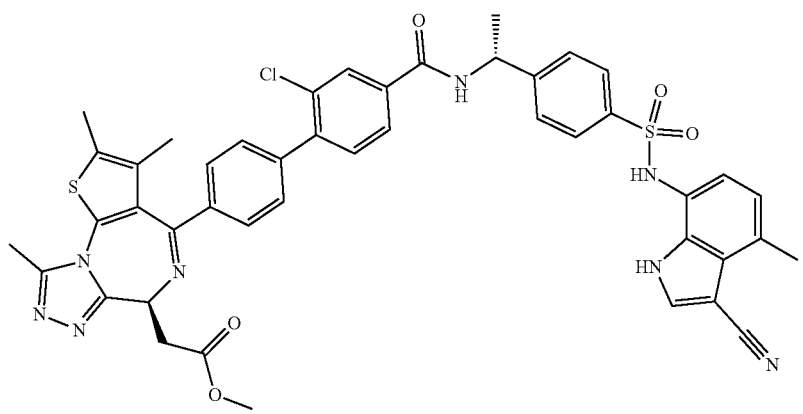

To a solution of Reference Example compound 19 (85 mg) and Reference Example compound 17 (68 mg) in N,N-dimethylformamide (1.7 mL) were added N,N-diisopropylethylamine (0.083 mL) and HATU (73 mg) at room temperature, and the mixture was stirred at the same temperature for 1 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (42 mg) as a beige powder.
MS(ESI) m/z: 871.4[M+H]$^+$ Example 85

(85-1) methyl [(6S)-4-(4'-{[(1R)-1-{4-[(3-cyano-4-methyl-1H-indol-7-yl)sulfamoyl]phenyl}ethyl]carbamoyl}-2'-fluoro[1,1'-biphenyl]-4-yl)-2,3,9-trimethyl-6H-thieno[3,2-f][1,2,4]triazolo[4,3-a][1,4]diazepin-6-yl]acetate (Example Compound 85)

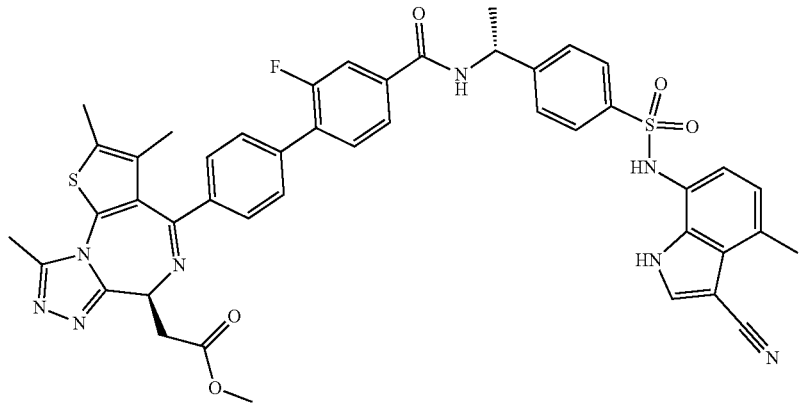

To a solution of Reference Example compound 18 (50 mg) and Reference Example compound 17 (42 mg) in N,N-dimethylformamide (1.0 mL) were added N,N-diisopropylethylamine (0.050 mL) and HATU (44 mg) at room temperature, and the mixture was stirred at the same temperature for 1 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (70 mg) as a beige powder.

MS(ESI) m/z: 855.5[M+H]$^+$

Example 86

(86-1) methyl [(6S)-4-(4'-{[(1R)-1-{4-[(3-cyano-4-methyl-1H-indol-7-yl)sulfamoyl]phenyl}ethyl]carbamoyl}-3'-methyl[1,1'-biphenyl]-4-yl)-2,3,9-trimethyl-6H-thieno[3,2-f][1,2,4]triazolo[4,3-a][1,4]diazepin-6-yl]acetate (Example Compound 86)

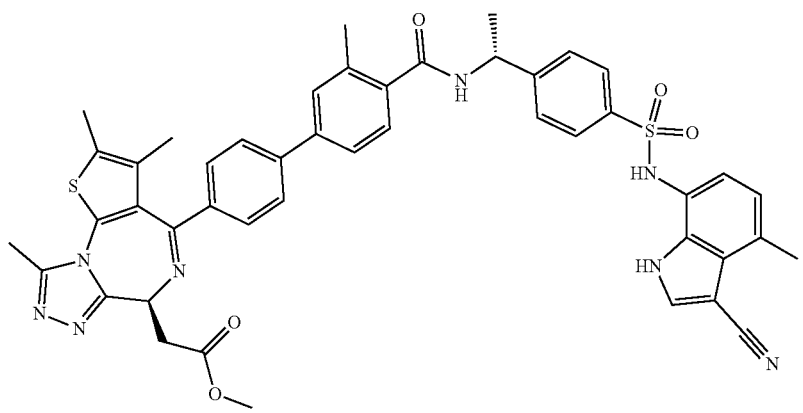

To a solution of Reference Example compound 20 (50 mg) and Reference Example compound 17 (42 mg) in N,N-dimethylformamide (1.0 mL) were added N,N-diisopropylethylamine (0.050 mL) and HATU (45 mg) at room temperature, and the mixture was stirred at the same temperature for 1 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (62 mg) as a beige powder.

MS(ESI) m/z: 851.4[M+H]$^+$

Example 87

(87-1) methyl [(6S)-4-{4'-[(2-{4-[(3-cyano-4-methyl-1H-indol-7-yl)sulfamoyl]phenyl}ethyl)carbamoyl]-3'-methyl[1,1'-biphenyl]-4-yl}-2,3,9-trimethyl-6H-thieno[3,2-f][1,2,4]triazolo[4,3-a][1,4]diazepin-6-yl]acetate (Example Compound 87)

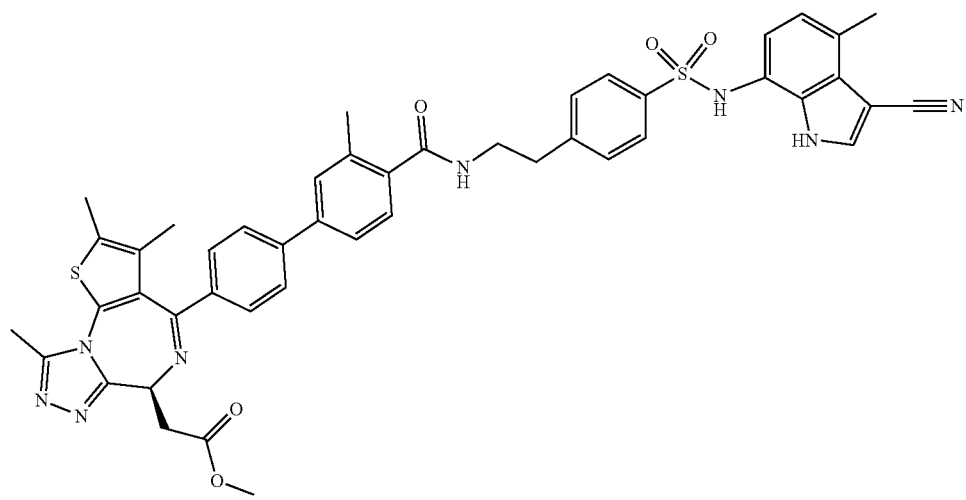 [SMILES: COC(=O)C[C@@H]1N=C(c2ccc(-c3ccc(C(=O)NCCc4ccc(S(=O)(=O)Nc5ccc(C)c6c(C#N)c[nH]c56)cc4)c(C)c3)cc2)c2c(sc(C)c2C)-n2c(C)nnc21]

To a solution of Reference Example compound 20 (50 mg) and Reference Example compound 11 (42 mg) in N,N-dimethylformamide (1.0 mL) were added N,N-diisopropylethylamine (0.050 mL) and HATU (45 mg) at room temperature, and the mixture was stirred at the same temperature for 1 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (60 mg) as a white powder.

MS(ESI) m/z: 851.5[M+H]$^+$

Example 88

(88-1) methyl [(6S)-4-(4'-{[(1R)-1-{4-[(3-cyano-4-methyl-1H-indol-7-yl)sulfamoyl]phenyl}ethyl]carbamoyl}-2'-methyl[1,1'-biphenyl]-4-yl)-2,3,9-trimethyl-6H-thieno[3,2-f][1,2,4]triazolo[4,3-a][1,4]diazepin-6-yl]acetate (Example Compound 88)

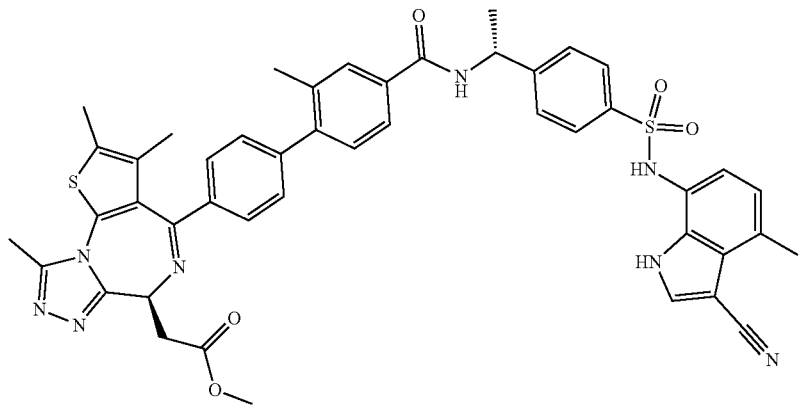

By reaction and treatment in the same manner as in Example 86 except that Example compound 75-1 (50 mg) was used instead of Reference Example compound 20, the title compound (63 mg) was obtained as a beige powder.
MS(ESI) m/z: 851.5[M+H]$^+$

Example 89

(89-1) methyl [(6S)-4-{4'-[(2-{4-[(3-cyano-4-methyl-1H-indol-7-yl)sulfamoyl]phenyl}ethyl)carbamoyl]-2'-methyl[1,1'-biphenyl]-4-yl}-2,3,9-trimethyl-6H-thieno[3,2-f][1,2,4]triazolo[4,3-a][1,4]diazepin-6-yl]acetate (Example Compound 89)

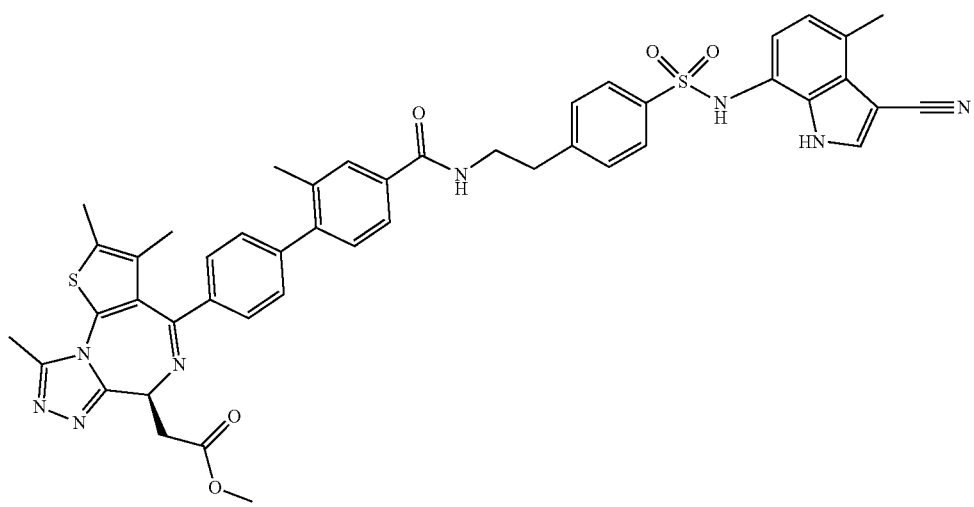 [SMILES: COC(=O)C[C@@H]1N=C(c2ccc(-c3ccc(C(=O)NCCc4ccc(S(=O)(=O)Nc5ccc(C)c6c(C#N)c[nH]c56)cc4)cc3C)cc2)c2c(sc(C)c2C)-n2c(C)nnc21]

By reaction and treatment in the same manner as in Example 87 except that Example compound 75-1 (50 mg) was used instead of Reference Example compound 20, the title compound (53 mg) was obtained as a white powder.
MS(ESI) m/z: 851.4[M+H]$^+$

Example 90

(90-1) methyl [(6S)-4-(4-{6-[(2-{4-[(3-cyano-4-methyl-1H-indol-7-yl)sulfamoyl]phenyl}ethyl)carbamoyl]pyridin-3-yl}phenyl)-2,3,9-trimethyl-6H-thieno[3,2-f][1,2,4]triazolo[4,3-a][1,4]diazepin-6-yl]acetate (Example Compound 90)

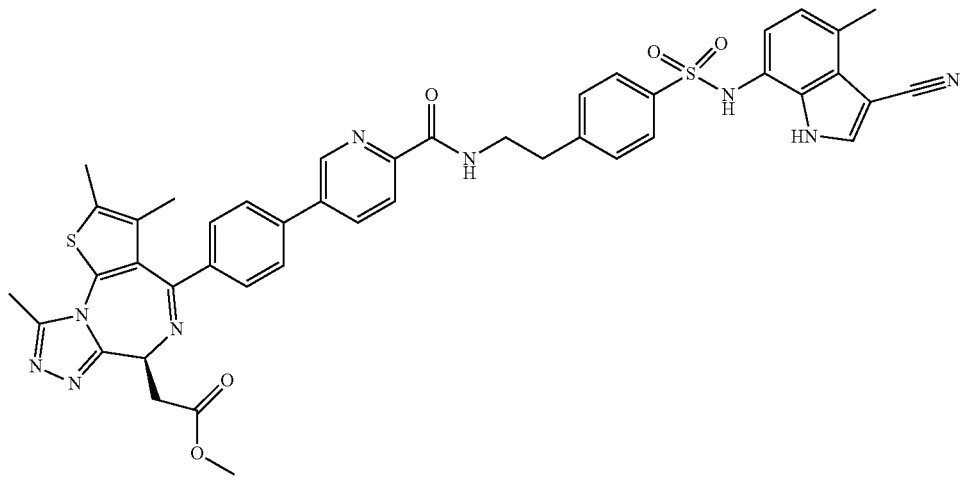 [SMILES: COC(=O)C[C@@H]1N=C(c2ccc(-c3ccc(C(=O)NCCc4ccc(S(=O)(=O)Nc5ccc(C)c6c(C#N)c[nH]c56)cc4)nc3)cc2)c2c(sc(C)c2C)-n2c(C)nnc21]

By reaction and treatment in the same manner as in (53-2) except that Reference Example compound 11 was used instead of Reference Example compound 5 in Example 53, the title compound was obtained as a beige solid. MS(ESI) m/z: 838.4[M+H]$^+$

Example 91

(91-1) methyl [(6S)-4-(4-{6-[({4-[(3-cyano-4-methyl-1H-indol-7-yl)sulfamoyl]phenyl}methyl)carbamoyl]-5-methylpyridin-3-yl}phenyl)-2,3,9-trimethyl-6H-thieno[3,2-f][1,2,4]triazolo[4,3-a][1,4]diazepin-6-yl]acetate (Example Compound 91)

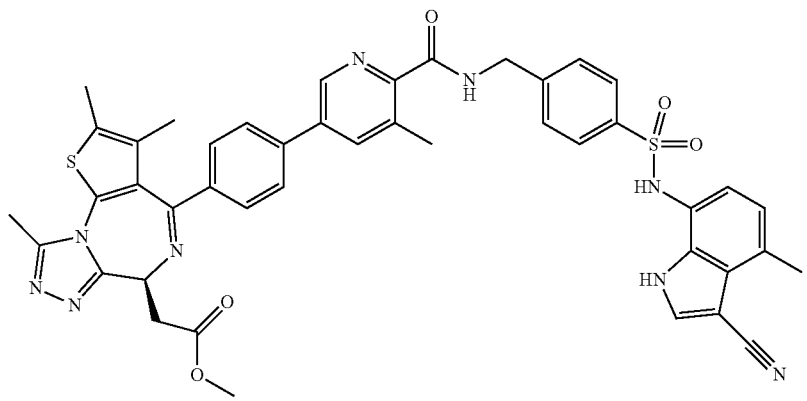

By reaction and treatment in the same manner as in (53-1)-(53-2) except that t-butyl 5-bromo-3-methylpyridine-2-carboxylate was used instead of t-butyl 5-bromopyridine-2-carboxylate in Example 53, the title compound was obtained as a milk-white solid. MS(ESI) m/z: 838.4[M+H]$^+$

Example 92

(92-1) methyl {(6S)-4-[4-(6-{[(1R)-1-{4-[(3-cyano-4-methyl-1H-indol-7-yl)sulfamoyl]phenyl}ethyl]carbamoyl}pyridin-3-yl)phenyl]-2,3,9-trimethyl-6H-thieno[3,2-f][1,2,4]triazolo[4,3-a][1,4]diazepin-6-yl}acetate (Example Compound 92)

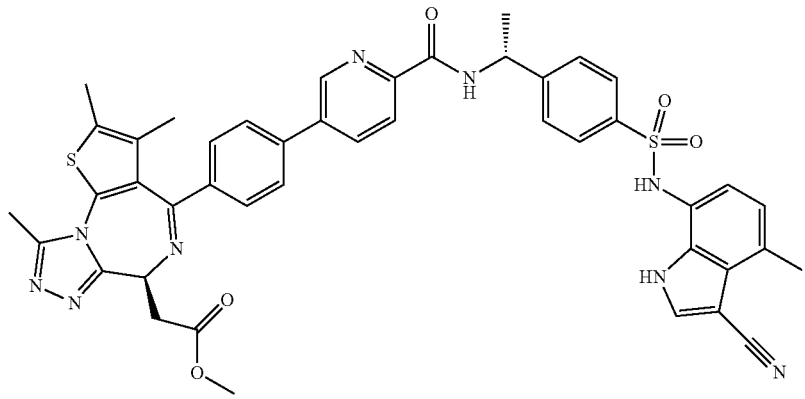

By reaction and treatment in the same manner as in (53-2) except that Reference Example compound 17 was used instead of Reference Example compound 5 in Example 53, the title compound was obtained as a milk-white solid. MS(ESI) m/z: 838.4[M+H]$^+$

Example 93

(93-1) 3-hydroxy-4'-[(6S)-6-(2-methoxy-2-oxo-ethyl)-2,3,9-trimethyl-6H-thieno[3,2-f][1,2,4]triazolo[4,3-a][1,4]diazepin-4-yl][1,1'-biphenyl]-4-carboxylic acid (Example Compound 93-1)

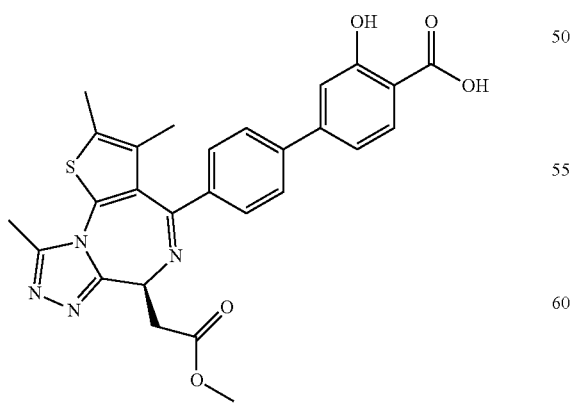

Reference Example compound 3 (204 mg) was dissolved in tetrahydrofuran (2.0 mL), 4-bromo-3-methylbenzoic acid (83 mg), 2-dicyclohexylphosphino-2',4',6'-triisopropylbiphenyl (X-Phos, 18 mg), X-Phos aminobiphenylpalladium chloride precatalyst (30 mg), cesium fluoride (175 mg) and water (0.5 mL) were added, and the mixture was stirred under a nitrogen atmosphere under microwave irradiation at 120° C. for 0.5 hr, and further at 160° C. for 0.5 hr. The reaction mixture was diluted with ethyl acetate and extracted twice with saturated aqueous sodium hydrogen carbonate. The aqueous layers were combined and 2N hydrochloric acid was added by small portions to pH=1 under ice-cooling. The aqueous layer was extracted twice with chloroform. The combined organic layer was dried over anhydrous sodium sulfate and filtered, and the solvent was evaporated under reduced pressure to give the title compound (130 mg) as a pale-yellow powder. MS(ESI) m/z: 517.3[M+H]$^+$ (93-2) methyl [(6S)-4-{4'-[({4-[(3-cyano-4-methyl-1H-indol-7-yl)sulfamoyl]phenyl}methyl)carbamoyl]-3'-hydroxy[1,1'-biphenyl]-4-yl}-2,3,9-trimethyl-6H-thieno[3,2-f][1,2,4]triazolo[4,3-a][1,4]diazepin-6-yl]acetate (Example Compound 93)

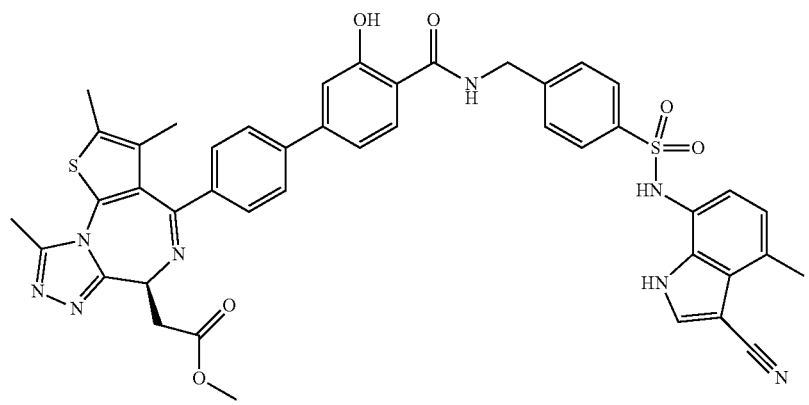

To a solution of Example compound 93-1 (68 mg) and Reference Example compound 5 (54 mg) in N,N-dimethylformamide (2.0 mL) were added 1-hydroxy-7-azabenzotriazole (HOAt, 22 mg) and 1-(3-dimethylaminopropyl)-3-ethylcarbodiimide hydrochloride (WSCI, 31 mg) at room temperature, and the mixture was stirred at the same temperature for 3 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-90:10) to give the title compound (72 mg) as a beige powder. MS(ESI) m/z: 839.4[M+H]$^+$ Example 94

(94-1) methyl [(6S)-4-{4'-[({4-[(3-cyano-4-methyl-1H-indol-7-yl)sulfamoyl]-2-methylphenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 94)

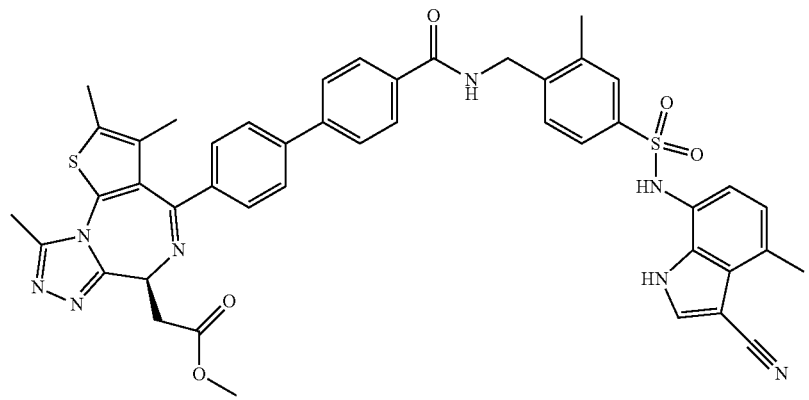

By reaction and treatment in the same manner as in (25-1)-(25-2) except that (4-bromo-2-methyl-phenyl)methanamine was used instead of 4-bromo-3-fluorophenylmethanamine hydrochloride in Example 25, the title compound was obtained as a gray powder.
MS(ESI) m/z: 837.4[M+H]$^+$ Example 95

(95-1) methyl [(6S)-4-(4'-{[(1R)-1-{4-[(3-cyano-4-methyl-1H-indol-7-yl)sulfamoyl]phenyl}propyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 95)

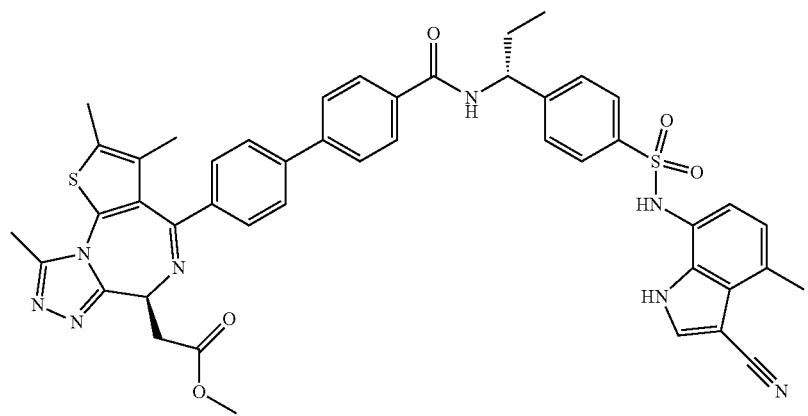

By reaction and treatment in the same manner as in (25-1)-(25-2) except that (1R)-1-(4-bromophenyl)propan-1-amine was used instead of 4-bromo-3-fluorophenylmethanamine hydrochloride in Example 25, the title compound was obtained as a gray powder.
MS(ESI) m/z: 851.4[M+H]$^+$

Example 96

(96-1) methyl [(6S)-4-{4'-[({4-[(3-cyano-4-methyl-1H-indol-7-yl)sulfamoyl]-3-methylphenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 96)

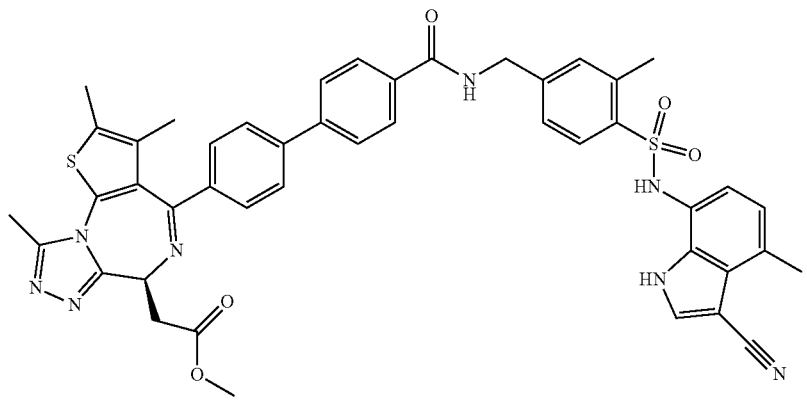

By reaction and treatment in the same manner as in (25-1)-(25-2) except that (4-bromo-3-methyl-phenyl)methanamine hydrochloride was used instead of 4-bromo-3-fluorophenylmethanamine hydrochloride in Example 25, the title compound was obtained as a beige powder.

MS(ESI) m/z: 837.7[M+H]$^+$

Example 97

(97-1) methyl [(6S)-4-(4'-{[(1R)-1-{4-[(3-cyano-4-methyl-1H-indol-7-yl)sulfamoyl]phenyl}ethyl]carbamoyl}-2',5'-difluoro[1,1'-biphenyl]-4-yl)-2,3,9-trimethyl-6H-thieno[3,2-f][1,2,4]triazolo[4,3-a][1,4]diazepin-6-yl]acetate (Example Compound 97)

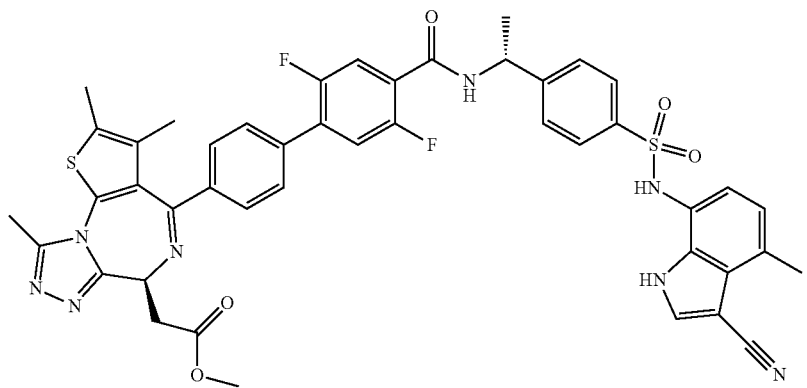

By reaction and treatment in the same manner as in Example 86 except that Example compound 82-1 (40 mg) was used instead of Reference Example compound 20, the title compound (48 mg) was obtained as a milk-white powder.

MS(ESI) m/z: 873.7[M+H]$^+$

Example 98

(98-1) methyl [(6S)-4-(4'-{[(1R)-1-{4-[(3-cyano-4-methyl-1H-indol-7-yl)sulfamoyl]phenyl}ethyl]carbamoyl}-2'-fluoro-5'-methyl[1,1'-biphenyl]-4-yl)-2,3,9-trimethyl-6H-thieno[3,2-f][1,2,4]triazolo[4,3-a][1,4]diazepin-6-yl]acetate (Example Compound 98)

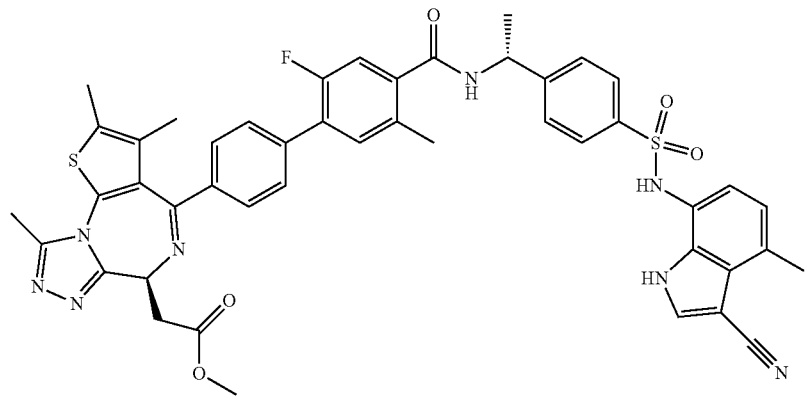

By reaction and treatment in the same manner as in Example 86 except that Example compound 83-1 (30 mg) was used instead of Reference Example compound 20, the title compound (34 mg) was obtained as a milk-white powder.

MS(ESI) m/z: 869.7[M+H]$^+$

Example 99

(99-1) 2,3-difluoro-4'-[(6S)-6-(2-methoxy-2-oxoethyl)-2,3,9-trimethyl-6H-thieno[3,2-f][1,2,4]triazolo[4,3-a][1,4]diazepin-4-yl][1,1'-biphenyl]-4-carboxylic acid (Example Compound 99-1)

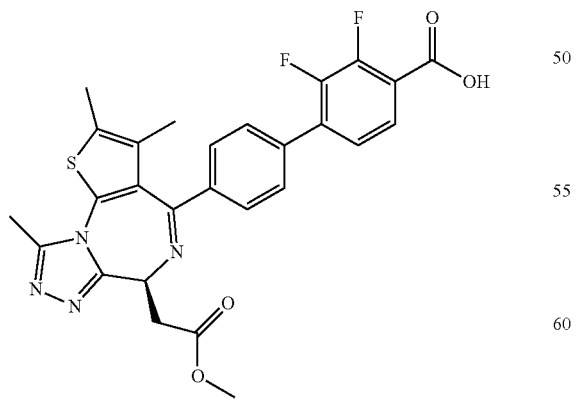

Reference Example compound 3 (362 mg) was dissolved in tetrahydrofuran (3.0 mL). 4-Bromo-2,3-difluorobenzoic acid (150 mg), 2-dicyclohexylphosphino-2',4',6'-triisopropylbiphenyl (X-Phos, 30 mg), X-Phos aminobiphenylpalladium chloride precatalyst (50 mg), cesium fluoride (289 mg) and water (0.75 mL) were added, and the mixture was stirred under a nitrogen atmosphere under microwave irradiation at 120° C. for 0.5 hr. The reaction mixture was diluted with ethyl acetate and extracted twice with saturated aqueous sodium hydrogen carbonate. The aqueous layers were combined, and 2N hydrochloric acid was added by small portions to pH=1 under ice-cooling. The aqueous layer was extracted twice with chloroform. The combined organic layer was dried over anhydrous sodium sulfate and filtered, and the solvent was evaporated under reduced pressure to give the title compound (365 mg) as a pale-yellow crudely-purified powder.

MS(ESI) m/z: 537.2[M+H]$^+$ (99-2) methyl [(6S)-4-(4'-{[(1R)-1-{4-[(3-cyano-4-methyl-1H-indol-7-yl)sulfamoyl]phenyl}ethyl]carbamoyl}-2',3'-difluoro[1,1'-biphenyl]-4-yl)-2,3,9-trimethyl-6H-thieno[3,2-f][1,2,4]triazolo[4,3-a][1,4]diazepin-6-yl]acetate (Example Compound 99)

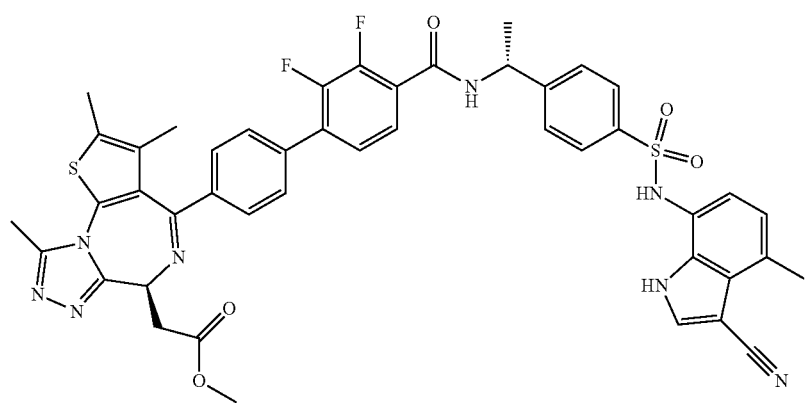

To a solution of Example compound 99-1 (50 mg) and Reference Example compound 17 (40 mg) in N,N-dimethylformamide (2.0 mL) were added N,N-diisopropylethylamine (0.49 mL) and HATU (43 mg) at room temperature, and the mixture was stirred at the same temperature for 1 hr. The reaction mixture was diluted with ethyl acetate-tetrahydrofuran, washed 3 times with saturated brine-water (1:1) and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (60 mg) as a beige powder.

MS(ESI) m/z: 873.7[M+H]$^+$

Example 100

(100-1) methyl [(6S)-4-{4'-[(2-{4-[(3-cyano-4-methyl-1H-indol-7-yl)sulfamoyl]phenyl}ethyl)carbamoyl]-2',3'-difluoro[1,1'-biphenyl]-4-yl}-2,3,9-trimethyl-6H-thieno[3,2-f][1,2,4]triazolo[4,3-a][1,4]diazepin-6-yl]acetate (Example Compound 100)

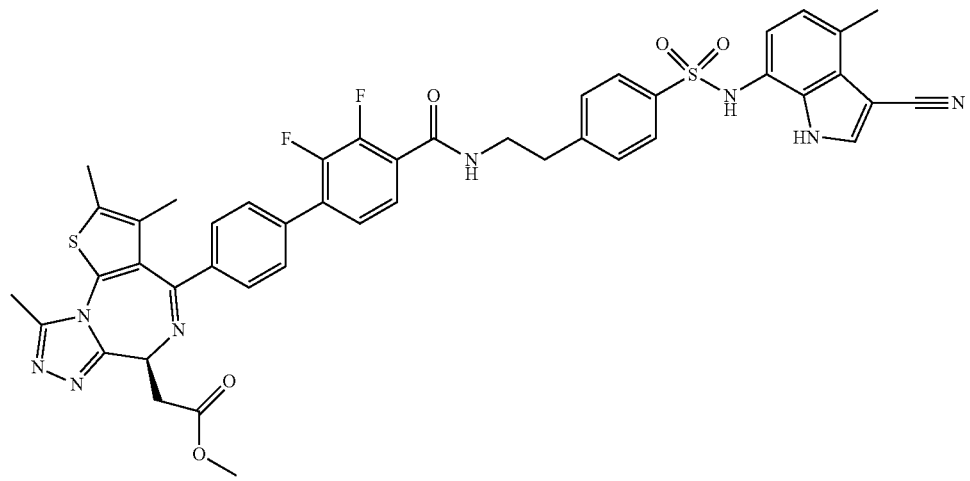 [SMILES: COC(=O)C[C@@H]1N=C(c2ccc(-c3ccc(C(=O)NCCc4ccc(S(=O)(=O)Nc5ccc(C)c6c(C#N)c[nH]c56)cc4)c(F)c3F)cc2)c2c(sc(C)c2C)-n2c(C)nnc21]

By reaction and treatment in the same manner as in Example 87 except that Example compound 99-1 (50 mg) was used instead of Reference Example compound 20, the title compound (60 mg) was obtained as a milk-white powder.

MS(ESI) m/z: 873.4[M+H]$^+$

Example 101

(101-1) 5-bromo-N-({4-[(3-cyano-4-methyl-1H-indol-7-yl)sulfamoyl]phenyl}methyl)-4-methylpyridine-2-carboxamide (Example Compound 101-1)

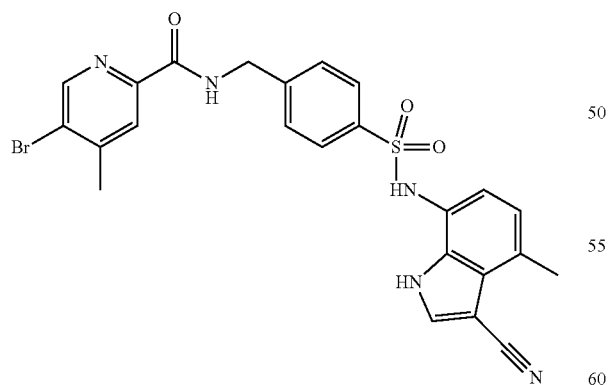

By reaction and treatment in the same manner as in (2-1) except that 5-bromo-4-methylpyridine-2-carboxylic acid was used instead of Reference Example compound 12 in Example 2, the title compound was obtained as a white solid.

MS(ESI) m/z: 536.1, 538.2[M−H]$^-$ (101-2) methyl [(6S)-4-(4-{6-[({4-[(3-cyano-4-methyl-1H-indol-7-yl)sulfamoyl]phenyl}methyl)carbamoyl]-4-methylpyridin-3-yl}phenyl)-2,3,9-trimethyl-6H-thieno[3,2-f][1,2,4]triazolo[4,3-a][1,4]diazepin-6-yl]acetate (Example Compound 101)

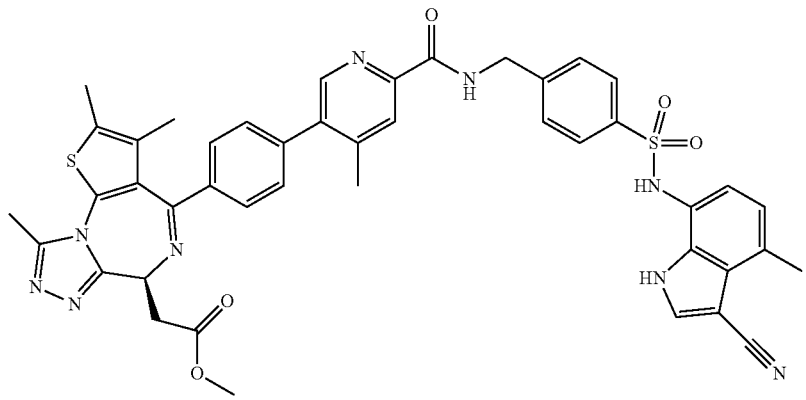

Under a nitrogen stream, Example compound 101-1 (134 mg), Reference Example compound 3 (126 mg), XPhos aminobiphenylpalladium chloride precatalyst (20 mg), XPhos (12 mg) and cesium fluoride (113 mg) were stirred in a water (1.0 mL)-tetrahydrofuran (4.0 mL) mixed solvent under microwave irradiation at 120° C. for 0.5 hr. The reaction mixture was directly purified by silica gel column chromatography (chloroform:methanol=100:0-95:5). The obtained solid was purified again by silica gel column chromatography (ethyl acetate:methanol=100:0-95:5) to give the title compound (114 mg) as a white solid. MS(ESI) m/z: 838.7[M+H]$^+$ Example 102

(102-1) methyl [(6S)-4-(4-{5-[(2-{4-[(3-cyano-4-methyl-1H-indol-7-yl)sulfamoyl]phenyl}ethyl)carbamoyl]pyrazin-2-yl}phenyl)-2,3,9-trimethyl-6H-thieno[3,2-f][1,2,4]triazolo[4,3-a][1, 4]diazepin-6-yl]acetate (Example Compound 102)

To a solution of Example compound 65-1 (68 mg) in chloroform (1.0 mL) was added trifluoroacetic acid (1.0 mL), and the mixture was stirred at room temperature for 2 hr. The reaction mixture was concentrated under reduced pressure, and azeotropically distilled twice with toluene. The residue and Reference Example compound 11 (47 mg), N,N-diisopropylethylamine (0.11 mL) and HATU (55 mg) were stirred in N,N-dimethylformamide (3.0 mL) at room temperature for 2 hr. To the reaction mixture was added water and the mixture was stirred. The resulting solid was collected by filtration, suspended and washed with water, and purified by silica gel column chromatography (chloroform:methanol=100:0-95:5) to give the title compound (79 mg) as a pale-yellow solid.

MS(ESI) m/z: 839.2[M+H]$^+$

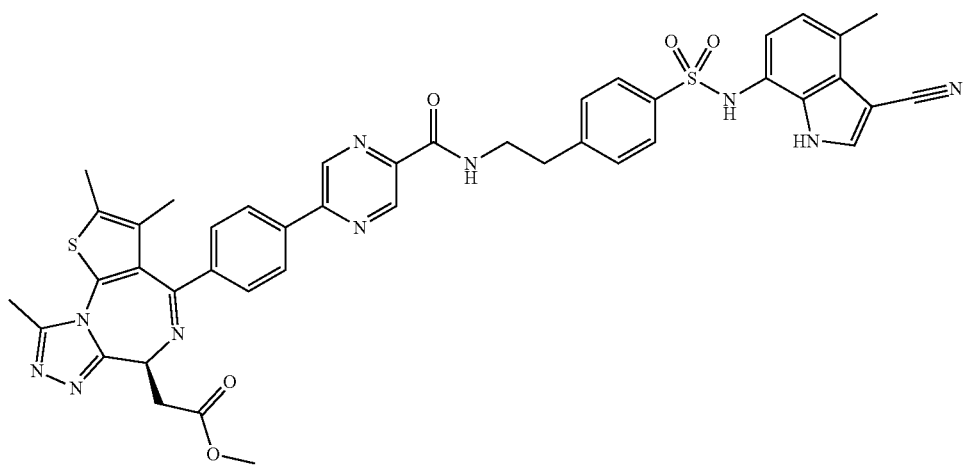 [SMILES: COC(=O)C[C@@H]1N=C(c2ccc(-c3cnc(C(=O)NCCc4ccc(S(=O)(=O)Nc5ccc(C)c6c(C#N)c[nH]c56)cc4)cn3)cc2)c2c(sc(C)c2C)-n2c(C)nnc21]

Example 103

(103-1) methyl {(6S)-4-[4-(5-{[(1R)-1-{4-[(3-cyano-4-methyl-1H-indol-7-yl)sulfamoyl]phenyl}ethyl]carbamoyl}pyrazin-2-yl)phenyl]-2,3,9-trimethyl-6H-thieno[3,2-f][1,2,4]triazolo[4,3-a][1,4]diazepin-6-yl}acetate (Example Compound 103)

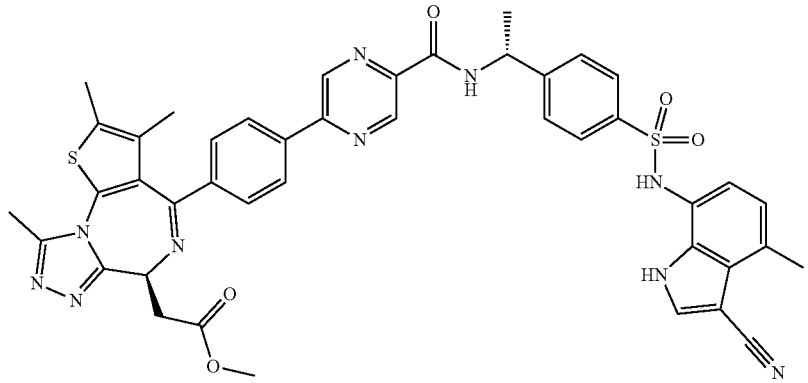

To a solution of Example compound 65-1 (68 mg) in chloroform (1.0 mL) was added trifluoroacetic acid (1.0 mL), and the mixture was stirred at room temperature for 2 hr. The reaction mixture was concentrated under reduced pressure, and azeotropically distilled twice with toluene. The residue and Reference Example compound 17 (47 mg), N,N-diisopropylethylamine (0.11 mL) and HATU (55 mg) were stirred in N,N-dimethylformamide (3.0 mL) at room temperature for 2 hr. To the reaction mixture was added water and the mixture was stirred. The resulting solid was collected by filtration, suspended and washed with water, and purified by silica gel column chromatography (chloroform:methanol=100:0-95:5) to give the title compound (74 mg) as a beige solid.

MS(ESI) m/z: 839.2[M+H]$^+$

Example 104

(104-1) di-t-butyl [(4-bromo-2-cyanophenyl)methyl]-2-imidodicarbonate (Example Compound 104-1)

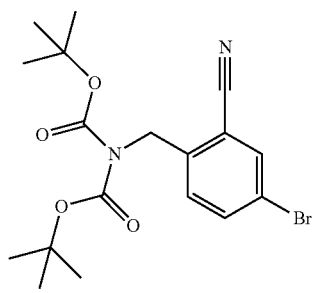 [SMILES: CC(C)(C)OC(=O)N(Cc1ccc(Br)cc1C#N)C(=O)OC(C)(C)C]

To a solution of 5-bromo-2-(bromomethyl)benzonitrile (500 mg) and di-t-butyl iminodicarboxylate (396 mg) in N,N-dimethylformamide (5.0 mL) was added cesium carbonate (1778 mg) at room temperature, and the mixture was stirred at 60° C. for 0.5 hr. The reaction mixture was diluted with ethyl acetate, washed 3 times with saturated brine-water (1:1) and once with saturated brine, dried over anhydrous sodium sulfate, and the solvent was evaporated under reduced pressure. The obtained residue was purified by silica gel column chromatography (hexane:ethyl acetate=98:2-90:10) to give the title compound (703 mg) as a colorless oil.

MS(ESI) m/z: 311.1, 313.2[M-Boc+2H]$^+$ (104-2) 2-(aminomethyl)-5-bromobenzonitrile hydrochloride (Example Compound 104-2)

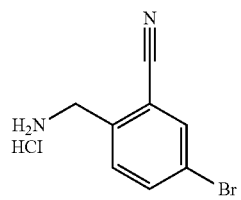

To Example compound 104-1 (400 mg) was added 4M hydrogen chloride/1,4-dioxane solution (4.0 mL) at room temperature. After stirring at the same temperature for 1 hr, the reaction mixture was concentrated under reduced pressure. The residue was suspended and washed with diethyl ether, and collected by filtration to give the title compound (233 mg) as a white solid.

MS(ESI) m/z: 211.1, 213.1[M+H]$^+$ (104-3) methyl [(6S)-4-{4'-[({2-cyano-4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 104)

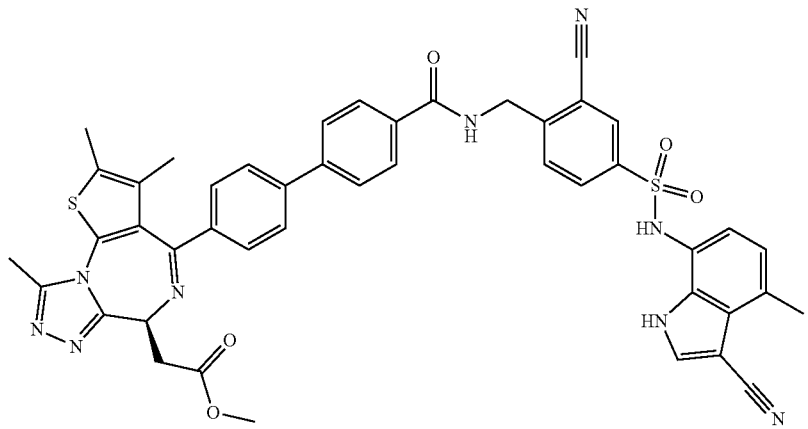

By reaction and treatment in the same manner as in (25-1)-(25-2) except that Example compound 104-2 was used instead of 4-bromo-3-fluorophenylmethanamine hydrochloride in Example 25, the title compound was obtained as a brown powder.

MS(ESI) m/z: 848.3[M+H]$^+$

Example 105

(105-1) 5-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyrazine-2-carboxylic acid (Example Compound 105-1)

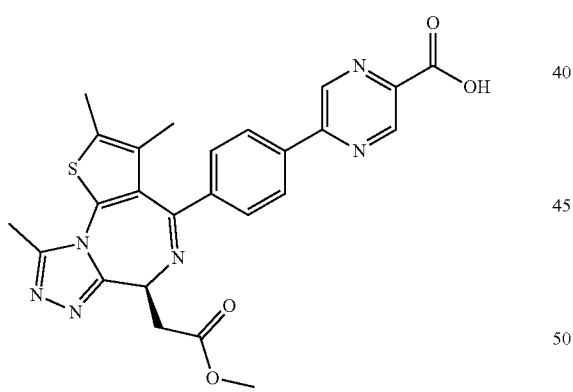

To a solution of Example compound 65-1 (218 mg) in chloroform (1.0 mL) was added trifluoroacetic acid (1.0 mL), and the mixture was stirred at room temperature for 2 hr. The reaction mixture was concentrated under reduced pressure, and toluene azeotropic distillation was performed twice. Ethyl acetate and water were added and the mixture was stirred. Saturated aqueous sodium hydrogen carbonate was added by small portions to pH8. The organic layer was removed, and the aqueous layer was washed with ethyl acetate. 1N Hydrochloric acid was slowly added to the aqueous layer to pH5, and the mixture was extracted 3 times with chloroform. The organic layer was concentrated under reduced pressure to give the title compound (161 mg) as a pale-yellow solid.

MS(ESI) m/z: 503.1[M+H]$^+$ (105-2) methyl [(6S)-4-(4-{5-[({4-[(3-cyano-4-ethyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1,4]diazepin-6-yl]acetate (Example Compound 105)

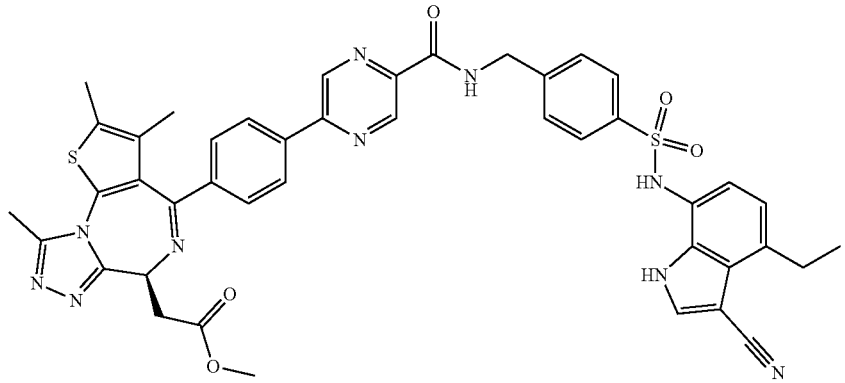

Example compound 105-1 (53 mg), and Reference Example compound 21 (45 mg), N,N-diisopropylethylamine (0.055 mL) and HATU (48 mg) were stirred in N,N-dimethylformamide (2.0 mL) at room temperature for 2 hr. To the reaction mixture was added water and the mixture was stirred. The resulting solid was collected by filtration, suspended and washed with water, and purified by silica gel column chromatography (chloroform:methanol=100:0-95:5) to give the title compound (65 mg) as a pale-yellow solid. MS(ESI) m/z: 839.2[M+H]$^+$ Example 106

(106-1) methyl {(6S)-4-[4-(5-{[(1R)-1-{4-[(3-cyano-4-ethyl-1H-indol-7-yl)sulfamoyl]phenyl}ethyl]carbamoyl}pyrazin-2-yl)phenyl]-2,3,9-trimethyl-6H-thieno[3,2-f][1,2,4]triazolo[4,3-a][1,4]diazepin-6-yl}acetate (Example Compound 106)

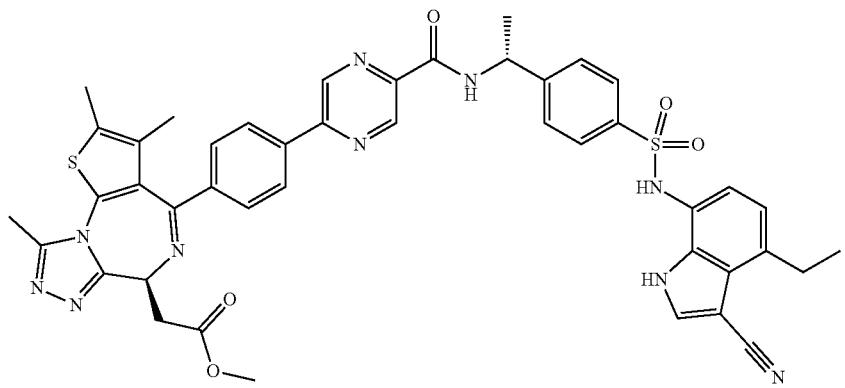

Example compound 105-1 (53 mg), and Reference Example compound 22 (47 mg), N,N-diisopropylethylamine (0.055 mL) and HATU (48 mg) were stirred in N,N-dimethylformamide (2.0 mL) at room temperature for 2 hr. To the reaction mixture was added water and the mixture was stirred. The resulting solid was collected by filtration, suspended and washed with water, and purified by silica gel column chromatography (chloroform:methanol=100:0-95:5) to give the title compound (70 mg) as a pale-yellow solid. MS(ESI) m/z: 853.2[M+H]$^+$

Example 107

(107-1) methyl [(6S)-4-(4-{5-[(2-{4-[(3-cyano-4-ethyl-1H-indol-7-yl)sulfamoyl]phenyl}ethyl)carbamoyl]pyrazin-2-yl}phenyl)-2,3,9-trimethyl-6H-thieno[3,2-f][1,2,4]triazolo[4,3-a][1, 4]diazepin-6-yl]acetate (Example Compound 107)

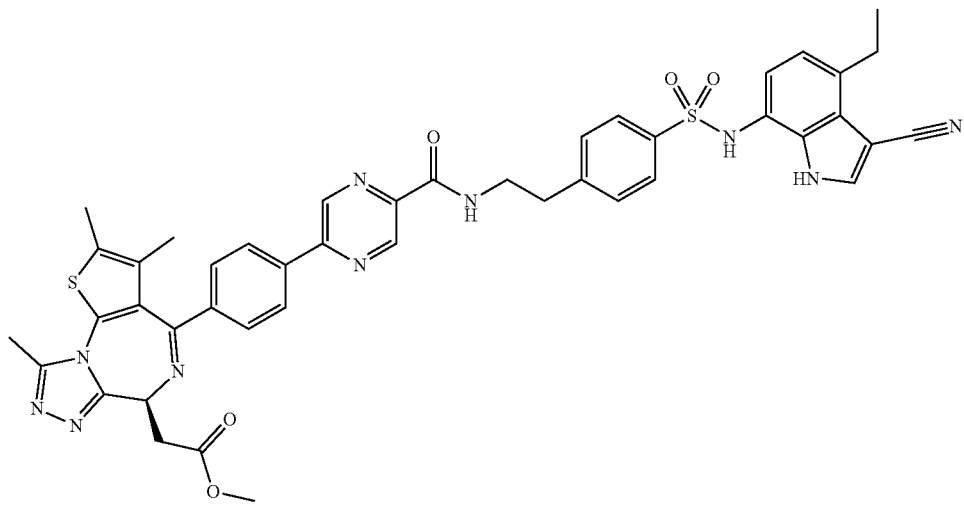

Example compound 105-1 (53 mg), and Reference Example compound 23 (47 mg), N,N-diisopropylethylamine (0.055 mL) and HATU (48 mg) were stirred in N,N-dimethylformamide (2.0 mL) at room temperature for 2 hr. To the reaction mixture was added water and the mixture was stirred. The resulting solid was collected by filtration, suspended and washed with water and purified by silica gel column chromatography (chloroform:methanol=100:0-95:5) to give the title compound (73 mg) as a pale-yellow solid.
MS(ESI) m/z: 853.2[M+H]$^+$

Example 108

(108-1) 5-{4-[(6S)-6-(2-methoxy-2-oxoethyl)-2,3,9-trimethyl-6H-thieno[3,2-f][1,2,4]triazolo[4,3-a][1,4]diazepin-4-yl]phenyl}pyridine-2-carboxylic acid (Example Compound 108-1)

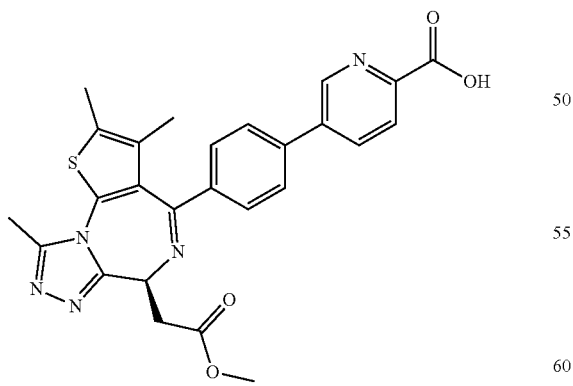

By reaction and treatment in the same manner as in (105-1) except that Example compound 53-1 (219 mg) was used instead of Example compound 65-1 in Example 105, the title compound (150 mg) was obtained as a pale-yellow solid.
MS(ESI) m/z: 502.1[M+H]$^+$ (108-2) methyl [(6S)-4-(4-{6-[({4-[(3-cyano-4-ethyl-1H-indol-7-yl)sulfamoyl]phenyl}methyl)carbamoyl]pyridin-3-yl}phenyl)-2,3,9-trimethyl-6H-thieno[3,2-f][1,2,4]triazolo[4,3-a][1,4]diazepin-6-yl]acetate (Example Compound 108)

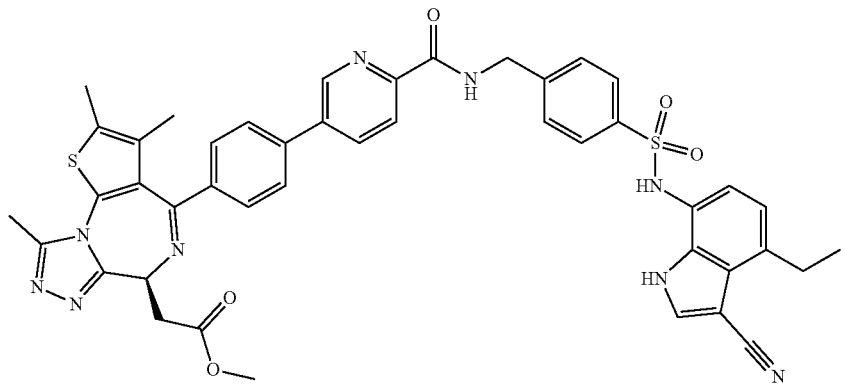 [SMILES: CCc1ccc(NS(=O)(=O)c2ccc(CNC(=O)c3ccc(-c4ccc(C5=N[C@@H](CC(=O)OC)c6nnc(C)n6-c6sc(C)c(C)c65)cc4)cn3)cc2)c2[nH]cc(C#N)c12]

By reaction and treatment in the same manner as in (105-2) except that Example compound 108-1 (50 mg) was used instead of Example compound 105-1 in Example 105, the title compound (51 mg) was obtained as a beige solid.
MS(ESI) m/z: 838.2[M+H]$^+$ Example 109

(109-1) methyl {(6S)-4-[4-(6-{[(1R)-1-{4-[(3-cyano-4-ethyl-1H-indol-7-yl)sulfamoyl]phenyl}ethyl]carbamoyl}pyridin-3-yl)phenyl]-2,3,9-trimethyl-6H-thieno[3,2-f][1,2,4]triazolo[4,3-a][1,4]diazepin-6-yl}acetate (Example Compound 109)

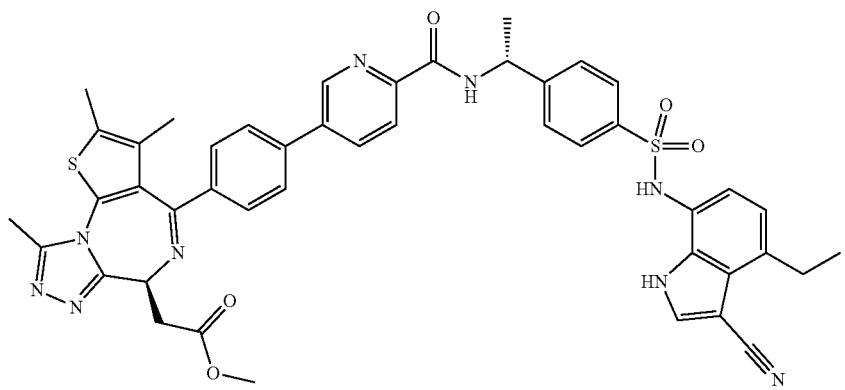 [SMILES: CCc1ccc(NS(=O)(=O)c2ccc([C@@H](C)NC(=O)c3ccc(-c4ccc(C5=N[C@@H](CC(=O)OC)c6nnc(C)n6-c6sc(C)c(C)c65)cc4)cn3)cc2)c2[nH]cc(C#N)c12]

By reaction and treatment in the same manner as in (106-1) except that Example compound 108-1 (50 mg) was used instead of Example compound 105-1 in Example 106, the title compound (68 mg) was obtained as a beige solid.
MS(ESI) m/z: 852.2[M+H]$^+$ Example 110

(110-1) methyl [(6S)-4-(4-{6-[(2-{4-[(3-cyano-4-ethyl-1H-indol-7-yl)sulfamoyl]phenyl}ethyl)carbamoyl]pyridin-3-yl}phenyl)-2,3,9-trimethyl-6H-thieno[3,2-f][1,2,4]triazolo[4,3-a][1, 4]diazepin-6-yl]acetate (Example Compound 110)

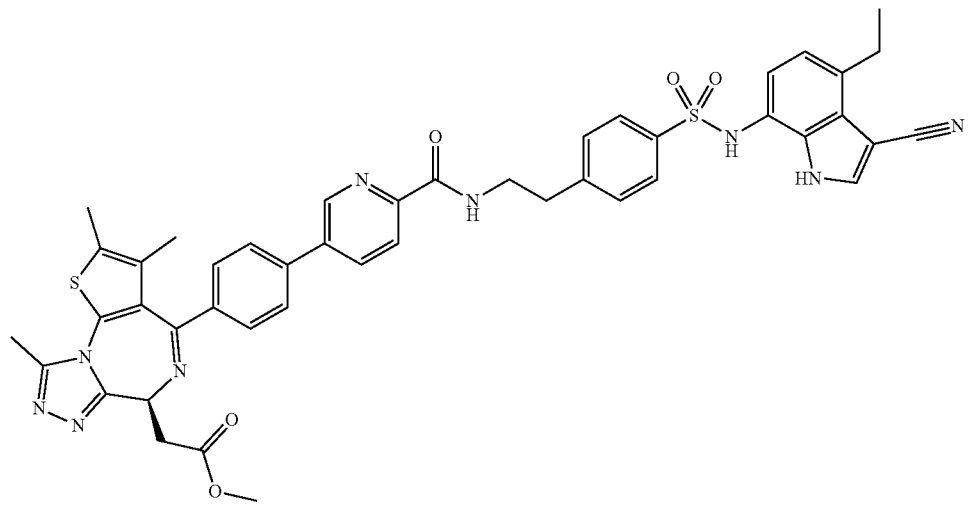 [SMILES: CCc1ccc(NS(=O)(=O)c2ccc(CCNC(=O)c3ccc(-c4ccc(C5=N[C@@H](CC(=O)OC)c6nnc(C)n6-c6sc(C)c(C)c65)cc4)cn3)cc2)c2[nH]cc(C#N)c12]

By reaction and treatment in the same manner as in (107-1) except that Example compound 108-1 (50 mg) was used instead of Example compound 105-1 in Example 107, the title compound (63 mg) was obtained as a beige solid. MS(ESI) m/z: 852.2[M+H]$^+$ Example 111

(111-1) methyl [(6S)-4-{4'-[(cyano{4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 111)

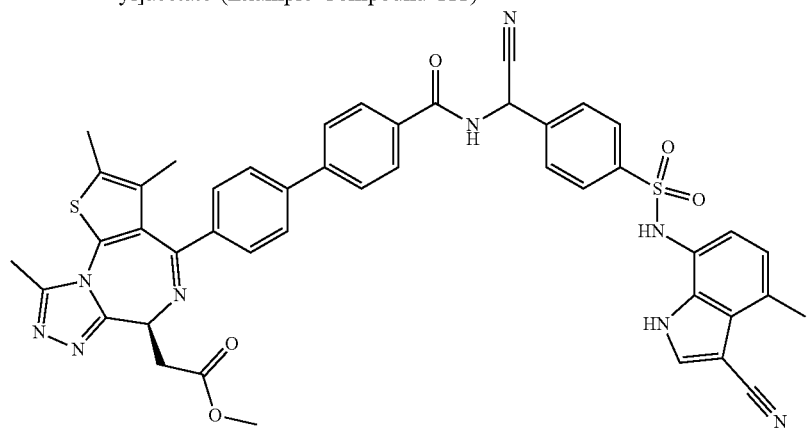

By reaction and treatment in the same manner as in (25-1)-(25-2) except that 2-amino-2-(4-bromophenyl)acetonitrile was used instead of 4-bromo-3-fluorophenylmethanamine hydrochloride in Example 25, the title compound was obtained as a pale-brown powder. MS(ESI) m/z: 848.3 [M+H]$^+$ Example 112

(112-1) methyl [(6S)-4-{4'-[({4-[(3-cyano-4-ethyl-1H-indol-7-yl)sulfamoyl]phenyl}methyl)carbamoyl]-3'-fluoro[1,1'-biphenyl]-4-yl}-2,3,9-trimethyl-6H-thieno[3,2-f][1,2,4]triazolo[4,3-a][1,4]diazepin-6-yl]acetate (Example Compound 112)

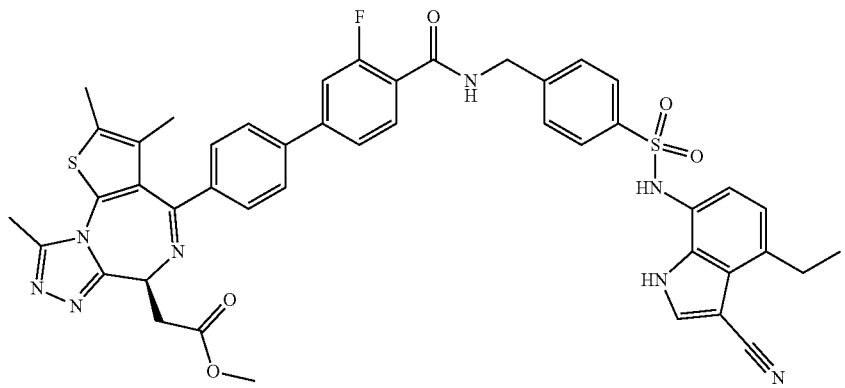 [SMILES: CCc1ccc(NS(=O)(=O)c2ccc(CNC(=O)c3ccc(-c4ccc(C5=N[C@@H](CC(=O)OC)c6nnc(C)n6-c6sc(C)c(C)c65)cc4)cc3F)cc2)c2[nH]cc(C#N)c12]

To a solution of Reference Example compound 12 (60 mg) and Reference Example compound 21 (50 mg) in N,N-dimethylformamide (1.0 mL) were added N,N-diisopropylethylamine (0.060 mL) and HATU (53 mg) at room temperature, and the mixture was stirred at the same temperature for 1 hr. The reaction mixture was directly purified by preparative HPLC (10 mM aqueous ammonium carbonate solution-acetonitrile) to give the title compound (78 mg) as a beige powder.

MS(ESI) m/z: 855.2[M+H]$^+$

Example 113

(113-1) methyl [(6S)-4-{3'-chloro-4'-[({4-[(3-cyano-4-ethyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 113)

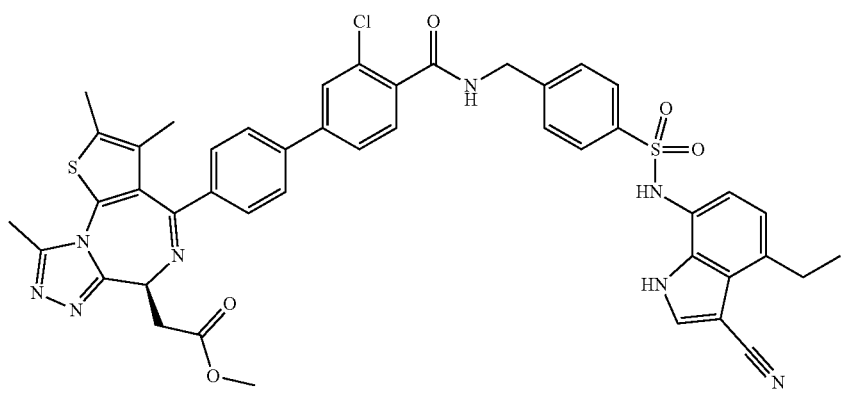 [SMILES: CCc1ccc(NS(=O)(=O)c2ccc(CNC(=O)c3ccc(-c4ccc(C5=N[C@@H](CC(=O)OC)c6nnc(C)n6-c6sc(C)c(C)c65)cc4)cc3Cl)cc2)c2[nH]cc(C#N)c12]

By reaction and treatment in the same manner as in Example 112 except that Reference Example compound 13 (68 mg) was used instead of Reference Example compound 12, the title compound (88 mg) was obtained as a white powder.

MS(ESI) m/z: 871.2, 873.1[M+H]$^+$

Example 114

(114-1) methyl [(6S)-4-{4'-[({4-[(3-cyano-4-ethyl-1H-indol-7-yl) sulfamoyl]phenyl}methyl) carbamoyl]-3'-methyl [1,1'-biphenyl]-4-yl}-2,3,9-trimethyl-6H-thieno[3,2-f][1,2,4]triazolo[4,3-a][1, 4]diazepin-6-yl]acetate (Example Compound 114)

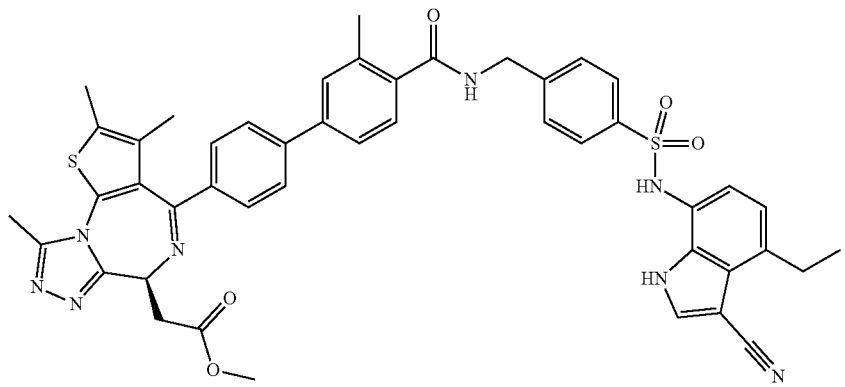 [SMILES: CCc1ccc(NS(=O)(=O)c2ccc(CNC(=O)c3ccc(-c4ccc(C5=N[C@@H](CC(=O)OC)c6nnc(C)n6-c6sc(C)c(C)c65)cc4)cc3C)cc2)c2[nH]cc(C#N)c12]

By reaction and treatment in the same manner as in Example 112 except that Reference Example compound 20 (50 mg) was used instead of Reference Example compound 12, the title compound (39 mg) was obtained as a beige powder.

MS(ESI) m/z: 851.3[M+H]$^+$

Example 115

(115-1) methyl [(6S)-4-{4'-[({4-[(3-cyano-4-ethyl-1H-indol-7-yl) sulfamoyl]phenyl}methyl) carbamoyl]-2'-fluoro[1,1'-biphenyl]-4-yl}-2,3,9-trimethyl-6H-thieno[3,2-f][1,2,4]triazolo[4,3-a][1, 4]diazepin-6-yl]acetate (Example Compound 115)

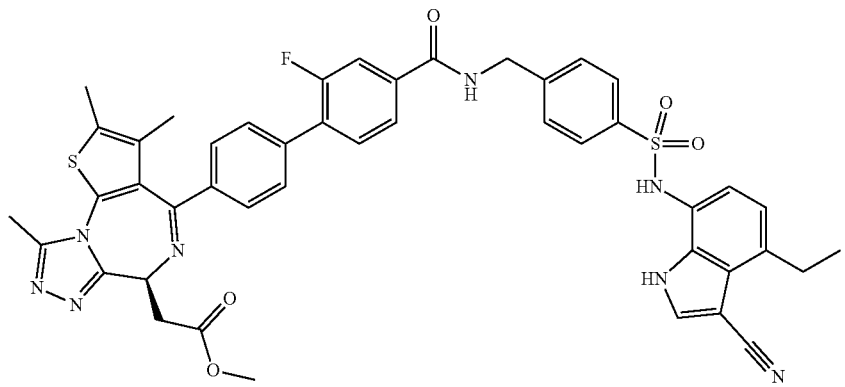 [SMILES: CCc1ccc(NS(=O)(=O)c2ccc(CNC(=O)c3ccc(-c4ccc(C5=N[C@@H](CC(=O)OC)c6nnc(C)n6-c6sc(C)c(C)c65)cc4)c(F)c3)cc2)c2[nH]cc(C#N)c12]

By reaction and treatment in the same manner as in Example 112 except that Reference Example compound 18 (50 mg) was used instead of Reference Example compound 12, the title compound (56 mg) was obtained as a beige powder.

MS(ESI) m/z: 855.3[M+H]$^+$

Example 116

(116-1) methyl [(6S)-4-{2'-chloro-4'-[({4-[(3-cyano-4-ethyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 116)

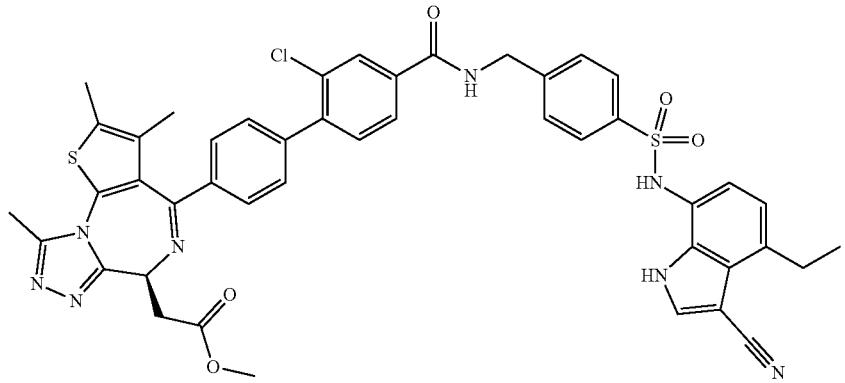 [SMILES: CCc1ccc(NS(=O)(=O)c2ccc(CNC(=O)c3ccc(-c4ccc(C5=N[C@@H](CC(=O)OC)c6nnc(C)n6-c6sc(C)c(C)c65)cc4)c(C)c3)cc2)c2[nH]cc(C#N)c12]

By reaction and treatment in the same manner as in Example 112 except that Reference Example compound 19 (50 mg) was used instead of Reference Example compound 12, the title compound (33 mg) was obtained as a white powder.
MS(ESI) m/z: 871.2, 873.2[M+H]+

Example 117

(117-1) methyl [(6S)-4-{4'-[({4-[(3-cyano-4-ethyl-1H-indol-7-yl)sulfamoyl]phenyl}methyl)carbamoyl]-2'-methyl[1,1'-biphenyl]-4-yl}-2,3,9-trimethyl-6H-thieno[3,2-f][1,2,4]triazolo[4,3-a][1,4]diazepin-6-yl]acetate (Example Compound 117)

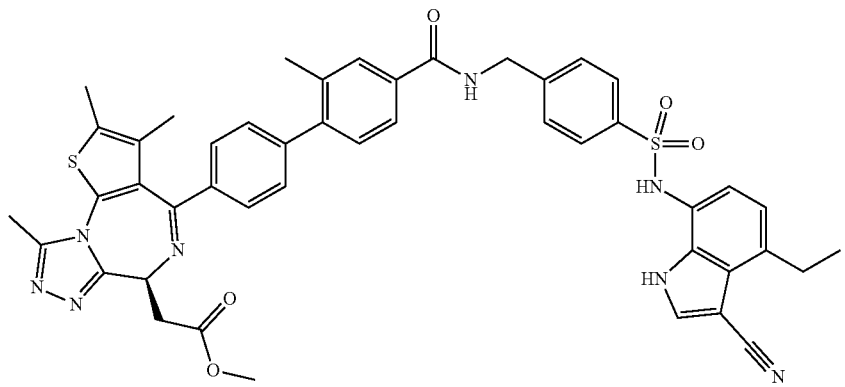

By reaction and treatment in the same manner as in Example 112 except that Example compound 75-1 (50 mg) was used instead of Reference Example compound 12, the title compound (39 mg) was obtained as a white powder.
MS(ESI) m/z: 851.3[M+H]+

Example 118

(118-1) methyl [(6S)-4-{4'-[({4-[(3-cyano-4-ethyl-1H-indol-7-yl)sulfamoyl]phenyl}methyl)carbamoyl]-2',3'-difluoro[1,1'-biphenyl]-4-yl}-2,3,9-trimethyl-6H-thieno[3,2-f][1,2,4]triazolo[4,3-a][1,4]diazepin-6-yl]acetate (Example Compound 118)

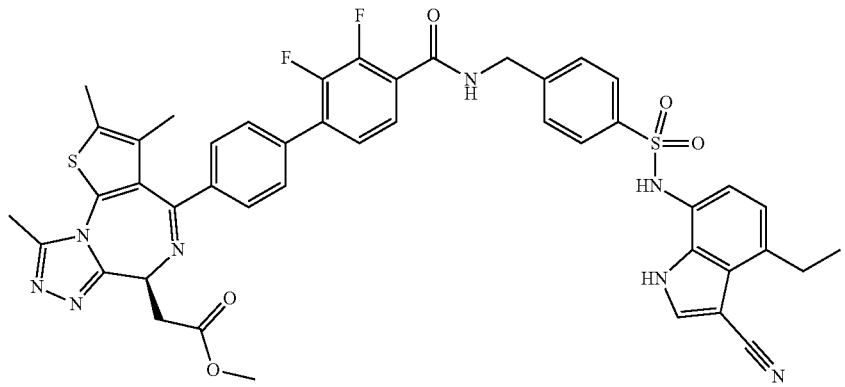 [SMILES: CCc1ccc(NS(=O)(=O)c2ccc(CNC(=O)c3ccc(-c4ccc(C5=N[C@@H](CC(=O)OC)c6nnc(C)n6-c6sc(C)c(C)c65)cc4)c(F)c3F)cc2)c2[nH]cc(C#N)c12]

By reaction and treatment in the same manner as in Example 112 except that Example compound 99-1 (50 mg) was used instead of Reference Example compound 12, the title compound (47 mg) was obtained as a white powder.
MS(ESI) m/z: 873.2[M+H]$^+$ Example 119

(119-1) methyl [(6S)-4-{4'-[({4-[(3-cyano-4-ethyl-1H-indol-7-yl)sulfamoyl]phenyl}methyl)carbamoyl]-2',5'-difluoro[1,1'-biphenyl]-4-yl}-2,3,9-trimethyl-6H-thieno[3,2-f][1,2,4]triazolo[4,3-a][1,4]diazepin-6-yl]acetate (Example Compound 119)

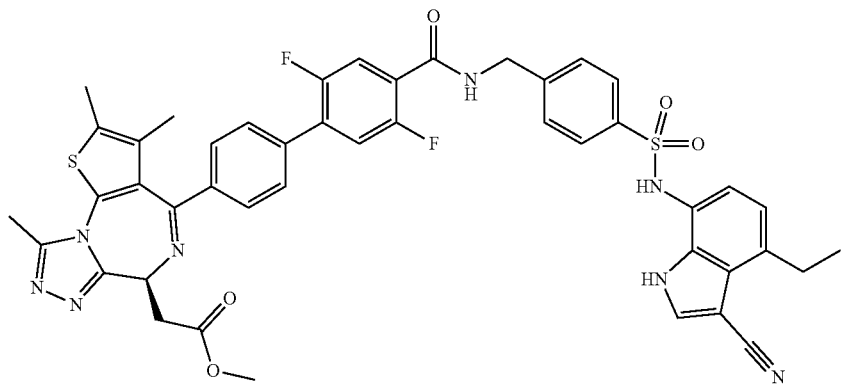 [SMILES: CCc1ccc(NS(=O)(=O)c2ccc(CNC(=O)c3cc(F)c(-c4ccc(C5=N[C@@H](CC(=O)OC)c6nnc(C)n6-c6sc(C)c(C)c65)cc4)cc3F)cc2)c2[nH]cc(C#N)c12]

By reaction and treatment in the same manner as in Example 112 except that Example compound 82-1 (26 mg) was used instead of Reference Example compound 12, the title compound (29 mg) was obtained as a white powder.
MS(ESI) m/z: 873.2[M+H]$^+$

Example 120

(120-1) methyl [(6S)-4-{4'-[({4-[(3-cyano-4-ethyl-1H-indol-7-yl) sulfamoyl]phenyl}methyl) carbamoyl]-2'-fluoro-5'-methyl [1,1'-biphenyl]-4-yl}-2,3,9-trimethyl-6H-thieno[3,2-f][1,2,4]triazolo[4,3-a][1,4]diazepin-6-yl]acetate (Example Compound 120)

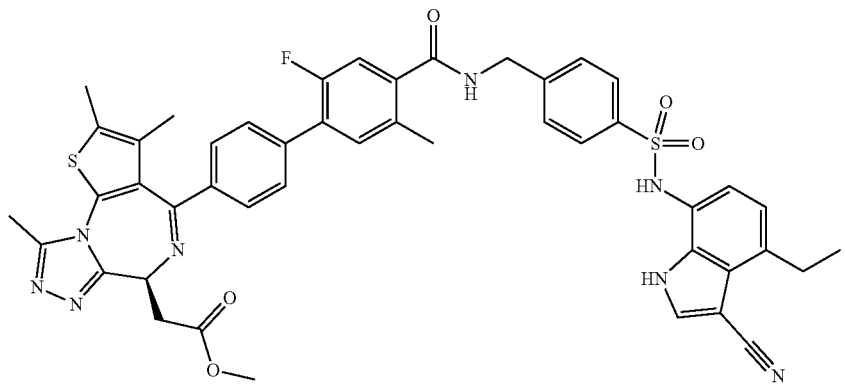 [SMILES: CCc1ccc(NS(=O)(=O)c2ccc(CNC(=O)c3cc(F)c(-c4ccc(C5=N[C@@H](CC(=O)OC)c6nnc(C)n6-c6sc(C)c(C)c65)cc4)cc3C)cc2)c2[nH]cc(C#N)c12]

By reaction and treatment in the same manner as in Example 112 except that Example compound 83-1 (19 mg) was used instead of Reference Example compound 12, the title compound (22 mg) was obtained as a white powder.
MS(ESI) m/z: 869.2[M+H]$^+$

Example 121

(121-1) methyl [(6S)-4-(4'-{[(1R)-1-{4-[(3-cyano-4-ethyl-1H-indol-7-yl)sulfamoyl]phenyl}ethyl]carbamoyl}-2'-fluoro[1,1'-biphenyl]-4-yl)-2,3,9-trimethyl-6H-thieno[3,2-f][1,2,4]triazolo[4,3-a][1,4]diazepin-6-yl]acetate (Example compound 121)

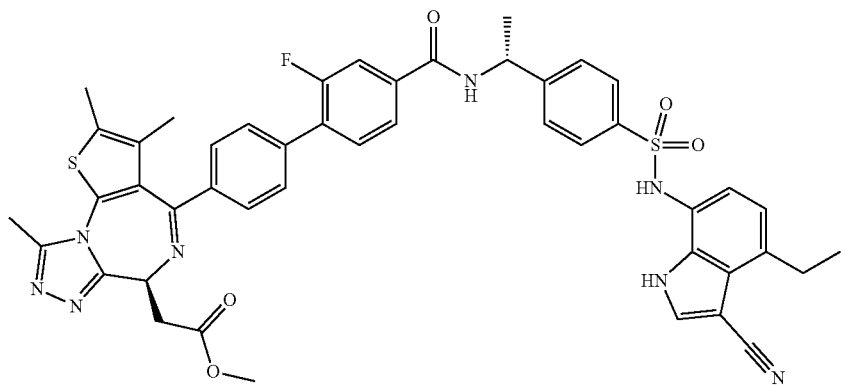 [SMILES: CCc1ccc(NS(=O)(=O)c2ccc([C@@H](C)NC(=O)c3ccc(-c4ccc(C5=N[C@@H](CC(=O)OC)c6nnc(C)n6-c6sc(C)c(C)c65)cc4)c(F)c3)cc2)c2[nH]cc(C#N)c12]

To a solution of Reference Example compound 18 (50 mg) and Reference Example compound 22 (43 mg) in N,N-dimethylformamide (1.0 mL) were added N,N-diisopropylethylamine (0.050 mL) and HATU (44 mg) at room temperature, and the mixture was stirred at the same temperature for 1 hr. The reaction mixture was directly purified by preparative HPLC (10 mM aqueous ammonium carbonate solution-acetonitrile) to give the title compound (35 mg) as a white powder.
MS(ESI) m/z: 869.2[M+H]$^+$

Example 122

(122-1) methyl [(6S)-4-(4'-{[(1R)-1-{4-[(3-cyano-4-ethyl-1H-indol-7-yl)sulfamoyl]phenyl}ethyl]carbamoyl}-2',3'-difluoro[1,1'-biphenyl]-4-yl)-2,3,9-trimethyl-6H-thieno[3,2-f][1,2,4]triazolo[4,3-a][1,4]diazepin-6-yl]acetate (Example Compound 122)

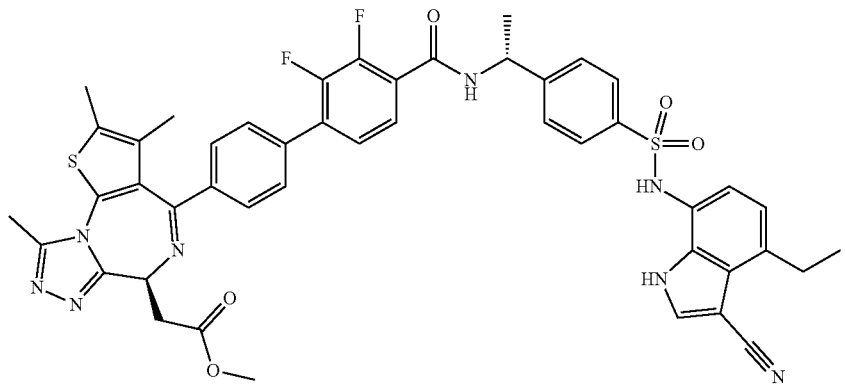 [SMILES: CCc1ccc(NS(=O)(=O)c2ccc([C@@H](C)NC(=O)c3ccc(-c4ccc(C5=N[C@@H](CC(=O)OC)c6nnc(C)n6-c6sc(C)c(C)c65)cc4)c(F)c3F)cc2)c2[nH]cc(C#N)c12]

By reaction and treatment in the same manner as in Example 121 except that Example compound 99-1 (50 mg) was used instead of Reference Example compound 18, the title compound (39 mg) was obtained as a white powder.
MS(ESI) m/z: 887.2[M+H]$^+$

Example 123

(123-1) methyl [(6S)-4-(4'-{[(1R)-1-{4-[(3-cyano-4-ethyl-1H-indol-7-yl)sulfamoyl]phenyl}ethyl]carbamoyl}-3'-methyl[1,1'-biphenyl]-4-yl)-2,3,9-trimethyl-6H-thieno[3,2-f][1,2,4]triazolo[4,3-a][1,4]diazepin-6-yl]acetate (Example Compound 123)

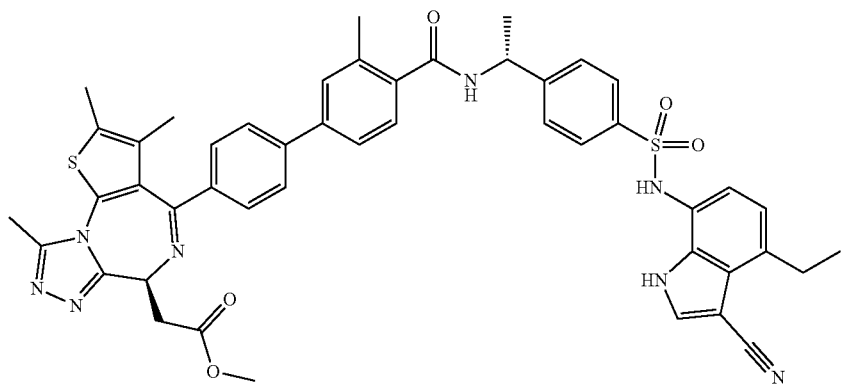 [SMILES: CCc1ccc(NS(=O)(=O)c2ccc([C@@H](C)NC(=O)c3ccc(-c4ccc(C5=N[C@@H](CC(=O)OC)c6nnc(C)n6-c6sc(C)c(C)c65)cc4)cc3C)cc2)c2[nH]cc(C#N)c12]

By reaction and treatment in the same manner as in Example 121 except that Reference Example compound 20 (30 mg) was used instead of Reference Example compound 18, the title compound (30 mg) was obtained as a beige powder.
MS(ESI) m/z: 865.3[M+H]$^+$ Example 124

(124-1) methyl [(6S)-4-{4'-[(2-{4-[(3-cyano-4-ethyl-1H-indol-7-yl)sulfamoyl]phenyl}ethyl)carbamoyl]-2'-fluoro[1,1'-biphenyl]-4-yl}-2,3,9-trimethyl-6H-thieno[3,2-f][1,2,4]triazolo[4,3-a][1,4]diazepin-6-yl]acetate (Example Compound 124)

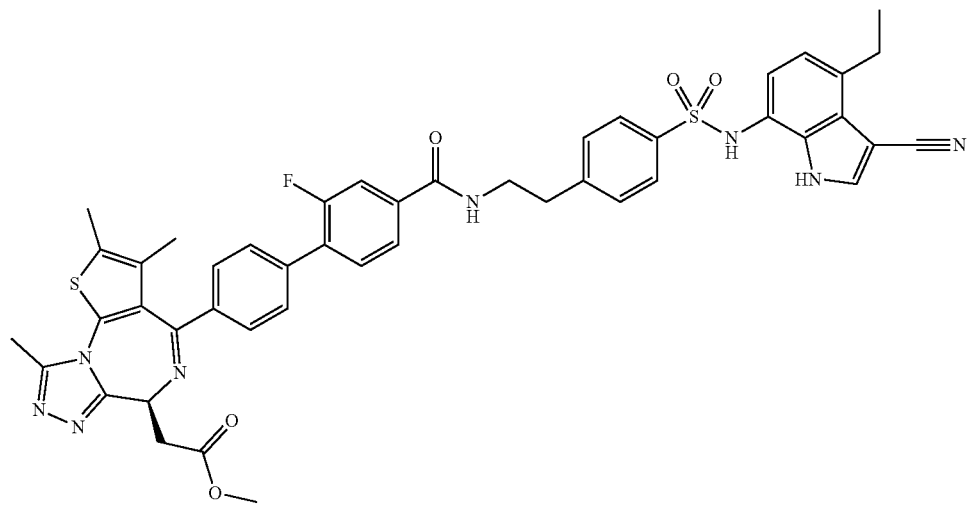 [SMILES: CCc1ccc(NS(=O)(=O)c2ccc(CCNC(=O)c3ccc(-c4ccc(C5=N[C@@H](CC(=O)OC)c6nnc(C)n6-c6sc(C)c(C)c65)cc4)c(F)c3)cc2)c2[nH]cc(C#N)c12]

To a solution of Reference Example compound 18 (50 mg) and Reference Example compound 23 (43 mg) in N,N-dimethylformamide (1.0 mL) were added N,N-diisopropylethylamine (0.050 mL) and HATU (44 mg) at room temperature, and the mixture was stirred at the same temperature for 1 hr. The reaction mixture was directly purified by preparative HPLC (10 mM aqueous ammonium carbonate solution-acetonitrile) to give the title compound (42 mg) as a beige powder.
MS(ESI) m/z: 869.3[M+H]$^+$ Example 125

(125-1) methyl [(6S)-4-{4'-[(2-{4-[(3-cyano-4-ethyl-1H-indol-7-yl)sulfamoyl]phenyl}ethyl)carbamoyl]-2',3'-difluoro[1,1'-biphenyl]-4-yl}-2,3,9-trimethyl-6H-thieno[3,2-f][1,2,4]triazolo[4,3-a][1,4]diazepin-6-yl]acetate (Example Compound 125)

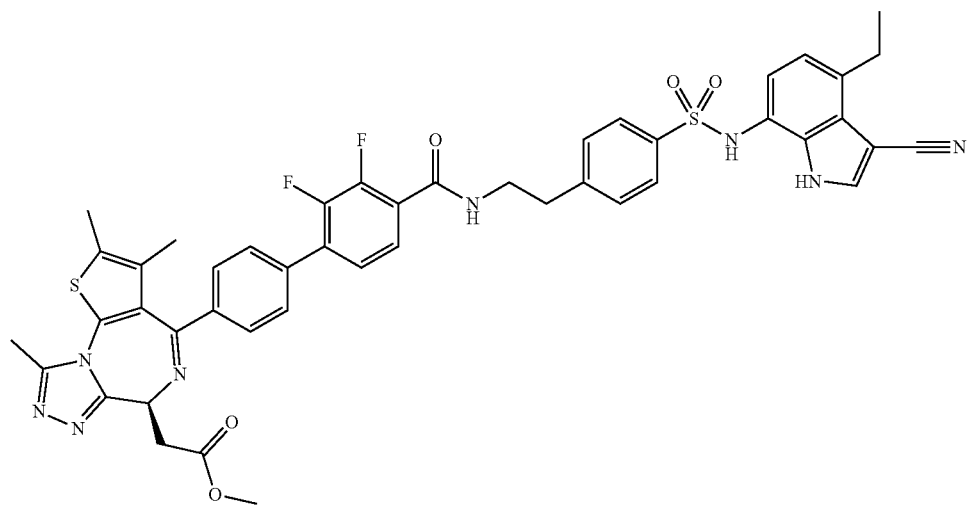

By reaction and treatment in the same manner as in Example 124 except that Example compound 99-1 (50 mg) was used instead of Reference Example compound 18, the title compound (48 mg) was obtained as a white powder.

MS(ESI) m/z: 887.2[M+H]$^+$

Example 126

(126-1) methyl [(6S)-4-{4'-[(2-{4-[(3-cyano-4-ethyl-1H-indol-7-yl)sulfamoyl]phenyl}ethyl)carbamoyl]-3'-methyl[1,1'-biphenyl]-4-yl}-2,3,9-trimethyl-6H-thieno[3,2-f][1,2,4]triazolo[4,3-a][1,4]diazepin-6-yl]acetate (Example Compound 126)

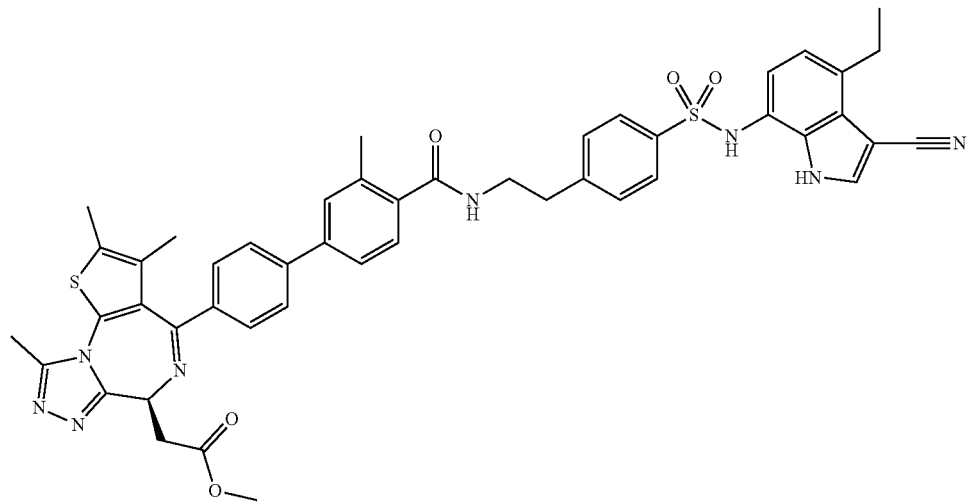 [SMILES: CCc1ccc(NS(=O)(=O)c2ccc(CCNC(=O)c3ccc(-c4ccc(C5=N[C@@H](CC(=O)OC)c6nnc(C)n6-c6sc(C)c(C)c65)cc4)cc3C)cc2)c2[nH]cc(C#N)c12]

By reaction and treatment in the same manner as in Example 124 except that Reference Example compound 20 (32 mg) was used instead of Reference Example compound 18, the title compound (28 mg) was obtained as a white powder.

MS(ESI) m/z: 865.3[M+H]$^+$

Example 127

(127-1) methyl [(6S)-4-(4'-{[(1R)-1-{4-[(3-cyano-4-ethyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate (Example Compound 127)

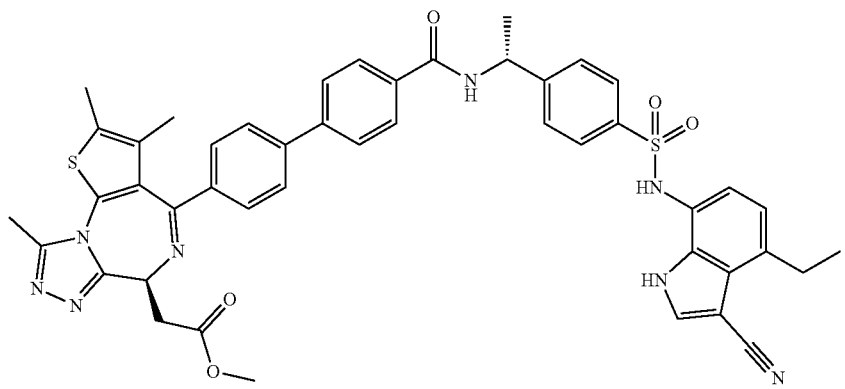 [SMILES: CCc1ccc(NS(=O)(=O)c2ccc([C@@H](C)NC(=O)c3ccc(-c4ccc(C5=N[C@@H](CC(=O)OC)c6nnc(C)n6-c6sc(C)c(C)c65)cc4)cc3)cc2)c2[nH]cc(C#N)c12]

By reaction and treatment in the same manner as in (1-1) except that Reference Example compound 22 (39 mg) was used instead of Reference Example compound 5 in Example 1, the title compound (58 mg) was obtained as a pale-yellow solid.

MS (ESI) m/z: 851.3[M+H]$^+$

Example 128

(128-1) methyl [(6S)-4-{4'-[(2-{4-[(3-cyano-4-ethyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 128)

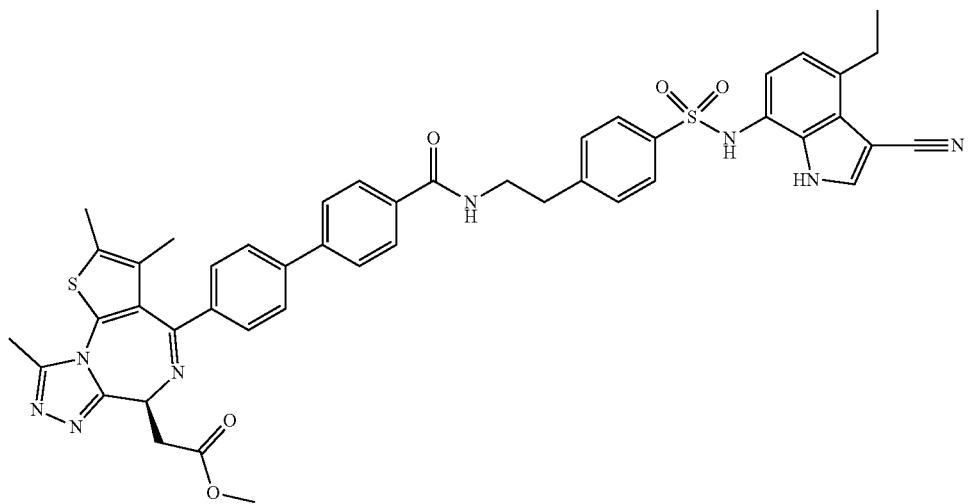 [SMILES: CCc1ccc(NS(=O)(=O)c2ccc(CCNC(=O)c3ccc(-c4ccc(C5=N[C@@H](CC(=O)OC)c6nnc(C)n6-c6sc(C)c(C)c65)cc4)cc3)cc2)c2[nH]cc(C#N)c12]

By reaction and treatment in the same manner as in Example 1 except that Reference Example compound 23 (39 mg) was used instead of Reference Example compound 5, the title compound (56 mg) was obtained as a pale-yellow solid.

MS(ESI) m/z: 851.2[M+H]$^+$

Example 129

(129-1) N-({4-[(3-cyano-4-methyl-1H-indol-7-yl)sulfamoyl]phenyl}methyl)-4-(4,4,5,5-tetramethyl-1,3,2-dioxaboronan-2-yl) benzamide (Example Compound 129-1)

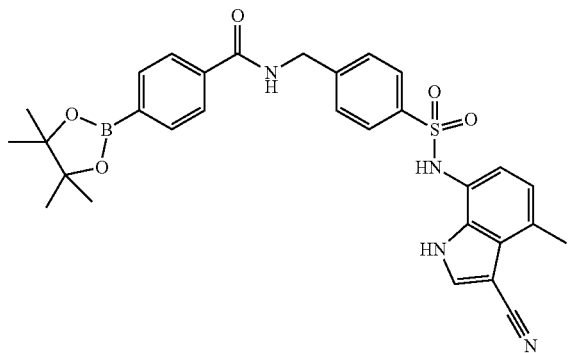

Under a nitrogen stream, to a solution of Reference Example compound 5 (300 mg), 4-(4,4,5,5-tetramethyl-1,3,2-dioxaborolan-2-yl)benzoic acid (198 mg) in N,N-dimethylformamide (6.0 mL) were added N,N-diisopropylethylamine (0.41 mL) and HATU (363 mg), and the mixture was stirred at the same temperature for 1 hr. Reference Example compound 5 (45 mg) was added, and the mixture was further stirred at room temperature for 1 hr. The reaction mixture was diluted with ethyl acetate, the organic layer was washed with saturated aqueous sodium hydrogen carbonate, water, saturated brine, and dried over anhydrous sodium sulfate. The solvent was evaporated under reduced pressure to give a crude title compound (499 mg) as a gray solid. MS(ESI) m/z: 571.0[M+H]$^+$

(129-2) ethyl [(6S)-4-(4-chlorophenyl)-2,3,9-trimethyl-6H-thieno[3,2-f][1,2,4]triazolo[4,3-a][1,4]diazepin-6-yl]acetate (Example Compound 129-2)

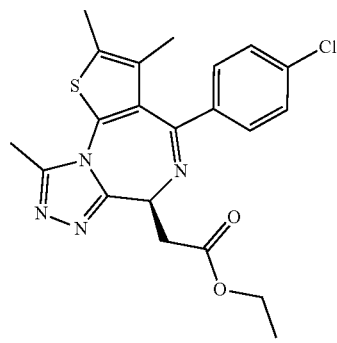 [SMILES: CCOC(=O)C[C@@H]1N=C(c2ccc(Cl)cc2)c2c(sc(C)c2C)-n2c(C)nnc21]

To a solution of (S)-4-(4-chlorophenyl)-2,3,9-trimethyl-6H-thieno[3,2-f][1,2,4]triazolo[4,3-a][1,4]diazepine-6-acetic acid (70 g) in ethanol (500 mL) was added concentrated sulfuric acid (4 mL), and the mixture was heated under reflux for 9 hr. After cooling, the solvent was evaporated under reduced pressure, aqueous potassium carbonate solution was added, and the mixture was extracted with chloroform. The extract was washed with water and saturated brine, and dried over anhydrous sodium sulfate. The solvent was evaporated and the residue was recrystallized from ethyl acetate to give the title compound (45 g).

$^1$H NMR (300 MHz, DMSO-d6) δ ppm 1.19 (3H, t, J=7.1H), 1.60 (3H, s), 2.39 (3H, s), 2.58 (3H, s), 3.3-3.5 (2H, m), 4.0-4.3 (2H, m), 4.47 (1H, dd, J=7.8, 6.8 Hz), 7.41 (2H, d, J=7.0 Hz), 7.47 (2H, d, J=7.0 Hz)

MS (ESI) m/z: 429 (M+H)$^+$

(129-3) ethyl [(6S)-4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 129)

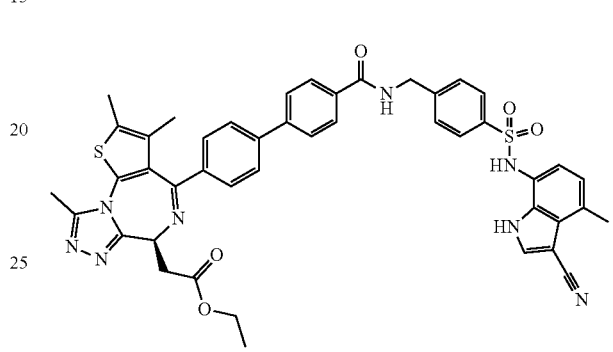

Under a nitrogen stream, a mixture of Example compound 129-1 (73 mg), Example compound 129-2 (50 mg), cesium fluoride (53 mg), water (0.2 mL), tetrahydrofuran (0.8 mL), X-Phos (5.6 mg) and X-Phos aminobiphenylpalladium chloride precatalyst (9.2 mg) was stirred under microwave irradiation at 130° C. for 90 min. The reaction mixture was diluted with ethyl acetate-tetrahydrofuran (1:1), washed twice with saturated brine, and dried over anhydrous sodium sulfate. The solvent was evaporated under reduced pressure. The residue was purified by NH silica gel column chromatography (chloroform:methanol=90:10-0:100) to give the title compound (14 mg) as a pale-yellow solid. MS(ESI) m/z: 837.3[M+H]$^+$

Example 130

(130-1) n-propyl [(6S)-4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 130)

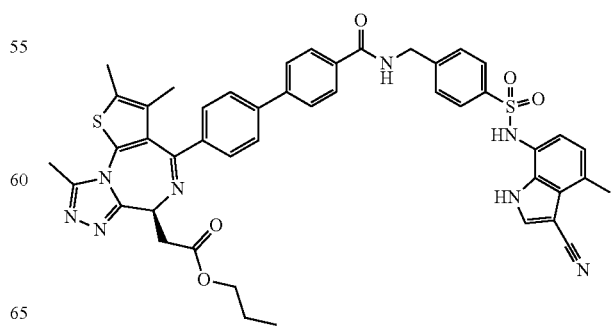

By reaction and treatment in the same manner as in (131-1)-(131-2) except that n-propyl alcohol was used instead of isopropyl alcohol in Example 131, the title compound (80 mg) was obtained as a pale-yellow solid. MS(ESI) m/z: 851.3[M+H]$^+$ Example 131

(131-1) isopropyl [(6S)-4-(4-chlorophenyl)-2,3,9-trimethyl-6H-thieno[3,2-f][1,2,4]triazolo[4,3-a][1,4]diazepin-6-yl]acetate (Example Compound 131-1)

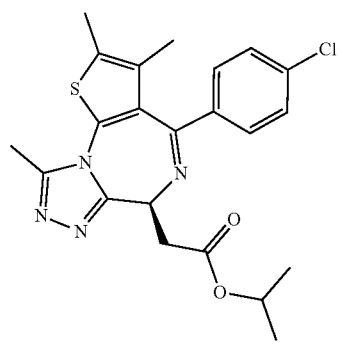 [SMILES: Cc1sc2c(c1C)C(c1ccc(Cl)cc1)=N[C@@H](CC(=O)OC(C)C)c1nnc(C)n1-2]

To a solution of (S)-4-(4-chlorophenyl)-2,3,9-trimethyl-6H-thieno[3,2-f][1,2,4]triazolo[4,3-a][1,4]diazepine-6-acetic acid (1.44 g), triethylamine (0.75 mL) in tetrahydrofuran (14 mL) was added pivaloyl chloride (0.53 mL) at −10° C. to −20° C., and the mixture was stirred at −10° C. for 2 hr. To the reaction mixture was added, at −10° C., sodium isopropoxide prepared from isopropyl alcohol (5 mL) and a suspension of sodium hydride (60%, 430 mg) in tetrahydrofuran (20 mL), and the mixture was stirred at room temperature for 1 hr. The reaction mixture was added to water (100 mL), and the mixture was extracted 3 times with ethyl acetate (100 mL), the mixture was washed twice with saturated brine, and the solvent was evaporated under reduced pressure. The obtained residue was purified by silica gel column chromatography (chloroform:methanol=19:1) to give the title compound (0.45 g) as a pale-yellow solid.

(131-2) isopropyl [(6S)-4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 131)

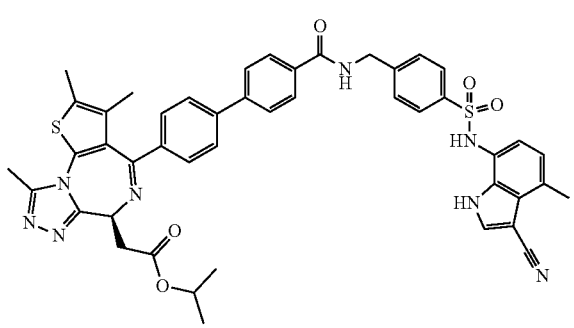

By reaction and treatment in the same manner as in (129-3) except that Example compound 131-1 (50 mg) was used instead of Example compound 129-2 in Example 129, the title compound (31 mg) was obtained as a pale-yellow solid.

MS(ESI) m/z: 851.3[M+H]$^+$

Example 132

(132-1) t-butyl [(4S)-6-{4'-[({4-[(3-cyano-4-methyl-1H-indol-7-yl)sulfamoyl]phenyl}methyl)carbamoyl][1,1'-biphenyl]-4-yl}-8-methoxy-1-methyl-4H-[1,2,4]triazolo[4,3-a][1,4]benzodiazepin-4-yl]acetate (Example Compound 132)

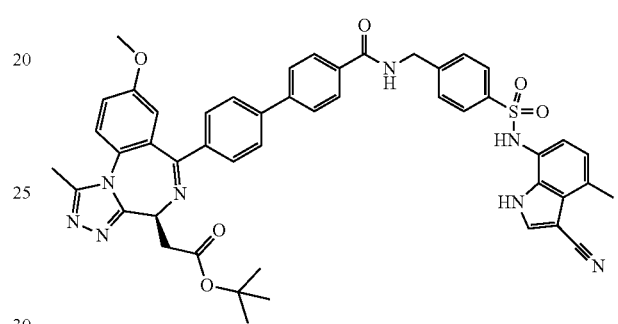

By reaction and treatment in the same manner as in (129-3) except that t-butyl [(4S)-6-(4-chlorophenyl)-1-methyl-8-(methyloxy)-4H-[1,2,4]triazolo[4,3-a][1,4]benzodiazepin-4-yl]acetate (43 mg) was used instead of Example compound 129-2 in Example 129, the title compound (49 mg) was obtained as a pale-yellow solid. MS(ESI) m/z: 861.4[M+H]$^+$ (133-1) methyl [(4S)-6-{4'-[({4-[(3-cyano-4-methyl-1H-indol-7-yl)sulfamoyl]phenyl}methyl)carbamoyl][1,1'-biphenyl]-4-yl}-8-methoxy-1-methyl-4H-[1,2,4]triazolo[4,3-a][1,4]benzodiazepin-4-yl]acetate (Example Compound 133)

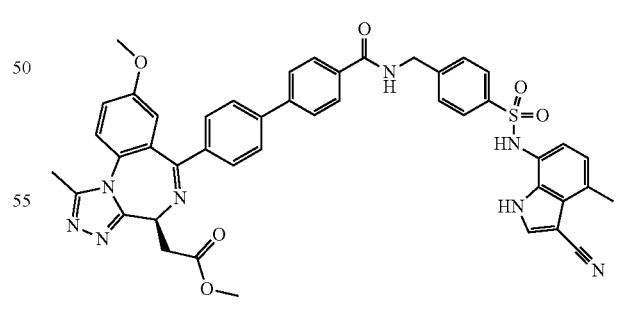

By reaction and treatment in the same manner as in (129-3) except that methyl [(4S)-6-(4-chlorophenyl)-1-methyl-8-(methyloxy)-4H-[1,2,4]triazolo[4,3-a][1,4]benzodiazepin-4-yl]acetate (40 mg) was used instead of Example compound 129-2 in Example 129, the title compound (41 mg) was obtained as a pale-yellow solid. MS(ESI) m/z: 819.4[M+H]$^+$

Example 134

(134-1) t-butyl [(6S)-4-(4'-{[(1R)-1-{4-[(3-cyano-4-methyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1, 4]diazepin-6-yl]acetate (Example Compound 134)

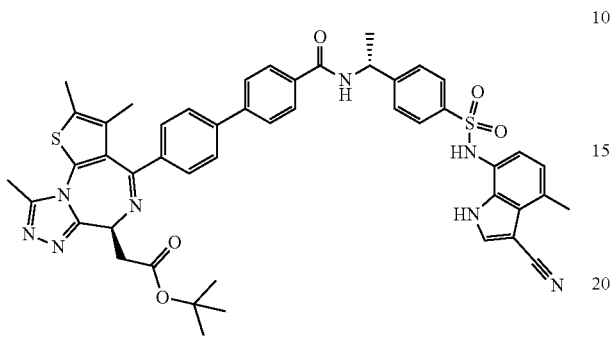

By reaction and treatment in the same manner as in (63-3) except that Reference Example compound 17 (40 mg) was used instead of Reference Example compound 5 in Example 63, the title compound (21 mg) was obtained as a pale-brown solid.

MS(ESI) m/z: 879.3[M+H]$^+$

Example 135

(135-1) t-butyl [(6S)-4-{4'-[({4-[(3-cyano-4-ethyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 135)

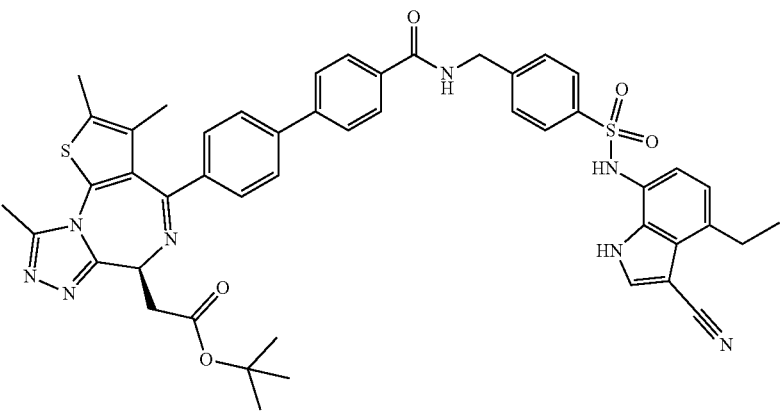 [SMILES: CCc1ccc(NS(=O)(=O)c2ccc(CNC(=O)c3ccc(-c4ccc(C5=N[C@@H](CC(=O)OC(C)(C)C)c6nnc(C)n6-c6sc(C)c(C)c65)cc4)cc3)cc2)c2[nH]cc(C#N)c12]

By reaction and treatment in the same manner as in (63-3) except that Reference Example compound 21 (40 mg) was used instead of Reference Example compound 5 in Example 63, the title compound (26 mg) was obtained as a pale-brown solid.

MS(ESI) m/z: 879.2[M+H]$^+$

Example 136

(136-1) t-butyl [(6S)-4-(4'-{[(1R)-1-{4-[(3-cyano-4-ethyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1, 4]diazepin-6-yl]acetate (Example Compound 136)

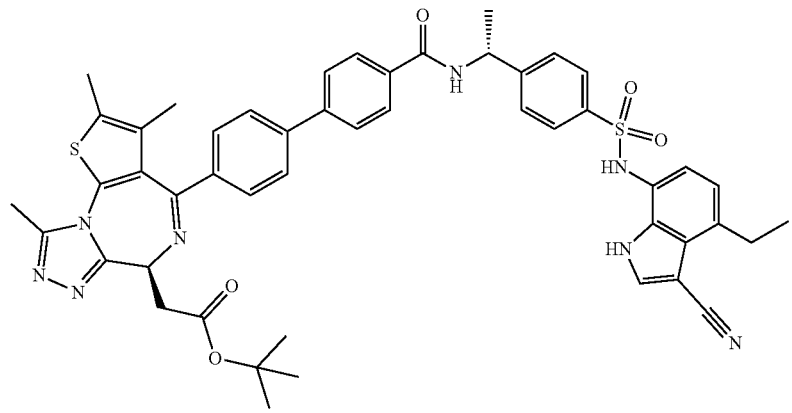 [SMILES: CCc1ccc(NS(=O)(=O)c2ccc([C@@H](C)NC(=O)c3ccc(-c4ccc(C5=N[C@@H](CC(=O)OC(C)(C)C)c6nnc(C)n6-c6sc(C)c(C)c65)cc4)cc3)cc2)c2[nH]cc(C#N)c12]

By reaction and treatment in the same manner as in (63-3) except that Reference Example compound 22 (41 mg) was used instead of Reference Example compound 5 in Example 63, the title compound (52 mg) was obtained as a pale-brown solid.

MS(ESI) m/z: 893.2[M+H]$^+$

Example 137

(137-1) t-butyl [(6S)-4-{4'-[(2-{4-[(3-cyano-4-ethyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1, 4]diazepin-6-yl]acetate (Example Compound 137)

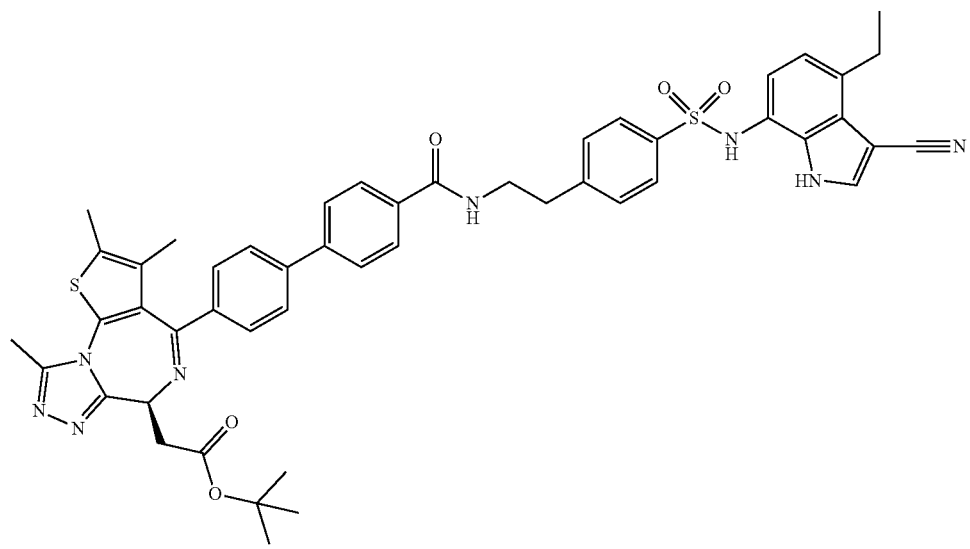 [SMILES: CCc1ccc(NS(=O)(=O)c2ccc(CCNC(=O)c3ccc(-c4ccc(C5=N[C@@H](CC(=O)OC(C)(C)C)c6nnc(C)n6-c6sc(C)c(C)c65)cc4)cc3)cc2)c2[nH]cc(C#N)c12]

By reaction and treatment in the same manner as in (63-3) except that Reference Example compound 23 (41 mg) was used instead of Reference Example compound 5 in Example 63, the title compound (36 mg) was obtained as a pale-brown solid.

MS(ESI) m/z: 893.2[M+H]$^+$

Example 138

(138-1) t-butyl {(6S)-2,3,9-trimethyl-4-[4-(4,4,5,5-tetramethyl-1,3,2-dioxaboronan-2-yl)phenyl]-6H-thieno[3,2-f][1,2,4]triazolo[4,3-a][1,4]diazepin-6-yl}acetate (Example Compound 138-1)

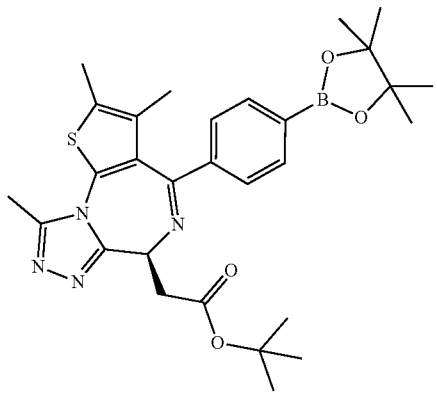

By reaction and treatment in the same manner as in (3-1) except that t-butyl [(6S)-4-(4-chlorophenyl)-2,3,9-trimethyl-6H-thieno[3,2-f][1,2,4]triazolo[4,3-a][1,4]diazepin-6-yl]acetate (1.47 g) was used instead of Reference Example compound 1 in Reference Example 3, the title compound (1.73 g) was obtained as a pale-yellow solid. MS(ESI) m/z: 549.4[M+H]$^+$ (138-2) t-butyl [(6S)-4-{4'-[({4-[(3-cyano-4-methyl-1H-indol-7-yl)sulfamoyl]phenyl}methyl)carbamoyl]-2',3'-difluoro[1,1'-biphenyl]-4-yl}-2,3,9-trimethyl-6H-thieno[3,2-f][1,2,4]triazolo[4,3-a][1,4]diazepin-6-yl]acetate (Example Compound 138)

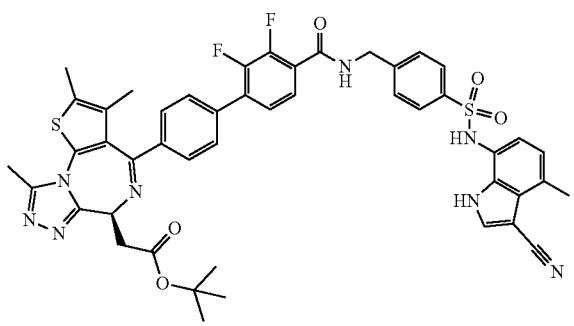

To a solution of 4-bromo-2,3-fluorobenzoic acid (28 mg) and Reference Example compound 5 (40 mg) in N,N-dimethylformamide (2.0 mL) were added N,N-diisopropylethylamine (0.061 mL) and HATU (54 mg), and the mixture was stirred at room temperature for 0.5 hr. The reaction mixture was diluted with ethyl acetate (30 mL)-tetrahydrofuran (5 mL), washed 3 times with half-saturated brine and once with saturated brine, dried over anhydrous sodium sulfate and filtered. The solvent was evaporated under reduced pressure.

To the obtained residue was added a mixture of Example compound 138-1 (71 mg), cesium fluoride (54 mg), water (0.5 mL), tetrahydrofuran (2.0 mL), X-Phos (6 mg), X-Phos aminobiphenylpalladium chloride precatalyst (10 mg), and the mixture was stirred under microwave irradiation at 120° C. for 30 min. The reaction mixture was diluted with ethyl acetate (40 mL)-tetrahydrofuran (10 mL) and washed with half-saturated brine. The aqueous layer was extracted with ethyl acetate-tetrahydrofuran (10 mL-2 mL). The organic layers were combined, dried over anhydrous sodium sulfate and filtered. The solvent was evaporated under reduced pressure. The obtained residue was purified twice by silica gel column chromatography (chloroform:methanol=98:2-95:5) to give the title compound (23 mg) as a pale-yellow solid. MS(ESI) m/z: 901.5[M+H]$^+$ Example 139

(139-1) t-butyl [(6S)-4-{4'-[({4-[(3-cyano-4-methyl-1H-indol-7-yl) sulfamoyl]phenyl}methyl) carbamoyl]-3'-fluoro[1,1'-biphenyl]-4-yl}-2,3,9-trimethyl-6H-thieno[3,2-f][1,2,4]triazolo[4,3-a][1, 4]diazepin-6-yl]acetate (Example Compound 139)

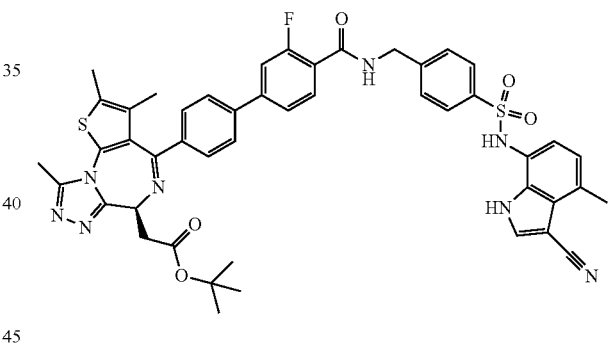

A mixture of Example compound 138-1 (83 mg), 4-bromo-2-fluorobenzoic acid (30 mg), cesium fluoride (63 mg), water (0.25 mL), tetrahydrofuran (1.0 mL), X-Phos (7 mg), X-Phos aminobiphenylpalladium chloride precatalyst (11 mg) was stirred under microwave irradiation at 120° C. for 30 min. To the reaction mixture was added an ethyl acetate-water (1:1) solution, and the organic layer was washed with saturated aqueous sodium hydrogen carbonate. The aqueous layer was set to pH1 with 2N hydrochloric acid, extracted twice with chloroform. The organic layers were combined, dried over anhydrous sodium sulfate and filtered. The solvent was evaporated under reduced pressure.

To the obtained residue were added a solution of Reference Example compound 5 (47 mg) in N,N-dimethylformamide (1.0 mL), N,N-diisopropylethylamine (0.071 mL) and HATU (63 mg), and the mixture was stirred at room temperature for 1 hr. The reaction mixture was purified by preparative HPLC (10 mM aqueous ammonium carbonate solution-acetonitrile) to give the title compound (43 mg) as a white solid.

MS(ESI) m/z: 883.2[M+H]$^+$

Example 140

(140-1) t-butyl [(6S)-4-{3'-chloro-4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 140)

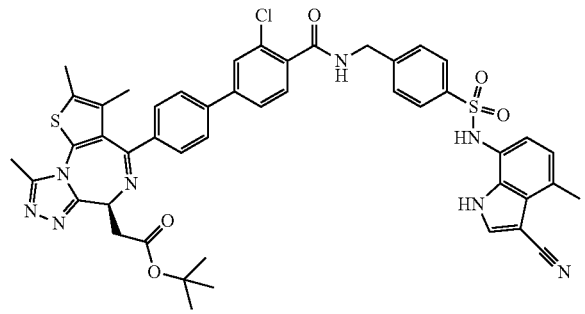

By reaction and treatment in the same manner as in (139-1) except that 4-bromo-2-chlorobenzoic acid (30 mg) was used instead of 4-bromo-2-fluorobenzoic acid in Example 139, the title compound (24 mg) was obtained as a white solid.

MS(ESI) m/z: 899.2[M+H]$^+$

Example 141

(141-1) t-butyl [(6S)-4-{4'-[({4-[(3-cyano-4-methyl-1H-indol-7-yl)sulfamoyl]phenyl}methyl)carbamoyl]-3'-methyl[1,1'-biphenyl]-4-yl}-2,3,9-trimethyl-6H-thieno[3,2-f][1,2,4]triazolo[4,3-a][1,4]diazepin-6-yl]acetate (Example Compound 141)

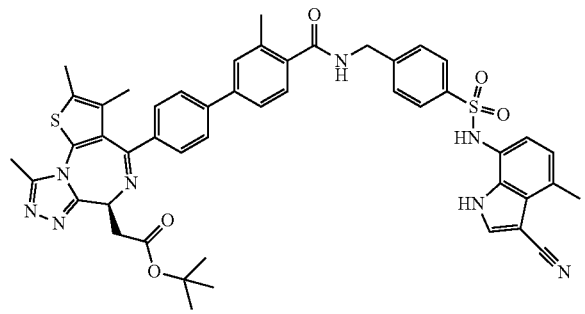

By reaction and treatment in the same manner as in (139-1) except that 4-bromo-2-methylbenzoic acid (30 mg) was used instead of 4-bromo-2-fluorobenzoic acid in Example 139, the title compound (39 mg) was obtained as a white solid.

MS(ESI) m/z: 879.3[M+H]$^+$

Example 142

(142-1) t-butyl [(6S)-4-{4'-[({4-[(3-cyano-4-methyl-1H-indol-7-yl)sulfamoyl]phenyl}methyl)carbamoyl]-2'-fluoro[1,1'-biphenyl]-4-yl)-2,3,9-trimethyl-6H-thieno[3,2-f][1,2,4]triazolo[4,3-a][1,4]diazepin-6-yl]acetate (Example Compound 142)

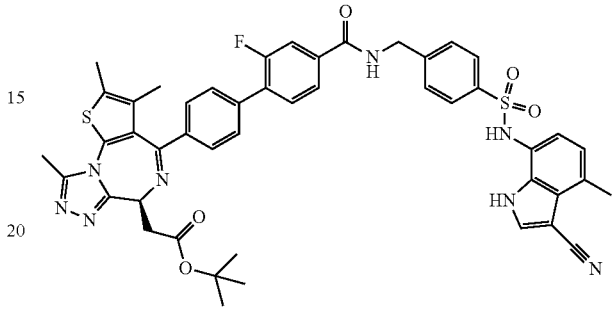

By reaction and treatment in the same manner as in (139-1) except that 4-bromo-3-fluorobenzoic acid (30 mg) was used instead of 4-bromo-2-fluorobenzoic acid in Example 139, the title compound (13 mg) was obtained as a white solid.

MS(ESI) m/z: 883.2[M+H]$^+$

Example 143

(143-1) t-butyl [(6S)-4-{2'-chloro-4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate (Example Compound 143)

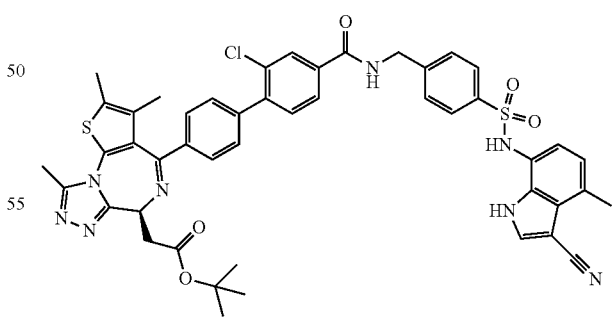

By reaction and treatment in the same manner as in (139-1) except that 4-bromo-3-chlorobenzoic acid (30 mg) was used instead of 4-bromo-2-fluorobenzoic acid in Example 139, the title compound (23 mg) was obtained as a white solid.

MS(ESI) m/z: 899.2[M+H]$^+$

Example 144

(144-1) t-butyl [(6S)-4-{4'-[({4-[(3-cyano-4-methyl-1H-indol-7-yl)sulfamoyl]phenyl}methyl)carbamoyl]-2'-methyl[1,1'-biphenyl]-4-yl}-2,3,9-trimethyl-6H-thieno[3,2-f][1,2,4]triazolo[4,3-a][1, 4]diazepin-6-yl]acetate (Example Compound 144)

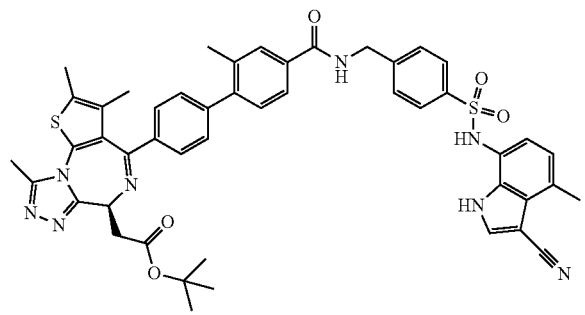

By reaction and treatment in the same manner as in (139-1) except that 4-bromo-3-methylbenzoic acid (30 mg) was used instead of 4-bromo-2-fluorobenzoic acid in Example 139, the title compound (24 mg) was obtained as a white solid.

MS(ESI) m/z: 879.3[M+H]$^+$

Example 145

(145-1) t-butyl [(6S)-4-(4-{6-[({4-[(3-cyano-4-methyl-1H-indol-7-yl)sulfamoyl]phenyl}methyl)carbamoyl]pyridin-3-yl}phenyl)-2,3,9-trimethyl-6H-thieno[3,2-f][1,2,4]triazolo[4,3-a][1, 4]diazepin-6-yl]acetate (Example Compound 145)

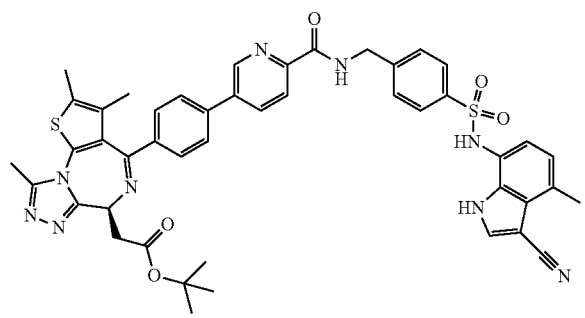

By reaction and treatment in the same manner as in (138-2) except that 5-bromopyridine-2-carboxylic acid (65 mg) was used instead of 4-bromo-2,3-fluorobenzoic acid in Example 138, the title compound (67 mg) was obtained as a white solid.

MS(ESI) m/z: 866.2[M+H]$^+$

Example 146

(146-1) methyl [(6S)-4-(4-{2-[({4-[(3-cyano-4-methyl-1H-indol-7-yl)sulfamoyl]phenyl}methyl)carbamoyl]pyrimidin-5-yl}phenyl)-2,3,9-trimethyl-6H-thieno[3,2-f][1,2,4]triazolo[4,3-a][1, 4]diazepin-6-yl]acetate (Example Compound 146)

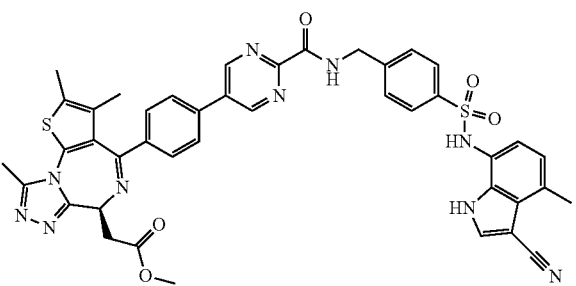

By reaction and treatment in the same manner as in (138-2) except that 5-bromopyrimidine-2-carboxylic acid (100 mg) was used instead of 4-bromo-2,3-fluorobenzoic acid, and Reference Example compound 3 (114 mg) was used instead of Example compound 138-1 in Example 138, the title compound (4.2 mg) was obtained as a pale-yellow solid. MS(ESI) m/z: 825.3[M+H]$^+$

Example 147

(147-1) t-butyl [(6S)-4-(4-{2-[({4-[(3-cyano-4-methyl-1H-indol-7-yl)sulfamoyl]phenyl}methyl)carbamoyl]pyrimidin-5-yl}phenyl)-2,3,9-trimethyl-6H-thieno[3,2-f][1,2,4]triazolo[4,3-a][1, 4]diazepin-6-yl]acetate (Example Compound 147)

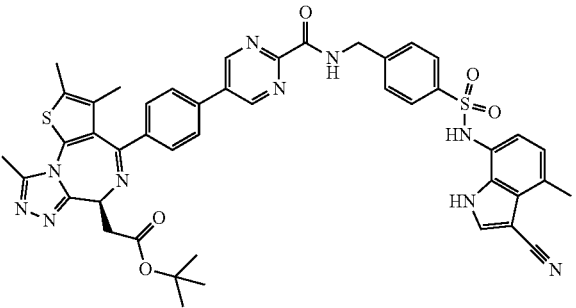

By reaction and treatment in the same manner as in (138-2) except that 5-bromopyrimidine-2-carboxylic acid (80 mg) was used instead of 4-bromo-2,3-fluorobenzoic acid in Example 138, the title compound (10 mg) was obtained as a white solid.

MS(ESI) m/z: 867.2[M+H]$^+$

Example 148

(148-1) benzyl 5-{4-[(6S)-6-(2-t-butoxy-2-oxo-ethyl)-2,3,9-trimethyl-6H-thieno[3,2-f][1,2,4]triazolo[4,3-a][1,4]diazepin-4-yl]phenyl}pyrazine-2-carboxylate (Example Compound 148-1)

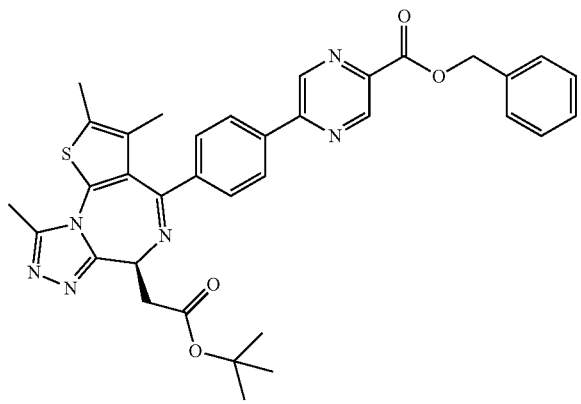 [SMILES: Cc1sc2c(c1C)C(c1ccc(-c3cnc(C(=O)OCc4ccccc4)cn3)cc1)=N[C@@H](CC(=O)OC(C)(C)C)c1nnc(C)n1-2]

Example compound 138-1 (89 mg), benzyl 5-bromopyrazine-2-carboxylate (71 mg), tetrakis(triphenylphosphine)palladium(0) (19 mg), potassium phosphate (103 mg) and water (0.011 mL) were stirred in tetrahydrofuran (1.0 mL) under a nitrogen atmosphere under microwave irradiation at 100° C. for 0.5 hr. The reaction mixture was diluted with ethyl acetate, insoluble materials were filtered off through celite. The filtrate was concentrated, and the residue was purified by silica gel column chromatography (hexane:ethyl acetate=50:50-0:100) to give the title compound (97 mg) as a pale-yellow solid.
MS(ESI) m/z: 635.4[M+H]$^+$ (148-2) 5-{4-[(6S)-6-(2-t-butoxy-2-oxoethyl)-2,3,9-trimethyl-6H-thieno[3,2-f][1,2,4]triazolo[4,3-a][1,4]diazepin-4-yl]phenyl}pyrazine-2-carboxylic acid (Example Compound 148-2)

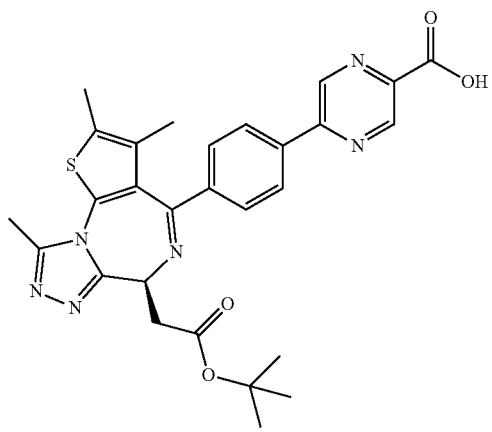 [SMILES: Cc1sc2c(c1C)C(c1ccc(-c3cnc(C(=O)O)cn3)cc1)=N[C@@H](CC(=O)OC(C)(C)C)c1nnc(C)n1-2]

Example compound 148-1 (33 mg) was dissolved in tetrahydrofuran (3.0 mL), 20% palladium hydroxide carbon (15 mg) was added. The reaction container was substituted with hydrogen, and the mixture was stirred at room temperature for 3 hr. Furthermore, 20% palladium hydroxide carbon (15 mg) was added, and the mixture was stirred at room temperature for 2 hr. The reaction mixture was filtered, and the solvent was concentrated under reduced pressure to give a crude title compound (24 mg) as a pale-yellow solid.
MS (ESI) m/z: 545.3[M+H]$^+$ (148-3) t-butyl [(6S)-4-(4-{5-[({4-[(3-cyano-4-methyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1, 4]diazepin-6-yl]acetate (Example Compound 148)

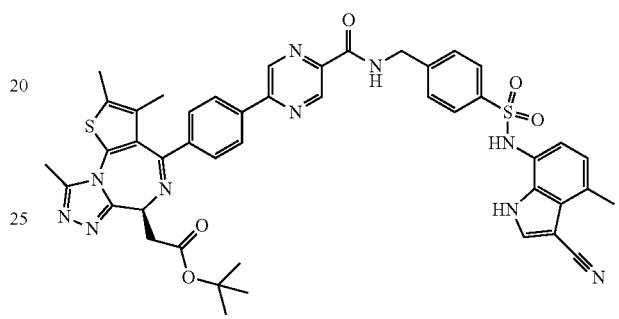

By reaction and treatment in the same manner as in (63-3) except that Example compound 148-2 (20 mg) was used instead of Example compound 63-2 in Example 63, the title compound (8.7 mg) was obtained as a yellow solid. MS(ESI) m/z: 867.5[M+H]$^+$

Example 149

(149-1) methyl [(6S)-4-(4-{6-[({4-[(3-cyano-4-methyl-1H-indol-7-yl)sulfamoyl]phenyl}methyl)carbamoyl]pyridazin-3-yl}phenyl)-2,3,9-trimethyl-6H-thieno[3,2-f][1,2,4]triazolo[4,3-a][1, 4]diazepin-6-yl]acetate (Example Compound 149)

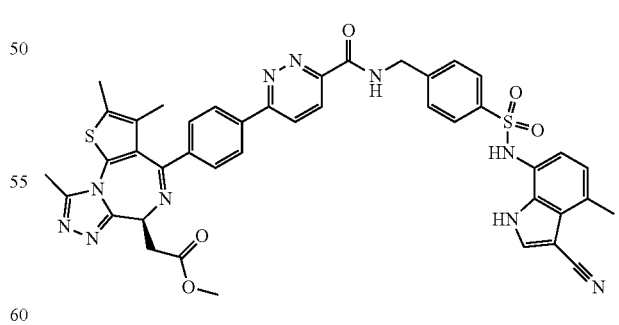

By reaction and treatment in the same manner as in (65-1)-(65-2) except that t-butyl 6-bromopyridazine-3-carboxylate (283 mg) was used instead of t-butyl 5-bromopyrazine-2-carboxylate in Example 65, the title compound (81 mg) was obtained as a pale-yellow solid. MS(ESI) m/z: 825.5[M+H]$^+$

Example 150

(150-1) methyl 6-{4-[(6S)-6-(2-t-butoxy-2-oxo-ethyl)-2,3,9-trimethyl-6H-thieno[3,2-f][1,2,4]triazolo[4,3-a][1,4]diazepin-4-yl]phenyl}pyridazine-3-carboxylate (Example Compound 150)

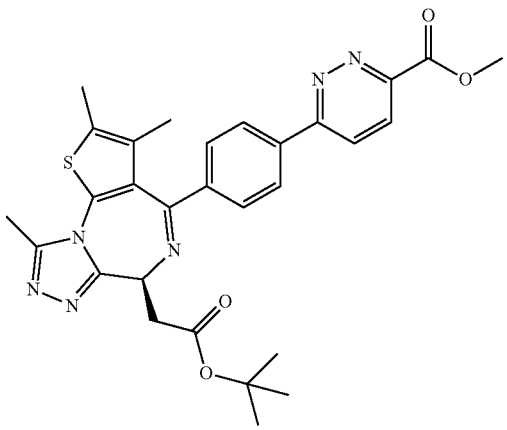

Under a nitrogen stream, a mixture of Example compound 138-1 (100 mg), methyl 6-chloropyridazine-3-carboxylate (95 mg), cesium fluoride (139 mg), water (0.02 mL), tetrahydrofuran (2.0 mL), X-Phos (18 mg), X-Phos aminobiphenylpalladium chloride precatalyst (29 mg) was stirred with heating under reflux for 3 hr. To the reaction mixture were added methyl 6-chloropyridazine-3-carboxylate (95 mg), cesium fluoride (139 mg), water (0.02 mL), X-Phos (18 mg), X-Phos aminobiphenylpalladium chloride precatalyst (29 mg), and the mixture was further stirred with heating under reflux for 2 hr. The reaction mixture was diluted with ethyl acetate, washed with saturated aqueous sodium hydrogen carbonate, and the organic layer was dried over anhydrous sodium sulfate. The solvent was evaporated under reduced pressure. The obtained residue was purified by silica gel column chromatography (chloroform:methanol=98:2-95:5) and NH silica gel column chromatography (hexane:ethyl acetate=50:50-0:100) to give the title compound (52 mg) as a pale-yellow oil.

MS(ESI) m/z: 559.3[M+H]$^+$ (150-2) t-butyl [(6S)-4-(4-{6-[({4-[(3-cyano-4-methyl-1H-indol-7-yl)sulfamoyl]phenyl}methyl)carbamoyl]pyridazin-3-yl}phenyl)-2,3,9-trimethyl-6H-thieno[3,2-f][1,2,4]triazolo[4,3-a][1,4]diazepin-6-yl]acetate (Example Compound 150)

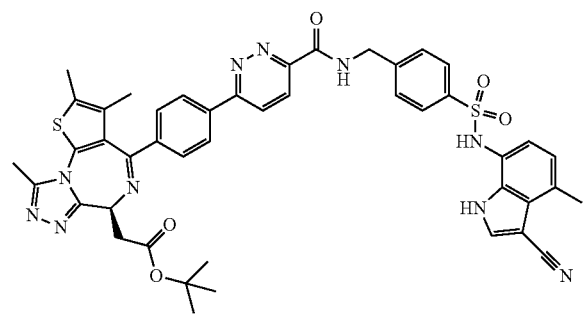

To a solution of Example compound 150-1 (50 mg) in tetrahydrofuran (1 mL), methanol (1 mL) was added, under ice-cooling, an aqueous solution (0.25 mL) of lithium hydroxide (7.5 mg), and the mixture was stirred at the same temperature for 1 hr. The reaction mixture was diluted with ethyl acetate, and washed twice with saturated aqueous sodium hydrogen carbonate. The aqueous layer was adjusted to pH3 by adding 2N hydrochloric acid under ice-cooling, and extracted 3 times with chloroform. The organic layers were combined and dried over anhydrous sodium sulfate, and the solvent was evaporated under reduced pressure.

To the obtained residue were added a solution of Reference Example compound 5 (21 mg) in N,N-dimethylformamide (1 mL), N,N-diisopropylethylamine (0.021 mL) and HATU (19 mg), and the mixture was stirred at room temperature for 1 hr. The reaction mixture was diluted with ethyl acetate (30 mL)-tetrahydrofuran (5 mL), washed 3 times with half-saturated brine and once with saturated brine, dried over anhydrous sodium sulfate and filtered. The solvent was evaporated under reduced pressure. The obtained residue was purified by silica gel column chromatography (chloroform:methanol=98:2-95:5) to give the title compound (29 mg) as a white solid.

MS(ESI) m/z: 867.4[M+H]$^+$

Experimental Example 1

Cytotoxic Action on Cancer Cells

The cytotoxic action of the compound of the present invention against human cancer cells was evaluated in vitro. In this experiment, (+)-JQ1 (Nature volume 468, pages 1067-1073 (23 Dec. 2010)) known to have an inhibitory activity on the binding of BRD4 protein and a ligand therefor was used as a positive control drug. Respective cells were suspended in 10% FBS/RPMI1640, seeded in a 96 well plate and cultured at 5% $CO_2$, 37° C. overnight. A test compound dissolved in DMSO was diluted with 10% FBS/RPMI1640 and added and the cells were further cultured for 96 hr. After culturing, the viable cell number was measured using a cell number measurement WST-8 kit (Kishida Chemical Co., Ltd.). As a control, the measurement was performed under conditions free of the test compound. The cytotoxic activity of the compound of the present invention against human prostate cancer LNCaP cells is shown in $IC_{50}$ value in Table 1. The $IC_{50}$ value is a concentration of the compound showing 50% cell survival rate when the cell survival rate thereof under compound untreated condition is 100%. It was calculated from the straight line connecting the cell survival rate at two points enclosing the 50% cell survival rate and the compound concentration. In addition, the cytotoxic activity against respective cancer cells of human acute myeloid leukemia MV-4-11 cell, human chronic myeloid leukemia K562 cell, human multiple myeloma MM.1S cell, human diffuse large B-cell lymphoma SU-DHL-6 cell, human T-cell leukemia Jurkat cells, human Burkitt lymphoma Raji cell, human castration-resistant prostate cancer PC-3 cell, human AR-V7 positive castration-resistant prostate cancer 22Rv1 cell, human ovarian cancer A2780 cell, human cisplatin-resistant ovarian cancer SK-OV-03 cell, human bladder cancer 5637 cell, human breast cancer ZR-75-1 cell, human triple negative breast cancer MDA-MB-231 cell, human uterus cervix cancer HeLa cell, human uterine sarcoma MES-SA cell, human stomach cancer SNU-16 cell, human non-small cell lung cancer NCI-H2126 cell, human EGFRT790M mutation-positive non-small cell lung cancer NCI-H1975 cell, human small cell lung cancer NCI-H82 cell, human large cell lung cancer NCI-H460 cell, human colon cancer HCT116 cell, human glioma U-87 MG cell, human pancreatic cancer BxPC-3 cell, human liver cancer HLF cell, human bile duct cancer HuCCT1 cell, human renal cell cancer 786-O cell, and human fibrosarcoma HT1080 cell is shown in $IC_{50}$ value in Table 2. The compound of the present invention showed a strong cytotoxic action on the cancer cells.

TABLE 1-1

| Example compound No. | LNCaP cytotoxic activity: $IC_{50}$ (nmol/L) |
|---|---|
| 1 | 0.14 |
| 2 | 0.35 |
| 3 | 0.092 |
| 4 | 16 |
| 5 | 4.1 |
| 8 | 2.8 |
| 11 | 0.074 |
| 15 | 0.28 |
| 21 | 9.8 |
| 25 | 0.24 |
| 26 | 0.10 |
| 31 | 4.2 |
| 32 | 0.69 |
| 35 | 7.2 |
| 36 | 1.4 |
| 37 | 3.0 |
| 38 | 5.8 |
| 40 | 0.42 |
| 41 | 1.1 |
| 43 | 0.23 |
| 45 | 0.22 |
| 46 | 0.19 |
| 47 | 0.46 |
| 48 | 0.49 |
| 50 | 0.23 |
| 52 | 0.55 |
| 53 | 0.16 |
| 55 | 3.0 |
| 59 | 0.23 |
| 62 | 0.97 |
| 63 | 0.45 |
| 64 | 0.25 |
| 65 | 0.071 |
| 67 | 2.1 |
| 69 | 0.12 |
| 70 | 0.23 |
| 71 | 0.61 |
| 72 | 5.5 |
| 73 | 1.7 |
| 74 | 0.21 |
| 75 | 0.47 |
| 77 | 0.16 |
| 82 | 0.27 |
| 83 | 0.33 |
| 84 | 0.58 |
| 85 | 0.26 |
| 86 | 0.35 |
| 88 | 0.17 |
| 89 | 0.33 |
| 90 | 0.19 |
| 91 | 0.26 |
| 92 | 0.087 |
| 94 | 0.42 |
| 97 | 0.12 |
| 98 | 0.22 |
| 99 | 0.14 |
| 100 | 0.16 |
| 101 | 0.27 |
| 102 | 0.071 |
| 103 | 0.067 |
| 105 | 0.13 |
| 106 | 0.079 |
| 107 | 0.26 |
| 108 | 0.23 |
| 109 | 0.36 |
| 110 | 0.28 |
| 112 | 0.44 |
| 113 | 0.30 |
| 114 | 0.34 |
| 115 | 0.32 |
| 116 | 0.65 |
| 117 | 0.41 |
| 118 | 0.32 |
| 119 | 0.45 |
| 120 | 0.41 |
| 121 | 0.22 |
| 122 | 0.39 |
| 123 | 0.32 |
| 124 | 0.27 |
| 125 | 0.37 |
| 127 | 0.032 |
| 128 | 0.074 |
| 129 | 0.048 |
| 130 | 0.050 |
| 131 | 0.065 |
| 132 | 0.21 |
| 133 | 0.49 |
| 134 | 0.55 |
| 135 | 0.66 |
| 136 | 0.60 |
| 137 | 0.48 |
| 138 | 0.77 |
| 139 | 0.45 |
| 140 | 0.52 |
| 141 | 0.92 |
| 142 | 1.3 |
| 143 | 2.4 |
| 144 | 1.2 |
| 145 | 0.44 |
| 146 | 1.3 |
| 147 | 0.42 |
| 148 | 0.20 |
| 149 | 0.54 |
| 150 | 0.43 |
| (+)-JQ1 | 19000 |

TABLE 2

| cell line | cytotoxic activity: $IC_{50}$ (nmol/L) Example compound 1 |
|---|---|
| MV-4-11 | 0.16 |
| K562 | 1.7 |
| MM.1S | 0.026 |
| SU-DHL-6 | 0.44 |
| Jurkat | 1.3 |
| Raji | 5.3 |
| PC-3 | 0.88 |
| 22Rv1 | 0.71 |
| A2780 | 0.19 |
| SK-OV-03 | 41 |
| 5637 | 1.9 |
| ZR-75-1 | 27 |
| MDA-MB-231 | 4.0 |
| HeLa | 27 |
| MES-SA | 1.8 |
| SNU-16 | 6.4 |
| NCI-H2126 | 6.6 |
| NCI-H1975 | 3.6 |
| NCI-H82 | 21 |
| NCI-H460 | 28 |
| HCT116 | 8.8 |
| U-87 MG | 6.0 |
| BxPC-3 | 3.3 |
| HLF | 2.9 |
| HuCCT1 | 26 |
| 786-O | 660 |
| HT1080 | 13 |

Experimental Example 2

BRD4 Protein Degradation Inducing Action in Cancer Cells

The degradation inducing action of the compound of the present invention on BRD4 proteins in cancer cells was evaluated in vitro using human prostate cancer LNCaP cells. LNCaP cells were suspended in 10% FBS/RPMI1640, seeded in a 96 well Cell carrier plate (Perkin Elmer) and cultured at 5% $CO_2$, 37° C. overnight. A test compound dissolved in DMSO was diluted with 10% FBS/RPMI1640 and added and the cells were further cultured for 6 hr. After culturing, the cells were immobilized with 4% para-formaldehyde/PBS and further subjected to a permeation treatment with 0.25% Triton X-100/PBS. Thereafter, the cells were blocked with 10% BSA/PBS, Anti-BRD4 (Sigma-Aldrich) solution was added and the cells were incubated at 4° C. overnight. Furthermore, Goat anti-Rabbit IgG (H+L) Cross-Adsorbed Secondary Antibody, Alexa Fluor 546 (Thermo Fisher Scientific) solution, 0.5 µg/mL Hoechst 33342 (Sigma-Aldrich), and 14 µM Acti-Stain 555 Fluorescent Phalloidin (Cytoskeleton) were added. After incubation for 1 hr, BRD4 protein amount was measured by Operetta (Perkin Elmer) as fluorescence intensity (excitation: 560 nm, emission: 572 nm). The BRD4 protein degradation inducing activity of the compound of the present invention in LNCaP cells is shown in $DC_{50}$ value in Table 3. The $DC_{50}$ value is a concentration of the compound showing 50% fluorescence intensity when the fluorescence intensity thereof under compound untreated condition is 100%. It was calculated from the straight line connecting the fluorescence intensity at two points enclosing the 50% fluorescence intensity and the compound concentration. The compound of the present invention induced degradation of BRD4 protein in the cancer cells at a concentration showing a cell proliferation suppressive action.

TABLE 3-1

| Example compound No. | BRD4 protein degradation inducing activity: $DC_{50}$ (nmol/L) |
|---|---|
| 1 | 0.15 |
| 2 | 0.23 |
| 3 | 0.42 |
| 4 | 38 |
| 5 | 15 |
| 8 | 2.4 |
| 11 | 0.083 |
| 15 | 0.22 |
| 21 | 6.7 |
| 25 | 0.16 |
| 26 | 0.14 |
| 31 | 5.9 |
| 32 | 0.42 |
| 35 | 2.7 |
| 36 | 0.41 |
| 37 | 1.4 |
| 38 | 5.6 |
| 40 | 0.19 |
| 41 | 0.41 |
| 43 | 0.12 |
| 45 | 0.19 |
| 46 | 0.11 |
| 47 | 0.30 |
| 48 | 0.30 |
| 50 | 0.13 |
| 52 | 0.30 |
| 53 | 0.078 |
| 55 | 1.4 |
| 59 | 0.22 |
| 62 | 0.64 |
| 63 | 0.23 |
| 64 | 0.13 |
| 65 | 0.036 |
| 67 | 2.0 |
| 69 | 0.056 |
| 70 | 0.13 |
| 71 | 0.32 |
| 72 | 65 |
| 73 | 0.75 |
| 74 | 0.092 |
| 75 | 0.32 |
| 77 | 0.048 |
| 82 | 0.25 |
| 83 | 0.25 |
| 84 | 0.23 |
| 85 | 0.074 |
| 86 | 0.059 |
| 88 | 0.37 |
| 89 | 0.80 |
| 90 | 0.091 |
| 91 | 0.029 |
| 92 | 0.041 |
| 94 | 0.13 |
| 97 | 0.064 |
| 98 | 0.098 |
| 99 | 0.091 |
| 100 | 0.085 |
| 101 | 0.15 |
| 102 | 0.036 |
| 103 | 0.030 |
| 105 | 0.054 |
| 106 | 0.059 |
| 107 | 0.046 |
| 108 | 0.069 |
| 109 | 0.082 |
| 110 | 0.063 |
| 112 | 0.25 |
| 113 | 0.33 |
| 114 | 0.28 |
| 115 | 0.13 |
| 116 | 0.42 |
| 117 | 0.16 |
| 118 | 0.14 |
| 119 | 0.27 |
| 120 | 0.26 |
| 121 | 0.17 |
| 122 | 0.14 |
| 123 | 0.21 |
| 124 | 0.095 |
| 125 | 0.17 |
| 127 | 0.024 |
| 128 | 0.039 |
| 129 | 0.033 |
| 130 | 0.028 |
| 131 | 0.035 |
| 132 | 0.13 |
| 133 | 0.34 |
| 134 | 0.31 |
| 135 | 0.38 |
| 136 | 0.25 |
| 137 | 0.13 |
| 138 | 0.32 |
| 139 | 0.25 |
| 140 | 0.38 |
| 141 | 0.47 |
| 142 | 0.51 |
| 143 | 1.6 |
| 144 | 0.59 |
| 145 | 0.17 |
| 146 | 0.26 |
| 147 | 0.13 |
| 148 | 0.042 |
| 149 | 0.18 |
| 150 | 0.12 |

Experimental Example 3

Cytotoxic Action Against Cancer Cells that Acquired Resistance to Conventional BRD4 Protein Degradation Inducing Agents The cytotoxic action of the compound of the present invention against cancer cells that acquired resistance to conventional BRD4 protein degradation inducing agents was evaluated in vitro. In this experiment, ARV-771 (Proc Natl Acad Sci USA. volume 113, pages 7124-7129 (28 Jun. 2016)) and MZ1 (ACS Chem Biol. Volume 10, pages 1770-1777 (21 Aug. 2015)), in which a ligand for VHL and BRD4 protein inhibitor are linked, were used as a conventional BRD4 protein degradation inducing agent serving as a comparison control. Human breast cancer MDA-MB-436 cells and MDA-MB-436 cells that acquired resistance to conventional BRD4 protein degradation inducing agents (MDA-MB-436 w/o2 cells) were suspended in 10% FBS/RPMI1640, seeded in a 96 well plate and cultured at 5% $CO_2$, 37° C. overnight. A test compound dissolved in DMSO was diluted with 10% FBS/RPMI1640 and added and the cells were further cultured for 96 hr. After culturing, the viable cell number was measured using a cell number measurement WST-8 kit (Kishida Chemical Co., Ltd.). As a control, the measurement was performed under conditions free of the test compound. The cytotoxic activity of the compound of the present invention against each cell is shown in $IC_{50}$ value in Table 4. The $IC_{50}$ value is a concentration of the compound showing 50% cell survival rate when the cell survival rate thereof under compound untreated condition is 100%. It was calculated from the straight line connecting the cell survival rate at two points enclosing the 50% cell survival rate and the compound concentration. In addition, the tolerance (fold) was calculated by dividing the $IC_{50}$ value in MDA-MB-436 w/o2 cells by the $IC_{50}$ value in MDA-MB-436 cells. MDA-MB-436 w/o2 cells showed resistance to ARV-771 and MZ1, but not to the compound of the present invention.

TABLE 4

| Example compound No. | cytotoxic activity: $IC_{50}$ (nmol/L) | | resistance: (fold) |
|---|---|---|---|
| | MDA-MB-436 | MDA-MB-436 w/o2 | |
| 1 | 0.39 | 0.51 | 1.3 |
| 11 | 0.27 | 0.31 | 1.2 |
| 43 | 0.34 | 0.42 | 1.3 |
| 46 | 0.20 | 0.26 | 1.3 |
| 53 | 0.21 | 0.32 | 1.5 |
| ARV-771 | 5.6 | 860 | 150 |
| MZ1 | 1900 | >50000 | >2 6 |

Experimental Example 4

BRD4 Protein Degradation Inducing Action on Cancer Cells that Acquired Resistance to Conventional BRD4 Protein Degradation Inducing Agent The BRD4 protein degradation inducing action of the compound of the present invention on the cancer cells that acquired resistance to conventional BRD4 protein degradation inducing agents was evaluated in vitro. In this experiment, ARV-771 and MZ1, in which a ligand for VHL and BRD4 protein inhibitor are linked, were used as a conventional BRD4 protein degradation inducing agent serving as a comparison control. Human breast cancer MDA-MB-436 cells and MDA-MB-436 cells that acquired resistance to conventional BRD4 protein degradation inducing agents (MDA-MB-436 w/o2 cells) were suspended in 10% FBS/RPMI1640, seeded in a 6 well plate and cultured at 5% $CO_2$, 37° C. overnight. A test compound dissolved in DMSO was diluted with 10% FBS/RPMI1640 and added and the cells were further cultured for 6 hr. After culturing, the cells were lysed in a solubilizing solution (10 mM Tris-HCl, pH 7.4, 0.1% NP-40, 0.1% sodium deoxycholate, 0.1% SDS, 0.15 M NaCl, 1 mM EDTA, 10 µg/mL aprotinin). The solution was electrophoresed and proteins in acrylamide gel were transferred to Immobilon PVDF membrane using a semi-dry transfer device. After transfer, the membrane was blocked and immersed in a primary antibody (Anti-BRD4: Sigma-Aldrich, Anti-R-Actin antibody:Sigma-Aldrich) solution at 4° C. overnight. After immersing in a secondary antibody solution for 1 hr, the object protein on the membrane was detected using ECL Prime Western Blotting Detection System or ECL Select Western Blotting Detection System (GE Healthcare). As a result, as shown in FIG. 1, ARV-771 and MZ1 induced degradation of BRD4 protein in MDA-MB-436 cell but did not induce degradation in MDA-MB-436 w/o2 cell. On the other hand, the compound of the present invention equivalently induced degradation of BRD4 protein in the both cell lines.

Experimental Example 5

Inhibitory Action on Binding of BRD4 Protein and Ligand

The inhibitory action of the compound of the present invention on the binding of BRD4 protein and a ligand thereof (acetylated histone H4) was evaluated by the time-resolved fluorescence resonance energy transfer (TR-FRET) method using EPIgeneous™ Binding Domain Kit A (Cisbio), BRD4-1 (GST) (Reaction Biology Corp) and [Lys(Ac)5/8/12/16]-Histone H4 (1-21)-GGK (Biotin) (Eurogentec). In this experiment, (+)-JQ1 (Nature volume 468, pages 1067-1073 (23 Dec. 2010)) known to have an inhibitory activity on the binding of BRD4 protein and acetylated histone H4 therefor was used as a positive control drug. A test compound dissolved in DMSO was diluted with attached Diluent Buffer, added to a 384 well white plate, and BRD4-1 (GST) and [Lys(Ac)5/8/12/16]-Histone H4 (1-21)-GGK (Biotin) were further added. Thereafter, Streptavidin-d2 conjugate and Anti-GST-$Eu^{3+}$ Cryptate Conjugate were added and the cells were incubated at room temperature for 3 hr. The binding amount of the BRD4 protein and acetylated histone H4 was measured as the fluorescence intensity (excitation: 314 nm/emission: 620 nm and excitation: 314 nm/emission: 665 nm). The BRD4 protein inhibitory activity of the compound of the present invention is shown in $IC_{50}$ value (concentration of compound that inhibits 50% of the binding of BRD4 protein and acetylated histone H4) in Table 5. The $IC_{50}$ value is a concentration of the compound showing 50% fluorescence intensity when the fluorescence intensity thereof under compound untreated condition is 100%. It was calculated from the straight line connecting the degradation rate at two points enclosing the 50% fluorescence intensity and the compound concentration. The compound of the present invention showed a strong inhibitory action on the binding of BRD4 protein and ligand.

TABLE 5

| Example compound No. | BRD4 protein inhibitory activity: $IC_{50}$ (nmol/L) |
|---|---|
| 1 | 29 |
| 11 | 5.7 |
| (+)-JQ1 | 550 |

Experimental Example 6

Antitumor Effect in Human Acute Myeloid Leukemia MV-4-11 Cell Transplanted Mouse The in vivo antitumor effect of the compound of the present invention was studied using human acute myeloid leukemia MV-4-11 cell transplanted mouse. MV-4-11 cells were subcutaneously transplanted into the inguinal region of male, 6-week-old BALB/c nude mouse ($5×10^6$ cells/mouse). The compound of the present invention was administered into the tail vein on days 1, 5, 9, 13 from the time point when the assumed tumor volume determined from $1/2ab^2$ (a is major axis and b is minor axis of tumor) reached about 100 mm$^3$ (day 1). The control group was administered with a solvent, 20% hydroxypropyl-β-cyclodextrin solution. On day 15, the tumor was isolated, the weight was measured, and the tumor growth inhibitory rate IR (%) was calculated by the following formula.

tumor growth inhibitory rate IR (%)={1−(average tumor weight of administration group/average tumor weight of nonadministration control group)}×100(%)

Figure 2:
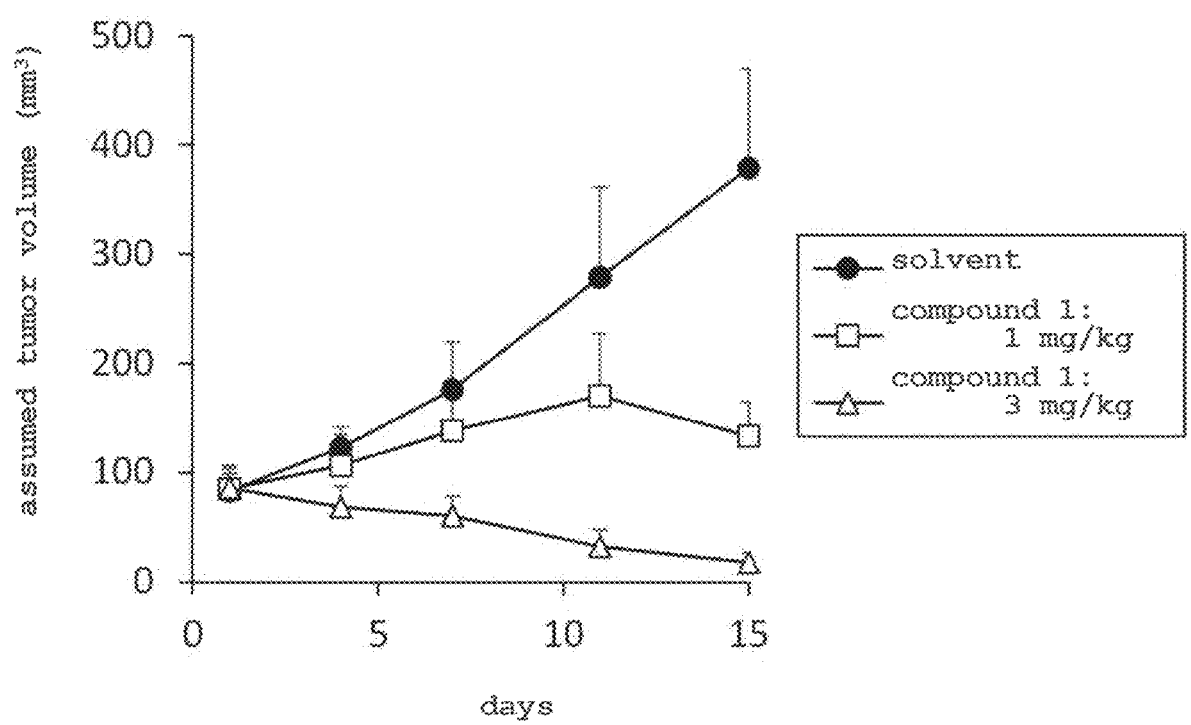
FIG. 2 shows the results of the antitumor effect in Experimental Example 6.

As a result, as shown in Table 6 and FIG. 2, it was demonstrated that the compound of the present invention exhibits an antitumor effect in human acute myeloid leukemia MV-4-11 cell transplanted mouse.

TABLE 6

| Example compound No. | dose (mg/kg/day) | tumor growth inhibitory rate (%) |
|---|---|---|
| 1 | 1 | 68.4* |
|   | 3 | 95.3* |

*$P < 0.001$;
significant difference from solvent administration group (Dunnett's test)

Experimental Example 7

Antitumor Effect of 1 Week Intermittent Administration to Human Acute Myeloid Leukemia MV-4-11 Cell Transplanted Mouse The in vivo antitumor effect of the compound of the present invention was studied using human acute myeloid leukemia MV-4-11 cell transplanted mouse. MV-4-11 cells were subcutaneously transplanted into the inguinal region of male, 6-week-old BALB/c nude mouse ($5×10^6$ cells/mouse). The compound of the present invention was administered into the tail vein on days 1 and 8 from the time point when the assumed tumor volume determined from $1/2ab^2$ (a is major axis and b is minor axis of tumor) reached about 200 mm$^3$ (day 1). The control group was administered with a solvent, 10% Kolliphor ELP/5% ethanol/85% saline solution. On day 15, the tumor was isolated, the weight was measured, and the tumor growth inhibitory rate IR (%) was calculated by the following formula.

tumor growth inhibitory rate IR (%)={1−(average tumor weight of administration group/average tumor weight of nonadministration control group)}×100(%)

As a result, as shown in Table 7, it was demonstrated that the compound of the present invention exhibits an antitumor effect in human acute myeloid leukemia MV-4-11 cell transplanted mouse even by 1 week intermittent administration.

TABLE 7

| Example compound No. | dose (mg/kg/day) | tumor growth inhibitory rate (%) |
|---|---|---|
| 1 | 4 | 56** |
|   | 12.5 | 92** |
| 47 | 4 | 32* |
|   | 12.5 | 68** |
| 74 | 4 | 43** |
|   | 12.5 | 94** |
| 106 | 4 | 96** |
|   | 12.5 | 98** |

*$P < 0.05$,
**$P < 0.001$;
significant difference from solvent administration group (Dunnett's test)

Experimental Example 8

Maximum Tolerated Dose

The maximum tolerated dose (MTD) in rats was determined for the compound of the present invention. In this experiment, control compound 157 (PCT/JP2019/026553), in which a ligand for VHL and BRD4 protein inhibitor are linked, was used as a conventional BRD4 protein degradation inducing agent serving as a comparison control. After a single tail vein administration of the compound of the present invention or compound 157 to male, 6-week-old CD (SD) rats, general condition was observed and MTD was determined.

As a result, as shown in Table 8, the compound of the present invention showed an improvement in MTD as compared with the BRD4 protein degradation inducing agent using the ligand for VHL.

TABLE 8

| Example compound No. | MTD (mg/kg) |
|---|---|
| Example 1 | >10 |
| control compound 157 | 0.5 |

INDUSTRIAL APPLICABILITY

The compound of the present invention is superior in a BRD4 protein degradation inducing action and useful as a therapeutic agent for cancer.

This application is based on patent application No. 2020-019227 filed in Japan, the contents of which are encompassed in full herein.

The invention claimed is:
1. A compound represented by the formula (I):

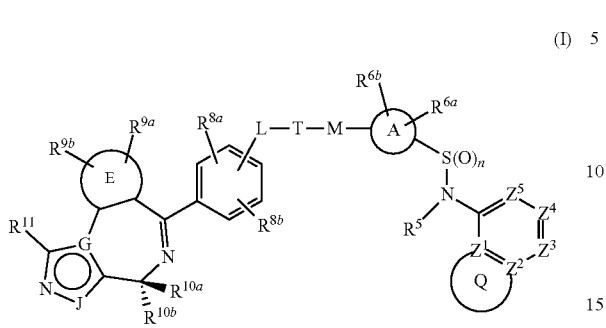

(I)

wherein
A and Q are each independently a ring selected from an aromatic hydrocarbocycle; an aromatic heterocycle containing 1 to 3 atoms selected from oxygen, sulfur and nitrogen; a cycloalkane ring; and an aliphatic heterocycle containing 1 to 3 atoms selected from oxygen, sulfur and nitrogen;
the ring is optionally substituted by a group selected from
a halogen atom;
a hydroxy group;
a cyano group;
a hydroxycarbonyl group;
an oxo group;
a thioxo group;
an alkyl group optionally substituted by a group selected from a halogen atom, a hydroxy group, an alkoxy group and a cyano group;
an alkoxy group optionally substituted by a group selected from a halogen atom, a hydroxy group, an alkoxy group and a cyano group;
an alkoxycarbonyl group optionally substituted by a group selected from a halogen atom, a hydroxy group, an alkoxy group and a cyano group;
—CO—N($R^{7a}$)($R^{7b}$);
—N($R^{7a}$)($R^{7b}$); and
—N($R^{7c}$)—CO—$R^{7d}$,
$Z^1$ is a group selected from C and N,
$Z^2$ is a group selected from C and N,
$Z^3$ is a group selected from =$CR^{23}$— and =N—,
$Z^4$ is a group selected from =$CR^{24}$— and =N—,
$Z^5$ is a group selected from =$CR^{25}$— and =N—,
$R^{Z3}$, $R^{Z4}$, and $R^{Z5}$ are each independently a group selected from a hydrogen atom; a halogen atom; a hydroxy group; a cyano group; a hydroxycarbonyl group; an alkyl group optionally substituted by a group selected from a halogen atom, a hydroxy group, an alkoxy group and a cyano group; a cycloalkyl group optionally substituted by a group selected from a halogen atom, a hydroxy group, an alkoxy group and a cyano group; an alkoxy group optionally substituted by a group selected from a halogen atom, a hydroxy group, an alkoxy group and a cyano group; an alkoxycarbonyl group optionally substituted by a group selected from a halogen atom, a hydroxy group, an alkoxy group and a cyano group; —CO—N($R^{7a}$)($R^{7b}$); —N($R^{7a}$)($R^{7b}$); —N($R^{7c}$)—CO—$R^{7d}$; an aromatic hydrocarbon group; and a 5- or 6-membered aromatic heterocyclic group containing 1 to 3 atoms selected from oxygen, sulfur and nitrogen;

a partial structure:

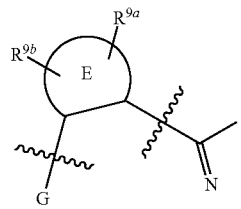

is any of the following formulas (Ea), (Eb) and (Ec):

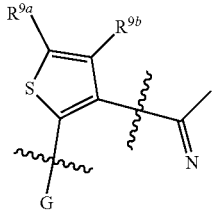
(Ea)

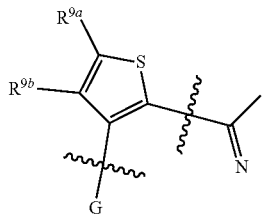
(Eb)

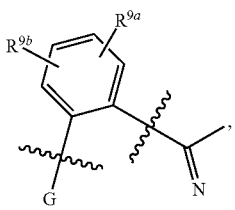
(Ec)

L, T, and M are each independently a single bond, a group selected from —O—; —S—; —$NR^{7a}$—; —CO—; —SO—; —$SO_2$—; —CO—$NR^{7c}$—; —$NR^{7c}$—CO—; —$SO_2$—$NR^{7c}$—; —$NR^{7c}$—$SO_2$—; —$NR^{7a}$—CO—$NR^{7b}$—; —(OCH_2CH_2)$_m$—; —O—$R^{7r}$—; —$R^{7r}$—O—; —S—$R^{7r}$—; —$R^{7r}$—S—; —$NR^{7a}$—$R^{7r}$—; —$R^{7r}$—$NR^{7a}$—; —CO—$NR^{7c}$—$R^{7r}$—; —$R^{7r}$—CO—$NR^{7c}$—; —$SO_2$—$NR^{7c}$—$R^{7r}$—; and —$R^{7r}$—$SO_2$—$NR^{7c}$—; or a group selected from a divalent aromatic hydrocarbon group; a divalent aliphatic heterocyclic group; an optionally partly hydrogenated divalent aromatic heterocyclic group; an alkylene group; a cycloalkylene group; an alkenylene group; and an alkynylene group;
the group is optionally substituted by a substituent selected from a halogen atom; a hydroxy group; a cyano group; an oxo group; a hydroxycarbonyl group; an alkyl group optionally substituted by a group selected from a halogen atom, a hydroxy group, an alkoxy group and a cyano group; and an alkoxy group optionally substituted by a group selected from a halogen atom, a hydroxy group, an alkoxy group and a cyano group;
-L-T-M-does not indicate a group selected from —O— O—, —S—S—, —$NR^{7a}$—$NR^{7a}$—, —O—S—, —S—

O—, —O—NR$^{7a}$—, —NR$^{7a}$—O—, —S—NR$^{7a}$-and-NR$^{7a}$—S—, as a whole or partial structure, G is N or C, J is N or O, a partial structure:

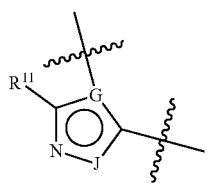

is a partial structure selected from

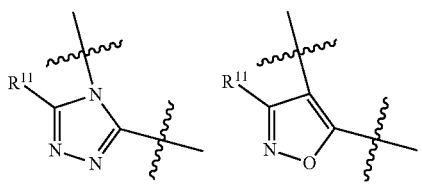

n is 1 or 2, m is an integer of 1 to 6,

R$^5$ is a group selected from a hydrogen atom; and an alkyl group optionally substituted by a group selected from a halogen atom, a hydroxy group, an alkoxy group and a cyano group;

R$^{6a}$ and R$^{6b}$ are each independently a group selected from a hydrogen atom; a halogen atom; a hydroxy group; a cyano group; an alkyl group optionally substituted by a group selected from a halogen atom, a hydroxy group, an alkoxy group and a cyano group; and an alkoxy group optionally substituted by a group selected from a halogen atom, a hydroxy group, an alkoxy group and a cyano group;

R$^{7a}$ and R$^{7b}$ are each independently a hydrogen atom; or an alkyl group optionally substituted by a group selected from a halogen atom, a hydroxy group, an alkoxy group and a cyano group, or R$^{7a}$ and R$^{7b}$ that are bonded to the same nitrogen atom are bonded to optionally form, together with the nitrogen atom, an aliphatic heterocycle having one nitrogen atom and optionally substituted by a group selected from a halogen atom, a hydroxy group, an alkoxy group and a cyano group, R$^{7c}$ and R$^{7d}$ are each independently a hydrogen atom; or an alkyl group optionally substituted by a group selected from a halogen atom, a hydroxy group, an alkoxy group and a cyano group, R$^{7r}$ is a group selected from an alkylene group optionally substituted by a group selected from a halogen atom, a hydroxy group, an alkoxy group and a cyano group; an alkenylene group optionally substituted by a group selected from a halogen atom, a hydroxy group, an alkoxy group and a cyano group; or an alkynylene group optionally substituted by a group selected from a halogen atom, a hydroxy group, an alkoxy group and a cyano group, R$^{8a}$ and R$^{8b}$ are each independently a group selected from a hydrogen atom; a halogen atom; a hydroxy group; a cyano group; an alkyl group optionally substituted by a group selected from a halogen atom, a hydroxy group, an alkoxy group and a cyano group; and an alkoxy group optionally substituted by a group selected from a halogen atom, a hydroxy group, an alkoxy group and a cyano group;

R$^{9a}$ and R$^{9b}$ are each independently a group selected from a hydrogen atom; a halogen atom; a hydroxy group; a cyano group; a hydroxycarbonyl group; an alkyl group optionally substituted by a group selected from a halogen atom, a hydroxy group, an alkoxy group and a cyano group; an alkoxy group optionally substituted by a group selected from a halogen atom, a hydroxy group, an alkoxy group and a cyano group; an alkoxycarbonyl group optionally substituted by a substituent selected from a halogen atom, a hydroxy group, an alkoxy group and a cyano group; and —CO—N(R$^{7a}$)(R$^{7b}$), or R$^{9a}$ and R$^{9b}$ are optionally joined by an alkylene group optionally substituted by a group selected from a halogen atom, a hydroxy group, an alkoxy group and a cyano group; or an alkenylene group optionally substituted by a group selected from a halogen atom, a hydroxy group, an alkoxy group and a cyano group, and optionally form a fused ring with the adjacent ring E, R$^{10a}$ and R$^{10b}$ are each independently a substituent selected from a hydrogen atom; a hydroxy group; a cyano group; —N(R$^{7a}$)(R$^{7b}$); —N(R$^{7c}$)—CO—OR$^{7d}$, and an alkyl group;

the alkyl group is optionally substituted by a substituent selected from a halogen atom; a hydroxy group; a cyano group; an alkoxy group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; a hydroxycarbonyl group; and —CO—N(R$^{7a}$)(R$^{7b}$); or R$^{10a}$ and R$^{10b}$ are optionally joined by an alkylene group optionally substituted by a group selected from a halogen atom, a hydroxy group, an alkoxy group and a cyano group and form a ring, and R$^{11}$ is a group selected from a hydrogen atom; and an alkyl group optionally substituted by a group selected from a halogen atom, a hydroxy group, an alkoxy group and a cyano group;

or a pharmaceutically acceptable salt thereof.

2. The compound according to claim 1, wherein a partial structure:

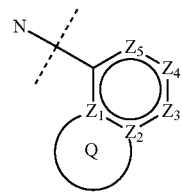

is represented by the following formula:

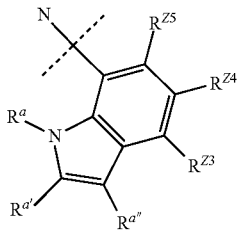

wherein
$R^a$ is a hydrogen atom; or an alkyl group optionally substituted by a substituent selected from a halogen atom, a hydroxy group, an alkoxy group and a cyano group;

$R^{a'}$ is a hydrogen atom; a halogen atom; a hydroxy group; a cyano group; an alkyl group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; or —CO—N($R^{7a}$)($R^{7b}$), $R^{a'}$ is a hydrogen atom; a halogen atom; a cyano group; an alkyl group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; or —CO—N($R^{7a}$)($R^{7b}$), or a pharmaceutically acceptable salt thereof.

3. The compound according to claim 2, wherein

A is a ring selected from an aromatic hydrocarbocycle, a 5- or 6-membered aromatic heterocycle containing 1 to 3 atoms selected from oxygen, sulfur and nitrogen, and a cycloalkane ring, $R^{Z3}$ is a group selected from a hydrogen atom; a halogen atom; a hydroxy group; a cyano group; a hydroxycarbonyl group; an alkyl group optionally substituted by a group selected from a halogen atom, a hydroxy group, an alkoxy group and a cyano group; a cycloalkyl group optionally substituted by a group selected from a halogen atom, a hydroxy group, an alkoxy group and a cyano group; an alkoxy group optionally substituted by a group selected from a halogen atom, a hydroxy group, an alkoxy group and a cyano group; an alkoxycarbonyl group optionally substituted by a group selected from a halogen atom, a hydroxy group, an alkoxy group and a cyano group;

$R^{Z4}$ and $R^{Z5}$ are each independently a group selected from a hydrogen atom; a halogen atom; a cyano group; an alkyl group optionally substituted by a substituent selected from a halogen atom, a hydroxy group, an alkoxy group and a cyano group; an alkoxy group optionally substituted by a group selected from a halogen atom, a hydroxy group, an alkoxy group and a cyano group;

a partial structure:

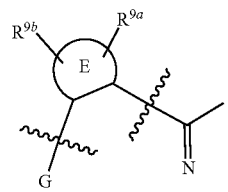

is represented by the following formula (Ea) or (Ec):

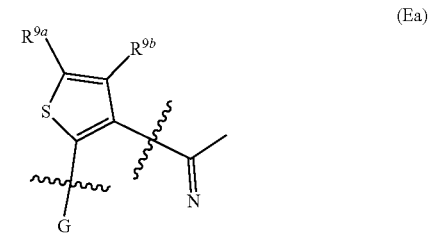

a partial structure:

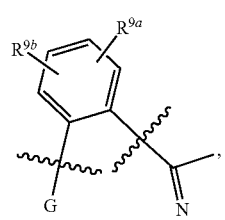

is represented by

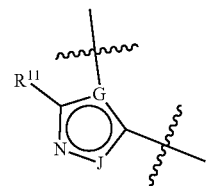

a partial structure:

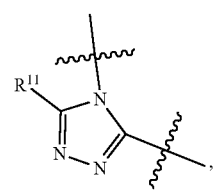

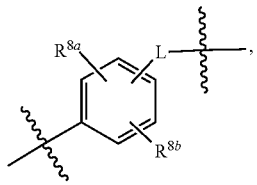

is represented by

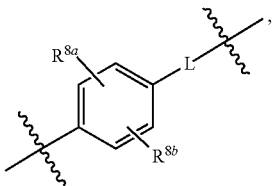

L is a group selected from a divalent aromatic hydrocarbon group; a divalent aliphatic heterocyclic group; an optionally partly hydrogenated divalent aromatic heterocyclic group; an alkylene group; a cycloalkylene group; an alkenylene group; and an alkynylene group;
the group is optionally substituted by a substituent selected from a halogen atom; a hydroxy group; a cyano group; a hydroxycarbonyl group; an alkyl group optionally substituted by a group selected from a halogen atom, a hydroxy group, an alkoxy group and a cyano group; and an alkoxy group optionally substituted by a group selected from a halogen atom, a hydroxy group, an alkoxy group and a cyano group;
T is a single bond, —CO—, —CO—$NR^{7c}$—, —$NR^{7c}$—CO—, or —O—, or an alkylene group optionally substituted by a substituent selected from a halogen atom; a hydroxy group; a cyano group; an oxo group; a hydroxycarbonyl group; an alkyl group optionally substituted by a substituent selected from a halogen atom, a hydroxy group, an alkoxy group and a cyano group; and an alkoxy group optionally substituted by substituent selected from a halogen atom, a hydroxy group, an alkoxy group and a cyano group;
M is a single bond, or a group selected from —O—; —S—; —$NR^{7a}$—; —CO—; —SO—; —$SO_2$—; —CO—$NR^{7c}$—; —$NR^{7c}$—CO—; —$SO_2$—$NR^{7c}$—; —$NR^{7c}$—$SO_2$—; —$NR^{7a}$—CO—$NR^{7b}$—; —$(OCH_2CH_2)_m$—; —O—$R^{7r}$—; —$R^{7r}$—O—; —S—$R^{7r}$—; —$R^{7r}$—S—; —$NR^{7a}$—$R^{7r}$—; —$R^{7r}$—$NR^{7a}$—; —CO—$NR^{7c}$—$R^{7r}$; —$R^{7r}$—CO—$NR^{7c}$—; an alkylene group optionally substituted by a substituent selected from a halogen atom, a hydroxy group, an alkoxy group and a cyano group; an alkynylene group optionally substituted by a substituent selected from a halogen atom, a hydroxy group, an alkoxy group and a cyano group; and a divalent aliphatic heterocyclic group optionally substituted by a substituent selected from a) a halogen atom, b) a hydroxy group, c) a cyano group, d) an oxo group, e) an alkyl group optionally substituted by a substituent selected from a halogen atom, a hydroxy group, an alkoxy group and a cyano group, and f) an alkoxy group optionally substituted by a substituent selected from a halogen atom, a hydroxy group, an alkoxy group and a cyano group,
$R^5$ is a hydrogen atom,
$R^{6a}$ and $R^{6b}$ are each independently a group selected from a hydrogen atom; a halogen atom; a hydroxy group; a cyano group; and an alkyl group optionally substituted by a substituent selected from a halogen atom, a hydroxy group and a cyano group;
$R^{7c}$ is a hydrogen atom,
$R^{8a}$ and $R^{8b}$ are each independently a group selected from a hydrogen atom; a halogen atom; a hydroxy group; and a cyano group;

$R^{9a}$ and $R^{9b}$ are each independently a group selected from a hydrogen atom; a halogen atom; a cyano group; an alkyl group optionally substituted by a substituent selected from a halogen atom, a hydroxy group and a cyano group;
$R^{10a}$ and $R^{10b}$ are each independently a substituent selected from a hydrogen atom; —$N(R^{7c})$—CO—$OR^{7d}$; and an alkyl group;
the alkyl group is optionally substituted by a substituent selected from a halogen atom; a hydroxy group; a cyano group; an alkoxy group optionally substituted by a substituent selected from a halogen atom, a hydroxy group, an alkoxy group and a cyano group; an alkoxycarbonyl group optionally substituted by a substituent selected from a halogen atom, a hydroxy group, an alkoxy group and a cyano group; —CO—$N(R^{7a})(R^{7b})$; and a hydroxycarbonyl group,
or a pharmaceutically acceptable salt thereof.

4. The compound according to claim 2, wherein
A is a ring selected from a benzene ring; a pyridine ring; and a cycloalkane ring,
$R^a$ is a hydrogen atom; or an alkyl group optionally substituted by a substituent selected from a halogen atom, a hydroxy group, and a cyano group,
$R^{a'}$ is a hydrogen atom; or an alkyl group optionally substituted by a substituent selected from a halogen atom, a hydroxy group, and a cyano group,
$R^{a''}$ is a hydrogen atom; a halogen atom; an alkyl group optionally substituted by a substituent selected from a halogen atom, a hydroxy group, and a cyano group; or a cyano group,
$R^{Z3}$ is a hydrogen atom; a halogen atom; a cyano group; an alkyl group optionally substituted by a substituent selected from a halogen atom, a hydroxy group and a cyano group; a cycloalkyl group optionally substituted by a substituent selected from a halogen atom, a hydroxy group and a cyano group; or an alkoxy group optionally substituted by a substituent selected from a halogen atom, a hydroxy group and a cyano group;
$R^{Z4}$ and $R^{Z5}$ are each independently a hydrogen atom; or an alkyl group optionally substituted by a substituent selected from a halogen atom, a hydroxy group and a cyano group,
a partial structure:

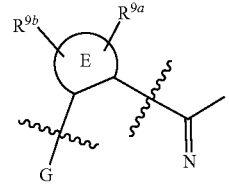

is represented by the following formula (Ea):

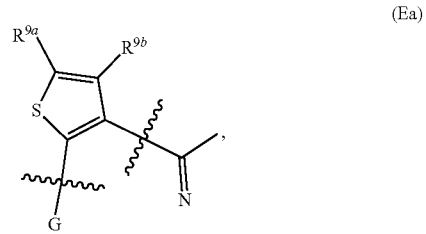

(Ea)

L is a group selected from an alkynyl group optionally substituted by a substituent selected from a halogen atom, a hydroxy group and a cyano group; a divalent aromatic hydrocarbon group optionally substituted by a substituent selected from a) a halogen atom, b) a hydroxy group, c) a cyano group, d) an alkyl group optionally substituted by a substituent selected from a halogen atom, a hydroxy group and a cyano group, and e) an alkoxy group optionally substituted by a substituent selected from a halogen atom, a hydroxy group and a cyano group; a divalent aliphatic heterocyclic group containing one nitrogen atom optionally substituted by a substituent selected from a halogen atom, a hydroxy group and a cyano group; and an optionally partially hydrogenated, divalent aromatic heterocyclic group containing 1-2 atoms selected from a nitrogen atom, an oxygen atom and a sulfur atom, the aromatic heterocyclic group is optionally substituted by a substituent selected from a halogen atom, a hydroxy group, a cyano group and an oxo group, T is a single bond; —CO—; —CO—$NR^{7c}$—; —$NR^{7c}$—CO—; or —O—, M is a single bond, or a group selected from —$R^{7r}$—O—; —$R^{7r}$—$NR^{7a}$—; an alkylene group optionally substituted by a substituent selected from a halogen atom, a hydroxy group, and a cyano group; an alkynylene group optionally substituted by a substituent selected from a halogen atom, a hydroxy group, and a cyano group; and a divalent aliphatic heterocyclic group, $R^{6a}$ and $R^{6b}$ are each independently a group selected from a hydrogen atom; a halogen atom; a cyano group; and an alkyl group optionally substituted by a substituent selected from a halogen atom, a hydroxy group and a cyano group, $R^{7a}$ and $R^{7b}$ are each independently a hydrogen atom; or an alkyl group optionally substituted by a substituent selected from a halogen atom, a hydroxy group and a cyano group, $R^{7c}$ is a hydrogen atom, $R^{7d}$ is an alkyl group optionally substituted by a substituent selected from a halogen atom, a hydroxy group and a cyano group, $R^{7r}$ is an alkylene group optionally substituted by a substituent selected from a halogen atom, a hydroxy group, and a cyano group, $R^{8a}$ and $R^{8b}$ are each a hydrogen atom, $R^{9a}$ and $R^{9b}$ are each independently an alkyl group optionally substituted by a substituent selected from a halogen atom, a hydroxy group and a cyano group, $R^{10a}$ is a group selected from a hydrogen atom; and an alkyl group optionally substituted by a substituent selected from a halogen atom, a hydroxy group, a cyano group, —NH—CO—$OR^{7d}$, —CO—N($R^{7a}$)($R^{7b}$), an alkoxycarbonyl group and a hydroxycarbonyl group, $R^{10b}$ is a hydrogen atom, and $R^{11}$ is an alkyl group optionally substituted by a substituent selected from a halogen atom, a hydroxy group and a cyano group, or a pharmaceutically acceptable salt thereof.

5. The compound according to claim 2, wherein
$R^a$ is a hydrogen atom; or an alkyl group,
$R^{a'}$ is a hydrogen atom; or an alkyl group,
$R^{a''}$ is a hydrogen atom; a halogen atom; an alkyl group; or a cyano group,
$R^{Z3}$ is a hydrogen atom; a halogen atom; a cyano group; an alkyl group optionally substituted by 1-3 substituents selected from a halogen atom and hydroxy group; a cycloalkyl group; or an alkoxy group, $RZ^4$ and $R^{Z5}$ are each independently a hydrogen atom; or an alkyl group, a partial structure:

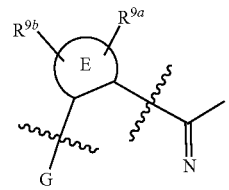

is represented by the following formula (Ea):

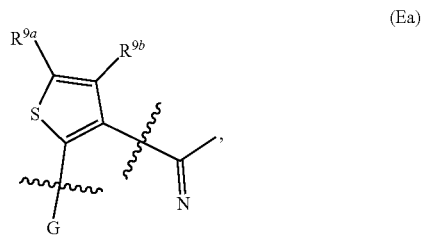

L is a group selected from an alkynylene group; a divalent aromatic hydrocarbon group optionally substituted by 1-2 substituents selected from a halogen atom, a hydroxy group, an alkyl group optionally substituted by 1 to 3 halogen atoms, and an alkoxy group; a divalent aliphatic heterocyclic group containing one nitrogen atom; and optionally partially hydrogenated, divalent aromatic heterocyclic group containing 1-2 atoms selected from a nitrogen atom, an oxygen atom and a sulfur atom, the aromatic heterocyclic group is optionally substituted by an oxo group when it is a partially hydrogenated, divalent aromatic heterocyclic group containing 1-2 atoms selected from a nitrogen atom, an oxygen atom and a sulfur atom, T is a single bond, or —CO—; —CO—$NR^{7c}$—; —$NR^{7c}$—CO—; or —O—, M is a single bond, or a group selected from —$R^{7r}$—O—; —$R^{7r}$—$NR^{7a}$—; an alkylene group optionally substituted by one hydroxy group; an alkynylene group; and a divalent aliphatic heterocyclic group, $R^{6a}$ and $R^{6b}$ are each independently a group selected from a hydrogen atom; a halogen atom; a cyano group; and an alkyl group, $R^{7a}$ and $R^{7b}$ are each independently a hydrogen atom; or an alkyl group, $R^{7c}$ is a hydrogen atom, $R^{7d}$ is an alkyl group, $R^{7r}$ is an alkylene group, $R^{8a}$ and $R^{8b}$ are each a hydrogen atom, $R^{9a}$ and $R^{9b}$ are each independently an alkyl group optionally substituted by one hydroxy group, $R^{10a}$ is a group selected from a hydrogen atom; and an alkyl group optionally substituted by one substituent selected from —NH—CO—$OR^{7d}$, —CO—N($R^{7a}$)($R^{7b}$), a cyano group, an alkoxycarbonyl group and a hydroxycarbonyl group, R$^{10b}$ is a hydrogen atom, and
R$^{11}$ is an alkyl group,
or a pharmaceutically acceptable salt thereof.

6. The compound according to claim 2, wherein
A is a benzene ring,
R$^a$ is a hydrogen atom,
R$^{10a}$ is an alkyl group optionally substituted by one alkoxycarbonyl group,
L is a group selected from a divalent aromatic hydrocarbon group optionally substituted by 1-2 substituents selected from a halogen atom, an alkyl group optionally substituted by 1 to 3 halogen atoms, and an alkoxy group; and optionally partially hydrogenated, divalent aromatic heterocyclic group containing 1-2 atoms selected from a nitrogen atom, an oxygen atom and a sulfur atom, and
M is an alkylene group optionally substituted by one substituent selected from a hydroxy group and a cyano group,
or a pharmaceutically acceptable salt thereof.

7. The compound according to claim 2, wherein
R$^{a'}$ is a hydrogen atom,
R$^{a''}$ is a cyano group,
R$^{Z3}$ is an alkyl group optionally substituted by 1 to 3 halogen atoms or a hydroxy group; or an alkoxy group,
R$^{Z4}$ is a hydrogen atom, and
R$^{Z5}$ is a hydrogen atom,
or a pharmaceutically acceptable salt thereof.

8. The compound according to claim 2, wherein
R$^{8a}$ and R$^{8b}$ are each a hydrogen atom,
R$^{9a}$ and R$^{9b}$ are each independently an alkyl group optionally substituted by one hydroxy group,
R$^{10a}$ is an alkyl group optionally substituted by one alkoxycarbonyl group,
R$^{10b}$ is a hydrogen atom, and
R$^{11}$ is an alkyl group,
or a pharmaceutically acceptable salt thereof.

9. The compound according to claim 2, wherein
L is a phenylene group optionally substituted by 1-2 substituents selected from a halogen atom and an alkyl group; or a pyrazinediyl group,
T is -CO—NR$^{7c}$—, R$^{7c}$ is a hydrogen atom, and
M is —CH$_2$— or —CH(CH$_3$)—,
or a pharmaceutically acceptable salt thereof.

10. A compound selected from
methyl [(6S)-4-{4'-[(2-{4-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate,
methyl [(6S)-4-{4'-[({4-[(3-cyano-4-methoxy-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate,
methyl [(6S)-4-(4'-{[(1R)-1-{4-[(3-cyano-4-methyl-1H-indol-7-yl)sulfamoyl]phenyl} ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate,
methyl [(6S)-4-{4'-[({4-[(3-cyano-4-ethyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate,
methyl [(6S)-4-{4'-[({4-[(3-cyano-4-methyl-1H-indol-7-yl)sulfamoyl]phenyl}methyl)carbamoyl]-2'-fluoro[1,1'-biphenyl]-4-yl}-2,3,9-trimethyl-6H-thieno[3,2-f][1,2,4]triazolo[4,3-a][1,4]diazepin-6-yl]acetate,
methyl [(6S)-4-{4'-[(2-{4-[(3-cyano-4-methyl-1H-indol-7-yl)sulfamoyl]phenyl}ethyl)carbamoyl]-2'-fluoro[1,1'-biphenyl]-4-yl}-2,3,9-trimethyl-6H-thieno[3,2-f][1,2,4]triazolo[4,3-a][1,4]diazepin-6-yl]acetate,
methyl [(6S)-4-{4'-[({4-[(3-cyano-4-methyl-1H-indol-7-yl)sulfamoyl]phenyl}methyl)carbamoyl]-3'-methyl[1,1'-biphenyl]-4-yl}-2,3,9-trimethyl-6H-thieno[3,2-f][1,2,4]triazolo[4,3-a][1,4]diazepin-6-yl]acetate,
methyl [(6S)-4-(4-{6-[({4-[(3-cyano-4-methyl-1H-indol-7-yl)sulfamoyl]phenyl}methyl)carbamoyl]pyridin-3-yl}phenyl)-2,3,9-trimethyl-6H-thieno[3,2-f][1,2,4]triazolo[4,3-a][1,4]diazepin-6-yl]acetate,
t-butyl [(6S)-4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate,
t-butyl [(6S)-4-{4'-[(2-{4-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate,
methyl [(6S)-4-(4-{5-[({4-[(3-cyano-4-methyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1,4]diazepin-6-yl]acetate,
methyl [(6S)-4-(4'-{[(1R)-1-{4-[(3-cyano-4-methyl-1H-indol-7-yl)sulfamoyl]phenyl}ethyl]carbamoyl}-3'-fluoro[1,1'-biphenyl]-4-yl)-2,3,9-trimethyl-6H-thieno[3,2-f][1,2,4]triazolo[4,3-a][1,4]diazepin-6-yl]acetate,
methyl [(6S)-4-(3'-chloro-4'-{[(1R)-1-{4-[(3-cyano-4-methyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate,
5-chloro-N-({4-[(3-cyano-4-methyl-1H-indol-7-yl)sulfamoyl]phenyl}methyl)-2-fluoro-4'-[(6S)-2,3,6,9-tetramethyl-6H-thieno[3,2-f][1,2,4]triazolo[4,3-a][1,4]diazepin-4-yl][1,1'-biphenyl]-4-carboxamide,
methyl [(6S)-4-(4'-{[(1R)-1-{4-[(3-cyano-4-methyl-1H-indol-7-yl)sulfamoyl]phenyl}ethyl]carbamoyl}-2'-fluoro[1,1'-biphenyl]-4-yl)-2,3,9-trimethyl-6H-thieno[3,2-f][1,2,4]triazolo[4,3-a][1,4]diazepin-6-yl]acetate,
methyl {(6S)-4-[4-(6-{[(1R)-1-{4-[(3-cyano-4-methyl-1H-indol-7-yl)sulfamoyl]phenyl}ethyl]carbamoyl}pyridin-3-yl)phenyl]-2,3,9-trimethyl-6H-thieno[3,2-f][1,2,4]triazolo[4,3-a][1,4]diazepin-6-yl}acetate,
methyl [(6S)-4-(4'-{[(1R)-1-{4-[(3-cyano-4-methyl-1H-indol-7-yl)sulfamoyl]phenyl}ethyl]carbamoyl}-2',5'-difluoro[1,1'-biphenyl]-4-yl)-2,3,9-trimethyl-6H-thieno[3,2-f][1,2,4]triazolo[4,3-a][1,4]diazepin-6-yl]acetate,
methyl [(6S)-4-(4'-{[(1R)-1-{4-[(3-cyano-4-methyl-1H-indol-7-yl)sulfamoyl]phenyl}ethyl]carbamoyl}-2'-fluoro-5'-methyl[1,1'-biphenyl]-4-yl)-2,3,9-trimethyl-6H-thieno[3,2-f][1,2,4]triazolo[4,3-a][1,4]diazepin-6-yl]acetate,
methyl [(6S)-4-(4'-{[(1R)-1-{4-[(3-cyano-4-methyl-1H-indol-7-yl)sulfamoyl]phenyl}ethyl]carbamoyl}-2',3'-difluoro[1,1'-biphenyl]-4-yl)-2,3,9-trimethyl-6H-thieno[3,2-f][1,2,4]triazolo[4,3-a][1,4]diazepin-6-yl]acetate,
methyl [(6S)-4-{4'-[(2-{4-[(3-cyano-4-methyl-1H-indol-7-yl)sulfamoyl]phenyl}ethyl)carbamoyl]-2',3'-difluoro[1,1'-biphenyl]-4-yl}-2,3,9-trimethyl-6H-thieno[3,2-f][1,2,4]triazolo[4,3-a][1,4]diazepin-6-yl]acetate,
methyl [(6S)-4-(4-{5-[(2-{4-[(3-cyano-4-methyl-1H-indol-7-yl)sulfamoyl]phenyl}ethyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl {(6S)-4-[4-(5-{[(1R)-1-{4-[(3-cyano-4-methyl-1H-indol-7-yl)sulfamoyl]phenyl}ethyl]carbamoyl}pyrazin-2-yl)phenyl]-2,3,9-trimethyl-6H-thieno[3,2-f][1,2,4]triazolo[4,3-a][1,4]diazepin-6-yl}acetate, methyl [(6S)-4-(4-{5-[({4-[(3-cyano-4-ethyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl [(6S)-4-(4-{5-[(2-{4-[(3-cyano-4-ethyl-1H-indol-7-yl)sulfamoyl]phenyl}ethyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl [(6S)-4-(4-{6-[({4-[(3-cyano-4-ethyl-1H-indol-7-yl)sulfamoyl]phenyl}methyl)carbamoyl]pyridin-3-yl}phenyl)-2,3,9-trimethyl-6H-thieno[3,2-f][1,2,4]triazolo[4,3-a][1,4]diazepin-6-yl]acetate, methyl {(6S)-4-[4-(6-{[(1R)-1-{4-[(3-cyano-4-ethyl-1H-indol-7-yl)sulfamoyl]phenyl}ethyl]carbamoyl}pyridin-3-yl)phenyl]-2,3,9-trimethyl-6H-thieno[3,2-f][1,2,4]triazolo[4,3-a][1,4]diazepin-6-yl}acetate, methyl [(6S)-4-(4-{6-[(2-{4-[(3-cyano-4-ethyl-1H-indol-7-yl)sulfamoyl]phenyl}ethyl)carbamoyl]pyridin-3-yl}phenyl)-2,3,9-trimethyl-6H-thieno[3,2-f][1,2,4]triazolo[4,3-a][1,4]diazepin-6-yl]acetate, methyl [(6S)-4-{4'-[({4-[(3-cyano-4-ethyl-1H-indol-7-yl)sulfamoyl]phenyl}methyl)carbamoyl]-2',3'-difluoro[1,1'-biphenyl]-4-yl}-2,3,9-trimethyl-6H-thieno[3,2-f][1,2,4]triazolo[4,3-a][1,4]diazepin-6-yl]acetate, methyl [(6S)-4-(4'-{[(1R)-1-{4-[(3-cyano-4-ethyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate, and t-butyl [(6S)-4-(4-{5-[({4-[(3-cyano-4-methyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1,4]diazepin-6-yl]acetate, or a pharmaceutically acceptable salt thereof.

11. A compound selected from methyl [(6S)-4-{4'-[(2-{4-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate, methyl [(6S)-4-(4'-{[(1R)-1-{4-[(3-cyano-4-methyl-1H-indol-7-yl)sulfamoyl]phenyl}ethyl]carbamoyl}[1,1'-biphenyl]-4-yl)-2,3,9-trimethyl-6H-thieno[3,2-f][1,2,4]triazolo[4,3-a][1,4]diazepin-6-yl]acetate, methyl [(6S)-4-{4'-[({4-[(3-cyano-4-ethyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate, methyl [(6S)-4-(4-{6-[({4-[(3-cyano-4-methyl-1H-indol-7-yl)sulfamoyl]phenyl}methyl)carbamoyl]pyridin-3-yl}phenyl)-2,3,9-trimethyl-6H-thieno[3,2-f][1,2,4]triazolo[4,3-a][1,4]diazepin-6-yl]acetate, t-butyl [(6S)-4-{4'-[({4-[(3-cyano-4-methyl-1H-indol-7-yl)sulfamoyl]phenyl}methyl)carbamoyl][1,1'-biphenyl]-4-yl}-2,3,9-trimethyl-6H-thieno[3,2-f][1,2,4]triazolo[4,3-a][1,4]diazepin-6-yl]acetate, t-butyl [(6S)-4-{4'-[(2-{4-[(3-cyano-4-methyl-1H-indol-7-yl)sulfamoyl]phenyl}ethyl)carbamoyl][1,1'-biphenyl]-4-yl}-2,3,9-trimethyl-6H-thieno[3,2-f][1,2,4]triazolo[4,3-a][1,4]diazepin-6-yl]acetate, methyl [(6S)-4-(4-{5-[({4-[(3-cyano-4-methyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl [(6S)-4-(4'-{[(1R)-1-{4-[(3-cyano-4-methyl-1H-indol-7-yl)sulfamoyl]phenyl}ethyl]carbamoyl}-3'-fluoro[1,1'-biphenyl]-4-yl)-2,3,9-trimethyl-6H-thieno[3,2-f][1,2,4]triazolo[4,3-a][1,4]diazepin-6-yl]acetate, 5-chloro-N-({4-[(3-cyano-4-methyl-1H-indol-7-yl)sulfamoyl]phenyl}methyl)-2-fluoro-4'-[(6S)-2,3,6,9-tetramethyl-6H-thieno[3,2-f][1,2,4]triazolo[4,3-a][1,4]diazepin-4-yl][1,1'-biphenyl]-4-carboxamide, methyl {(6S)-4-[4-(6-{[(1R)-1-{4-[(3-cyano-4-methyl-1H-indol-7-yl)sulfamoyl]phenyl}ethyl]carbamoyl}pyridin-3-yl)phenyl]-2,3,9-trimethyl-6H-thieno[3,2-f][1,2,4]triazolo[4,3-a][1,4]diazepin-6-yl}acetate, methyl [(6S)-4-(4-{5-[(2-{4-[(3-cyano-4-methyl-1H-indol-7-yl)sulfamoyl]phenyl}ethyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl {(6S)-4-[4-(5-{[(1R)-1-{4-[(3-cyano-4-methyl-1H-indol-7-yl)sulfamoyl]phenyl}ethyl]carbamoyl}pyrazin-2-yl)phenyl]-2,3,9-trimethyl-6H-thieno[3,2-f][1,2,4]triazolo[4,3-a][1,4]diazepin-6-yl}acetate, methyl [(6S)-4-(4-{5-[({4-[(3-cyano-4-ethyl-1H-indol-7-yl)sulfamoyl]phenyl}methyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl [(6S)-4-(4-{5-[(2-{4-[(3-cyano-4-ethyl-1H-indol-7-yl)sulfamoyl]phenyl}ethyl)carbamoyl]pyrazin-2-yl}phenyl)-2,3,9-trimethyl-6H-thieno[3,2-f][1,2,4]triazolo[4,3-a][1,4]diazepin-6-yl]acetate, methyl [(6S)-4-(4-{6-[({4-[(3-cyano-4-ethyl-1H-indol-7-yl)sulfamoyl]phenyl}methyl)carbamoyl]pyridin-3-yl}phenyl)-2,3,9-trimethyl-6H-thieno[3,2-f][1,2,4]triazolo[4,3-a][1,4]diazepin-6-yl]acetate, methyl {(6S)-4-[4-(6-{[(1R)-1-{4-[(3-cyano-4-ethyl-1H-indol-7-yl)sulfamoyl]phenyl}ethyl]carbamoyl}pyridin-3-yl)phenyl]-2,3,9-trimethyl-6H-thieno[3,2-f][1,2,4]triazolo[4,3-a][1,4]diazepin-6-yl}acetate, and methyl [(6S)-4-(4-{6-[(2-{4-[(3-cyano-4-ethyl-1H-indol-7-yl)sulfamoyl]phenyl}ethyl)carbamoyl]pyridin-3-yl}phenyl)-2,3,9-trimethyl-6H-thieno[3,2-f][1,2,4]triazolo[4,3-a][1,4]diazepin-6-yl]acetate, or a pharmaceutically acceptable salt thereof.

12. A pharmaceutical composition comprising the compound according to claim 1 or a pharmaceutically acceptable salt thereof.

13. The pharmaceutical composition according to claim 12 for inducing BRD4 proteolysis.

14. The pharmaceutical composition according to claim 12 for treating cancer.

15. The pharmaceutical composition according to claim 14, wherein the cancer is selected from acute myeloid leukemia, acute lymphocytic leukemia, chronic myeloid leukemia, multiple myeloma, diffuse large B-cell lymphoma, adult T-cell leukemia lymphoma, Burkitt lymphoma, prostate cancer, ovarian cancer, bladder cancer, breast cancer, uterus cervix cancer, uterine sarcoma, gastric cancer, lung cancer, colorectal cancer, glioma, pancreatic cancer, liver cancer, bile duct cancer, renal cell cancer, and fibrosarcoma.

16. The pharmaceutical composition according to claim 15, wherein the cancer is selected from acute myeloid leukemia, chronic myeloid leukemia, acute lymphocytic leukemia, diffuse large B-cell lymphoma, multiple myeloma, Burkitt lymphoma, glioma, gastric cancer, colorectal cancer, pancreatic cancer, liver cancer, prostate cancer, non-small cell lung cancer, breast cancer, ovarian cancer and uterine sarcoma.

17. The pharmaceutical composition according to claim 16, wherein the cancer is selected from acute myeloid leukemia, diffuse large B-cell lymphoma, multiple myeloma, prostate cancer, ovarian cancer and breast cancer.

18. A method for treating cancer, comprising administering the compound according to claim 1 or a pharmaceutically acceptable salt thereof.

19. A method for treating cancer, comprising administering the pharmaceutical composition according to claim 12.

* * * * *

UNITED STATES PATENT AND TRADEMARK OFFICE
CERTIFICATE OF CORRECTION

PATENT NO. : 12,102,641 B2
APPLICATION NO. : 17/796258
DATED : October 1, 2024
INVENTOR(S) : Kiyomi Ohba et al.

Page 1 of 1

It is certified that error appears in the above-identified patent and that said Letters Patent is hereby corrected as shown below:

In the Claims

At Claim 1, Column 327, Lines 47-49, -- $CR^{23}$, $CR^{24}$, and $CR^{25}$ -- should be -- $CR^{Z3}$, $CR^{Z4}$, and $CR^{Z5}$ --

At Claim 1, Column 329, Line 4, -- Nor O -- should be -- N or O --

At Claim 2, Column 331, Line 29, -- $R^{a\prime\prime}$ -- should be -- $R^{a\prime\prime\prime}$ --

Signed and Sealed this
Fourth Day of February, 2025

Coke Morgan Stewart
*Acting Director of the United States Patent and Trademark Office*